US012715860B2

(12) United States Patent
Ozawa et al.

(10) Patent No.: US 12,715,860 B2
(45) Date of Patent: Aug. 25, 2026

(54) COMPOUND, LIGHT-EMITTING MATERIAL, DELAYED FLUORESCENCE MATERIAL, AND ORGANIC OPTICAL DEVICE

(71) Applicant: KYULUX, INC., Fukuoka (JP)

(72) Inventors: Hiroaki Ozawa, Fukuoka (JP); Masataka Yamashita, Fukuoka (JP); Shuo-Hsien Cheng, Fukuoka (JP); YuSeok Yang, Fukuoka (JP)

(73) Assignee: KYULUX, INC., Fukuoka (JP)

( * ) Notice: Subject to any disclaimer, the term of this patent is extended or adjusted under 35 U.S.C. 154(b) by 1057 days.

(21) Appl. No.: 17/760,127

(22) PCT Filed: Feb. 3, 2021

(86) PCT No.: PCT/JP2021/003845
§ 371 (c)(1),
(2) Date: Aug. 4, 2022

(87) PCT Pub. No.: WO2021/157599
PCT Pub. Date: Aug. 12, 2021

(65) Prior Publication Data

US 2023/0106096 A1 Apr. 6, 2023

(30) Foreign Application Priority Data

Feb. 5, 2020 (JP) ................................ 2020-018374

(51) Int. Cl.
*C07D 403/14* (2006.01)
*H10K 50/11* (2023.01)
*H10K 85/60* (2023.01)

(52) U.S. Cl.
CPC ........... *C07D 403/14* (2013.01); *H10K 50/11* (2023.02); *H10K 85/652* (2023.02); *H10K 85/654* (2023.02); *H10K 85/6572* (2023.02)

(58) Field of Classification Search
CPC .... C07D 403/14; H10K 50/11; H10K 85/652; H10K 85/654; H10K 85/6572; H10K 50/14; C09K 11/06
See application file for complete search history.

(56) References Cited

U.S. PATENT DOCUMENTS

| | | | | |
|---|---|---|---|---|
| 2016/0172601 A1* | 6/2016 | Kawamura | C07D 209/82 | 257/40 |
| 2016/0380205 A1* | 12/2016 | Adachi | C09K 11/06 | 544/102 |
| 2017/0256720 A1* | 9/2017 | Adachi | C09K 11/06 | |
| 2018/0323394 A1* | 11/2018 | Haldi | H10K 50/11 | |
| 2019/0237679 A1 | 8/2019 | Lee et al. | | |
| 2020/0168814 A1 | 5/2020 | Suzuki et al. | | |

FOREIGN PATENT DOCUMENTS

| | | | | |
|---|---|---|---|---|
| CN | 110105281 A | 8/2019 | | |
| CN | 110183426 A | 8/2019 | | |
| CN | 114249684 A * | 3/2022 | C07D 405/10 | |
| JP | 2014043541 A | 3/2014 | | |
| JP | 2020-050650 A1 | 4/2020 | | |
| TW | 201524961 A | 7/2015 | | |
| WO | 2018/206520 A1 | 11/2018 | | |
| WO | WO-2019001838 A1 * | 1/2019 | C09K 11/06 | |
| WO | WO-2019078700 A1 * | 4/2019 | C07D 209/82 | |
| WO | 2019/191665 A1 | 10/2019 | | |
| WO | 2019/195104 A1 | 10/2019 | | |
| WO | 2020/022378 A1 | 1/2020 | | |

OTHER PUBLICATIONS

Office Action dated Mar. 18, 2025 issued in the corresponding Japanese patent application No. 2021-575823 with its English Machine Translation.
Office Action dated Dec. 10, 2024 issued in the corresponding Japanese patent application No. 2021-575823 with its English Machine Translation.
Office Action dated Oct. 7, 2024 issued in the corresponding Taiwanese patent application No. 110104137 with its English Translation.
Office Action dated Jun. 17, 2025, issued in the corresponding Japanese patentapplication No. 2021-575823 with its English Machine Translation.
Japanese and English version of International Preliminary Report on Patentability of Chapter I, i.e., International Search Opinion which we received from the WIPO as the International Bureau of the PCT issued in International Application No. PCT/JP2021/003845 (Jul. 28, 2022).
International Search Report and Search Opinion issued in International Application No. PCT/JP2021/003845 (Apr. 6, 2021).

* cited by examiner

*Primary Examiner* — Michael M Dollinger
(74) *Attorney, Agent, or Firm* — Troutman Pepper Locke LLP; James E. Armstrong, IV

(57) ABSTRACT

The compound represented by the following formula is useful as a light-emitting material. One of $R^1$ to $R^5$ is CN; another is Het-$L^A$-*; other two or three are each a carbazolyl group, etc.; and the rest are others. Het is a heteroaryl group; and $L^A$ is a single bond or an arylene group.

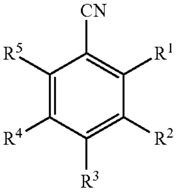

11 Claims, No Drawings

COMPOUND, LIGHT-EMITTING MATERIAL, DELAYED FLUORESCENCE MATERIAL, AND ORGANIC OPTICAL DEVICE

TECHNICAL FIELD

The present invention relates to a compound having good luminescence characteristics. Further, the present invention also relates to a light-emitting material using the compound, a delayed fluorescence material, and an organic optical device.

BACKGROUND ART

Research has been actively conducted to improve the luminous efficiency of organic optical devices such as organic light emitting diodes (OLEDs). For example, in relation to the material of a light emitting layer, research on the use of compounds in which inverse intersystem crossing can be caused from an excited triplet state to an excited singlet state have been energetically conducted. When a normal fluorescent light-emitting material is current-excited at room temperature, singlet excitons and triplet excitons are generated with a probability of 25:75. Among these, the singlet excitons are radiatively deactivated to a ground singlet state and emit fluorescence. Whereas the triplet excitons have a long lifetime, and thus lose energy due to thermal radiation prior to transition to a ground state and are deactivated without radiation. Therefore, the energy of triplet excitons having a high generation probability cannot be effectively used for light emission. On the other hand, in compounds in which inverse intersystem crossing can be caused from the excited triplet state to the excited singlet state, since singlet excitons generated by inverse intersystem crossing from the excited triplet state to the excited singlet state also emit fluorescence during the transition to the ground singlet state, the energy of triplet excitons having a high generation probability can also be indirectly allowed to contribute to the fluorescence emission. Therefore, a significantly high luminous efficiency can be expected as compared to in the case where the normal fluorescent light-emitting material not causing inverse intersystem crossing is used.

As for an organic optical device using a compound capable of causing such inverse intersystem crossing, many things having a single light emitting layer formed by co-depositing a thermal activation-type delayed fluorophore and a host material have been suggested (see, for example, Patent Documents 1 and 2). Here, the thermal activation-type delayed fluorophore is a compound in which inverse intersystem crossing occurs from the excited triplet state to the excited singlet state due to absorption of heat energy. After the fluorescence radiation from the singlet excitons directly excited from the ground singlet state is observed, the fluorescence radiation (delayed fluorescence radiation) from the singlet excitons generated via the inverse intersystem crossing is observed with a delay.

CITATION LIST

Patent Literature

Patent Document 1 WO2019/195104A1
Patent Document 2 US2019/237679A1

SUMMARY OF INVENTION

Technical Problem

However, in the conventionally suggested light-emitting material, there is room for further improvement in terms of luminescence characteristics. Thus, the present inventors have found a light-emitting material having good luminescence characteristics, and have conducted intensive studies for the purpose of providing an excellent organic optical device.

Solution to Problem

The present inventors have conducted the intensive studies, and as a result, have found that a compound having a specific structure has excellent luminescence characteristics. The present invention is suggested on the basis of such findings, and has the following configurations.

[1] A compound represented by the following formula (I).

Formula (I)

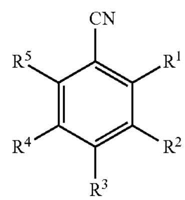

[In the formula (I), among $R^1$ to $R^5$, one is CN, another is A, other p groups are each independently D, and the remaining 3-p group is a hydrogen atom or a substituent (but, other than CN, A, and D).

Here,

A is a group represented by Het-$L^A$-*, in which Het represents a substituted or unsubstituted heteroaryl group bonded via a carbon atom (meanwhile, at least two nitrogen atoms are included as ring skeleton-forming atoms of the heteroaryl group), $L^A$ represents a single bond or a substituted or unsubstituted arylene group, and * represents a bond position.

D is a group represented the following formula (IIa), (IIb), (IIc) or (IId).

Formula (IIa)

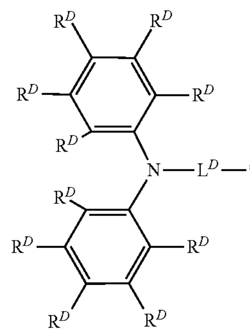

-continued

Formula (IIb)

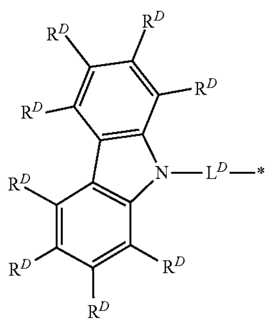

Formula (IIc)

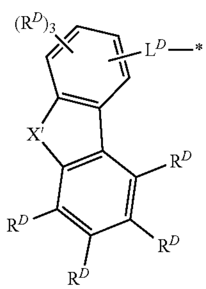

Formula (IId)

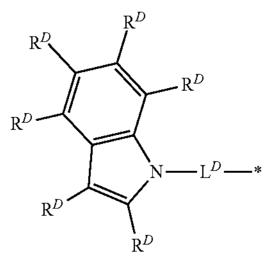

Here, X' represents N—$R^{D\prime}$, an oxygen atom or a sulfur atom, each $R^D$ independently represents a hydrogen atom, a deuterium atom, a substituted or unsubstituted alkyl group, a substituted or unsubstituted alkoxy group, a substituted or unsubstituted amino group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $R^{D\prime}$ represents a hydrogen atom, a deuterium atom, a substituted or unsubstituted alkyl group, a substituted or unsubstituted aryl group, or a substituted or unsubstituted heteroaryl group, and $R^{D\prime}$ may be bonded to one or more $R^D$'s to form a cyclic structure, each $L^D$ independently represents a single bond, a substituted or unsubstituted arylene group, or a substituted or unsubstituted heteroarylene group, and

* represents a bond position.

p is 2 or 3. The plurality of D's present in the molecule may be the same or different.]

[2] The compound described in [1], in which $R^1$ is A.

[3] The compound described in [1] or [2], in which $R^3$ is CN.

[4] The compound described in [3], in which $R^2$ is H.

[5] The compound described in [3], in which $R^2$ is D.

[6] The compound described in [1] or [2], in which $R^2$ is CN.

[7] The compound described in [6], in which $R^3$ is D.

[8] The compound described in any one of [1] to [7], in which $R^4$ and $R^5$ are D.

[9] The compound described in any one of [1] to [8], in which all p D's are the same.

[10] The compound described in any one of [1] to [9], in which each $R^D$ is independently a hydrogen atom, a deuterium atom, a substituted or unsubstituted alkyl group, or a substituted or unsubstituted aryl group.

[11] The compound described in any one of [1] to [10], in which two or more $R^D$'s are bonded to each other to form a cyclic structure.

[12] The compound described in any one of [1] to [11], in which D is a group represented by the formula (IIb).

[13] The compound described in any one of [1] to [12], in which p is 2.

[14] The compound described in any one of [1] to [12], in which p is 3.

[15] The compound described in any one of [1] to [14], in which any one of $R^1$ to $R^5$ is a hydrogen atom.

[16] The compound described in any one of [1] to [15], in which $R^m$ is A, and $R^{m+1}$ is a hydrogen atom, or $R^m$ is a hydrogen atom, and $R^{m+1}$ is A, and m is any integer of 1 to 4.

[17] The compound described in any one of [1] to [16], in which Het-$L^A$-* is a group represented by any of the following formulas (IIIa), (IIIb) and (IIIc).

Formula (IIIa)

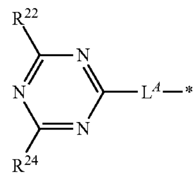

Formula (IIIb)

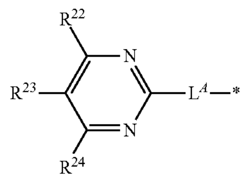

Formula (IIIc)

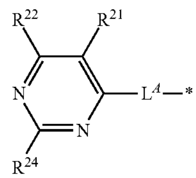

[each of $R^{21}$ to $R^{24}$ independently represents a hydrogen atom or a substituent. $L^A$ represents a single bond or a substituted or unsubstituted arylene group. * represents a bond position.]

[18] The compound described in [17], in which Het-$L^A$-* is a group represented by the formula (IIIa).

[19] The compound described in [18], in which each of $R^{22}$ and $R^{24}$ is independently a substituted or unsubstituted aryl group.

[20] The compound described in any one of [1] to [19], in which $L^D$ is a single bond.

[21] The compound described in any one of [1] to [19], in which $L^D$ is a substituted or unsubstituted arylene group.

[22] A light-emitting material made of the compound described in any one of [1] to [21].

[23] A delayed fluorescence material made of the compound described in any one of [1] to [21].

[24] An organic optical device containing the compound described in any one of [1] to [21].

[25] The organic optical device described in [24], in which the device has a layer containing the compound, and the layer also contains a host material.

[26] The organic optical device described in [24], in which the device has a layer containing the compound, and the layer also contains a light-emitting material.

[27] The organic optical device described in any one of [24] to [26], in which among the materials contained in the device, the compound emits the maximum amount of light.

[28] The organic optical device described in [26], in which the amount of light emitted from the light-emitting material is larger than the amount of light emitted from the compound.

[29] The organic optical device described in any one of [24] to [28], which is an organic light emitting diode (OLED).

[30] The organic optical device described in any one of [24] to [29], which emits delayed fluorescence.

[31] A compound represented by the following formula (I').

Formula (I')

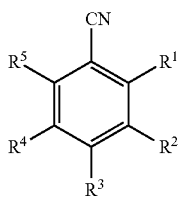

[$R^1$ to $R^5$ in the formula (I') satisfy the following condition 1 or condition 2, (condition 1)

among $R^1$ to $R^5$, one is CN, another is a halogen atom, other p groups are each independently D, and the remaining 3-p group is a hydrogen atom or a substituent (but, other than CN, A, and D).

(condition 2)

among $R^1$ to $R^5$, one is CN, another is a first halogen atom, another is a second halogen atom, other p-1 groups are each independently D, and the remaining 3-p group is a hydrogen atom or a substituent (but, other than CN, A, and D).

Here,

A is a group represented by Het-$L^A$-*, in which Het represents a substituted or unsubstituted heteroaryl group bonded via a carbon atom (meanwhile, at least two nitrogen atoms are included as ring skeleton-forming atoms of the heteroaryl group), $L^A$ represents a single bond or a substituted or unsubstituted arylene group, and * represents a bond position.

D is a group represented by the following formula (IIa), (IIb), (IIc) or (IId).

Formular (IIa)

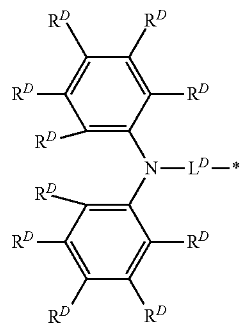

Formula (IIb)

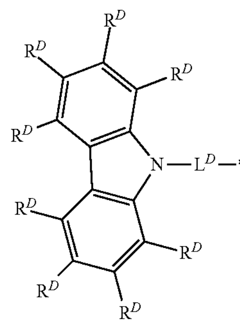

Formula (IIc)

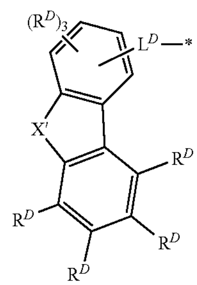

Formula (IId)

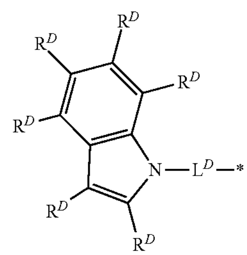

Here, X' represents N—$R^{D'}$, an oxygen atom or a sulfur atom, each $R^D$ independently represents a hydrogen atom, a deuterium atom, a substituted or unsubstituted alkyl group, a substituted or unsubstituted alkoxy group, a substituted or unsubstituted amino group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $R^{D'}$ represents a hydrogen atom, a deuterium atom, a substituted or unsubstituted alkyl group, a substituted or unsubstituted aryl group, or a substituted or unsubstituted heteroaryl group, and $R^{D'}$ may be bonded to one or more $R^D$'s to form a cyclic structure, each $L^D$ independently represents a single bond, a substituted or unsubstituted arylene group, or a substituted or unsubstituted heteroarylene group, and

* represents a bond position.

p is 2 or 3. The plurality of D's present in the molecule may be the same or different.]

[32] The compound described in [31], which satisfies the condition 1.

[33] The compound described in [32], in which p is 2.

[34] The compound described in [32], in which p is 3.

[35] The compound described in any one of [32] to [34], in which the halogen atom is a bromine atom.

[36] The compound described in [31], which satisfies the condition 2.

[37] The compound described in [36], in which p is 2.

[38] The compound described in [36] or [37], in which one of $R^1$ to $R^5$ is a hydrogen atom.

[39] The compound described in any one of [36] to [38], in which the first halogen atom is a fluorine atom.

[40] The compound described in any one of [36] to [39], in which the first halogen atom is a bromine atom.

Advantageous Effects of Invention

According to the present invention, it is possible to provide a light-emitting material having good luminescence characteristics. Further, according to the present invention, it is possible to provide an organic optical device having high luminous efficiency.

DESCRIPTION OF EMBODIMENTS

Hereinafter, the contents of the present invention will be described in detail. The descriptions on constituent elements to be described below may be made on the basis of representative embodiments or specific examples of the present invention but the present invention is not limited to such embodiments or specific examples. The numerical value range represented by using "to" in the present specification means a range including numerical values described before and after "to", as the lower limit value and the upper limit value. The entire specification of Japanese Application No. 2020-018374, which is the basis of the priority claim of the present application, is cited herein as a part of the specification of the present application.

The present invention provides a compound represented by the following formula (I).

Formula (I)

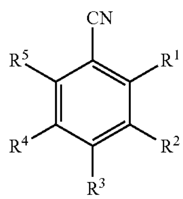

In the formula (I), among $R^1$ to $R^5$, one is CN, another is A, other p are each independently D, and the remaining 3-p is a hydrogen atom or a substituent (but, other than CN, A, and D). Here, p is 2 or 3.

In some embodiments, $R^3$ is CN. In some embodiments, $R^3$ is CN, $R^1$ is A, two of $R^2$, $R^4$ and $R^5$ are each independently D, and the remaining one is a hydrogen atom. In some embodiments, $R^3$ is CN, $R^1$ is A, two of $R^2$, $R^4$ and $R^5$ are each independently D, and the remaining one is a substituted or unsubstituted aryl group (but, other than a group that may be A or D). In some embodiments, $R^3$ is CN, $R^1$ is A, two of $R^2$, $R^4$ and $R^5$ are each independently D, and the remaining one is a substituted or unsubstituted alkyl group. In some embodiments, $R^3$ is CN, $R^1$ is A, each of $R^2$, $R^4$, and $R^5$ is independently D. In a preferred embodiment, $R^3$ is CN, $R^1$ is A, and $R^2$ is a hydrogen atom. In some embodiments, $R^3$ is CN, $R^1$ is A, and $R^2$ is D. In some embodiments, $R^3$ is CN, $R^1$ is A, and $R^2$ is a substituted or unsubstituted aryl group (but, other than a group that may be A or D). In some embodiments, $R^3$ is CN, $R^1$ is A, and $R^4$ is D. In some embodiments, $R^3$ is CN, $R^1$ is A, and $R^5$ is D. In some embodiments, $R^3$ is CN, $R^1$ is A, and each of $R^4$ and $R^5$ is independently D. In some embodiments, $R^3$ is CN, $R^1$ is A, and each of $R^2$ and $R^4$ is independently D. In some embodiments, $R^3$ is CN, $R^1$ is A, and each of $R^2$ and $R^5$ is independently D.

In some embodiments, $R^2$ is CN. In some embodiments, $R^2$ is CN, $R^1$ is A, two of $R^3$, $R^4$ and $R^5$ are each independently D, and the remaining one is a hydrogen atom. In some embodiments, $R^2$ is CN, $R^1$ is A, two of $R^3$, $R^4$ and $R^5$ are each independently D, and the remaining one is a substituted or unsubstituted aryl group (but, other than a group that may be A or D). In some embodiments, $R^2$ is CN, $R^1$ is A, two of $R^3$, $R^4$ and $R^5$ are each independently D, and the remaining one is a substituted or unsubstituted alkyl group. In some embodiments, $R^2$ is CN, $R^1$ is A, and each of $R^3$, $R^4$ and $R^5$ is independently D. In some embodiments, $R^2$ is CN, $R^1$ is A, and $R^3$ is D. In some embodiments, $R^2$ is CN, $R^1$ is A, and $R^4$ is D. In some embodiments, $R^2$ is CN, $R^1$ is A, and $R^3$ and $R^4$ are D's. In some embodiments, $R^2$ is CN, $R^1$ is A, and $R^3$ and $R^5$ are D's. In some embodiments, $R^2$ is CN, and $R^3$ is A. In a preferred embodiment, $R^2$ is CN, $R^3$ is A, and $R^4$ is a hydrogen atom. In some embodiments, $R^2$ is CN, $R^3$ is A, and $R^4$ is a hydrogen atom. In some embodiments, $R^2$ is CN, $R^3$ is A, and $R^5$ is a hydrogen atom. In some embodiments, $R^2$ is CN, and $R^4$ is A. In a preferred embodiment, $R^2$ is CN, $R^4$ is A, and $R^3$ is a hydrogen atom. In some embodiments, $R^2$ is CN, $R^4$ is A, and $R^1$ is a hydrogen atom.

In some embodiments, $R^1$ is CN. In some embodiments, $R^1$ is CN, and $R^2$ is A. In some embodiments, $R^1$ is CN, $R^2$ is A, two of $R^3$, $R^4$ and $R^5$ are each independently D, and the remaining one is a hydrogen atom. In a preferred embodiment, $R^1$ is CN, $R^2$ is A, and $R^3$ is a hydrogen atom. In some embodiments, $R^1$ is CN, $R^2$ is A, two of $R^3$, $R^4$ and $R^5$ are each independently D, and the remaining one is a substituted or unsubstituted aryl group (but, other than a group that may be A or D). In some embodiments, $R^1$ is CN, $R^2$ is A, two of $R^3$, $R^4$ and $R^5$ are each independently D, and the remaining one is a substituted or unsubstituted alkyl group. In some embodiments, $R^1$ is CN, $R^2$ is A, and each of $R^3$, $R^4$, and $R^5$ is independently D. In some embodiments, $R^1$ is CN, and $R^3$ is A. In some embodiments, $R^1$ is CN, $R^3$ is A, two of $R^2$, $R^4$ and $R^5$ are each independently D, and the remaining one is a hydrogen atom. In a preferred embodiment, $R^1$ is CN, $R^3$ is A, and $R^2$ is a hydrogen atom. In a preferred embodiment, $R^1$ is CN, $R^3$ is A, and $R^4$ is a hydrogen atom. In some embodiments, $R^1$ is CN, $R^3$ is A, two of $R^2$, $R^4$ and $R^5$ are each independently D, and the remaining one is a substituted or unsubstituted aryl group (but, other than a group that may be A or D). In some embodiments, $R^1$ is CN, $R^3$ is A, two of $R^2$, $R^4$ and $R^5$ are each independently D, and the remaining one is a substituted or unsubstituted alkyl group. In some embodiments, $R^1$ is CN, $R^3$ is A, and each of $R^2$, $R^4$, and $R^5$ is independently D.

In the compound represented by the formula (I), it is desirable that $R^m$ is A and $R^{m+1}$ is a hydrogen atom, or $R^m$ is a hydrogen atom, and $R^{m+1}$ is A. Here, m is an integer of 1 to 4. In some embodiments, $R^1$ is A, and $R^2$ is a hydrogen atom. In some embodiments, $R^2$ is A, and $R^3$ is a hydrogen atom. In some embodiments, $R^3$ is A, and $R^4$ is a hydrogen atom. In some embodiments, $R^1$ is a hydrogen atom, and $R^2$ is A. In some embodiments, $R^2$ is a hydrogen atom, and $R^3$ is A.

In some embodiments, each of $R^4$ and $R^5$ is independently D. In some embodiments, each of $R^3$ and $R^5$ is independently D. In some embodiments, each of $R^2$ and $R^5$ is independently D. In some embodiments, each of $R^3$, $R^4$, and $R^5$ is independently D. In some embodiments, each of $R^2$, $R^4$, and $R^5$ is independently D. In some embodiments, each of $R^2$, $R^3$, and $R^5$ is independently D.

In some embodiments, $R^1$ to $R^5$ are not substituted or unsubstituted aryl groups (but, other than a group that may be A or D). In some embodiments, $R^1$ to $R^5$ are not substituted or unsubstituted aryl groups (also including a group that may be A or D). In some embodiments, only one of $R^1$ to $R^5$ is a substituted or unsubstituted aryl group (but, other than a group that may be A or D). In some embodiments, only one of $R^1$ to $R^5$ is a substituted or unsubstituted aryl group (also including a group that may be A or D). In some embodiments, two of $R^1$ to $R^5$ are substituted or unsubstituted aryl groups (also including a group that may be A or D). In some embodiments, one of $R^1$ to $R^5$ is CN, another is A, and the other three are not groups bonded with carbon atoms. In some embodiments, each of $R^1$ to $R^5$ is independently a group composed of two or more atoms selected from the group including a hydrogen atom, a carbon atom, and a nitrogen atom. In some embodiments, $R^1$ to $R^5$ are not groups having repeating units.

As a group of particularly preferable combinations of $R^1$ to $R^5$, a group in which ($R^1$, $R^2$, $R^3$, $R^4$, $R^5$) is (A, H, CN, D, D), (D, CN, A, H, D) or (D, CN, H, A, D) may be exemplified. As another group, a group of (A, H, CN, D, D), (A, D, CN, H, D), (A, D, CN, D, H), (A, Ar, CN, D, D), (A, D, CN, Ar, D), (A, D, CN, D, Ar) and (A, D, CN, D, D) may be exemplified. As another group, a group of (A, H, CN, D, D), (A, D, CN, H, D), (A, D, CN, D, H) and (A, D, CN, D, D) may be exemplified. Further, as another group, a group of (A, H, CN, D, D), (A, D, CN, H, D) and (A, D, CN, D, H) may be exemplified. As another group, a group of (A, H, CN, D, D), (A, D, CN, H, D), (A, D, CN, D, H), (A, Ar, CN, D, D), (A, D, CN, Ar, D), (A, D, CN, D, Ar) and (A, D, CN, D, D) may be exemplified. As another group, a group of (A, H, CN, D, D), (A, D, CN, H, D), (A, D, CN, D, H) and (A, D, CN, D, D) may be exemplified. As another group, a group of (A, H, CN, D, D), (A, D, CN, H, D) and (A, D, CN, D, H) may be exemplified. H represents a hydrogen atom, and Ar represents a substituted or unsubstituted aryl group (but, other than a group that may be A or D). In the present invention, combinations of $R^1$ to $R^5$, which do not belong to the groups exemplified herein, can also be adopted.

In the formula (I), A is a group represented by Het-$L^A$-*. Here, Het is a substituted or unsubstituted heteroaryl group bonded via a carbon atom, and the heteroaryl group mentioned herein contains at least two nitrogen atoms as ring skeleton-forming atoms. $L^A$ represents a single bond or a substituted or unsubstituted arylene group. * represents a bond position.

Het has a heteroaryl ring in which two or more nitrogen atoms are contained as ring skeleton-forming atoms, and it is desirable that the ring skeleton-forming carbon atom of the heteroaryl ring is bonded to $L^A$ (bonded to a ring skeleton-forming carbon atom of a benzene ring of the formula (1) when $L^A$ is a single bond). Het-$L^A$-* is preferably a group represented by any of the following formulas (IIIa), (IIIb) and (IIIc).

Formula (IIIa)

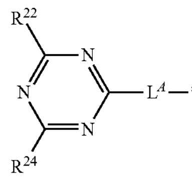

Formula (IIIb)

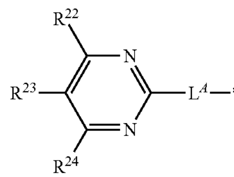

Formula (IIIc)

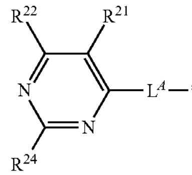

Each of $R^{21}$ to $R^{24}$ independently represents a hydrogen atom or a substituent. $L^A$ represents a single bond or a substituted or unsubstituted arylene group. * represents a bond position. In some embodiments, each of $R^{21}$ to $R^{24}$ is independently a hydrogen atom, a deuterium atom, a cyano group, a substituted or unsubstituted alkyl group, a substituted or unsubstituted aryl group, or a substituted or unsubstituted heteroaryl group. The alkyl group mentioned herein may be substituted with, for example, one or more substituents selected from a deuterium atom, a substituted or unsubstituted aryl group, and a substituted or unsubstituted heteroaryl group. Each of the aryl group and the heteroaryl group mentioned herein may be independently substituted with, for example, one or more substituents selected from a deuterium atom, a substituted or unsubstituted alkyl group, a substituted or unsubstituted aryl group, and a substituted or unsubstituted heteroaryl group. Two or more of these substituents may be bonded to form a cyclic structure. Further, $R^{21}$ and $R^{22}$, $R^{22}$ and $R^{23}$, and $R^{23}$ and $R^{24}$ may be bonded to each other to form a cyclic structure. The cyclic structure mentioned herein may be a substituted or unsubstituted aromatic ring, or a substituted or unsubstituted aliphatic ring. Further, it may be a carbon ring or a hetero ring. In a preferred embodiment, each of $R^{21}$ to $R^{24}$ is independently a substituted or unsubstituted alkyl group, or a substituted or unsubstituted aryl group. In a more preferred embodiment, each of $R^{21}$ to $R^{24}$ is independently a substituted or unsubstituted aryl group. In another preferred embodiment, at least one of $R^{21}$ to $R^{24}$ is an aryl group that may be substituted with an aryl group. $R^{21}$ to $R^{24}$ may be the same or different, and, for example, can be the same. Further, in a preferred embodiment, in one of $R^{21}$ and $R^{22}$, $R^{22}$ and $R^{23}$, and $R^{23}$ and $R^{24}$, these are bonded to each other to form a benzene ring. In another preferred embodiment, in one of $R^{21}$ and $R^{22}$, $R^{22}$ and $R^{23}$, and $R^{23}$ and $R^{24}$, these are bonded to each other to form a benzofuran ring or a benzothiophene ring.

In a preferred embodiment, Het-$L^A$-* is a group represented by the formula (IIIa). Further, Het-$L^A$-* can also be a group represented by either the formula (IIIb) or (IIIc).

In some embodiments, $L^A$ is a single bond.

Further, in another embodiment of the present invention, $L^A$ is a substituted or unsubstituted arylene group. $L^A$ may be a linking group in which two or three substituted or unsubstituted arylene groups are linked. Further, $L^A$ may be composed of only one substituted or unsubstituted arylene group. In some embodiments, $L^A$ is an unsubstituted arylene group. Further, in some embodiments, $L^A$ is a substituted arylene group. here, the arylene group may be substituted with, for example, one or more substituents selected from a deuterium atom, a substituted or unsubstituted alkyl group, a substituted or unsubstituted aryl group, and a substituted or unsubstituted heteroaryl group, and two or more of these substituents may be combined to form a cyclic structure. The cyclic structure mentioned herein may be a substituted or unsubstituted aromatic ring, or a substituted or unsubstituted aliphatic ring. Further, it may be a carbon ring, or may be a hetero ring.

$R^{21}$ and $L^A$ do not combine with each other to form a cyclic structure.

In some embodiments, $L^A$ is a single bond, an unsubstituted phenylene group, or a phenylene group substituted with at least one alkyl group. Examples of the phenylene group include a 1,4-phenylene group, a 1,3-phenylene group, and a 1,2-phenylene group, and a 1,4-phenylene group and a 1,3-phenylene group are preferred.

In some embodiments, A is selected from the group including A1 to A12 illustrated below. * represents a bond position.

A1

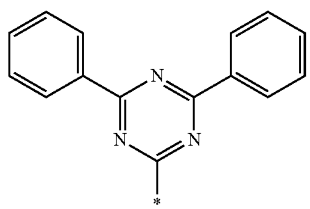

A2

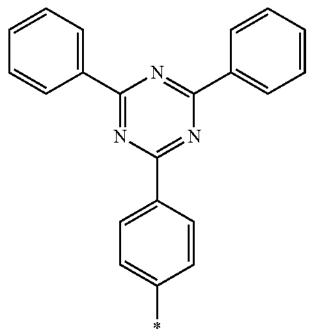

A3

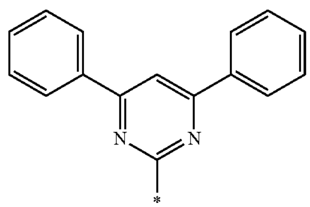

-continued

A4

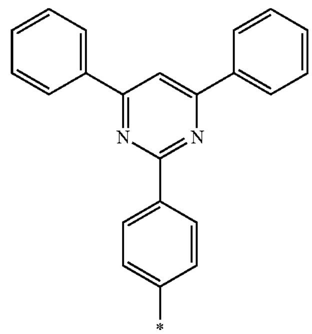

A5

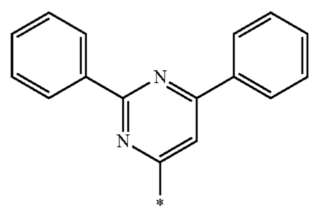

A6

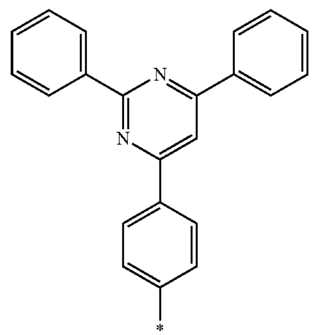

A7

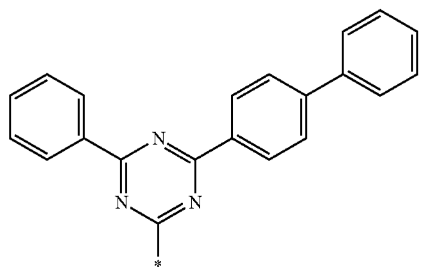

A8

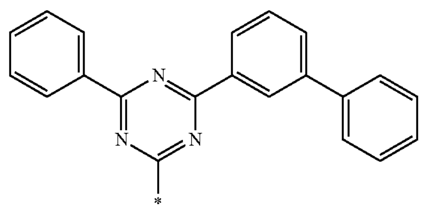

-continued

A9

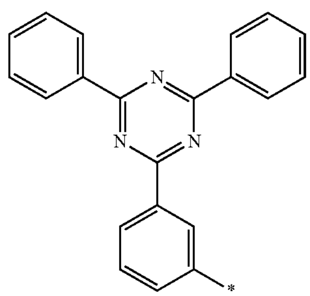

A10

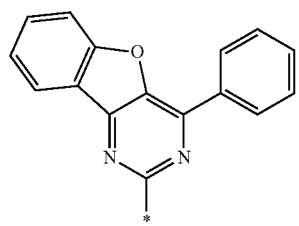

A11

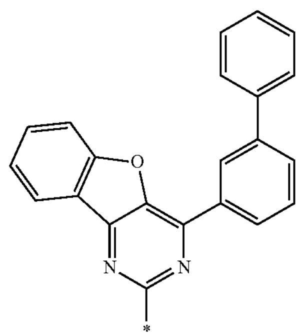

A12

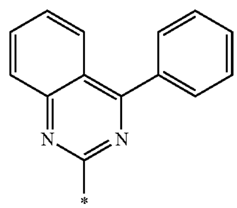

In the formula (I), D is a group represented by the following formula (IIa), (IIb), (IIc) or (IId). In some embodiments, D is a group represented by the formula (IIa), (IIb) or (IId). In some embodiments, D is a group represented by the formula (IIa). In some embodiments, D is a group represented by the formula (IIb). In some embodiments, D is a group represented by the formula (IId).

Formula (IIa)

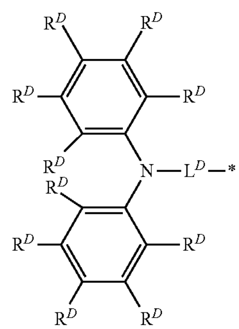

Formula (IIb)

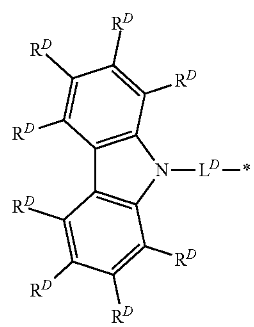

Formula (IIc)

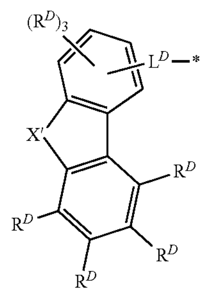

Formula (IId)

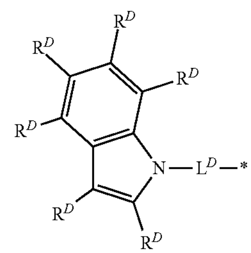

Each $R^D$ independently represents a hydrogen atom, a deuterium atom, a substituted or unsubstituted alkyl group, a substituted or unsubstituted alkoxy group, a substituted or unsubstituted amino group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure. In some embodiments of the present invention, each $R^D$ is independently selected from the group including a hydrogen atom, a deuterium atom, a substituted or unsubstituted alkyl group, and a substituted or unsubstituted alkoxy group. In some embodiments of the present invention, each $R^D$ is independently selected from the group including a hydrogen atom, a deuterium atom, a substituted or unsubstituted aryl group, and a substituted or unsubstituted aryloxy group. In some embodiments of the present invention, each $R^D$ is independently selected from the group including a hydrogen atom, a deuterium atom, a substituted or unsubstituted heteroaryl group, and a substituted or unsubstituted heteroaryloxy group. In some embodiments of the present invention, each $R^D$ is independently a hydrogen atom or a deuterium atom. Among $R^D$'s present in D, the number of substituents that are neither hydrogen atoms nor deuterium atoms is three or four in some embodiments, two in other embodiments of the present invention, or one in some embodiments.

X' represents N—$R^{D'}$, an oxygen atom or a sulfur atom. In some embodiments, X' is N—$R^{D'}$. In some embodiments, X' is an oxygen atom. In some embodiments, X' is a sulfur atom.

$R^{D'}$ represents a hydrogen atom, a deuterium atom, a substituted or unsubstituted alkyl group, a substituted or unsubstituted aryl group, or a substituted or unsubstituted heteroaryl group, and $R^{D'}$ may be bonded to one or more other $R^{D'}$s to form a cyclic structure. In some embodiments of the present invention, each $R^{D'}$ is independently a hydrogen atom or a deuterium atom. In some embodiments of the present invention, $R^{D'}$ is a substituted or unsubstituted alkyl group. In some embodiments of the present invention, $R^{D'}$ is a substituted or unsubstituted aryl group.

The cyclic structure formed by combining two or more $R^{D'}$s, or $R^{D'}$ and one or more other $R^D$s may be a substituted or unsubstituted aromatic ring, or a substituted or unsubstituted aliphatic ring. Further, it may be a carbon ring, or may be a hetero ring.

$R^D$ and $L^D$, and $R^{D'}$ and $L^D$ do not bond to each other to form a cyclic structure.

Each $L^D$ independently represents a single bond, a substituted or unsubstituted arylene group, or a substituted or unsubstituted heteroarylene group. In some embodiments, $L^D$ is a single bond. In some embodiments, $L^D$ is a substituted or unsubstituted arylene group. $L^D$ may be a linking group in which two or three selected from the group including a substituted or unsubstituted arylene group and a substituted or unsubstituted heteroarylene group are linked to each other. In some embodiments, $L^D$ is a linking group in which two or three substituted or unsubstituted arylene groups are linked. In some embodiments, $L^D$ is composed of only one substituted or unsubstituted arylene group. In some embodiments, $L^D$ is an unsubstituted arylene group. Further, in some embodiments, $L^D$ is a substituted arylene group. Here, an arylene group may be substituted with, for example, one or more substituents selected from a deuterium atom, a substituted or unsubstituted alkyl group, a substituted or unsubstituted aryl group, and a substituted or unsubstituted heteroaryl group, and two or more of these substituents may be combined to form a cyclic structure. The cyclic structure mentioned herein may be a substituted or unsubstituted aromatic ring, or a substituted or unsubstituted aliphatic ring. Further, it may be a carbon ring, or may be a hetero ring.

In some embodiments, $L^D$ is a single bond, an unsubstituted phenylene group, or a phenylene group substituted with at least one alkyl group. Examples of the phenylene group include a 1,4-phenylene group, a 1,3-phenylene group, and a 1,2-phenylene group, and the 1,4-phenylene group and the 1,3-phenylene group are preferred.

In some embodiments, D is selected from the group including D1 to D45 illustrated below. In some embodiments, D is selected from the group including D1 to D6. In some embodiments, D is selected from the group including D7 and D8. In some embodiments, D is selected from the group including D9 to D16. In some embodiments, D is selected from the group including D17 to D40. In some embodiments, D is selected from the group including D41 to D45. * represents a bond position. Ph represents an unsubstituted phenyl group.

D1

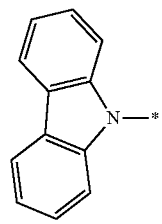

D2

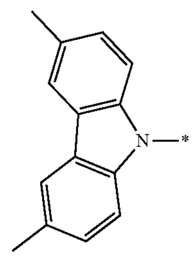

D3

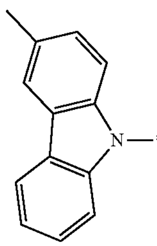

D4

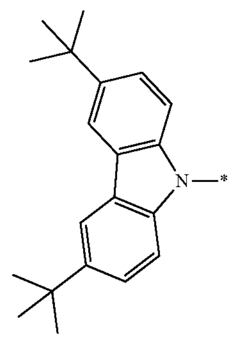

D5

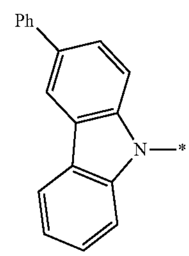

-continued
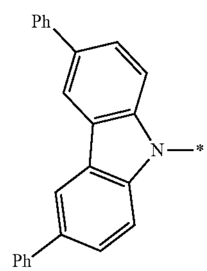
D6
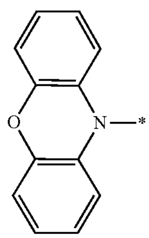
D7
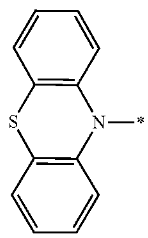
D8
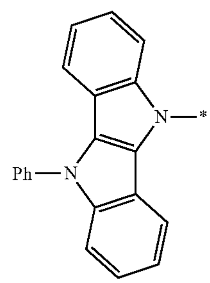
D9
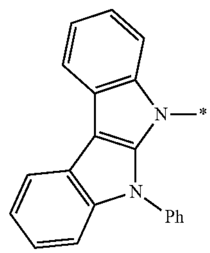
D10
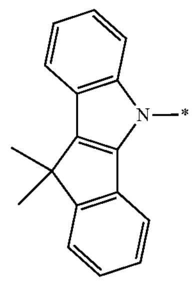
D11
-continued
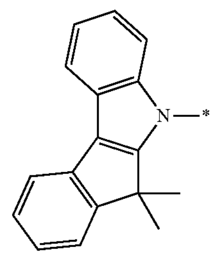
D12
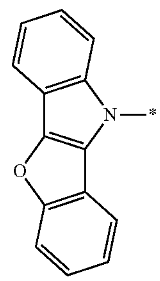
D13
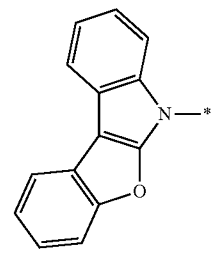
D14
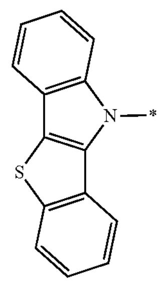
D15
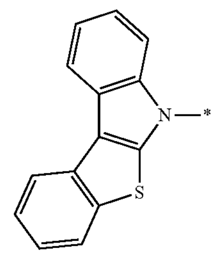
D16
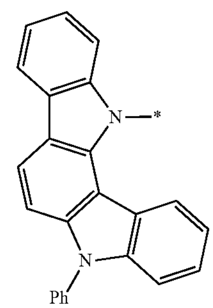
D17

-continued
D18
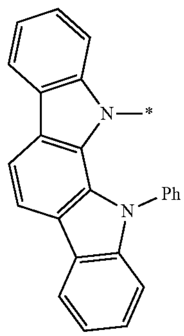
D19
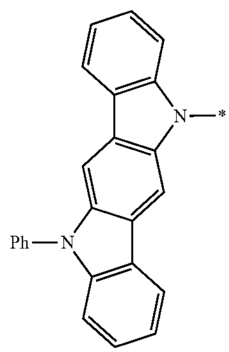
D20
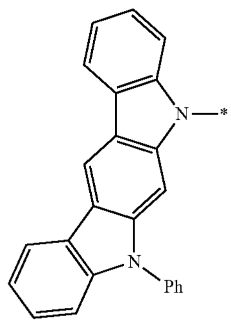
D21
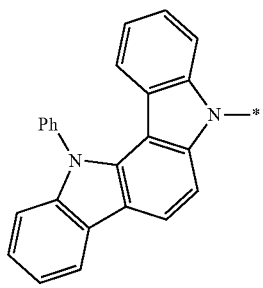
D22
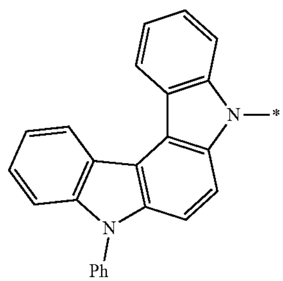
-continued
D23
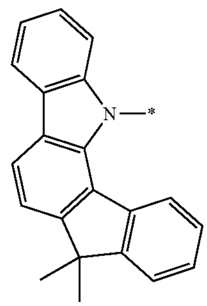
D24
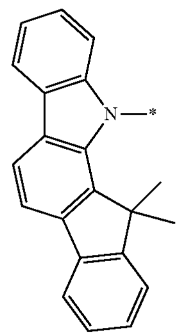
D25
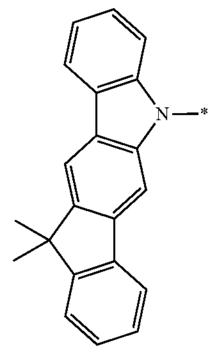
D26
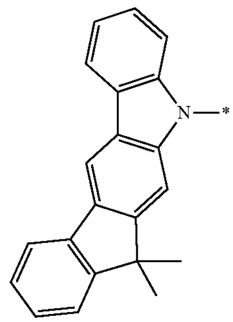
D27
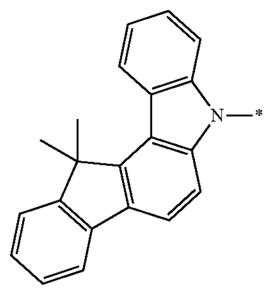

-continued
D28
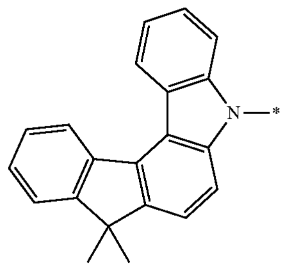
D29
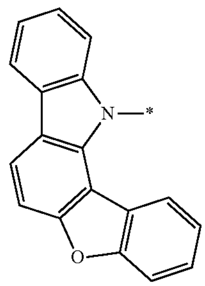
D30
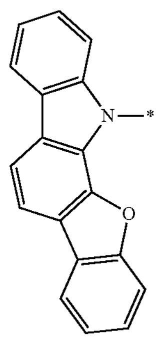
D31
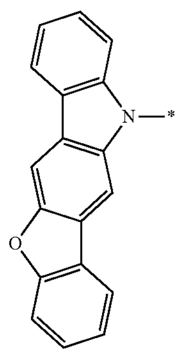
D32
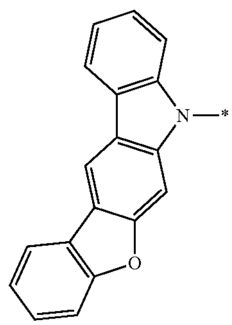
-continued
D33
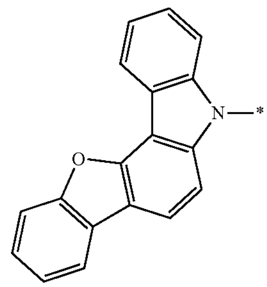
D34
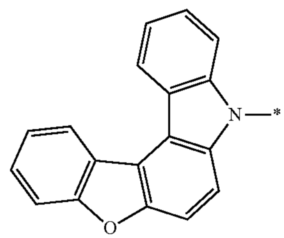
D35
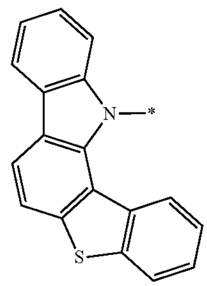
D36
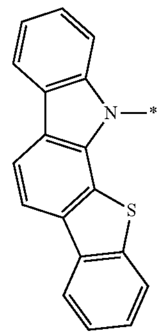
D37
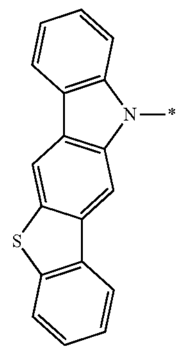

-continued

D38

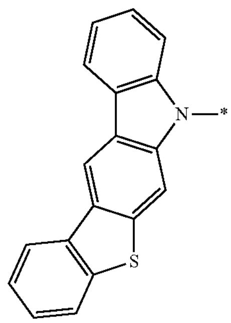

D39

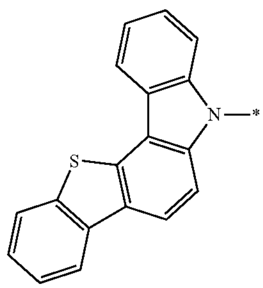

D40

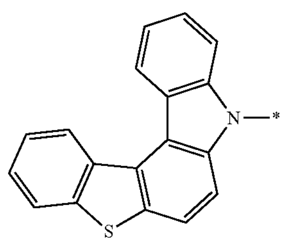

D41

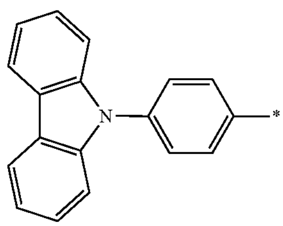

D42

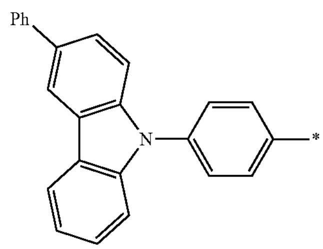

D43

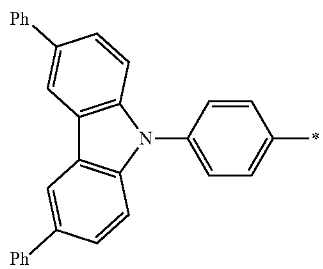

-continued

D44

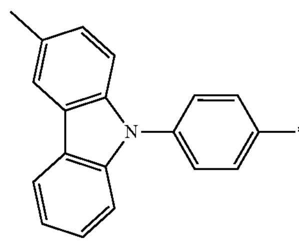

D45

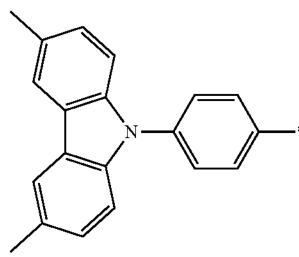

In the formula (I), 3-p of $R^1$ to $R^5$ is a hydrogen atom or a substituent (but, other than groups that may be CN, A, and D). When p is 3, no hydrogen atom or substituent (but, other than groups that may be CN, A, and D) is present. When p is 2, only one hydrogen atom or substituent (but, other than groups that may be CN, A, and D) is present.

The substituent (but, other than groups that may be CN, A, and D) is preferably a deuterium atom, or a substituted or unsubstituted aryl group (but, other than a group that may be A or D), a substituted or unsubstituted alkyl group, a substituted or unsubstituted aryloxy group, or a substituted or unsubstituted alkoxy group, more preferably a deuterium atom, a substituted or unsubstituted aryl group (but, other than a group that may be A or D), or a substituted or unsubstituted alkyl group, further preferably a substituted or unsubstituted aryl group (but, other than a group that may be A or D). Examples thereof include a substituted or unsubstituted phenyl group, an unsubstituted phenyl group or the like.

In some embodiments, one of $R^1$ to $R^5$ is a hydrogen atom. In some embodiments, one of $R^1$ to $R^5$ is a substituted or unsubstituted aryl group (but, other than a group that may be A or D), and is, for example, an unsubstituted aryl group. The aryl group as a substituted aryl group may be substituted with, for example, one or more substituents selected from a deuterium atom, a substituted or unsubstituted alkyl group, and a substituted or unsubstituted aryl group. Two or more of these substituents may be bonded to form a cyclic structure. The cyclic structure mentioned herein may be a substituted or unsubstituted aromatic ring, or may be a substituted or unsubstituted aliphatic ring. Further, it may be a carbon ring, or may be a hetero ring.

In the formula (I), p is an integer of either 2 or 3. When p is 2 or 3, D's present in the molecule may be the same or different. In some embodiments, p is 3. In some embodiments, p is 2.

In a preferred embodiment, in $R^1$ and $R^2$, $R^2$ and $R^3$, $R^3$ and $R^4$, and $R^4$ and $R^5$ in the formula (I), none of these are bonded to each other to form a cyclic structure.

The molecular weight of the compound represented by the formula (I) is preferably 1500 or less, more preferably 1200 or less, further preferably 1000 or less, still further preferably 900 or less, for example, when there is an intention to form and use a film of an organic layer containing the compound represented by the formula (I), through a deposition method. The lower limit value of the molecular weight is the molecular weight of the smallest compound represented by the formula (I).

The compound represented by the formula (I) may be formed into a film through a coating method regardless of the molecular weight. When the coating method is used, it is possible to form a film even if the compound has a relatively large molecular weight.

Through an application of the present invention, a compound in which a plurality of structures represented by the formula (I) is included in the molecule may be prepared. The use of such a compound as, for example, a charge transport material may be taken into consideration.

For example, it is possible to obtain a polymer by allowing a polymerizable group to exist in the structure represented by the formula (I) in advance and polymerizing the polymerizable group. Specifically, a monomer including a polymerizable functional group may be prepared in any of $R^1$ to $R^5$ of the formula (I), and this may be polymerized alone or copolymerized with another monomer so as to obtain a polymer having repeating units. Alternatively, a dimer or a trimer may also be obtained by coupling compounds having the structures represented by the formula (I) with each other.

In some embodiments, the compound represented by the formula (I) does not include a metal atom. In some embodiments, the compound represented by the formula (I) is composed of only a hydrogen atom, a carbon atom, and a nitrogen atom. In some embodiments, the compound represented by the formula (I) is composed of only atoms selected from the group including a hydrogen atom, a carbon atom, a nitrogen atom, and an oxygen atom. In some embodiments, the compound represented by the formula (I) is composed of only atoms selected from the group including a hydrogen atom, a carbon atom, a nitrogen atom, and a sulfur atom. In some embodiments, the compound represented by the formula (I) is composed of only atoms selected from the group including a hydrogen atom, a carbon atom, a nitrogen atom, an oxygen atom, a sulfur atom, and a silicon atom. In some embodiments, the compound represented by the formula (I) does not include a diarylamino group (meanwhile, two aryl groups constituting the diarylamino group are not bonded to each other by a single bond or a linking group to form a cyclic structure).

Specific examples of a compound represented by the formula (I) will be mentioned below. Meanwhile, the scope of compounds of the present invention should not be construed as limiting to these specific examples.

TABLE 1-1

| No. | $R^1$ | $R^2$ | $R^3$ | $R^4$ | $R^5$ |
|---|---|---|---|---|---|
| 1 | A1 | D1 | CN | D1 | D1 |
| 2 | A1 | D1 | CN | D1 | D2 |
| 3 | A1 | D1 | CN | D1 | D3 |
| 4 | A1 | D1 | CN | D1 | D4 |
| 5 | A1 | D1 | CN | D1 | D5 |
| 6 | A1 | D1 | CN | D1 | D6 |
| 7 | A1 | D1 | CN | D2 | D1 |
| 8 | A1 | D1 | CN | D2 | D2 |
| 9 | A1 | D1 | CN | D2 | D3 |
| 10 | A1 | D1 | CN | D2 | D4 |
| 11 | A1 | D1 | CN | D2 | D5 |
| 12 | A1 | D1 | CN | D2 | D6 |
| 13 | A1 | D1 | CN | D3 | D1 |
| 14 | A1 | D1 | CN | D3 | D2 |
| 15 | A1 | D1 | CN | D3 | D3 |

TABLE 1-1-continued

| No. | $R^1$ | $R^2$ | $R^3$ | $R^4$ | $R^5$ |
|---|---|---|---|---|---|
| 16 | A1 | D1 | CN | D3 | D4 |
| 17 | A1 | D1 | CN | D3 | D5 |
| 18 | A1 | D1 | CN | D3 | D6 |
| 19 | A1 | D1 | CN | D4 | D1 |
| 20 | A1 | D1 | CN | D4 | D2 |
| 21 | A1 | D1 | CN | D4 | D3 |
| 22 | A1 | D1 | CN | D4 | D4 |
| 23 | A1 | D1 | CN | D4 | D5 |
| 24 | A1 | D1 | CN | D4 | D6 |
| 25 | A1 | D1 | CN | D5 | D1 |
| 26 | A1 | D1 | CN | D5 | D2 |
| 27 | A1 | D1 | CN | D5 | D3 |
| 28 | A1 | D1 | CN | D5 | D4 |
| 29 | A1 | D1 | CN | D5 | D5 |
| 30 | A1 | D1 | CN | D5 | D6 |
| 31 | A1 | D1 | CN | D6 | D1 |
| 32 | A1 | D1 | CN | D6 | D2 |
| 33 | A1 | D1 | CN | D6 | D3 |
| 34 | A1 | D1 | CN | D6 | D4 |
| 35 | A1 | D1 | CN | D6 | D5 |
| 36 | A1 | D1 | CN | D6 | D6 |
| 37 | A1 | D2 | CN | D1 | D1 |
| 38 | A1 | D2 | CN | D1 | D2 |
| 39 | A1 | D2 | CN | D1 | D3 |
| 40 | A1 | D2 | CN | D1 | D4 |
| 41 | A1 | D2 | CN | D1 | D5 |
| 42 | A1 | D2 | CN | D1 | D6 |
| 43 | A1 | D2 | CN | D2 | D1 |
| 44 | A1 | D2 | CN | D2 | D2 |
| 45 | A1 | D2 | CN | D2 | D3 |
| 46 | A1 | D2 | CN | D2 | D4 |
| 47 | A1 | D2 | CN | D2 | D5 |
| 48 | A1 | D2 | CN | D2 | D6 |
| 49 | A1 | D2 | CN | D3 | D1 |
| 50 | A1 | D2 | CN | D3 | D2 |
| 51 | A1 | D2 | CN | D3 | D3 |
| 52 | A1 | D2 | CN | D3 | D4 |
| 53 | A1 | D2 | CN | D3 | D5 |
| 54 | A1 | D2 | CN | D3 | D6 |
| 55 | A1 | D2 | CN | D4 | D1 |
| 56 | A1 | D2 | CN | D4 | D2 |
| 57 | A1 | D2 | CN | D4 | D3 |
| 58 | A1 | D2 | CN | D4 | D4 |
| 59 | A1 | D2 | CN | D4 | D5 |
| 60 | A1 | D2 | CN | D4 | D6 |
| 61 | A1 | D2 | CN | D5 | D1 |
| 62 | A1 | D2 | CN | D5 | D2 |
| 63 | A1 | D2 | CN | D5 | D3 |
| 64 | A1 | D2 | CN | D5 | D4 |
| 65 | A1 | D2 | CN | D5 | D5 |
| 66 | A1 | D2 | CN | D5 | D6 |
| 67 | A1 | D2 | CN | D6 | D1 |
| 68 | A1 | D2 | CN | D6 | D2 |
| 69 | A1 | D2 | CN | D6 | D3 |
| 70 | A1 | D2 | CN | D6 | D4 |
| 71 | A1 | D2 | CN | D6 | D5 |
| 72 | A1 | D2 | CN | D6 | D6 |
| 73 | A1 | D3 | CN | D1 | D1 |
| 74 | A1 | D3 | CN | D1 | D2 |
| 75 | A1 | D3 | CN | D1 | D3 |
| 76 | A1 | D3 | CN | D1 | D4 |
| 77 | A1 | D3 | CN | D1 | D5 |
| 78 | A1 | D3 | CN | D1 | D6 |
| 79 | A1 | D3 | CN | D2 | D1 |
| 80 | A1 | D3 | CN | D2 | D2 |
| 81 | A1 | D3 | CN | D2 | D3 |
| 82 | A1 | D3 | CN | D2 | D4 |
| 83 | A1 | D3 | CN | D2 | D5 |
| 84 | A1 | D3 | CN | D2 | D6 |
| 85 | A1 | D3 | CN | D3 | D1 |
| 86 | A1 | D3 | CN | D3 | D2 |
| 87 | A1 | D3 | CN | D3 | D3 |
| 88 | A1 | D3 | CN | D3 | D4 |
| 89 | A1 | D3 | CN | D3 | D5 |
| 90 | A1 | D3 | CN | D3 | D6 |
| 91 | A1 | D3 | CN | D4 | D1 |
| 92 | A1 | D3 | CN | D4 | D2 |
| 93 | A1 | D3 | CN | D4 | D3 |

TABLE 1-1-continued

| No. | $R^1$ | $R^2$ | $R^3$ | $R^4$ | $R^5$ |
|---|---|---|---|---|---|
| 94 | A1 | D3 | CN | D4 | D4 |
| 95 | A1 | D3 | CN | D4 | D5 |
| 96 | A1 | D3 | CN | D4 | D6 |
| 97 | A1 | D3 | CN | D5 | D1 |
| 98 | A1 | D3 | CN | D5 | D2 |
| 99 | A1 | D3 | CN | D5 | D3 |
| 100 | A1 | D3 | CN | D5 | D4 |
| 101 | A1 | D3 | CN | D5 | D5 |
| 102 | A1 | D3 | CN | D5 | D6 |
| 103 | A1 | D3 | CN | D6 | D1 |
| 104 | A1 | D3 | CN | D6 | D2 |
| 105 | A1 | D3 | CN | D6 | D3 |
| 106 | A1 | D3 | CN | D6 | D4 |
| 107 | A1 | D3 | CN | D6 | D5 |
| 108 | A1 | D3 | CN | D6 | D6 |
| 109 | A1 | D4 | CN | D1 | D1 |
| 110 | A1 | D4 | CN | D1 | D2 |
| 111 | A1 | D4 | CN | D1 | D3 |
| 112 | A1 | D4 | CN | D1 | D4 |
| 113 | A1 | D4 | CN | D1 | D5 |
| 114 | A1 | D4 | CN | D1 | D6 |
| 115 | A1 | D4 | CN | D2 | D1 |
| 116 | A1 | D4 | CN | D2 | D2 |
| 117 | A1 | D4 | CN | D2 | D3 |
| 118 | A1 | D4 | CN | D2 | D4 |
| 119 | A1 | D4 | CN | D2 | D5 |
| 120 | A1 | D4 | CN | D2 | D6 |
| 121 | A1 | D4 | CN | D3 | D1 |
| 122 | A1 | D4 | CN | D3 | D2 |
| 123 | A1 | D4 | CN | D3 | D3 |
| 124 | A1 | D4 | CN | D3 | D4 |
| 125 | A1 | D4 | CN | D3 | D5 |
| 126 | A1 | D4 | CN | D3 | D6 |
| 127 | A1 | D4 | CN | D4 | D1 |
| 128 | A1 | D4 | CN | D4 | D2 |
| 129 | A1 | D4 | CN | D4 | D3 |
| 130 | A1 | D4 | CN | D4 | D4 |
| 131 | A1 | D4 | CN | D4 | D5 |
| 132 | A1 | D4 | CN | D4 | D6 |
| 133 | A1 | D4 | CN | D5 | D1 |
| 134 | A1 | D4 | CN | D5 | D2 |
| 135 | A1 | D4 | CN | D5 | D3 |
| 136 | A1 | D4 | CN | D5 | D4 |
| 137 | A1 | D4 | CN | D5 | D5 |
| 138 | A1 | D4 | CN | D5 | D6 |
| 139 | A1 | D4 | CN | D6 | D1 |
| 140 | A1 | D4 | CN | D6 | D2 |
| 141 | A1 | D4 | CN | D6 | D3 |
| 142 | A1 | D4 | CN | D6 | D4 |
| 143 | A1 | D4 | CN | D6 | D5 |
| 144 | A1 | D4 | CN | D6 | D6 |
| 145 | A1 | D5 | CN | D1 | D1 |
| 146 | A1 | D5 | CN | D1 | D2 |
| 147 | A1 | D5 | CN | D1 | D3 |
| 148 | A1 | D5 | CN | D1 | D4 |
| 149 | A1 | D5 | CN | D1 | D5 |
| 150 | A1 | D5 | CN | D1 | D6 |

TABLE 1-2

| No. | $R^1$ | $R^2$ | $R^3$ | $R^4$ | $R^5$ |
|---|---|---|---|---|---|
| 151 | A1 | D5 | CN | D2 | D1 |
| 152 | A1 | D5 | CN | D2 | D2 |
| 153 | A1 | D5 | CN | D2 | D3 |
| 154 | A1 | D5 | CN | D2 | D4 |
| 155 | A1 | D5 | CN | D2 | D5 |
| 156 | A1 | D5 | CN | D2 | D6 |
| 157 | A1 | D5 | CN | D3 | D1 |
| 158 | A1 | D5 | CN | D3 | D2 |
| 159 | A1 | D5 | CN | D3 | D3 |
| 160 | A1 | D5 | CN | D3 | D4 |
| 161 | A1 | D5 | CN | D3 | D5 |
| 162 | A1 | D5 | CN | D3 | D6 |
| 163 | A1 | D5 | CN | D4 | D1 |

TABLE 1-2-continued

| No. | $R^1$ | $R^2$ | $R^3$ | $R^4$ | $R^5$ |
|---|---|---|---|---|---|
| 164 | A1 | D5 | CN | D4 | D2 |
| 165 | A1 | D5 | CN | D4 | D3 |
| 166 | A1 | D5 | CN | D4 | D4 |
| 167 | A1 | D5 | CN | D4 | D5 |
| 168 | A1 | D5 | CN | D4 | D6 |
| 169 | A1 | D5 | CN | D5 | D1 |
| 170 | A1 | D5 | CN | D5 | D2 |
| 171 | A1 | D5 | CN | D5 | D3 |
| 172 | A1 | D5 | CN | D5 | D4 |
| 173 | A1 | D5 | CN | D5 | D5 |
| 174 | A1 | D5 | CN | D5 | D6 |
| 175 | A1 | D5 | CN | D6 | D1 |
| 176 | A1 | D5 | CN | D6 | D2 |
| 177 | A1 | D5 | CN | D6 | D3 |
| 178 | A1 | D5 | CN | D6 | D4 |
| 179 | A1 | D5 | CN | D6 | D5 |
| 180 | A1 | D5 | CN | D6 | D6 |
| 181 | A1 | D6 | CN | D1 | D1 |
| 182 | A1 | D6 | CN | D1 | D2 |
| 183 | A1 | D6 | CN | D1 | D3 |
| 184 | A1 | D6 | CN | D1 | D4 |
| 185 | A1 | D6 | CN | D1 | D5 |
| 186 | A1 | D6 | CN | D1 | D6 |
| 187 | A1 | D6 | CN | D2 | D1 |
| 188 | A1 | D6 | CN | D2 | D2 |
| 189 | A1 | D6 | CN | D2 | D3 |
| 190 | A1 | D6 | CN | D2 | D4 |
| 191 | A1 | D6 | CN | D2 | D5 |
| 192 | A1 | D6 | CN | D2 | D6 |
| 193 | A1 | D6 | CN | D3 | D1 |
| 194 | A1 | D6 | CN | D3 | D2 |
| 195 | A1 | D6 | CN | D3 | D3 |
| 196 | A1 | D6 | CN | D3 | D4 |
| 197 | A1 | D6 | CN | D3 | D5 |
| 198 | A1 | D6 | CN | D3 | D6 |
| 199 | A1 | D6 | CN | D4 | D1 |
| 200 | A1 | D6 | CN | D4 | D2 |
| 201 | A1 | D6 | CN | D4 | D3 |
| 202 | A1 | D6 | CN | D4 | D4 |
| 203 | A1 | D6 | CN | D4 | D5 |
| 204 | A1 | D6 | CN | D4 | D6 |
| 205 | A1 | D6 | CN | D5 | D1 |
| 206 | A1 | D6 | CN | D5 | D2 |
| 207 | A1 | D6 | CN | D5 | D3 |
| 208 | A1 | D6 | CN | D5 | D4 |
| 209 | A1 | D6 | CN | D5 | D5 |
| 210 | A1 | D6 | CN | D5 | D6 |
| 211 | A1 | D6 | CN | D6 | D1 |
| 212 | A1 | D6 | CN | D6 | D2 |
| 213 | A1 | D6 | CN | D6 | D3 |
| 214 | A1 | D6 | CN | D6 | D4 |
| 215 | A1 | D6 | CN | D6 | D5 |
| 216 | A1 | D6 | CN | D6 | D6 |
| 217 | A2 | D1 | CN | D1 | D1 |
| 218 | A2 | D1 | CN | D1 | D2 |
| 219 | A2 | D1 | CN | D1 | D3 |
| 220 | A2 | D1 | CN | D1 | D4 |
| 221 | A2 | D1 | CN | D1 | D5 |
| 222 | A2 | D1 | CN | D1 | D6 |
| 223 | A2 | D1 | CN | D2 | D1 |
| 224 | A2 | D1 | CN | D2 | D2 |
| 225 | A2 | D1 | CN | D2 | D3 |
| 226 | A2 | D1 | CN | D2 | D4 |
| 227 | A2 | D1 | CN | D2 | D5 |
| 228 | A2 | D1 | CN | D2 | D6 |
| 229 | A2 | D1 | CN | D3 | D1 |
| 230 | A2 | D1 | CN | D3 | D2 |
| 231 | A2 | D1 | CN | D3 | D3 |
| 232 | A2 | D1 | CN | D3 | D4 |
| 233 | A2 | D1 | CN | D3 | D5 |
| 234 | A2 | D1 | CN | D3 | D6 |
| 235 | A2 | D1 | CN | D4 | D1 |
| 236 | A2 | D1 | CN | D4 | D2 |
| 237 | A2 | D1 | CN | D4 | D3 |
| 238 | A2 | D1 | CN | D4 | D4 |
| 239 | A2 | D1 | CN | D4 | D5 |
| 240 | A2 | D1 | CN | D4 | D6 |
| 241 | A2 | D1 | CN | D5 | D1 |

TABLE 1-2-continued

| No. | $R^1$ | $R^2$ | $R^3$ | $R^4$ | $R^5$ |
|---|---|---|---|---|---|
| 242 | A2 | D1 | CN | D5 | D2 |
| 243 | A2 | D1 | CN | D5 | D3 |
| 244 | A2 | D1 | CN | D5 | D4 |
| 245 | A2 | D1 | CN | D5 | D5 |
| 246 | A2 | D1 | CN | D5 | D6 |
| 247 | A2 | D1 | CN | D6 | D1 |
| 248 | A2 | D1 | CN | D6 | D2 |
| 249 | A2 | D1 | CN | D6 | D3 |
| 250 | A2 | D1 | CN | D6 | D4 |
| 251 | A2 | D1 | CN | D6 | D5 |
| 252 | A2 | D1 | CN | D6 | D6 |
| 253 | A2 | D2 | CN | D1 | D1 |
| 254 | A2 | D2 | CN | D1 | D2 |
| 255 | A2 | D2 | CN | D1 | D3 |
| 256 | A2 | D2 | CN | D1 | D4 |
| 257 | A2 | D2 | CN | D1 | D5 |
| 258 | A2 | D2 | CN | D1 | D6 |
| 259 | A2 | D2 | CN | D2 | D1 |
| 260 | A2 | D2 | CN | D2 | D2 |
| 261 | A2 | D2 | CN | D2 | D3 |
| 262 | A2 | D2 | CN | D2 | D4 |
| 263 | A2 | D2 | CN | D2 | D5 |
| 264 | A2 | D2 | CN | D2 | D6 |
| 265 | A2 | D2 | CN | D3 | D1 |
| 266 | A2 | D2 | CN | D3 | D2 |
| 267 | A2 | D2 | CN | D3 | D3 |
| 268 | A2 | D2 | CN | D3 | D4 |
| 269 | A2 | D2 | CN | D3 | D5 |
| 270 | A2 | D2 | CN | D3 | D6 |
| 271 | A2 | D2 | CN | D4 | D1 |
| 272 | A2 | D2 | CN | D4 | D2 |
| 273 | A2 | D2 | CN | D4 | D3 |
| 274 | A2 | D2 | CN | D4 | D4 |
| 275 | A2 | D2 | CN | D4 | D5 |
| 276 | A2 | D2 | CN | D4 | D6 |
| 277 | A2 | D2 | CN | D5 | D1 |
| 278 | A2 | D2 | CN | D5 | D2 |
| 279 | A2 | D2 | CN | D5 | D3 |
| 280 | A2 | D2 | CN | D5 | D4 |
| 281 | A2 | D2 | CN | D5 | D5 |
| 282 | A2 | D2 | CN | D5 | D6 |
| 283 | A2 | D2 | CN | D6 | D1 |
| 284 | A2 | D2 | CN | D6 | D2 |
| 285 | A2 | D2 | CN | D6 | D3 |
| 286 | A2 | D2 | CN | D6 | D4 |
| 287 | A2 | D2 | CN | D6 | D5 |
| 288 | A2 | D2 | CN | D6 | D6 |
| 289 | A2 | D3 | CN | D1 | D1 |
| 290 | A2 | D3 | CN | D1 | D2 |
| 291 | A2 | D3 | CN | D1 | D3 |
| 292 | A2 | D3 | CN | D1 | D4 |
| 293 | A2 | D3 | CN | D1 | D5 |
| 294 | A2 | D3 | CN | D1 | D6 |
| 295 | A2 | D3 | CN | D2 | D1 |
| 296 | A2 | D3 | CN | D2 | D2 |
| 297 | A2 | D3 | CN | D2 | D3 |
| 298 | A2 | D3 | CN | D2 | D4 |
| 299 | A2 | D3 | CN | D2 | D5 |
| 300 | A2 | D3 | CN | D2 | D6 |

TABLE 1-3

| No. | $R^1$ | $R^2$ | $R^3$ | $R^4$ | $R^5$ |
|---|---|---|---|---|---|
| 301 | A2 | D3 | CN | D3 | D1 |
| 302 | A2 | D3 | CN | D3 | D2 |
| 303 | A2 | D3 | CN | D3 | D3 |
| 304 | A2 | D3 | CN | D3 | D4 |
| 305 | A2 | D3 | CN | D3 | D5 |
| 306 | A2 | D3 | CN | D3 | D6 |
| 307 | A2 | D3 | CN | D4 | D1 |
| 308 | A2 | D3 | CN | D4 | D2 |
| 309 | A2 | D3 | CN | D4 | D3 |
| 310 | A2 | D3 | CN | D4 | D4 |
| 311 | A2 | D3 | CN | D4 | D5 |

TABLE 1-3-continued

| No. | $R^1$ | $R^2$ | $R^3$ | $R^4$ | $R^5$ |
|---|---|---|---|---|---|
| 312 | A2 | D3 | CN | D4 | D6 |
| 313 | A2 | D3 | CN | D5 | D1 |
| 314 | A2 | D3 | CN | D5 | D2 |
| 315 | A2 | D3 | CN | D5 | D3 |
| 316 | A2 | D3 | CN | D5 | D4 |
| 317 | A2 | D3 | CN | D5 | D5 |
| 318 | A2 | D3 | CN | D5 | D6 |
| 319 | A2 | D3 | CN | D6 | D1 |
| 320 | A2 | D3 | CN | D6 | D2 |
| 321 | A2 | D3 | CN | D6 | D3 |
| 322 | A2 | D3 | CN | D6 | D4 |
| 323 | A2 | D3 | CN | D6 | D5 |
| 324 | A2 | D3 | CN | D6 | D6 |
| 325 | A2 | D4 | CN | D1 | D1 |
| 326 | A2 | D4 | CN | D1 | D2 |
| 327 | A2 | D4 | CN | D1 | D3 |
| 328 | A2 | D4 | CN | D1 | D4 |
| 329 | A2 | D4 | CN | D1 | D5 |
| 330 | A2 | D4 | CN | D1 | D6 |
| 331 | A2 | D4 | CN | D2 | D1 |
| 332 | A2 | D4 | CN | D2 | D2 |
| 333 | A2 | D4 | CN | D2 | D3 |
| 334 | A2 | D4 | CN | D2 | D4 |
| 335 | A2 | D4 | CN | D2 | D5 |
| 336 | A2 | D4 | CN | D2 | D6 |
| 337 | A2 | D4 | CN | D3 | D1 |
| 338 | A2 | D4 | CN | D3 | D2 |
| 339 | A2 | D4 | CN | D3 | D3 |
| 340 | A2 | D4 | CN | D3 | D4 |
| 341 | A2 | D4 | CN | D3 | D5 |
| 342 | A2 | D4 | CN | D3 | D6 |
| 343 | A2 | D4 | CN | D4 | D1 |
| 344 | A2 | D4 | CN | D4 | D2 |
| 345 | A2 | D4 | CN | D4 | D3 |
| 346 | A2 | D4 | CN | D4 | D4 |
| 347 | A2 | D4 | CN | D4 | D5 |
| 348 | A2 | D4 | CN | D4 | D6 |
| 349 | A2 | D4 | CN | D5 | D1 |
| 350 | A2 | D4 | CN | D5 | D2 |
| 351 | A2 | D4 | CN | D5 | D3 |
| 352 | A2 | D4 | CN | D5 | D4 |
| 353 | A2 | D4 | CN | D5 | D5 |
| 354 | A2 | D4 | CN | D5 | D6 |
| 355 | A2 | D4 | CN | D6 | D1 |
| 356 | A2 | D4 | CN | D6 | D2 |
| 357 | A2 | D4 | CN | D6 | D3 |
| 358 | A2 | D4 | CN | D6 | D4 |
| 359 | A2 | D4 | CN | D6 | D5 |
| 360 | A2 | D4 | CN | D6 | D6 |
| 361 | A2 | D5 | CN | D1 | D1 |
| 362 | A2 | D5 | CN | D1 | D2 |
| 363 | A2 | D5 | CN | D1 | D3 |
| 364 | A2 | D5 | CN | D1 | D4 |
| 365 | A2 | D5 | CN | D1 | D5 |
| 366 | A2 | D5 | CN | D1 | D6 |
| 367 | A2 | D5 | CN | D2 | D1 |
| 368 | A2 | D5 | CN | D2 | D2 |
| 369 | A2 | D5 | CN | D2 | D3 |
| 370 | A2 | D5 | CN | D2 | D4 |
| 371 | A2 | D5 | CN | D2 | D5 |
| 372 | A2 | D5 | CN | D2 | D6 |
| 373 | A2 | D5 | CN | D3 | D1 |
| 374 | A2 | D5 | CN | D3 | D2 |
| 375 | A2 | D5 | CN | D3 | D3 |
| 376 | A2 | D5 | CN | D3 | D4 |
| 377 | A2 | D5 | CN | D3 | D5 |
| 378 | A2 | D5 | CN | D3 | D6 |
| 379 | A2 | D5 | CN | D4 | D1 |
| 380 | A2 | D5 | CN | D4 | D2 |
| 381 | A2 | D5 | CN | D4 | D3 |
| 382 | A2 | D5 | CN | D4 | D4 |
| 383 | A2 | D5 | CN | D4 | D5 |
| 384 | A2 | D5 | CN | D4 | D6 |
| 385 | A2 | D5 | CN | D5 | D1 |
| 386 | A2 | D5 | CN | D5 | D2 |
| 387 | A2 | D5 | CN | D5 | D3 |
| 388 | A2 | D5 | CN | D5 | D4 |
| 389 | A2 | D5 | CN | D5 | D5 |

TABLE 1-3-continued

| No. | R1 | R2 | R3 | R4 | R5 |
|---|---|---|---|---|---|
| 390 | A2 | D5 | CN | D5 | D6 |
| 391 | A2 | D5 | CN | D6 | D1 |
| 392 | A2 | D5 | CN | D6 | D2 |
| 393 | A2 | D5 | CN | D6 | D3 |
| 394 | A2 | D5 | CN | D6 | D4 |
| 395 | A2 | D5 | CN | D6 | D5 |
| 396 | A2 | D5 | CN | D6 | D6 |
| 397 | A2 | D6 | CN | D1 | D1 |
| 398 | A2 | D6 | CN | D1 | D2 |
| 399 | A2 | D6 | CN | D1 | D3 |
| 400 | A2 | D6 | CN | D1 | D4 |
| 401 | A2 | D6 | CN | D1 | D5 |
| 402 | A2 | D6 | CN | D1 | D6 |
| 403 | A2 | D6 | CN | D2 | D1 |
| 404 | A2 | D6 | CN | D2 | D2 |
| 405 | A2 | D6 | CN | D2 | D3 |
| 406 | A2 | D6 | CN | D2 | D4 |
| 407 | A2 | D6 | CN | D2 | D5 |
| 408 | A2 | D6 | CN | D2 | D6 |
| 409 | A2 | D6 | CN | D3 | D1 |
| 410 | A2 | D6 | CN | D3 | D2 |
| 411 | A2 | D6 | CN | D3 | D3 |
| 412 | A2 | D6 | CN | D3 | D4 |
| 413 | A2 | D6 | CN | D3 | D5 |
| 414 | A2 | D6 | CN | D3 | D6 |
| 415 | A2 | D6 | CN | D4 | D1 |
| 416 | A2 | D6 | CN | D4 | D2 |
| 417 | A2 | D6 | CN | D4 | D3 |
| 418 | A2 | D6 | CN | D4 | D4 |
| 419 | A2 | D6 | CN | D4 | D5 |
| 420 | A2 | D6 | CN | D4 | D6 |
| 421 | A2 | D6 | CN | D5 | D1 |
| 422 | A2 | D6 | CN | D5 | D2 |
| 423 | A2 | D6 | CN | D5 | D3 |
| 424 | A2 | D6 | CN | D5 | D4 |
| 425 | A2 | D6 | CN | D5 | D5 |
| 426 | A2 | D6 | CN | D5 | D6 |
| 427 | A2 | D6 | CN | D6 | D1 |
| 428 | A2 | D6 | CN | D6 | D2 |
| 429 | A2 | D6 | CN | D6 | D3 |
| 430 | A2 | D6 | CN | D6 | D4 |
| 431 | A2 | D6 | CN | D6 | D5 |
| 432 | A2 | D6 | CN | D6 | D6 |
| 433 | A1 | H | CN | D1 | D1 |
| 434 | A1 | H | CN | D1 | D2 |
| 435 | A1 | H | CN | D1 | D3 |
| 436 | A1 | H | CN | D1 | D4 |
| 437 | A1 | H | CN | D1 | D5 |
| 438 | A1 | H | CN | D1 | D6 |
| 439 | A1 | H | CN | D1 | D7 |
| 440 | A1 | H | CN | D1 | D8 |
| 441 | A1 | H | CN | D1 | D9 |
| 442 | A1 | H | CN | D1 | D10 |
| 443 | A1 | H | CN | D1 | D11 |
| 444 | A1 | H | CN | D1 | D12 |
| 445 | A1 | H | CN | D1 | D13 |
| 446 | A1 | H | CN | D1 | D14 |
| 447 | A1 | H | CN | D1 | D15 |
| 448 | A1 | H | CN | D1 | D16 |
| 449 | A1 | H | CN | D2 | D1 |
| 450 | A1 | H | CN | D2 | D2 |

TABLE 1-4

| No. | R1 | R2 | R3 | R4 | R5 |
|---|---|---|---|---|---|
| 451 | A1 | H | CN | D2 | D3 |
| 452 | A1 | H | CN | D2 | D4 |
| 453 | A1 | H | CN | D2 | D5 |
| 454 | A1 | H | CN | D2 | D6 |
| 455 | A1 | H | CN | D2 | D7 |
| 456 | A1 | H | CN | D2 | D8 |
| 457 | A1 | H | CN | D2 | D9 |
| 458 | A1 | H | CN | D2 | D10 |
| 459 | A1 | H | CN | D2 | D11 |

TABLE 1-4-continued

| No. | R1 | R2 | R3 | R4 | R5 |
|---|---|---|---|---|---|
| 460 | A1 | H | CN | D2 | D12 |
| 461 | A1 | H | CN | D2 | D13 |
| 462 | A1 | H | CN | D2 | D14 |
| 463 | A1 | H | CN | D2 | D15 |
| 464 | A1 | H | CN | D2 | D16 |
| 465 | A1 | H | CN | D3 | D1 |
| 466 | A1 | H | CN | D3 | D2 |
| 467 | A1 | H | CN | D3 | D3 |
| 468 | A1 | H | CN | D3 | D4 |
| 469 | A1 | H | CN | D3 | D5 |
| 470 | A1 | H | CN | D3 | D6 |
| 471 | A1 | H | CN | D3 | D7 |
| 472 | A1 | H | CN | D3 | D8 |
| 473 | A1 | H | CN | D3 | D9 |
| 474 | A1 | H | CN | D3 | D10 |
| 475 | A1 | H | CN | D3 | D11 |
| 476 | A1 | H | CN | D3 | D12 |
| 477 | A1 | H | CN | D3 | D13 |
| 478 | A1 | H | CN | D3 | D14 |
| 479 | A1 | H | CN | D3 | D15 |
| 480 | A1 | H | CN | D3 | D16 |
| 481 | A1 | H | CN | D4 | D1 |
| 482 | A1 | H | CN | D4 | D2 |
| 483 | A1 | H | CN | D4 | D3 |
| 484 | A1 | H | CN | D4 | D4 |
| 485 | A1 | H | CN | D4 | D5 |
| 486 | A1 | H | CN | D4 | D6 |
| 487 | A1 | H | CN | D4 | D7 |
| 488 | A1 | H | CN | D4 | D8 |
| 489 | A1 | H | CN | D4 | D9 |
| 490 | A1 | H | CN | D4 | D10 |
| 491 | A1 | H | CN | D4 | D11 |
| 492 | A1 | H | CN | D4 | D12 |
| 493 | A1 | H | CN | D4 | D13 |
| 494 | A1 | H | CN | D4 | D14 |
| 495 | A1 | H | CN | D4 | D15 |
| 496 | A1 | H | CN | D4 | D16 |
| 497 | A1 | H | CN | D5 | D1 |
| 498 | A1 | H | CN | D5 | D2 |
| 499 | A1 | H | CN | D5 | D3 |
| 500 | A1 | H | CN | D5 | D4 |
| 501 | A1 | H | CN | D5 | D5 |
| 502 | A1 | H | CN | D5 | D6 |
| 503 | A1 | H | CN | D5 | D7 |
| 504 | A1 | H | CN | D5 | D8 |
| 505 | A1 | H | CN | D5 | D9 |
| 506 | A1 | H | CN | D5 | D10 |
| 507 | A1 | H | CN | D5 | D11 |
| 508 | A1 | H | CN | D5 | D12 |
| 509 | A1 | H | CN | D5 | D13 |
| 510 | A1 | H | CN | D5 | D14 |
| 511 | A1 | H | CN | D5 | D15 |
| 512 | A1 | H | CN | D5 | D16 |
| 513 | A1 | H | CN | D6 | D1 |
| 514 | A1 | H | CN | D6 | D2 |
| 515 | A1 | H | CN | D6 | D3 |
| 516 | A1 | H | CN | D6 | D4 |
| 517 | A1 | H | CN | D6 | D5 |
| 518 | A1 | H | CN | D6 | D6 |
| 519 | A1 | H | CN | D6 | D7 |
| 520 | A1 | H | CN | D6 | D8 |
| 521 | A1 | H | CN | D6 | D9 |
| 522 | A1 | H | CN | D6 | D10 |
| 523 | A1 | H | CN | D6 | D11 |
| 524 | A1 | H | CN | D6 | D12 |
| 525 | A1 | H | CN | D6 | D13 |
| 526 | A1 | H | CN | D6 | D14 |
| 527 | A1 | H | CN | D6 | D15 |
| 528 | A1 | H | CN | D6 | D16 |
| 529 | A1 | H | CN | D7 | D1 |
| 530 | A1 | H | CN | D7 | D2 |
| 531 | A1 | H | CN | D7 | D3 |
| 532 | A1 | H | CN | D7 | D4 |
| 533 | A1 | H | CN | D7 | D5 |
| 534 | A1 | H | CN | D7 | D6 |
| 535 | A1 | H | CN | D7 | D7 |
| 536 | A1 | H | CN | D7 | D8 |
| 537 | A1 | H | CN | D7 | D9 |

TABLE 1-4-continued

| No. | $R^1$ | $R^2$ | $R^3$ | $R^4$ | $R^5$ |
|---|---|---|---|---|---|
| 538 | A1 | H | CN | D7 | D10 |
| 539 | A1 | H | CN | D7 | D11 |
| 540 | A1 | H | CN | D7 | D12 |
| 541 | A1 | H | CN | D7 | D13 |
| 542 | A1 | H | CN | D7 | D14 |
| 543 | A1 | H | CN | D7 | D15 |
| 544 | A1 | H | CN | D7 | D16 |
| 545 | A1 | H | CN | D8 | D1 |
| 546 | A1 | H | CN | D8 | D2 |
| 547 | A1 | H | CN | D8 | D3 |
| 548 | A1 | H | CN | D8 | D4 |
| 549 | A1 | H | CN | D8 | D5 |
| 550 | A1 | H | CN | D8 | D6 |
| 551 | A1 | H | CN | D8 | D7 |
| 552 | A1 | H | CN | D8 | D8 |
| 553 | A1 | H | CN | D8 | D9 |
| 554 | A1 | H | CN | D8 | D10 |
| 555 | A1 | H | CN | D8 | D11 |
| 556 | A1 | H | CN | D8 | D12 |
| 557 | A1 | H | CN | D8 | D13 |
| 558 | A1 | H | CN | D8 | D14 |
| 559 | A1 | H | CN | D8 | D15 |
| 560 | A1 | H | CN | D8 | D16 |
| 561 | A1 | H | CN | D9 | D1 |
| 562 | A1 | H | CN | D9 | D2 |
| 563 | A1 | H | CN | D9 | D3 |
| 564 | A1 | H | CN | D9 | D4 |
| 565 | A1 | H | CN | D9 | D5 |
| 566 | A1 | H | CN | D9 | D6 |
| 567 | A1 | H | CN | D9 | D7 |
| 568 | A1 | H | CN | D9 | D8 |
| 569 | A1 | H | CN | D9 | D9 |
| 570 | A1 | H | CN | D9 | D10 |
| 571 | A1 | H | CN | D9 | D11 |
| 572 | A1 | H | CN | D9 | D12 |
| 573 | A1 | H | CN | D9 | D13 |
| 574 | A1 | H | CN | D9 | D14 |
| 575 | A1 | H | CN | D9 | D15 |
| 576 | A1 | H | CN | D9 | D16 |
| 577 | A1 | H | CN | D10 | D1 |
| 578 | A1 | H | CN | D10 | D2 |
| 579 | A1 | H | CN | D10 | D3 |
| 580 | A1 | H | CN | D10 | D4 |
| 581 | A1 | H | CN | D10 | D5 |
| 582 | A1 | H | CN | D10 | D6 |
| 583 | A1 | H | CN | D10 | D7 |
| 584 | A1 | H | CN | D10 | D8 |
| 585 | A1 | H | CN | D10 | D9 |
| 586 | A1 | H | CN | D10 | D10 |
| 587 | A1 | H | CN | D10 | D11 |
| 588 | A1 | H | CN | D10 | D12 |
| 589 | A1 | H | CN | D10 | D13 |
| 590 | A1 | H | CN | D10 | D14 |
| 591 | A1 | H | CN | D10 | D15 |
| 592 | A1 | H | CN | D10 | D16 |
| 593 | A1 | H | CN | D11 | D1 |
| 594 | A1 | H | CN | D11 | D2 |
| 595 | A1 | H | CN | D11 | D3 |
| 596 | A1 | H | CN | D11 | D4 |
| 597 | A1 | H | CN | D11 | D5 |
| 598 | A1 | H | CN | D11 | D6 |
| 599 | A1 | H | CN | D11 | D7 |
| 600 | A1 | H | CN | D11 | D8 |

TABLE 1-5

| No. | $R^1$ | $R^2$ | $R^3$ | $R^4$ | $R^5$ |
|---|---|---|---|---|---|
| 601 | A1 | H | CN | D11 | D9 |
| 602 | A1 | H | CN | D11 | D10 |
| 603 | A1 | H | CN | D11 | D11 |
| 604 | A1 | H | CN | D11 | D12 |
| 605 | A1 | H | CN | D11 | D13 |
| 606 | A1 | H | CN | D11 | D14 |
| 607 | A1 | H | CN | D11 | D15 |

TABLE 1-5-continued

| No. | $R^1$ | $R^2$ | $R^3$ | $R^4$ | $R^5$ |
|---|---|---|---|---|---|
| 608 | A1 | H | CN | D11 | D16 |
| 609 | A1 | H | CN | D12 | D1 |
| 610 | A1 | H | CN | D12 | D2 |
| 611 | A1 | H | CN | D12 | D3 |
| 612 | A1 | H | CN | D12 | D4 |
| 613 | A1 | H | CN | D12 | D5 |
| 614 | A1 | H | CN | D12 | D6 |
| 615 | A1 | H | CN | D12 | D7 |
| 616 | A1 | H | CN | D12 | D8 |
| 617 | A1 | H | CN | D12 | D9 |
| 618 | A1 | H | CN | D12 | D10 |
| 619 | A1 | H | CN | D12 | D11 |
| 620 | A1 | H | CN | D12 | D12 |
| 621 | A1 | H | CN | D12 | D13 |
| 622 | A1 | H | CN | D12 | D14 |
| 623 | A1 | H | CN | D12 | D15 |
| 624 | A1 | H | CN | D12 | D16 |
| 625 | A1 | H | CN | D13 | D1 |
| 626 | A1 | H | CN | D13 | D2 |
| 627 | A1 | H | CN | D13 | D3 |
| 628 | A1 | H | CN | D13 | D4 |
| 629 | A1 | H | CN | D13 | D5 |
| 630 | A1 | H | CN | D13 | D6 |
| 631 | A1 | H | CN | D13 | D7 |
| 632 | A1 | H | CN | D13 | D8 |
| 633 | A1 | H | CN | D13 | D9 |
| 634 | A1 | H | CN | D13 | D10 |
| 635 | A1 | H | CN | D13 | D11 |
| 636 | A1 | H | CN | D13 | D12 |
| 637 | A1 | H | CN | D13 | D13 |
| 638 | A1 | H | CN | D13 | D14 |
| 639 | A1 | H | CN | D13 | D15 |
| 640 | A1 | H | CN | D13 | D16 |
| 641 | A1 | H | CN | D14 | D1 |
| 642 | A1 | H | CN | D14 | D2 |
| 643 | A1 | H | CN | D14 | D3 |
| 644 | A1 | H | CN | D14 | D4 |
| 645 | A1 | H | CN | D14 | D5 |
| 646 | A1 | H | CN | D14 | D6 |
| 647 | A1 | H | CN | D14 | D7 |
| 648 | A1 | H | CN | D14 | D8 |
| 649 | A1 | H | CN | D14 | D9 |
| 650 | A1 | H | CN | D14 | D10 |
| 651 | A1 | H | CN | D14 | D11 |
| 652 | A1 | H | CN | D14 | D12 |
| 653 | A1 | H | CN | D14 | D13 |
| 654 | A1 | H | CN | D14 | D14 |
| 655 | A1 | H | CN | D14 | D15 |
| 656 | A1 | H | CN | D14 | D16 |
| 657 | A1 | H | CN | D15 | D1 |
| 658 | A1 | H | CN | D15 | D2 |
| 659 | A1 | H | CN | D15 | D3 |
| 660 | A1 | H | CN | D15 | D4 |
| 661 | A1 | H | CN | D15 | D5 |
| 662 | A1 | H | CN | D15 | D6 |
| 663 | A1 | H | CN | D15 | D7 |
| 664 | A1 | H | CN | D15 | D8 |
| 665 | A1 | H | CN | D15 | D9 |
| 666 | A1 | H | CN | D15 | D10 |
| 667 | A1 | H | CN | D15 | D11 |
| 668 | A1 | H | CN | D15 | D12 |
| 669 | A1 | H | CN | D15 | D13 |
| 670 | A1 | H | CN | D15 | D14 |
| 671 | A1 | H | CN | D15 | D15 |
| 672 | A1 | H | CN | D15 | D16 |
| 673 | A1 | H | CN | D16 | D1 |
| 674 | A1 | H | CN | D16 | D2 |
| 675 | A1 | H | CN | D16 | D3 |
| 676 | A1 | H | CN | D16 | D4 |
| 677 | A1 | H | CN | D16 | D5 |
| 678 | A1 | H | CN | D16 | D6 |
| 679 | A1 | H | CN | D16 | D7 |
| 680 | A1 | H | CN | D16 | D8 |
| 681 | A1 | H | CN | D16 | D9 |
| 682 | A1 | H | CN | D16 | D10 |
| 683 | A1 | H | CN | D16 | D11 |
| 684 | A1 | H | CN | D16 | D12 |
| 685 | A1 | H | CN | D16 | D13 |

TABLE 1-5-continued

| No. | $R^1$ | $R^2$ | $R^3$ | $R^4$ | $R^5$ |
|---|---|---|---|---|---|
| 686 | A1 | H | CN | D16 | D14 |
| 687 | A1 | H | CN | D16 | D15 |
| 688 | A1 | H | CN | D16 | D16 |
| 689 | A2 | H | CN | D1 | D1 |
| 690 | A2 | H | CN | D1 | D2 |
| 691 | A2 | H | CN | D1 | D3 |
| 692 | A2 | H | CN | D1 | D4 |
| 693 | A2 | H | CN | D1 | D5 |
| 694 | A2 | H | CN | D1 | D6 |
| 695 | A2 | H | CN | D1 | D7 |
| 696 | A2 | H | CN | D1 | D8 |
| 697 | A2 | H | CN | D1 | D9 |
| 698 | A2 | H | CN | D1 | D10 |
| 699 | A2 | H | CN | D1 | D11 |
| 700 | A2 | H | CN | D1 | D12 |
| 701 | A2 | H | CN | D1 | D13 |
| 702 | A2 | H | CN | D1 | D14 |
| 703 | A2 | H | CN | D1 | D15 |
| 704 | A2 | H | CN | D1 | D16 |
| 705 | A2 | H | CN | D2 | D1 |
| 706 | A2 | H | CN | D2 | D2 |
| 707 | A2 | H | CN | D2 | D3 |
| 708 | A2 | H | CN | D2 | D4 |
| 709 | A2 | H | CN | D2 | D5 |
| 710 | A2 | H | CN | D2 | D6 |
| 711 | A2 | H | CN | D2 | D7 |
| 712 | A2 | H | CN | D2 | D8 |
| 713 | A2 | H | CN | D2 | D9 |
| 714 | A2 | H | CN | D2 | D10 |
| 715 | A2 | H | CN | D2 | D11 |
| 716 | A2 | H | CN | D2 | D12 |
| 717 | A2 | H | CN | D2 | D13 |
| 718 | A2 | H | CN | D2 | D14 |
| 719 | A2 | H | CN | D2 | D15 |
| 720 | A2 | H | CN | D2 | D16 |
| 721 | A2 | H | CN | D3 | D1 |
| 722 | A2 | H | CN | D3 | D2 |
| 723 | A2 | H | CN | D3 | D3 |
| 724 | A2 | H | CN | D3 | D4 |
| 725 | A2 | H | CN | D3 | D5 |
| 726 | A2 | H | CN | D3 | D6 |
| 727 | A2 | H | CN | D3 | D7 |
| 728 | A2 | H | CN | D3 | D8 |
| 729 | A2 | H | CN | D3 | D9 |
| 730 | A2 | H | CN | D3 | D10 |
| 731 | A2 | H | CN | D3 | D11 |
| 732 | A2 | H | CN | D3 | D12 |
| 733 | A2 | H | CN | D3 | D13 |
| 734 | A2 | H | CN | D3 | D14 |
| 735 | A2 | H | CN | D3 | D15 |
| 736 | A2 | H | CN | D3 | D16 |
| 737 | A2 | H | CN | D4 | D1 |
| 738 | A2 | H | CN | D4 | D2 |
| 739 | A2 | H | CN | D4 | D3 |
| 740 | A2 | H | CN | D4 | D4 |
| 741 | A2 | H | CN | D4 | D5 |
| 742 | A2 | H | CN | D4 | D6 |
| 743 | A2 | H | CN | D4 | D7 |
| 744 | A2 | H | CN | D4 | D8 |
| 745 | A2 | H | CN | D4 | D9 |
| 746 | A2 | H | CN | D4 | D10 |
| 747 | A2 | H | CN | D4 | D11 |
| 748 | A2 | H | CN | D4 | D12 |
| 749 | A2 | H | CN | D4 | D13 |
| 750 | A2 | H | CN | D4 | D14 |

TABLE 1-6

| No. | $R^1$ | $R^2$ | $R^3$ | $R^4$ | $R^5$ |
|---|---|---|---|---|---|
| 751 | A2 | H | CN | D4 | D15 |
| 752 | A2 | H | CN | D4 | D16 |
| 753 | A2 | H | CN | D5 | D1 |
| 754 | A2 | H | CN | D5 | D2 |
| 755 | A2 | H | CN | D5 | D3 |

TABLE 1-6-continued

| No. | $R^1$ | $R^2$ | $R^3$ | $R^4$ | $R^5$ |
|---|---|---|---|---|---|
| 756 | A2 | H | CN | D5 | D4 |
| 757 | A2 | H | CN | D5 | D5 |
| 758 | A2 | H | CN | D5 | D6 |
| 759 | A2 | H | CN | D5 | D7 |
| 760 | A2 | H | CN | D5 | D8 |
| 761 | A2 | H | CN | D5 | D9 |
| 762 | A2 | H | CN | D5 | D10 |
| 763 | A2 | H | CN | D5 | D11 |
| 764 | A2 | H | CN | D5 | D12 |
| 765 | A2 | H | CN | D5 | D13 |
| 766 | A2 | H | CN | D5 | D14 |
| 767 | A2 | H | CN | D5 | D15 |
| 768 | A2 | H | CN | D5 | D16 |
| 769 | A2 | H | CN | D6 | D1 |
| 770 | A2 | H | CN | D6 | D2 |
| 771 | A2 | H | CN | D6 | D3 |
| 772 | A2 | H | CN | D6 | D4 |
| 773 | A2 | H | CN | D6 | D5 |
| 774 | A2 | H | CN | D6 | D6 |
| 775 | A2 | H | CN | D6 | D7 |
| 776 | A2 | H | CN | D6 | D8 |
| 777 | A2 | H | CN | D6 | D9 |
| 778 | A2 | H | CN | D6 | D10 |
| 779 | A2 | H | CN | D6 | D11 |
| 780 | A2 | H | CN | D6 | D12 |
| 781 | A2 | H | CN | D6 | D13 |
| 782 | A2 | H | CN | D6 | D14 |
| 783 | A2 | H | CN | D6 | D15 |
| 784 | A2 | H | CN | D6 | D16 |
| 785 | A2 | H | CN | D7 | D1 |
| 786 | A2 | H | CN | D7 | D2 |
| 787 | A2 | H | CN | D7 | D3 |
| 788 | A2 | H | CN | D7 | D4 |
| 789 | A2 | H | CN | D7 | D5 |
| 790 | A2 | H | CN | D7 | D6 |
| 791 | A2 | H | CN | D7 | D7 |
| 792 | A2 | H | CN | D7 | D8 |
| 793 | A2 | H | CN | D7 | D9 |
| 794 | A2 | H | CN | D7 | D10 |
| 795 | A2 | H | CN | D7 | D11 |
| 796 | A2 | H | CN | D7 | D12 |
| 797 | A2 | H | CN | D7 | D13 |
| 798 | A2 | H | CN | D7 | D14 |
| 799 | A2 | H | CN | D7 | D15 |
| 800 | A2 | H | CN | D7 | D16 |
| 801 | A2 | H | CN | D8 | D1 |
| 802 | A2 | H | CN | D8 | D2 |
| 803 | A2 | H | CN | D8 | D3 |
| 804 | A2 | H | CN | D8 | D4 |
| 805 | A2 | H | CN | D8 | D5 |
| 806 | A2 | H | CN | D8 | D6 |
| 807 | A2 | H | CN | D8 | D7 |
| 808 | A2 | H | CN | D8 | D8 |
| 809 | A2 | H | CN | D8 | D9 |
| 810 | A2 | H | CN | D8 | D10 |
| 811 | A2 | H | CN | D8 | D11 |
| 812 | A2 | H | CN | D8 | D12 |
| 813 | A2 | H | CN | D8 | D13 |
| 814 | A2 | H | CN | D8 | D14 |
| 815 | A2 | H | CN | D8 | D15 |
| 816 | A2 | H | CN | D8 | D16 |
| 817 | A2 | H | CN | D9 | D1 |
| 818 | A2 | H | CN | D9 | D2 |
| 819 | A2 | H | CN | D9 | D3 |
| 820 | A2 | H | CN | D9 | D4 |
| 821 | A2 | H | CN | D9 | D5 |
| 822 | A2 | H | CN | D9 | D6 |
| 823 | A2 | H | CN | D9 | D7 |
| 824 | A2 | H | CN | D9 | D8 |
| 825 | A2 | H | CN | D9 | D9 |
| 826 | A2 | H | CN | D9 | D10 |
| 827 | A2 | H | CN | D9 | D11 |
| 828 | A2 | H | CN | D9 | D12 |
| 829 | A2 | H | CN | D9 | D13 |
| 830 | A2 | H | CN | D9 | D14 |
| 831 | A2 | H | CN | D9 | D15 |
| 832 | A2 | H | CN | D9 | D16 |
| 833 | A2 | H | CN | D10 | D1 |

TABLE 1-6-continued

| No. | $R^1$ | $R^2$ | $R^3$ | $R^4$ | $R^5$ |
|---|---|---|---|---|---|
| 834 | A2 | H | CN | D10 | D2 |
| 835 | A2 | H | CN | D10 | D3 |
| 836 | A2 | H | CN | D10 | D4 |
| 837 | A2 | H | CN | D10 | D5 |
| 838 | A2 | H | CN | D10 | D6 |
| 839 | A2 | H | CN | D10 | D7 |
| 840 | A2 | H | CN | D10 | D8 |
| 841 | A2 | H | CN | D10 | D9 |
| 842 | A2 | H | CN | D10 | D10 |
| 843 | A2 | H | CN | D10 | D11 |
| 844 | A2 | H | CN | D10 | D12 |
| 845 | A2 | H | CN | D10 | D13 |
| 846 | A2 | H | CN | D10 | D14 |
| 847 | A2 | H | CN | D10 | D15 |
| 848 | A2 | H | CN | D10 | D16 |
| 849 | A2 | H | CN | D11 | D1 |
| 850 | A2 | H | CN | D11 | D2 |
| 851 | A2 | H | CN | D11 | D3 |
| 852 | A2 | H | CN | D11 | D4 |
| 853 | A2 | H | CN | D11 | D5 |
| 854 | A2 | H | CN | D11 | D6 |
| 855 | A2 | H | CN | D11 | D7 |
| 856 | A2 | H | CN | D11 | D8 |
| 857 | A2 | H | CN | D11 | D9 |
| 858 | A2 | H | CN | D11 | D10 |
| 859 | A2 | H | CN | D11 | D11 |
| 860 | A2 | H | CN | D11 | D12 |
| 861 | A2 | H | CN | D11 | D13 |
| 862 | A2 | H | CN | D11 | D14 |
| 863 | A2 | H | CN | D11 | D15 |
| 864 | A2 | H | CN | D11 | D16 |
| 865 | A2 | H | CN | D12 | D1 |
| 866 | A2 | H | CN | D12 | D2 |
| 867 | A2 | H | CN | D12 | D3 |
| 868 | A2 | H | CN | D12 | D4 |
| 869 | A2 | H | CN | D12 | D5 |
| 870 | A2 | H | CN | D12 | D6 |
| 871 | A2 | H | CN | D12 | D7 |
| 872 | A2 | H | CN | D12 | D8 |
| 873 | A2 | H | CN | D12 | D9 |
| 874 | A2 | H | CN | D12 | D10 |
| 875 | A2 | H | CN | D12 | D11 |
| 876 | A2 | H | CN | D12 | D12 |
| 877 | A2 | H | CN | D12 | D13 |
| 878 | A2 | H | CN | D12 | D14 |
| 879 | A2 | H | CN | D12 | D15 |
| 880 | A2 | H | CN | D12 | D16 |
| 881 | A2 | H | CN | D13 | D1 |
| 882 | A2 | H | CN | D13 | D2 |
| 883 | A2 | H | CN | D13 | D3 |
| 884 | A2 | H | CN | D13 | D4 |
| 885 | A2 | H | CN | D13 | D5 |
| 886 | A2 | H | CN | D13 | D6 |
| 887 | A2 | H | CN | D13 | D7 |
| 888 | A2 | H | CN | D13 | D8 |
| 889 | A2 | H | CN | D13 | D9 |
| 890 | A2 | H | CN | D13 | D10 |
| 891 | A2 | H | CN | D13 | D11 |
| 892 | A2 | H | CN | D13 | D12 |
| 893 | A2 | H | CN | D13 | D13 |
| 894 | A2 | H | CN | D13 | D14 |
| 895 | A2 | H | CN | D13 | D15 |
| 896 | A2 | H | CN | D13 | D16 |
| 897 | A2 | H | CN | D14 | D1 |
| 898 | A2 | H | CN | D14 | D2 |
| 899 | A2 | H | CN | D14 | D3 |
| 900 | A2 | H | CN | D14 | D4 |

TABLE 1-7

| No. | $R^1$ | $R^2$ | $R^3$ | $R^4$ | $R^5$ |
|---|---|---|---|---|---|
| 901 | A2 | H | CN | D14 | D5 |
| 902 | A2 | H | CN | D14 | D6 |
| 903 | A2 | H | CN | D14 | D7 |

TABLE 1-7-continued

| No. | $R^1$ | $R^2$ | $R^3$ | $R^4$ | $R^5$ |
|---|---|---|---|---|---|
| 904 | A2 | H | CN | D14 | D8 |
| 905 | A2 | H | CN | D14 | D9 |
| 906 | A2 | H | CN | D14 | D10 |
| 907 | A2 | H | CN | D14 | D11 |
| 908 | A2 | H | CN | D14 | D12 |
| 909 | A2 | H | CN | D14 | D13 |
| 910 | A2 | H | CN | D14 | D14 |
| 911 | A2 | H | CN | D14 | D15 |
| 912 | A2 | H | CN | D14 | D16 |
| 913 | A2 | H | CN | D15 | D1 |
| 914 | A2 | H | CN | D15 | D2 |
| 915 | A2 | H | CN | D15 | D3 |
| 916 | A2 | H | CN | D15 | D4 |
| 917 | A2 | H | CN | D15 | D5 |
| 918 | A2 | H | CN | D15 | D6 |
| 919 | A2 | H | CN | D15 | D7 |
| 920 | A2 | H | CN | D15 | D8 |
| 921 | A2 | H | CN | D15 | D9 |
| 922 | A2 | H | CN | D15 | D10 |
| 923 | A2 | H | CN | D15 | D11 |
| 924 | A2 | H | CN | D15 | D12 |
| 925 | A2 | H | CN | D15 | D13 |
| 926 | A2 | H | CN | D15 | D14 |
| 927 | A2 | H | CN | D15 | D15 |
| 928 | A2 | H | CN | D15 | D16 |
| 929 | A2 | H | CN | D16 | D1 |
| 930 | A2 | H | CN | D16 | D2 |
| 931 | A2 | H | CN | D16 | D3 |
| 932 | A2 | H | CN | D16 | D4 |
| 933 | A2 | H | CN | D16 | D5 |
| 934 | A2 | H | CN | D16 | D6 |
| 935 | A2 | H | CN | D16 | D7 |
| 936 | A2 | H | CN | D16 | D8 |
| 937 | A2 | H | CN | D16 | D9 |
| 938 | A2 | H | CN | D16 | D10 |
| 939 | A2 | H | CN | D16 | D11 |
| 940 | A2 | H | CN | D16 | D12 |
| 941 | A2 | H | CN | D16 | D13 |
| 942 | A2 | H | CN | D16 | D14 |
| 943 | A2 | H | CN | D16 | D15 |
| 944 | A2 | H | CN | D16 | D16 |
| 945 | CN | D1 | A1 | D1 | D1 |
| 946 | CN | D1 | A1 | D1 | D2 |
| 947 | CN | D1 | A1 | D1 | D3 |
| 948 | CN | D1 | A1 | D1 | D4 |
| 949 | CN | D1 | A1 | D1 | D5 |
| 950 | CN | D1 | A1 | D1 | D6 |
| 951 | CN | D1 | A1 | D2 | D1 |
| 952 | CN | D1 | A1 | D2 | D2 |
| 953 | CN | D1 | A1 | D2 | D3 |
| 954 | CN | D1 | A1 | D2 | D4 |
| 955 | CN | D1 | A1 | D2 | D5 |
| 956 | CN | D1 | A1 | D2 | D6 |
| 957 | CN | D1 | A1 | D3 | D1 |
| 958 | CN | D1 | A1 | D3 | D2 |
| 959 | CN | D1 | A1 | D3 | D3 |
| 960 | CN | D1 | A1 | D3 | D4 |
| 961 | CN | D1 | A1 | D3 | D5 |
| 962 | CN | D1 | A1 | D3 | D6 |
| 963 | CN | D1 | A1 | D4 | D1 |
| 964 | CN | D1 | A1 | D4 | D2 |
| 965 | CN | D1 | A1 | D4 | D3 |
| 966 | CN | D1 | A1 | D4 | D4 |
| 967 | CN | D1 | A1 | D4 | D5 |
| 968 | CN | D1 | A1 | D4 | D6 |
| 969 | CN | D1 | A1 | D5 | D1 |
| 970 | CN | D1 | A1 | D5 | D2 |
| 971 | CN | D1 | A1 | D5 | D3 |
| 972 | CN | D1 | A1 | D5 | D4 |
| 973 | CN | D1 | A1 | D5 | D5 |
| 974 | CN | D1 | A1 | D5 | D6 |
| 975 | CN | D1 | A1 | D6 | D1 |
| 976 | CN | D1 | A1 | D6 | D2 |
| 977 | CN | D1 | A1 | D6 | D3 |
| 978 | CN | D1 | A1 | D6 | D4 |
| 979 | CN | D1 | A1 | D6 | D5 |
| 980 | CN | D1 | A1 | D6 | D6 |
| 981 | CN | D2 | A1 | D1 | D1 |

TABLE 1-7-continued

| No. | $R^1$ | $R^2$ | $R^3$ | $R^4$ | $R^5$ |
|---|---|---|---|---|---|
| 982 | CN | D2 | A1 | D1 | D2 |
| 983 | CN | D2 | A1 | D1 | D3 |
| 984 | CN | D2 | A1 | D1 | D4 |
| 985 | CN | D2 | A1 | D1 | D5 |
| 986 | CN | D2 | A1 | D1 | D6 |
| 987 | CN | D2 | A1 | D2 | D1 |
| 988 | CN | D2 | A1 | D2 | D2 |
| 989 | CN | D2 | A1 | D2 | D3 |
| 990 | CN | D2 | A1 | D2 | D4 |
| 991 | CN | D2 | A1 | D2 | D5 |
| 992 | CN | D2 | A1 | D2 | D6 |
| 993 | CN | D2 | A1 | D3 | D1 |
| 994 | CN | D2 | A1 | D3 | D2 |
| 995 | CN | D2 | A1 | D3 | D3 |
| 996 | CN | D2 | A1 | D3 | D4 |
| 997 | CN | D2 | A1 | D3 | D5 |
| 998 | CN | D2 | A1 | D3 | D6 |
| 999 | CN | D2 | A1 | D4 | D1 |
| 1000 | CN | D2 | A1 | D4 | D2 |
| 1001 | CN | D2 | A1 | D4 | D3 |
| 1002 | CN | D2 | A1 | D4 | D4 |
| 1003 | CN | D2 | A1 | D4 | D5 |
| 1004 | CN | D2 | A1 | D4 | D6 |
| 1005 | CN | D2 | A1 | D5 | D1 |
| 1006 | CN | D2 | A1 | D5 | D2 |
| 1007 | CN | D2 | A1 | D5 | D3 |
| 1008 | CN | D2 | A1 | D5 | D4 |
| 1009 | CN | D2 | A1 | D5 | D5 |
| 1010 | CN | D2 | A1 | D5 | D6 |
| 1011 | CN | D2 | A1 | D6 | D1 |
| 1012 | CN | D2 | A1 | D6 | D2 |
| 1013 | CN | D2 | A1 | D6 | D3 |
| 1014 | CN | D2 | A1 | D6 | D4 |
| 1015 | CN | D2 | A1 | D6 | D5 |
| 1016 | CN | D2 | A1 | D6 | D6 |
| 1017 | CN | D3 | A1 | D1 | D1 |
| 1018 | CN | D3 | A1 | D1 | D2 |
| 1019 | CN | D3 | A1 | D1 | D3 |
| 1020 | CN | D3 | A1 | D1 | D4 |
| 1021 | CN | D3 | A1 | D1 | D5 |
| 1022 | CN | D3 | A1 | D1 | D6 |
| 1023 | CN | D3 | A1 | D2 | D1 |
| 1024 | CN | D3 | A1 | D2 | D2 |
| 1025 | CN | D3 | A1 | D2 | D3 |
| 1026 | CN | D3 | A1 | D2 | D4 |
| 1027 | CN | D3 | A1 | D2 | D5 |
| 1028 | CN | D3 | A1 | D2 | D6 |
| 1029 | CN | D3 | A1 | D3 | D1 |
| 1030 | CN | D3 | A1 | D3 | D2 |
| 1031 | CN | D3 | A1 | D3 | D3 |
| 1032 | CN | D3 | A1 | D3 | D4 |
| 1033 | CN | D3 | A1 | D3 | D5 |
| 1034 | CN | D3 | A1 | D3 | D6 |
| 1035 | CN | D3 | A1 | D4 | D1 |
| 1036 | CN | D3 | A1 | D4 | D2 |
| 1037 | CN | D3 | A1 | D4 | D3 |
| 1038 | CN | D3 | A1 | D4 | D4 |
| 1039 | CN | D3 | A1 | D4 | D5 |
| 1040 | CN | D3 | A1 | D4 | D6 |
| 1041 | CN | D3 | A1 | D5 | D1 |
| 1042 | CN | D3 | A1 | D5 | D2 |
| 1043 | CN | D3 | A1 | D5 | D3 |
| 1044 | CN | D3 | A1 | D5 | D4 |
| 1045 | CN | D3 | A1 | D5 | D5 |
| 1046 | CN | D3 | A1 | D5 | D6 |
| 1047 | CN | D3 | A1 | D6 | D1 |
| 1048 | CN | D3 | A1 | D6 | D2 |
| 1049 | CN | D3 | A1 | D6 | D3 |
| 1050 | CN | D3 | A1 | D6 | D4 |

TABLE 1-8

| No. | $R^1$ | $R^2$ | $R^3$ | $R^4$ | $R^5$ |
|---|---|---|---|---|---|
| 1051 | CN | D3 | A1 | D6 | D5 |
| 1052 | CN | D3 | A1 | D6 | D6 |
| 1053 | CN | D4 | A1 | D1 | D1 |
| 1054 | CN | D4 | A1 | D1 | D2 |
| 1055 | CN | D4 | A1 | D1 | D3 |
| 1056 | CN | D4 | A1 | D1 | D4 |
| 1057 | CN | D4 | A1 | D1 | D5 |
| 1058 | CN | D4 | A1 | D1 | D6 |
| 1059 | CN | D4 | A1 | D2 | D1 |
| 1060 | CN | D4 | A1 | D2 | D2 |
| 1061 | CN | D4 | A1 | D2 | D3 |
| 1062 | CN | D4 | A1 | D2 | D4 |
| 1063 | CN | D4 | A1 | D2 | D5 |
| 1064 | CN | D4 | A1 | D2 | D6 |
| 1065 | CN | D4 | A1 | D3 | D1 |
| 1066 | CN | D4 | A1 | D3 | D2 |
| 1067 | CN | D4 | A1 | D3 | D3 |
| 1068 | CN | D4 | A1 | D3 | D4 |
| 1069 | CN | D4 | A1 | D3 | D5 |
| 1070 | CN | D4 | A1 | D3 | D6 |
| 1071 | CN | D4 | A1 | D4 | D1 |
| 1072 | CN | D4 | A1 | D4 | D2 |
| 1073 | CN | D4 | A1 | D4 | D3 |
| 1074 | CN | D4 | A1 | D4 | D4 |
| 1075 | CN | D4 | A1 | D4 | D5 |
| 1076 | CN | D4 | A1 | D4 | D6 |
| 1077 | CN | D4 | A1 | D5 | D1 |
| 1078 | CN | D4 | A1 | D5 | D2 |
| 1079 | CN | D4 | A1 | D5 | D3 |
| 1080 | CN | D4 | A1 | D5 | D4 |
| 1081 | CN | D4 | A1 | D5 | D5 |
| 1082 | CN | D4 | A1 | D5 | D6 |
| 1083 | CN | D4 | A1 | D6 | D1 |
| 1084 | CN | D4 | A1 | D6 | D2 |
| 1085 | CN | D4 | A1 | D6 | D3 |
| 1086 | CN | D4 | A1 | D6 | D4 |
| 1087 | CN | D4 | A1 | D6 | D5 |
| 1088 | CN | D4 | A1 | D6 | D6 |
| 1089 | CN | D5 | A1 | D1 | D1 |
| 1090 | CN | D5 | A1 | D1 | D2 |
| 1091 | CN | D5 | A1 | D1 | D3 |
| 1092 | CN | D5 | A1 | D1 | D4 |
| 1093 | CN | D5 | A1 | D1 | D5 |
| 1094 | CN | D5 | A1 | D1 | D6 |
| 1095 | CN | D5 | A1 | D2 | D1 |
| 1096 | CN | D5 | A1 | D2 | D2 |
| 1097 | CN | D5 | A1 | D2 | D3 |
| 1098 | CN | D5 | A1 | D2 | D4 |
| 1099 | CN | D5 | A1 | D2 | D5 |
| 1100 | CN | D5 | A1 | D2 | D6 |
| 1101 | CN | D5 | A1 | D3 | D1 |
| 1102 | CN | D5 | A1 | D3 | D2 |
| 1103 | CN | D5 | A1 | D3 | D3 |
| 1104 | CN | D5 | A1 | D3 | D4 |
| 1105 | CN | D5 | A1 | D3 | D5 |
| 1106 | CN | D5 | A1 | D3 | D6 |
| 1107 | CN | D5 | A1 | D4 | D1 |
| 1108 | CN | D5 | A1 | D4 | D2 |
| 1109 | CN | D5 | A1 | D4 | D3 |
| 1110 | CN | D5 | A1 | D4 | D4 |
| 1111 | CN | D5 | A1 | D4 | D5 |
| 1112 | CN | D5 | A1 | D4 | D6 |
| 1113 | CN | D5 | A1 | D5 | D1 |
| 1114 | CN | D5 | A1 | D5 | D2 |
| 1115 | CN | D5 | A1 | D5 | D3 |
| 1116 | CN | D5 | A1 | D5 | D4 |
| 1117 | CN | D5 | A1 | D5 | D5 |
| 1118 | CN | D5 | A1 | D5 | D6 |
| 1119 | CN | D5 | A1 | D6 | D1 |
| 1120 | CN | D5 | A1 | D6 | D2 |
| 1121 | CN | D5 | A1 | D6 | D3 |
| 1122 | CN | D5 | A1 | D6 | D4 |
| 1123 | CN | D5 | A1 | D6 | D5 |
| 1124 | CN | D5 | A1 | D6 | D6 |
| 1125 | CN | D6 | A1 | D1 | D1 |
| 1126 | CN | D6 | A1 | D1 | D2 |
| 1127 | CN | D6 | A1 | D1 | D3 |
| 1128 | CN | D6 | A1 | D1 | D4 |

TABLE 1-8-continued

| No. | $R^1$ | $R^2$ | $R^3$ | $R^4$ | $R^5$ |
|---|---|---|---|---|---|
| 1129 | CN | D6 | A1 | D1 | D5 |
| 1130 | CN | D6 | A1 | D1 | D6 |
| 1131 | CN | D6 | A1 | D2 | D1 |
| 1132 | CN | D6 | A1 | D2 | D2 |
| 1133 | CN | D6 | A1 | D2 | D3 |
| 1134 | CN | D6 | A1 | D2 | D4 |
| 1135 | CN | D6 | A1 | D2 | D5 |
| 1136 | CN | D6 | A1 | D2 | D6 |
| 1137 | CN | D6 | A1 | D3 | D1 |
| 1138 | CN | D6 | A1 | D3 | D2 |
| 1139 | CN | D6 | A1 | D3 | D3 |
| 1140 | CN | D6 | A1 | D3 | D4 |
| 1141 | CN | D6 | A1 | D3 | D5 |
| 1142 | CN | D6 | A1 | D3 | D6 |
| 1143 | CN | D6 | A1 | D4 | D1 |
| 1144 | CN | D6 | A1 | D4 | D2 |
| 1145 | CN | D6 | A1 | D4 | D3 |
| 1146 | CN | D6 | A1 | D4 | D4 |
| 1147 | CN | D6 | A1 | D4 | D5 |
| 1148 | CN | D6 | A1 | D4 | D6 |
| 1149 | CN | D6 | A1 | D5 | D1 |
| 1150 | CN | D6 | A1 | D5 | D2 |
| 1151 | CN | D6 | A1 | D5 | D3 |
| 1152 | CN | D6 | A1 | D5 | D4 |
| 1153 | CN | D6 | A1 | D5 | D5 |
| 1154 | CN | D6 | A1 | D5 | D6 |
| 1155 | CN | D6 | A1 | D6 | D1 |
| 1156 | CN | D6 | A1 | D6 | D2 |
| 1157 | CN | D6 | A1 | D6 | D3 |
| 1158 | CN | D6 | A1 | D6 | D4 |
| 1159 | CN | D6 | A1 | D6 | D5 |
| 1160 | CN | D6 | A1 | D6 | D6 |
| 1161 | CN | D1 | A2 | D1 | D1 |
| 1162 | CN | D1 | A2 | D1 | D2 |
| 1163 | CN | D1 | A2 | D1 | D3 |
| 1164 | CN | D1 | A2 | D1 | D4 |
| 1165 | CN | D1 | A2 | D1 | D5 |
| 1166 | CN | D1 | A2 | D1 | D6 |
| 1167 | CN | D1 | A2 | D2 | D1 |
| 1168 | CN | D1 | A2 | D2 | D2 |
| 1169 | CN | D1 | A2 | D2 | D3 |
| 1170 | CN | D1 | A2 | D2 | D4 |
| 1171 | CN | D1 | A2 | D2 | D5 |
| 1172 | CN | D1 | A2 | D2 | D6 |
| 1173 | CN | D1 | A2 | D3 | D1 |
| 1174 | CN | D1 | A2 | D3 | D2 |
| 1175 | CN | D1 | A2 | D3 | D3 |
| 1176 | CN | D1 | A2 | D3 | D4 |
| 1177 | CN | D1 | A2 | D3 | D5 |
| 1178 | CN | D1 | A2 | D3 | D6 |
| 1179 | CN | D1 | A2 | D4 | D1 |
| 1180 | CN | D1 | A2 | D4 | D2 |
| 1181 | CN | D1 | A2 | D4 | D3 |
| 1182 | CN | D1 | A2 | D4 | D4 |
| 1183 | CN | D1 | A2 | D4 | D5 |
| 1184 | CN | D1 | A2 | D4 | D6 |
| 1185 | CN | D1 | A2 | D5 | D1 |
| 1186 | CN | D1 | A2 | D5 | D2 |
| 1187 | CN | D1 | A2 | D5 | D3 |
| 1188 | CN | D1 | A2 | D5 | D4 |
| 1189 | CN | D1 | A2 | D5 | D5 |
| 1190 | CN | D1 | A2 | D5 | D6 |
| 1191 | CN | D1 | A2 | D6 | D1 |
| 1192 | CN | D1 | A2 | D6 | D2 |
| 1193 | CN | D1 | A2 | D6 | D3 |
| 1194 | CN | D1 | A2 | D6 | D4 |
| 1195 | CN | D1 | A2 | D6 | D5 |
| 1196 | CN | D1 | A2 | D6 | D6 |
| 1197 | CN | D2 | A2 | D1 | D1 |
| 1198 | CN | D2 | A2 | D1 | D2 |
| 1199 | CN | D2 | A2 | D1 | D3 |
| 1200 | CN | D2 | A2 | D1 | D4 |

TABLE 1-9

| No. | $R^1$ | $R^2$ | $R^3$ | $R^4$ | $R^5$ |
|---|---|---|---|---|---|
| 1201 | CN | D2 | A2 | D1 | D5 |
| 1202 | CN | D2 | A2 | D1 | D6 |
| 1203 | CN | D2 | A2 | D2 | D1 |
| 1204 | CN | D2 | A2 | D2 | D2 |
| 1205 | CN | D2 | A2 | D2 | D3 |
| 1206 | CN | D2 | A2 | D2 | D4 |
| 1207 | CN | D2 | A2 | D2 | D5 |
| 1208 | CN | D2 | A2 | D2 | D6 |
| 1209 | CN | D2 | A2 | D3 | D1 |
| 1210 | CN | D2 | A2 | D3 | D2 |
| 1211 | CN | D2 | A2 | D3 | D3 |
| 1212 | CN | D2 | A2 | D3 | D4 |
| 1213 | CN | D2 | A2 | D3 | D5 |
| 1214 | CN | D2 | A2 | D3 | D6 |
| 1215 | CN | D2 | A2 | D4 | D1 |
| 1216 | CN | D2 | A2 | D4 | D2 |
| 1217 | CN | D2 | A2 | D4 | D3 |
| 1218 | CN | D2 | A2 | D4 | D4 |
| 1219 | CN | D2 | A2 | D4 | D5 |
| 1220 | CN | D2 | A2 | D4 | D6 |
| 1221 | CN | D2 | A2 | D5 | D1 |
| 1222 | CN | D2 | A2 | D5 | D2 |
| 1223 | CN | D2 | A2 | D5 | D3 |
| 1224 | CN | D2 | A2 | D5 | D4 |
| 1225 | CN | D2 | A2 | D5 | D5 |
| 1226 | CN | D2 | A2 | D5 | D6 |
| 1227 | CN | D2 | A2 | D6 | D1 |
| 1228 | CN | D2 | A2 | D6 | D2 |
| 1229 | CN | D2 | A2 | D6 | D3 |
| 1230 | CN | D2 | A2 | D6 | D4 |
| 1231 | CN | D2 | A2 | D6 | D5 |
| 1232 | CN | D2 | A2 | D6 | D6 |
| 1233 | CN | D3 | A2 | D1 | D1 |
| 1234 | CN | D3 | A2 | D1 | D2 |
| 1235 | CN | D3 | A2 | D1 | D3 |
| 1236 | CN | D3 | A2 | D1 | D4 |
| 1237 | CN | D3 | A2 | D1 | D5 |
| 1238 | CN | D3 | A2 | D1 | D6 |
| 1239 | CN | D3 | A2 | D2 | D1 |
| 1240 | CN | D3 | A2 | D2 | D2 |
| 1241 | CN | D3 | A2 | D2 | D3 |
| 1242 | CN | D3 | A2 | D2 | D4 |
| 1243 | CN | D3 | A2 | D2 | D5 |
| 1244 | CN | D3 | A2 | D2 | D6 |
| 1245 | CN | D3 | A2 | D3 | D1 |
| 1246 | CN | D3 | A2 | D3 | D2 |
| 1247 | CN | D3 | A2 | D3 | D3 |
| 1248 | CN | D3 | A2 | D3 | D4 |
| 1249 | CN | D3 | A2 | D3 | D5 |
| 1250 | CN | D3 | A2 | D3 | D6 |
| 1251 | CN | D3 | A2 | D4 | D1 |
| 1252 | CN | D3 | A2 | D4 | D2 |
| 1253 | CN | D3 | A2 | D4 | D3 |
| 1254 | CN | D3 | A2 | D4 | D4 |
| 1255 | CN | D3 | A2 | D4 | D5 |
| 1256 | CN | D3 | A2 | D4 | D6 |
| 1257 | CN | D3 | A2 | D5 | D1 |
| 1258 | CN | D3 | A2 | D5 | D2 |
| 1259 | CN | D3 | A2 | D5 | D3 |
| 1260 | CN | D3 | A2 | D5 | D4 |
| 1261 | CN | D3 | A2 | D5 | D5 |
| 1262 | CN | D3 | A2 | D5 | D6 |
| 1263 | CN | D3 | A2 | D6 | D1 |
| 1264 | CN | D3 | A2 | D6 | D2 |
| 1265 | CN | D3 | A2 | D6 | D3 |
| 1266 | CN | D3 | A2 | D6 | D4 |
| 1267 | CN | D3 | A2 | D6 | D5 |
| 1268 | CN | D3 | A2 | D6 | D6 |
| 1269 | CN | D4 | A2 | D1 | D1 |
| 1270 | CN | D4 | A2 | D1 | D2 |
| 1271 | CN | D4 | A2 | D1 | D3 |
| 1272 | CN | D4 | A2 | D1 | D4 |
| 1273 | CN | D4 | A2 | D1 | D5 |
| 1274 | CN | D4 | A2 | D1 | D6 |
| 1275 | CN | D4 | A2 | D2 | D1 |
| 1276 | CN | D4 | A2 | D2 | D2 |
| 1277 | CN | D4 | A2 | D2 | D3 |
| 1278 | CN | D4 | A2 | D2 | D4 |

TABLE 1-9-continued

| No. | $R^1$ | $R^2$ | $R^3$ | $R^4$ | $R^5$ |
|---|---|---|---|---|---|
| 1279 | CN | D4 | A2 | D2 | D5 |
| 1280 | CN | D4 | A2 | D2 | D6 |
| 1281 | CN | D4 | A2 | D3 | D1 |
| 1282 | CN | D4 | A2 | D3 | D2 |
| 1283 | CN | D4 | A2 | D3 | D3 |
| 1284 | CN | D4 | A2 | D3 | D4 |
| 1285 | CN | D4 | A2 | D3 | D5 |
| 1286 | CN | D4 | A2 | D3 | D6 |
| 1287 | CN | D4 | A2 | D4 | D1 |
| 1288 | CN | D4 | A2 | D4 | D2 |
| 1289 | CN | D4 | A2 | D4 | D3 |
| 1290 | CN | D4 | A2 | D4 | D4 |
| 1291 | CN | D4 | A2 | D4 | D5 |
| 1292 | CN | D4 | A2 | D4 | D6 |
| 1293 | CN | D4 | A2 | D5 | D1 |
| 1294 | CN | D4 | A2 | D5 | D2 |
| 1295 | CN | D4 | A2 | D5 | D3 |
| 1296 | CN | D4 | A2 | D5 | D4 |
| 1297 | CN | D4 | A2 | D5 | D5 |
| 1298 | CN | D4 | A2 | D5 | D6 |
| 1299 | CN | D4 | A2 | D6 | D1 |
| 1300 | CN | D4 | A2 | D6 | D2 |
| 1301 | CN | D4 | A2 | D6 | D3 |
| 1302 | CN | D4 | A2 | D6 | D4 |
| 1303 | CN | D4 | A2 | D6 | D5 |
| 1304 | CN | D4 | A2 | D6 | D6 |
| 1305 | CN | D5 | A2 | D1 | D1 |
| 1306 | CN | D5 | A2 | D1 | D2 |
| 1307 | CN | D5 | A2 | D1 | D3 |
| 1308 | CN | D5 | A2 | D1 | D4 |
| 1309 | CN | D5 | A2 | D1 | D5 |
| 1310 | CN | D5 | A2 | D1 | D6 |
| 1311 | CN | D5 | A2 | D2 | D1 |
| 1312 | CN | D5 | A2 | D2 | D2 |
| 1313 | CN | D5 | A2 | D2 | D3 |
| 1314 | CN | D5 | A2 | D2 | D4 |
| 1315 | CN | D5 | A2 | D2 | D5 |
| 1316 | CN | D5 | A2 | D2 | D6 |
| 1317 | CN | D5 | A2 | D3 | D1 |
| 1318 | CN | D5 | A2 | D3 | D2 |
| 1319 | CN | D5 | A2 | D3 | D3 |
| 1320 | CN | D5 | A2 | D3 | D4 |
| 1321 | CN | D5 | A2 | D3 | D5 |
| 1322 | CN | D5 | A2 | D3 | D6 |
| 1323 | CN | D5 | A2 | D4 | D1 |
| 1324 | CN | D5 | A2 | D4 | D2 |
| 1325 | CN | D5 | A2 | D4 | D3 |
| 1326 | CN | D5 | A2 | D4 | D4 |
| 1327 | CN | D5 | A2 | D4 | D5 |
| 1328 | CN | D5 | A2 | D4 | D6 |
| 1329 | CN | D5 | A2 | D5 | D1 |
| 1330 | CN | D5 | A2 | D5 | D2 |
| 1331 | CN | D5 | A2 | D5 | D3 |
| 1332 | CN | D5 | A2 | D5 | D4 |
| 1333 | CN | D5 | A2 | D5 | D5 |
| 1334 | CN | D5 | A2 | D5 | D6 |
| 1335 | CN | D5 | A2 | D6 | D1 |
| 1336 | CN | D5 | A2 | D6 | D2 |
| 1337 | CN | D5 | A2 | D6 | D3 |
| 1338 | CN | D5 | A2 | D6 | D4 |
| 1339 | CN | D5 | A2 | D6 | D5 |
| 1340 | CN | D5 | A2 | D6 | D6 |
| 1341 | CN | D6 | A2 | D1 | D1 |
| 1342 | CN | D6 | A2 | D1 | D2 |
| 1343 | CN | D6 | A2 | D1 | D3 |
| 1344 | CN | D6 | A2 | D1 | D4 |
| 1345 | CN | D6 | A2 | D1 | D5 |
| 1346 | CN | D6 | A2 | D1 | D6 |
| 1347 | CN | D6 | A2 | D2 | D1 |
| 1348 | CN | D6 | A2 | D2 | D2 |
| 1349 | CN | D6 | A2 | D2 | D3 |
| 1350 | CN | D6 | A2 | D2 | D4 |

TABLE 1-10

| No. | $R^1$ | $R^2$ | $R^3$ | $R^4$ | $R^5$ |
|---|---|---|---|---|---|
| 1351 | CN | D6 | A2 | D2 | D5 |
| 1352 | CN | D6 | A2 | D2 | D6 |
| 1353 | CN | D6 | A2 | D3 | D1 |
| 1354 | CN | D6 | A2 | D3 | D2 |
| 1355 | CN | D6 | A2 | D3 | D3 |
| 1356 | CN | D6 | A2 | D3 | D4 |
| 1357 | CN | D6 | A2 | D3 | D5 |
| 1358 | CN | D6 | A2 | D3 | D6 |
| 1359 | CN | D6 | A2 | D4 | D1 |
| 1360 | CN | D6 | A2 | D4 | D2 |
| 1361 | CN | D6 | A2 | D4 | D3 |
| 1362 | CN | D6 | A2 | D4 | D4 |
| 1363 | CN | D6 | A2 | D4 | D5 |
| 1364 | CN | D6 | A2 | D4 | D6 |
| 1365 | CN | D6 | A2 | D5 | D1 |
| 1366 | CN | D6 | A2 | D5 | D2 |
| 1367 | CN | D6 | A2 | D5 | D3 |
| 1368 | CN | D6 | A2 | D5 | D4 |
| 1369 | CN | D6 | A2 | D5 | D5 |
| 1370 | CN | D6 | A2 | D5 | D6 |
| 1371 | CN | D6 | A2 | D6 | D1 |
| 1372 | CN | D6 | A2 | D6 | D2 |
| 1373 | CN | D6 | A2 | D6 | D3 |
| 1374 | CN | D6 | A2 | D6 | D4 |
| 1375 | CN | D6 | A2 | D6 | D5 |
| 1376 | CN | D6 | A2 | D6 | D6 |
| 1377 | CN | H | A1 | D1 | D1 |
| 1378 | CN | H | A1 | D1 | D2 |
| 1379 | CN | H | A1 | D1 | D3 |
| 1380 | CN | H | A1 | D1 | D4 |
| 1381 | CN | H | A1 | D1 | D5 |
| 1382 | CN | H | A1 | D1 | D6 |
| 1383 | CN | H | A1 | D1 | D7 |
| 1384 | CN | H | A1 | D1 | D8 |
| 1385 | CN | H | A1 | D1 | D9 |
| 1386 | CN | H | A1 | D1 | D10 |
| 1387 | CN | H | A1 | D1 | D11 |
| 1388 | CN | H | A1 | D1 | D12 |
| 1389 | CN | H | A1 | D1 | D13 |
| 1390 | CN | H | A1 | D1 | D14 |
| 1391 | CN | H | A1 | D1 | D15 |
| 1392 | CN | H | A1 | D1 | D16 |
| 1393 | CN | H | A1 | D2 | D1 |
| 1394 | CN | H | A1 | D2 | D2 |
| 1395 | CN | H | A1 | D2 | D3 |
| 1396 | CN | H | A1 | D2 | D4 |
| 1397 | CN | H | A1 | D2 | D5 |
| 1398 | CN | H | A1 | D2 | D6 |
| 1399 | CN | H | A1 | D2 | D7 |
| 1400 | CN | H | A1 | D2 | D8 |
| 1401 | CN | H | A1 | D2 | D9 |
| 1402 | CN | H | A1 | D2 | D10 |
| 1403 | CN | H | A1 | D2 | D11 |
| 1404 | CN | H | A1 | D2 | D12 |
| 1405 | CN | H | A1 | D2 | D13 |
| 1406 | CN | H | A1 | D2 | D14 |
| 1407 | CN | H | A1 | D2 | D15 |
| 1408 | CN | H | A1 | D2 | D16 |
| 1409 | CN | H | A1 | D3 | D1 |
| 1410 | CN | H | A1 | D3 | D2 |
| 1411 | CN | H | A1 | D3 | D3 |
| 1412 | CN | H | A1 | D3 | D4 |
| 1413 | CN | H | A1 | D3 | D5 |
| 1414 | CN | H | A1 | D3 | D6 |
| 1415 | CN | H | A1 | D3 | D7 |
| 1416 | CN | H | A1 | D3 | D8 |
| 1417 | CN | H | A1 | D3 | D9 |
| 1418 | CN | H | A1 | D3 | D10 |
| 1419 | CN | H | A1 | D3 | D11 |
| 1420 | CN | H | A1 | D3 | D12 |
| 1421 | CN | H | A1 | D3 | D13 |
| 1422 | CN | H | A1 | D3 | D14 |
| 1423 | CN | H | A1 | D3 | D15 |
| 1424 | CN | H | A1 | D3 | D16 |
| 1425 | CN | H | A1 | D4 | D1 |
| 1426 | CN | H | A1 | D4 | D2 |
| 1427 | CN | H | A1 | D4 | D3 |
| 1428 | CN | H | A1 | D4 | D4 |

TABLE 1-10-continued

| No. | $R^1$ | $R^2$ | $R^3$ | $R^4$ | $R^5$ |
|---|---|---|---|---|---|
| 1429 | CN | H | A1 | D4 | D5 |
| 1430 | CN | H | A1 | D4 | D6 |
| 1431 | CN | H | A1 | D4 | D7 |
| 1432 | CN | H | A1 | D4 | D8 |
| 1433 | CN | H | A1 | D4 | D9 |
| 1434 | CN | H | A1 | D4 | D10 |
| 1435 | CN | H | A1 | D4 | D11 |
| 1436 | CN | H | A1 | D4 | D12 |
| 1437 | CN | H | A1 | D4 | D13 |
| 1438 | CN | H | A1 | D4 | D14 |
| 1439 | CN | H | A1 | D4 | D15 |
| 1440 | CN | H | A1 | D4 | D16 |
| 1441 | CN | H | A1 | D5 | D1 |
| 1442 | CN | H | A1 | D5 | D2 |
| 1443 | CN | H | A1 | D5 | D3 |
| 1444 | CN | H | A1 | D5 | D4 |
| 1445 | CN | H | A1 | D5 | D5 |
| 1446 | CN | H | A1 | D5 | D6 |
| 1447 | CN | H | A1 | D5 | D7 |
| 1448 | CN | H | A1 | D5 | D8 |
| 1449 | CN | H | A1 | D5 | D9 |
| 1450 | CN | H | A1 | D5 | D10 |
| 1451 | CN | H | A1 | D5 | D11 |
| 1452 | CN | H | A1 | D5 | D12 |
| 1453 | CN | H | A1 | D5 | D13 |
| 1454 | CN | H | A1 | D5 | D14 |
| 1455 | CN | H | A1 | D5 | D15 |
| 1456 | CN | H | A1 | D5 | D16 |
| 1457 | CN | H | A1 | D6 | D1 |
| 1458 | CN | H | A1 | D6 | D2 |
| 1459 | CN | H | A1 | D6 | D3 |
| 1460 | CN | H | A1 | D6 | D4 |
| 1461 | CN | H | A1 | D6 | D5 |
| 1462 | CN | H | A1 | D6 | D6 |
| 1463 | CN | H | A1 | D6 | D7 |
| 1464 | CN | H | A1 | D6 | D8 |
| 1465 | CN | H | A1 | D6 | D9 |
| 1466 | CN | H | A1 | D6 | D10 |
| 1467 | CN | H | A1 | D6 | D11 |
| 1468 | CN | H | A1 | D6 | D12 |
| 1469 | CN | H | A1 | D6 | D13 |
| 1470 | CN | H | A1 | D6 | D14 |
| 1471 | CN | H | A1 | D6 | D15 |
| 1472 | CN | H | A1 | D6 | D16 |
| 1473 | CN | H | A1 | D7 | D1 |
| 1474 | CN | H | A1 | D7 | D2 |
| 1475 | CN | H | A1 | D7 | D3 |
| 1476 | CN | H | A1 | D7 | D4 |
| 1477 | CN | H | A1 | D7 | D5 |
| 1478 | CN | H | A1 | D7 | D6 |
| 1479 | CN | H | A1 | D7 | D7 |
| 1480 | CN | H | A1 | D7 | D8 |
| 1481 | CN | H | A1 | D7 | D9 |
| 1482 | CN | H | A1 | D7 | D10 |
| 1483 | CN | H | A1 | D7 | D11 |
| 1484 | CN | H | A1 | D7 | D12 |
| 1485 | CN | H | A1 | D7 | D13 |
| 1486 | CN | H | A1 | D7 | D14 |
| 1487 | CN | H | A1 | D7 | D15 |
| 1488 | CN | H | A1 | D7 | D16 |
| 1489 | CN | H | A1 | D8 | D1 |
| 1490 | CN | H | A1 | D8 | D2 |
| 1491 | CN | H | A1 | D8 | D3 |
| 1492 | CN | H | A1 | D8 | D4 |
| 1493 | CN | H | A1 | D8 | D5 |
| 1494 | CN | H | A1 | D8 | D6 |
| 1495 | CN | H | A1 | D8 | D7 |
| 1496 | CN | H | A1 | D8 | D8 |
| 1497 | CN | H | A1 | D8 | D9 |
| 1498 | CN | H | A1 | D8 | D10 |
| 1499 | CN | H | A1 | D8 | D11 |
| 1500 | CN | H | A1 | D8 | D12 |

TABLE 1-11

| No. | $R^1$ | $R^2$ | $R^3$ | $R^4$ | $R^5$ |
|---|---|---|---|---|---|
| 1501 | CN | H | A1 | D8 | D13 |
| 1502 | CN | H | A1 | D8 | D14 |
| 1503 | CN | H | A1 | D8 | D15 |
| 1504 | CN | H | A1 | D8 | D16 |
| 1505 | CN | H | A1 | D9 | D1 |
| 1506 | CN | H | A1 | D9 | D2 |
| 1507 | CN | H | A1 | D9 | D3 |
| 1508 | CN | H | A1 | D9 | D4 |
| 1509 | CN | H | A1 | D9 | D5 |
| 1510 | CN | H | A1 | D9 | D6 |
| 1511 | CN | H | A1 | D9 | D7 |
| 1512 | CN | H | A1 | D9 | D8 |
| 1513 | CN | H | A1 | D9 | D9 |
| 1514 | CN | H | A1 | D9 | D10 |
| 1515 | CN | H | A1 | D9 | D11 |
| 1516 | CN | H | A1 | D9 | D12 |
| 1517 | CN | H | A1 | D9 | D13 |
| 1518 | CN | H | A1 | D9 | D14 |
| 1519 | CN | H | A1 | D9 | D15 |
| 1520 | CN | H | A1 | D9 | D16 |
| 1521 | CN | H | A1 | D10 | D1 |
| 1522 | CN | H | A1 | D10 | D2 |
| 1523 | CN | H | A1 | D10 | D3 |
| 1524 | CN | H | A1 | D10 | D4 |
| 1525 | CN | H | A1 | D10 | D5 |
| 1526 | CN | H | A1 | D10 | D6 |
| 1527 | CN | H | A1 | D10 | D7 |
| 1528 | CN | H | A1 | D10 | D8 |
| 1529 | CN | H | A1 | D10 | D9 |
| 1530 | CN | H | A1 | D10 | D10 |
| 1531 | CN | H | A1 | D10 | D11 |
| 1532 | CN | H | A1 | D10 | D12 |
| 1533 | CN | H | A1 | D10 | D13 |
| 1534 | CN | H | A1 | D10 | D14 |
| 1535 | CN | H | A1 | D10 | D15 |
| 1536 | CN | H | A1 | D10 | D16 |
| 1537 | CN | H | A1 | D11 | D1 |
| 1538 | CN | H | A1 | D11 | D2 |
| 1539 | CN | H | A1 | D11 | D3 |
| 1540 | CN | H | A1 | D11 | D4 |
| 1541 | CN | H | A1 | D11 | D5 |
| 1542 | CN | H | A1 | D11 | D6 |
| 1543 | CN | H | A1 | D11 | D7 |
| 1544 | CN | H | A1 | D11 | D8 |
| 1545 | CN | H | A1 | D11 | D9 |
| 1546 | CN | H | A1 | D11 | D10 |
| 1547 | CN | H | A1 | D11 | D11 |
| 1548 | CN | H | A1 | D11 | D12 |
| 1549 | CN | H | A1 | D11 | D13 |
| 1550 | CN | H | A1 | D11 | D14 |
| 1551 | CN | H | A1 | D11 | D15 |
| 1552 | CN | H | A1 | D11 | D16 |
| 1553 | CN | H | A1 | D12 | D1 |
| 1554 | CN | H | A1 | D12 | D2 |
| 1555 | CN | H | A1 | D12 | D3 |
| 1556 | CN | H | A1 | D12 | D4 |
| 1557 | CN | H | A1 | D12 | D5 |
| 1558 | CN | H | A1 | D12 | D6 |
| 1559 | CN | H | A1 | D12 | D7 |
| 1560 | CN | H | A1 | D12 | D8 |
| 1561 | CN | H | A1 | D12 | D9 |
| 1562 | CN | H | A1 | D12 | D10 |
| 1563 | CN | H | A1 | D12 | D11 |
| 1564 | CN | H | A1 | D12 | D12 |
| 1565 | CN | H | A1 | D12 | D13 |
| 1566 | CN | H | A1 | D12 | D14 |
| 1567 | CN | H | A1 | D12 | D15 |
| 1568 | CN | H | A1 | D12 | D16 |
| 1569 | CN | H | A1 | D13 | D1 |
| 1570 | CN | H | A1 | D13 | D2 |
| 1571 | CN | H | A1 | D13 | D3 |
| 1572 | CN | H | A1 | D13 | D4 |
| 1573 | CN | H | A1 | D13 | D5 |
| 1574 | CN | H | A1 | D13 | D6 |
| 1575 | CN | H | A1 | D13 | D7 |
| 1576 | CN | H | A1 | D13 | D8 |
| 1577 | CN | H | A1 | D13 | D9 |
| 1578 | CN | H | A1 | D13 | D10 |

TABLE 1-11-continued

| No. | $R^1$ | $R^2$ | $R^3$ | $R^4$ | $R^5$ |
|---|---|---|---|---|---|
| 1579 | CN | H | A1 | D13 | D11 |
| 1580 | CN | H | A1 | D13 | D12 |
| 1581 | CN | H | A1 | D13 | D13 |
| 1582 | CN | H | A1 | D13 | D14 |
| 1583 | CN | H | A1 | D13 | D15 |
| 1584 | CN | H | A1 | D13 | D16 |
| 1585 | CN | H | A1 | D14 | D1 |
| 1586 | CN | H | A1 | D14 | D2 |
| 1587 | CN | H | A1 | D14 | D3 |
| 1588 | CN | H | A1 | D14 | D4 |
| 1589 | CN | H | A1 | D14 | D5 |
| 1590 | CN | H | A1 | D14 | D6 |
| 1591 | CN | H | A1 | D14 | D7 |
| 1592 | CN | H | A1 | D14 | D8 |
| 1593 | CN | H | A1 | D14 | D9 |
| 1594 | CN | H | A1 | D14 | D10 |
| 1595 | CN | H | A1 | D14 | D11 |
| 1596 | CN | H | A1 | D14 | D12 |
| 1597 | CN | H | A1 | D14 | D13 |
| 1598 | CN | H | A1 | D14 | D14 |
| 1599 | CN | H | A1 | D14 | D15 |
| 1600 | CN | H | A1 | D14 | D16 |
| 1601 | CN | H | A1 | D15 | D1 |
| 1602 | CN | H | A1 | D15 | D2 |
| 1603 | CN | H | A1 | D15 | D3 |
| 1604 | CN | H | A1 | D15 | D4 |
| 1605 | CN | H | A1 | D15 | D5 |
| 1606 | CN | H | A1 | D15 | D6 |
| 1607 | CN | H | A1 | D15 | D7 |
| 1608 | CN | H | A1 | D15 | D8 |
| 1609 | CN | H | A1 | D15 | D9 |
| 1610 | CN | H | A1 | D15 | D10 |
| 1611 | CN | H | A1 | D15 | D11 |
| 1612 | CN | H | A1 | D15 | D12 |
| 1613 | CN | H | A1 | D15 | D13 |
| 1614 | CN | H | A1 | D15 | D14 |
| 1615 | CN | H | A1 | D15 | D15 |
| 1616 | CN | H | A1 | D15 | D16 |
| 1617 | CN | H | A1 | D16 | D1 |
| 1618 | CN | H | A1 | D16 | D2 |
| 1619 | CN | H | A1 | D16 | D3 |
| 1620 | CN | H | A1 | D16 | D4 |
| 1621 | CN | H | A1 | D16 | D5 |
| 1622 | CN | H | A1 | D16 | D6 |
| 1623 | CN | H | A1 | D16 | D7 |
| 1624 | CN | H | A1 | D16 | D8 |
| 1625 | CN | H | A1 | D16 | D9 |
| 1626 | CN | H | A1 | D16 | D10 |
| 1627 | CN | H | A1 | D16 | D11 |
| 1628 | CN | H | A1 | D16 | D12 |
| 1629 | CN | H | A1 | D16 | D13 |
| 1630 | CN | H | A1 | D16 | D14 |
| 1631 | CN | H | A1 | D16 | D15 |
| 1632 | CN | H | A1 | D16 | D16 |
| 1633 | CN | H | A2 | D1 | D1 |
| 1634 | CN | H | A2 | D1 | D2 |
| 1635 | CN | H | A2 | D1 | D3 |
| 1636 | CN | H | A2 | D1 | D4 |
| 1637 | CN | H | A2 | D1 | D5 |
| 1638 | CN | H | A2 | D1 | D6 |
| 1639 | CN | H | A2 | D1 | D7 |
| 1640 | CN | H | A2 | D1 | D8 |
| 1641 | CN | H | A2 | D1 | D9 |
| 1642 | CN | H | A2 | D1 | D10 |
| 1643 | CN | H | A2 | D1 | D11 |
| 1644 | CN | H | A2 | D1 | D12 |
| 1645 | CN | H | A2 | D1 | D13 |
| 1646 | CN | H | A2 | D1 | D14 |
| 1647 | CN | H | A2 | D1 | D15 |
| 1648 | CN | H | A2 | D1 | D16 |
| 1649 | CN | H | A2 | D2 | D1 |
| 1650 | CN | H | A2 | D2 | D2 |

TABLE 1-12

| No. | $R^1$ | $R^2$ | $R^3$ | $R^4$ | $R^5$ |
|---|---|---|---|---|---|
| 1651 | CN | H | A2 | D2 | D3 |
| 1652 | CN | H | A2 | D2 | D4 |
| 1653 | CN | H | A2 | D2 | D5 |
| 1654 | CN | H | A2 | D2 | D6 |
| 1655 | CN | H | A2 | D2 | D7 |
| 1656 | CN | H | A2 | D2 | D8 |
| 1657 | CN | H | A2 | D2 | D9 |
| 1658 | CN | H | A2 | D2 | D10 |
| 1659 | CN | H | A2 | D2 | D11 |
| 1660 | CN | H | A2 | D2 | D12 |
| 1661 | CN | H | A2 | D2 | D13 |
| 1662 | CN | H | A2 | D2 | D14 |
| 1663 | CN | H | A2 | D2 | D15 |
| 1664 | CN | H | A2 | D2 | D16 |
| 1665 | CN | H | A2 | D3 | D1 |
| 1666 | CN | H | A2 | D3 | D2 |
| 1667 | CN | H | A2 | D3 | D3 |
| 1668 | CN | H | A2 | D3 | D4 |
| 1669 | CN | H | A2 | D3 | D5 |
| 1670 | CN | H | A2 | D3 | D6 |
| 1671 | CN | H | A2 | D3 | D7 |
| 1672 | CN | H | A2 | D3 | D8 |
| 1673 | CN | H | A2 | D3 | D9 |
| 1674 | CN | H | A2 | D3 | D10 |
| 1675 | CN | H | A2 | D3 | D11 |
| 1676 | CN | H | A2 | D3 | D12 |
| 1677 | CN | H | A2 | D3 | D13 |
| 1678 | CN | H | A2 | D3 | D14 |
| 1679 | CN | H | A2 | D3 | D15 |
| 1680 | CN | H | A2 | D3 | D16 |
| 1681 | CN | H | A2 | D4 | D1 |
| 1682 | CN | H | A2 | D4 | D2 |
| 1683 | CN | H | A2 | D4 | D3 |
| 1684 | CN | H | A2 | D4 | D4 |
| 1685 | CN | H | A2 | D4 | D5 |
| 1686 | CN | H | A2 | D4 | D6 |
| 1687 | CN | H | A2 | D4 | D7 |
| 1688 | CN | H | A2 | D4 | D8 |
| 1689 | CN | H | A2 | D4 | D9 |
| 1690 | CN | H | A2 | D4 | D10 |
| 1691 | CN | H | A2 | D4 | D11 |
| 1692 | CN | H | A2 | D4 | D12 |
| 1693 | CN | H | A2 | D4 | D13 |
| 1694 | CN | H | A2 | D4 | D14 |
| 1695 | CN | H | A2 | D4 | D15 |
| 1696 | CN | H | A2 | D4 | D16 |
| 1697 | CN | H | A2 | D5 | D1 |
| 1698 | CN | H | A2 | D5 | D2 |
| 1699 | CN | H | A2 | D5 | D3 |
| 1700 | CN | H | A2 | D5 | D4 |
| 1701 | CN | H | A2 | D5 | D5 |
| 1702 | CN | H | A2 | D5 | D6 |
| 1703 | CN | H | A2 | D5 | D7 |
| 1704 | CN | H | A2 | D5 | D8 |
| 1705 | CN | H | A2 | D5 | D9 |
| 1706 | CN | H | A2 | D5 | D10 |
| 1707 | CN | H | A2 | D5 | D11 |
| 1708 | CN | H | A2 | D5 | D12 |
| 1709 | CN | H | A2 | D5 | D13 |
| 1710 | CN | H | A2 | D5 | D14 |
| 1711 | CN | H | A2 | D5 | D15 |
| 1712 | CN | H | A2 | D5 | D16 |
| 1713 | CN | H | A2 | D6 | D1 |
| 1714 | CN | H | A2 | D6 | D2 |
| 1715 | CN | H | A2 | D6 | D3 |
| 1716 | CN | H | A2 | D6 | D4 |
| 1717 | CN | H | A2 | D6 | D5 |
| 1718 | CN | H | A2 | D6 | D6 |
| 1719 | CN | H | A2 | D6 | D7 |
| 1720 | CN | H | A2 | D6 | D8 |
| 1721 | CN | H | A2 | D6 | D9 |
| 1722 | CN | H | A2 | D6 | D10 |
| 1723 | CN | H | A2 | D6 | D11 |
| 1724 | CN | H | A2 | D6 | D12 |
| 1725 | CN | H | A2 | D6 | D13 |
| 1726 | CN | H | A2 | D6 | D14 |
| 1727 | CN | H | A2 | D6 | D15 |
| 1728 | CN | H | A2 | D6 | D16 |

TABLE 1-12-continued

| No. | $R^1$ | $R^2$ | $R^3$ | $R^4$ | $R^5$ |
|---|---|---|---|---|---|
| 1729 | CN | H | A2 | D7 | D1 |
| 1730 | CN | H | A2 | D7 | D2 |
| 1731 | CN | H | A2 | D7 | D3 |
| 1732 | CN | H | A2 | D7 | D4 |
| 1733 | CN | H | A2 | D7 | D5 |
| 1734 | CN | H | A2 | D7 | D6 |
| 1735 | CN | H | A2 | D7 | D7 |
| 1736 | CN | H | A2 | D7 | D8 |
| 1737 | CN | H | A2 | D7 | D9 |
| 1738 | CN | H | A2 | D7 | D10 |
| 1739 | CN | H | A2 | D7 | D11 |
| 1740 | CN | H | A2 | D7 | D12 |
| 1741 | CN | H | A2 | D7 | D13 |
| 1742 | CN | H | A2 | D7 | D14 |
| 1743 | CN | H | A2 | D7 | D15 |
| 1744 | CN | H | A2 | D7 | D16 |
| 1745 | CN | H | A2 | D8 | D1 |
| 1746 | CN | H | A2 | D8 | D2 |
| 1747 | CN | H | A2 | D8 | D3 |
| 1748 | CN | H | A2 | D8 | D4 |
| 1749 | CN | H | A2 | D8 | D5 |
| 1750 | CN | H | A2 | D8 | D6 |
| 1751 | CN | H | A2 | D8 | D7 |
| 1752 | CN | H | A2 | D8 | D8 |
| 1753 | CN | H | A2 | D8 | D9 |
| 1754 | CN | H | A2 | D8 | D10 |
| 1755 | CN | H | A2 | D8 | D11 |
| 1756 | CN | H | A2 | D8 | D12 |
| 1757 | CN | H | A2 | D8 | D13 |
| 1758 | CN | H | A2 | D8 | D14 |
| 1759 | CN | H | A2 | D8 | D15 |
| 1760 | CN | H | A2 | D8 | D16 |
| 1761 | CN | H | A2 | D9 | D1 |
| 1762 | CN | H | A2 | D9 | D2 |
| 1763 | CN | H | A2 | D9 | D3 |
| 1764 | CN | H | A2 | D9 | D4 |
| 1765 | CN | H | A2 | D9 | D5 |
| 1766 | CN | H | A2 | D9 | D6 |
| 1767 | CN | H | A2 | D9 | D7 |
| 1768 | CN | H | A2 | D9 | D8 |
| 1769 | CN | H | A2 | D9 | D9 |
| 1770 | CN | H | A2 | D9 | D10 |
| 1771 | CN | H | A2 | D9 | D11 |
| 1772 | CN | H | A2 | D9 | D12 |
| 1773 | CN | H | A2 | D9 | D13 |
| 1774 | CN | H | A2 | D9 | D14 |
| 1775 | CN | H | A2 | D9 | D15 |
| 1776 | CN | H | A2 | D9 | D16 |
| 1777 | CN | H | A2 | D10 | D1 |
| 1778 | CN | H | A2 | D10 | D2 |
| 1779 | CN | H | A2 | D10 | D3 |
| 1780 | CN | H | A2 | D10 | D4 |
| 1781 | CN | H | A2 | D10 | D5 |
| 1782 | CN | H | A2 | D10 | D6 |
| 1783 | CN | H | A2 | D10 | D7 |
| 1784 | CN | H | A2 | D10 | D8 |
| 1785 | CN | H | A2 | D10 | D9 |
| 1786 | CN | H | A2 | D10 | D10 |
| 1787 | CN | H | A2 | D10 | D11 |
| 1788 | CN | H | A2 | D10 | D12 |
| 1789 | CN | H | A2 | D10 | D13 |
| 1790 | CN | H | A2 | D10 | D14 |
| 1791 | CN | H | A2 | D10 | D15 |
| 1792 | CN | H | A2 | D10 | D16 |
| 1793 | CN | H | A2 | D11 | D1 |
| 1794 | CN | H | A2 | D11 | D2 |
| 1795 | CN | H | A2 | D11 | D3 |
| 1796 | CN | H | A2 | D11 | D4 |
| 1797 | CN | H | A2 | D11 | D5 |
| 1798 | CN | H | A2 | D11 | D6 |
| 1799 | CN | H | A2 | D11 | D7 |
| 1800 | CN | H | A2 | D11 | D8 |

TABLE 1-13

| No. | $R^1$ | $R^2$ | $R^3$ | $R^4$ | $R^5$ |
|---|---|---|---|---|---|
| 1801 | CN | H | A2 | D11 | D9 |
| 1802 | CN | H | A2 | D11 | D10 |
| 1803 | CN | H | A2 | D11 | D11 |
| 1804 | CN | H | A2 | D11 | D12 |
| 1805 | CN | H | A2 | D11 | D13 |
| 1806 | CN | H | A2 | D11 | D14 |
| 1807 | CN | H | A2 | D11 | D15 |
| 1808 | CN | H | A2 | D11 | D16 |
| 1809 | CN | H | A2 | D12 | D1 |
| 1810 | CN | H | A2 | D12 | D2 |
| 1811 | CN | H | A2 | D12 | D3 |
| 1812 | CN | H | A2 | D12 | D4 |
| 1813 | CN | H | A2 | D12 | D5 |
| 1814 | CN | H | A2 | D12 | D6 |
| 1815 | CN | H | A2 | D12 | D7 |
| 1816 | CN | H | A2 | D12 | D8 |
| 1817 | CN | H | A2 | D12 | D9 |
| 1818 | CN | H | A2 | D12 | D10 |
| 1819 | CN | H | A2 | D12 | D11 |
| 1820 | CN | H | A2 | D12 | D12 |
| 1821 | CN | H | A2 | D12 | D13 |
| 1822 | CN | H | A2 | D12 | D14 |
| 1823 | CN | H | A2 | D12 | D15 |
| 1824 | CN | H | A2 | D12 | D16 |
| 1825 | CN | H | A2 | D13 | D1 |
| 1826 | CN | H | A2 | D13 | D2 |
| 1827 | CN | H | A2 | D13 | D3 |
| 1828 | CN | H | A2 | D13 | D4 |
| 1829 | CN | H | A2 | D13 | D5 |
| 1830 | CN | H | A2 | D13 | D6 |
| 1831 | CN | H | A2 | D13 | D7 |
| 1832 | CN | H | A2 | D13 | D8 |
| 1833 | CN | H | A2 | D13 | D9 |
| 1834 | CN | H | A2 | D13 | D10 |
| 1835 | CN | H | A2 | D13 | D11 |
| 1836 | CN | H | A2 | D13 | D12 |
| 1837 | CN | H | A2 | D13 | D13 |
| 1838 | CN | H | A2 | D13 | D14 |
| 1839 | CN | H | A2 | D13 | D15 |
| 1840 | CN | H | A2 | D13 | D16 |
| 1841 | CN | H | A2 | D14 | D1 |
| 1842 | CN | H | A2 | D14 | D2 |
| 1843 | CN | H | A2 | D14 | D3 |
| 1844 | CN | H | A2 | D14 | D4 |
| 1845 | CN | H | A2 | D14 | D5 |
| 1846 | CN | H | A2 | D14 | D6 |
| 1847 | CN | H | A2 | D14 | D7 |
| 1848 | CN | H | A2 | D14 | D8 |
| 1849 | CN | H | A2 | D14 | D9 |
| 1850 | CN | H | A2 | D14 | D10 |
| 1851 | CN | H | A2 | D14 | D11 |
| 1852 | CN | H | A2 | D14 | D12 |
| 1853 | CN | H | A2 | D14 | D13 |
| 1854 | CN | H | A2 | D14 | D14 |
| 1855 | CN | H | A2 | D14 | D15 |
| 1856 | CN | H | A2 | D14 | D16 |
| 1857 | CN | H | A2 | D15 | D1 |
| 1858 | CN | H | A2 | D15 | D2 |
| 1859 | CN | H | A2 | D15 | D3 |
| 1860 | CN | H | A2 | D15 | D4 |
| 1861 | CN | H | A2 | D15 | D5 |
| 1862 | CN | H | A2 | D15 | D6 |
| 1863 | CN | H | A2 | D15 | D7 |
| 1864 | CN | H | A2 | D15 | D8 |
| 1865 | CN | H | A2 | D15 | D9 |
| 1866 | CN | H | A2 | D15 | D10 |
| 1867 | CN | H | A2 | D15 | D11 |
| 1868 | CN | H | A2 | D15 | D12 |
| 1869 | CN | H | A2 | D15 | D13 |
| 1870 | CN | H | A2 | D15 | D14 |
| 1871 | CN | H | A2 | D15 | D15 |
| 1872 | CN | H | A2 | D15 | D16 |
| 1873 | CN | H | A2 | D16 | D1 |
| 1874 | CN | H | A2 | D16 | D2 |
| 1875 | CN | H | A2 | D16 | D3 |
| 1876 | CN | H | A2 | D16 | D4 |
| 1877 | CN | H | A2 | D16 | D5 |
| 1878 | CN | H | A2 | D16 | D6 |

TABLE 1-13-continued

| No. | $R^1$ | $R^2$ | $R^3$ | $R^4$ | $R^5$ |
|---|---|---|---|---|---|
| 1879 | CN | H | A2 | D16 | D7 |
| 1880 | CN | H | A2 | D16 | D8 |
| 1881 | CN | H | A2 | D16 | D9 |
| 1882 | CN | H | A2 | D16 | D10 |
| 1883 | CN | H | A2 | D16 | D11 |
| 1884 | CN | H | A2 | D16 | D12 |
| 1885 | CN | H | A2 | D16 | D13 |
| 1886 | CN | H | A2 | D16 | D14 |
| 1887 | CN | H | A2 | D16 | D15 |
| 1888 | CN | D1 | A1 | H | D1 |
| 1889 | CN | D1 | A1 | H | D2 |
| 1890 | CN | D1 | A1 | H | D3 |
| 1891 | CN | D1 | A1 | H | D4 |
| 1892 | CN | D1 | A1 | H | D5 |
| 1893 | CN | D1 | A1 | H | D6 |
| 1894 | CN | D1 | A1 | H | D7 |
| 1895 | CN | D1 | A1 | H | D8 |
| 1896 | CN | D1 | A1 | H | D9 |
| 1897 | CN | D1 | A1 | H | D10 |
| 1898 | CN | D1 | A1 | H | D11 |
| 1899 | CN | D1 | A1 | H | D12 |
| 1900 | CN | D1 | A1 | H | D13 |
| 1901 | CN | D1 | A1 | H | D14 |
| 1902 | CN | D1 | A1 | H | D15 |
| 1903 | CN | D1 | A1 | H | D16 |
| 1904 | CN | D2 | A1 | H | D1 |
| 1905 | CN | D2 | A1 | H | D2 |
| 1906 | CN | D2 | A1 | H | D3 |
| 1907 | CN | D2 | A1 | H | D4 |
| 1908 | CN | D2 | A1 | H | D5 |
| 1909 | CN | D2 | A1 | H | D6 |
| 1910 | CN | D2 | A1 | H | D7 |
| 1911 | CN | D2 | A1 | H | D8 |
| 1912 | CN | D2 | A1 | H | D9 |
| 1913 | CN | D2 | A1 | H | D10 |
| 1914 | CN | D2 | A1 | H | D11 |
| 1915 | CN | D2 | A1 | H | D12 |
| 1916 | CN | D2 | A1 | H | D13 |
| 1917 | CN | D2 | A1 | H | D14 |
| 1918 | CN | D2 | A1 | H | D15 |
| 1919 | CN | D2 | A1 | H | D16 |
| 1920 | CN | D3 | A1 | H | D1 |
| 1921 | CN | D3 | A1 | H | D2 |
| 1922 | CN | D3 | A1 | H | D3 |
| 1923 | CN | D3 | A1 | H | D4 |
| 1924 | CN | D3 | A1 | H | D5 |
| 1925 | CN | D3 | A1 | H | D6 |
| 1926 | CN | D3 | A1 | H | D7 |
| 1927 | CN | D3 | A1 | H | D8 |
| 1928 | CN | D3 | A1 | H | D9 |
| 1929 | CN | D3 | A1 | H | D10 |
| 1930 | CN | D3 | A1 | H | D11 |
| 1931 | CN | D3 | A1 | H | D12 |
| 1932 | CN | D3 | A1 | H | D13 |
| 1933 | CN | D3 | A1 | H | D14 |
| 1934 | CN | D3 | A1 | H | D15 |
| 1935 | CN | D3 | A1 | H | D16 |
| 1936 | CN | D4 | A1 | H | D1 |
| 1937 | CN | D4 | A1 | H | D2 |
| 1938 | CN | D4 | A1 | H | D3 |
| 1939 | CN | D4 | A1 | H | D4 |
| 1940 | CN | D4 | A1 | H | D5 |
| 1941 | CN | D4 | A1 | H | D6 |
| 1942 | CN | D4 | A1 | H | D7 |
| 1943 | CN | D4 | A1 | H | D8 |
| 1944 | CN | D4 | A1 | H | D9 |
| 1945 | CN | D4 | A1 | H | D10 |
| 1946 | CN | D4 | A1 | H | D11 |
| 1947 | CN | D4 | A1 | H | D12 |
| 1948 | CN | D4 | A1 | H | D13 |
| 1949 | CN | D4 | A1 | H | D14 |
| 1950 | CN | D4 | A1 | H | D15 |

TABLE 1-14

| No. | $R^1$ | $R^2$ | $R^3$ | $R^4$ | $R^5$ |
|---|---|---|---|---|---|
| 1951 | CN | D4 | A1 | H | D16 |
| 1952 | CN | D5 | A1 | H | D1 |
| 1953 | CN | D5 | A1 | H | D2 |
| 1954 | CN | D5 | A1 | H | D3 |
| 1955 | CN | D5 | A1 | H | D4 |
| 1956 | CN | D5 | A1 | H | D5 |
| 1957 | CN | D5 | A1 | H | D6 |
| 1958 | CN | D5 | A1 | H | D7 |
| 1959 | CN | D5 | A1 | H | D8 |
| 1960 | CN | D5 | A1 | H | D9 |
| 1961 | CN | D5 | A1 | H | D10 |
| 1962 | CN | D5 | A1 | H | D11 |
| 1963 | CN | D5 | A1 | H | D12 |
| 1964 | CN | D5 | A1 | H | D13 |
| 1965 | CN | D5 | A1 | H | D14 |
| 1966 | CN | D5 | A1 | H | D15 |
| 1967 | CN | D5 | A1 | H | D16 |
| 1968 | CN | D6 | A1 | H | D1 |
| 1969 | CN | D6 | A1 | H | D2 |
| 1970 | CN | D6 | A1 | H | D3 |
| 1971 | CN | D6 | A1 | H | D4 |
| 1972 | CN | D6 | A1 | H | D5 |
| 1973 | CN | D6 | A1 | H | D6 |
| 1974 | CN | D6 | A1 | H | D7 |
| 1975 | CN | D6 | A1 | H | D8 |
| 1976 | CN | D6 | A1 | H | D9 |
| 1977 | CN | D6 | A1 | H | D10 |
| 1978 | CN | D6 | A1 | H | D11 |
| 1979 | CN | D6 | A1 | H | D12 |
| 1980 | CN | D6 | A1 | H | D13 |
| 1981 | CN | D6 | A1 | H | D14 |
| 1982 | CN | D6 | A1 | H | D15 |
| 1983 | CN | D6 | A1 | H | D16 |
| 1984 | CN | D7 | A1 | H | D1 |
| 1985 | CN | D7 | A1 | H | D2 |
| 1986 | CN | D7 | A1 | H | D3 |
| 1987 | CN | D7 | A1 | H | D4 |
| 1988 | CN | D7 | A1 | H | D5 |
| 1989 | CN | D7 | A1 | H | D6 |
| 1990 | CN | D7 | A1 | H | D7 |
| 1991 | CN | D7 | A1 | H | D8 |
| 1992 | CN | D7 | A1 | H | D9 |
| 1993 | CN | D7 | A1 | H | D10 |
| 1994 | CN | D7 | A1 | H | D11 |
| 1995 | CN | D7 | A1 | H | D12 |
| 1996 | CN | D7 | A1 | H | D13 |
| 1997 | CN | D7 | A1 | H | D14 |
| 1998 | CN | D7 | A1 | H | D15 |
| 1999 | CN | D7 | A1 | H | D16 |
| 2000 | CN | D8 | A1 | H | D1 |
| 2001 | CN | D8 | A1 | H | D2 |
| 2002 | CN | D8 | A1 | H | D3 |
| 2003 | CN | D8 | A1 | H | D4 |
| 2004 | CN | D8 | A1 | H | D5 |
| 2005 | CN | D8 | A1 | H | D6 |
| 2006 | CN | D8 | A1 | H | D7 |
| 2007 | CN | D8 | A1 | H | D8 |
| 2008 | CN | D8 | A1 | H | D9 |
| 2009 | CN | D8 | A1 | H | D10 |
| 2010 | CN | D8 | A1 | H | D11 |
| 2011 | CN | D8 | A1 | H | D12 |
| 2012 | CN | D8 | A1 | H | D13 |
| 2013 | CN | D8 | A1 | H | D14 |
| 2014 | CN | D8 | A1 | H | D15 |
| 2015 | CN | D8 | A1 | H | D16 |
| 2016 | CN | D9 | A1 | H | D1 |
| 2017 | CN | D9 | A1 | H | D2 |
| 2018 | CN | D9 | A1 | H | D3 |
| 2019 | CN | D9 | A1 | H | D4 |
| 2020 | CN | D9 | A1 | H | D5 |
| 2021 | CN | D9 | A1 | H | D6 |
| 2022 | CN | D9 | A1 | H | D7 |
| 2023 | CN | D9 | A1 | H | D8 |
| 2024 | CN | D9 | A1 | H | D9 |
| 2025 | CN | D9 | A1 | H | D10 |
| 2026 | CN | D9 | A1 | H | D11 |
| 2027 | CN | D9 | A1 | H | D12 |
| 2028 | CN | D9 | A1 | H | D13 |

TABLE 1-14-continued

| No. | $R^1$ | $R^2$ | $R^3$ | $R^4$ | $R^5$ |
|---|---|---|---|---|---|
| 2029 | CN | D9 | A1 | H | D14 |
| 2030 | CN | D9 | A1 | H | D15 |
| 2031 | CN | D9 | A1 | H | D16 |
| 2032 | CN | D10 | A1 | H | D1 |
| 2033 | CN | D10 | A1 | H | D2 |
| 2034 | CN | D10 | A1 | H | D3 |
| 2035 | CN | D10 | A1 | H | D4 |
| 2036 | CN | D10 | A1 | H | D5 |
| 2037 | CN | D10 | A1 | H | D6 |
| 2038 | CN | D10 | A1 | H | D7 |
| 2039 | CN | D10 | A1 | H | D8 |
| 2040 | CN | D10 | A1 | H | D9 |
| 2041 | CN | D10 | A1 | H | D10 |
| 2042 | CN | D10 | A1 | H | D11 |
| 2043 | CN | D10 | A1 | H | D12 |
| 2044 | CN | D10 | A1 | H | D13 |
| 2045 | CN | D10 | A1 | H | D14 |
| 2046 | CN | D10 | A1 | H | D15 |
| 2047 | CN | D10 | A1 | H | D16 |
| 2048 | CN | D11 | A1 | H | D1 |
| 2049 | CN | D11 | A1 | H | D2 |
| 2050 | CN | D11 | A1 | H | D3 |
| 2051 | CN | D11 | A1 | H | D4 |
| 2052 | CN | D11 | A1 | H | D5 |
| 2053 | CN | D11 | A1 | H | D6 |
| 2054 | CN | D11 | A1 | H | D7 |
| 2055 | CN | D11 | A1 | H | D8 |
| 2056 | CN | D11 | A1 | H | D9 |
| 2057 | CN | D11 | A1 | H | D10 |
| 2058 | CN | D11 | A1 | H | D11 |
| 2059 | CN | D11 | A1 | H | D12 |
| 2060 | CN | D11 | A1 | H | D13 |
| 2061 | CN | D11 | A1 | H | D14 |
| 2062 | CN | D11 | A1 | H | D15 |
| 2063 | CN | D11 | A1 | H | D16 |
| 2064 | CN | D12 | A1 | H | D1 |
| 2065 | CN | D12 | A1 | H | D2 |
| 2066 | CN | D12 | A1 | H | D3 |
| 2067 | CN | D12 | A1 | H | D4 |
| 2068 | CN | D12 | A1 | H | D5 |
| 2069 | CN | D12 | A1 | H | D6 |
| 2070 | CN | D12 | A1 | H | D7 |
| 2071 | CN | D12 | A1 | H | D8 |
| 2072 | CN | D12 | A1 | H | D9 |
| 2073 | CN | D12 | A1 | H | D10 |
| 2074 | CN | D12 | A1 | H | D11 |
| 2075 | CN | D12 | A1 | H | D12 |
| 2076 | CN | D12 | A1 | H | D13 |
| 2077 | CN | D12 | A1 | H | D14 |
| 2078 | CN | D12 | A1 | H | D15 |
| 2079 | CN | D12 | A1 | H | D16 |
| 2080 | CN | D13 | A1 | H | D1 |
| 2081 | CN | D13 | A1 | H | D2 |
| 2082 | CN | D13 | A1 | H | D3 |
| 2083 | CN | D13 | A1 | H | D4 |
| 2084 | CN | D13 | A1 | H | D5 |
| 2085 | CN | D13 | A1 | H | D6 |
| 2086 | CN | D13 | A1 | H | D7 |
| 2087 | CN | D13 | A1 | H | D8 |
| 2088 | CN | D13 | A1 | H | D9 |
| 2089 | CN | D13 | A1 | H | D10 |
| 2090 | CN | D13 | A1 | H | D11 |
| 2091 | CN | D13 | A1 | H | D12 |
| 2092 | CN | D13 | A1 | H | D13 |
| 2093 | CN | D13 | A1 | H | D14 |
| 2094 | CN | D13 | A1 | H | D15 |
| 2095 | CN | D13 | A1 | H | D16 |
| 2096 | CN | D14 | A1 | H | D1 |
| 2097 | CN | D14 | A1 | H | D2 |
| 2098 | CN | D14 | A1 | H | D3 |
| 2099 | CN | D14 | A1 | H | D4 |
| 2100 | CN | D14 | A1 | H | D5 |

TABLE 1-15

| No. | $R^1$ | $R^2$ | $R^3$ | $R^4$ | $R^5$ |
|---|---|---|---|---|---|
| 2101 | CN | D14 | A1 | H | D6 |
| 2102 | CN | D14 | A1 | H | D7 |
| 2103 | CN | D14 | A1 | H | D8 |
| 2104 | CN | D14 | A1 | H | D9 |
| 2105 | CN | D14 | A1 | H | D10 |
| 2106 | CN | D14 | A1 | H | D11 |
| 2107 | CN | D14 | A1 | H | D12 |
| 2108 | CN | D14 | A1 | H | D13 |
| 2109 | CN | D14 | A1 | H | D14 |
| 2110 | CN | D14 | A1 | H | D15 |
| 2111 | CN | D14 | A1 | H | D16 |
| 2112 | CN | D15 | A1 | H | D1 |
| 2113 | CN | D15 | A1 | H | D2 |
| 2114 | CN | D15 | A1 | H | D3 |
| 2115 | CN | D15 | A1 | H | D4 |
| 2116 | CN | D15 | A1 | H | D5 |
| 2117 | CN | D15 | A1 | H | D6 |
| 2118 | CN | D15 | A1 | H | D7 |
| 2119 | CN | D15 | A1 | H | D8 |
| 2120 | CN | D15 | A1 | H | D9 |
| 2121 | CN | D15 | A1 | H | D10 |
| 2122 | CN | D15 | A1 | H | D11 |
| 2123 | CN | D15 | A1 | H | D12 |
| 2124 | CN | D15 | A1 | H | D13 |
| 2125 | CN | D15 | A1 | H | D14 |
| 2126 | CN | D15 | A1 | H | D15 |
| 2127 | CN | D15 | A1 | H | D16 |
| 2128 | CN | D16 | A1 | H | D1 |
| 2129 | CN | D16 | A1 | H | D2 |
| 2130 | CN | D16 | A1 | H | D3 |
| 2131 | CN | D16 | A1 | H | D4 |
| 2132 | CN | D16 | A1 | H | D5 |
| 2133 | CN | D16 | A1 | H | D6 |
| 2134 | CN | D16 | A1 | H | D7 |
| 2135 | CN | D16 | A1 | H | D8 |
| 2136 | CN | D16 | A1 | H | D9 |
| 2137 | CN | D16 | A1 | H | D10 |
| 2138 | CN | D16 | A1 | H | D11 |
| 2139 | CN | D16 | A1 | H | D12 |
| 2140 | CN | D16 | A1 | H | D13 |
| 2141 | CN | D16 | A1 | H | D14 |
| 2142 | CN | D16 | A1 | H | D15 |
| 2143 | CN | D16 | A1 | H | D16 |
| 2144 | CN | D1 | A2 | H | D1 |
| 2145 | CN | D1 | A2 | H | D2 |
| 2146 | CN | D1 | A2 | H | D3 |
| 2147 | CN | D1 | A2 | H | D4 |
| 2148 | CN | D1 | A2 | H | D5 |
| 2149 | CN | D1 | A2 | H | D6 |
| 2150 | CN | D1 | A2 | H | D7 |
| 2151 | CN | D1 | A2 | H | D8 |
| 2152 | CN | D1 | A2 | H | D9 |
| 2153 | CN | D1 | A2 | H | D10 |
| 2154 | CN | D1 | A2 | H | D11 |
| 2155 | CN | D1 | A2 | H | D12 |
| 2156 | CN | D1 | A2 | H | D13 |
| 2157 | CN | D1 | A2 | H | D14 |
| 2158 | CN | D1 | A2 | H | D15 |
| 2159 | CN | D1 | A2 | H | D16 |
| 2160 | CN | D2 | A2 | H | D1 |
| 2161 | CN | D2 | A2 | H | D2 |
| 2162 | CN | D2 | A2 | H | D3 |
| 2163 | CN | D2 | A2 | H | D4 |
| 2164 | CN | D2 | A2 | H | D5 |
| 2165 | CN | D2 | A2 | H | D6 |
| 2166 | CN | D2 | A2 | H | D7 |
| 2167 | CN | D2 | A2 | H | D8 |
| 2168 | CN | D2 | A2 | H | D9 |
| 2169 | CN | D2 | A2 | H | D10 |
| 2170 | CN | D2 | A2 | H | D11 |
| 2171 | CN | D2 | A2 | H | D12 |
| 2172 | CN | D2 | A2 | H | D13 |
| 2173 | CN | D2 | A2 | H | D14 |
| 2174 | CN | D2 | A2 | H | D15 |
| 2175 | CN | D2 | A2 | H | D16 |
| 2176 | CN | D3 | A2 | H | D1 |
| 2177 | CN | D3 | A2 | H | D2 |
| 2178 | CN | D3 | A2 | H | D3 |

TABLE 1-15-continued

| No. | $R^1$ | $R^2$ | $R^3$ | $R^4$ | $R^5$ |
|---|---|---|---|---|---|
| 2179 | CN | D3 | A2 | H | D4 |
| 2180 | CN | D3 | A2 | H | D5 |
| 2181 | CN | D3 | A2 | H | D6 |
| 2182 | CN | D3 | A2 | H | D7 |
| 2183 | CN | D3 | A2 | H | D8 |
| 2184 | CN | D3 | A2 | H | D9 |
| 2185 | CN | D3 | A2 | H | D10 |
| 2186 | CN | D3 | A2 | H | D11 |
| 2187 | CN | D3 | A2 | H | D12 |
| 2188 | CN | D3 | A2 | H | D13 |
| 2189 | CN | D3 | A2 | H | D14 |
| 2190 | CN | D3 | A2 | H | D15 |
| 2191 | CN | D3 | A2 | H | D16 |
| 2192 | CN | D4 | A2 | H | D1 |
| 2193 | CN | D4 | A2 | H | D2 |
| 2194 | CN | D4 | A2 | H | D3 |
| 2195 | CN | D4 | A2 | H | D4 |
| 2196 | CN | D4 | A2 | H | D5 |
| 2197 | CN | D4 | A2 | H | D6 |
| 2198 | CN | D4 | A2 | H | D7 |
| 2199 | CN | D4 | A2 | H | D8 |
| 2200 | CN | D4 | A2 | H | D9 |
| 2201 | CN | D4 | A2 | H | D10 |
| 2202 | CN | D4 | A2 | H | D11 |
| 2203 | CN | D4 | A2 | H | D12 |
| 2204 | CN | D4 | A2 | H | D13 |
| 2205 | CN | D4 | A2 | H | D14 |
| 2206 | CN | D4 | A2 | H | D15 |
| 2207 | CN | D4 | A2 | H | D16 |
| 2208 | CN | D5 | A2 | H | D1 |
| 2209 | CN | D5 | A2 | H | D2 |
| 2210 | CN | D5 | A2 | H | D3 |
| 2211 | CN | D5 | A2 | H | D4 |
| 2212 | CN | D5 | A2 | H | D5 |
| 2213 | CN | D5 | A2 | H | D6 |
| 2214 | CN | D5 | A2 | H | D7 |
| 2215 | CN | D5 | A2 | H | D8 |
| 2216 | CN | D5 | A2 | H | D9 |
| 2217 | CN | D5 | A2 | H | D10 |
| 2218 | CN | D5 | A2 | H | D11 |
| 2219 | CN | D5 | A2 | H | D12 |
| 2220 | CN | D5 | A2 | H | D13 |
| 2221 | CN | D5 | A2 | H | D14 |
| 2222 | CN | D5 | A2 | H | D15 |
| 2223 | CN | D5 | A2 | H | D16 |
| 2224 | CN | D6 | A2 | H | D1 |
| 2225 | CN | D6 | A2 | H | D2 |
| 2226 | CN | D6 | A2 | H | D3 |
| 2227 | CN | D6 | A2 | H | D4 |
| 2228 | CN | D6 | A2 | H | D5 |
| 2229 | CN | D6 | A2 | H | D6 |
| 2230 | CN | D6 | A2 | H | D7 |
| 2231 | CN | D6 | A2 | H | D8 |
| 2232 | CN | D6 | A2 | H | D9 |
| 2233 | CN | D6 | A2 | H | D10 |
| 2234 | CN | D6 | A2 | H | D11 |
| 2235 | CN | D6 | A2 | H | D12 |
| 2236 | CN | D6 | A2 | H | D13 |
| 2237 | CN | D6 | A2 | H | D14 |
| 2238 | CN | D6 | A2 | H | D15 |
| 2239 | CN | D6 | A2 | H | D16 |
| 2240 | CN | D7 | A2 | H | D1 |
| 2241 | CN | D7 | A2 | H | D2 |
| 2242 | CN | D7 | A2 | H | D3 |
| 2243 | CN | D7 | A2 | H | D4 |
| 2244 | CN | D7 | A2 | H | D5 |
| 2245 | CN | D7 | A2 | H | D6 |
| 2246 | CN | D7 | A2 | H | D7 |
| 2247 | CN | D7 | A2 | H | D8 |
| 2248 | CN | D7 | A2 | H | D9 |
| 2249 | CN | D7 | A2 | H | D10 |
| 2250 | CN | D7 | A2 | H | D11 |

TABLE 1-16

| No. | $R^1$ | $R^2$ | $R^3$ | $R^4$ | $R^5$ |
|---|---|---|---|---|---|
| 2251 | CN | D7 | A2 | H | D12 |
| 2252 | CN | D7 | A2 | H | D13 |
| 2253 | CN | D7 | A2 | H | D14 |
| 2254 | CN | D7 | A2 | H | D15 |
| 2255 | CN | D7 | A2 | H | D16 |
| 2256 | CN | D8 | A2 | H | D1 |
| 2257 | CN | D8 | A2 | H | D2 |
| 2258 | CN | D8 | A2 | H | D3 |
| 2259 | CN | D8 | A2 | H | D4 |
| 2260 | CN | D8 | A2 | H | D5 |
| 2261 | CN | D8 | A2 | H | D6 |
| 2262 | CN | D8 | A2 | H | D7 |
| 2263 | CN | D8 | A2 | H | D8 |
| 2264 | CN | D8 | A2 | H | D9 |
| 2265 | CN | D8 | A2 | H | D10 |
| 2266 | CN | D8 | A2 | H | D11 |
| 2267 | CN | D8 | A2 | H | D12 |
| 2268 | CN | D8 | A2 | H | D13 |
| 2269 | CN | D8 | A2 | H | D14 |
| 2270 | CN | D8 | A2 | H | D15 |
| 2271 | CN | D8 | A2 | H | D16 |
| 2272 | CN | D9 | A2 | H | D1 |
| 2273 | CN | D9 | A2 | H | D2 |
| 2274 | CN | D9 | A2 | H | D3 |
| 2275 | CN | D9 | A2 | H | D4 |
| 2276 | CN | D9 | A2 | H | D5 |
| 2277 | CN | D9 | A2 | H | D6 |
| 2278 | CN | D9 | A2 | H | D7 |
| 2279 | CN | D9 | A2 | H | D8 |
| 2280 | CN | D9 | A2 | H | D9 |
| 2281 | CN | D9 | A2 | H | D10 |
| 2282 | CN | D9 | A2 | H | D11 |
| 2283 | CN | D9 | A2 | H | D12 |
| 2284 | CN | D9 | A2 | H | D13 |
| 2285 | CN | D9 | A2 | H | D14 |
| 2286 | CN | D9 | A2 | H | D15 |
| 2287 | CN | D9 | A2 | H | D16 |
| 2288 | CN | D10 | A2 | H | D1 |
| 2289 | CN | D10 | A2 | H | D2 |
| 2290 | CN | D10 | A2 | H | D3 |
| 2291 | CN | D10 | A2 | H | D4 |
| 2292 | CN | D10 | A2 | H | D5 |
| 2293 | CN | D10 | A2 | H | D6 |
| 2294 | CN | D10 | A2 | H | D7 |
| 2295 | CN | D10 | A2 | H | D8 |
| 2296 | CN | D10 | A2 | H | D9 |
| 2297 | CN | D10 | A2 | H | D10 |
| 2298 | CN | D10 | A2 | H | D11 |
| 2299 | CN | D10 | A2 | H | D12 |
| 2300 | CN | D10 | A2 | H | D13 |
| 2301 | CN | D10 | A2 | H | D14 |
| 2302 | CN | D10 | A2 | H | D15 |
| 2303 | CN | D10 | A2 | H | D16 |
| 2304 | CN | D11 | A2 | H | D1 |
| 2305 | CN | D11 | A2 | H | D2 |
| 2306 | CN | D11 | A2 | H | D3 |
| 2307 | CN | D11 | A2 | H | D4 |
| 2308 | CN | D11 | A2 | H | D5 |
| 2309 | CN | D11 | A2 | H | D6 |
| 2310 | CN | D11 | A2 | H | D7 |
| 2311 | CN | D11 | A2 | H | D8 |
| 2312 | CN | D11 | A2 | H | D9 |
| 2313 | CN | D11 | A2 | H | D10 |
| 2314 | CN | D11 | A2 | H | D11 |
| 2315 | CN | D11 | A2 | H | D12 |
| 2316 | CN | D11 | A2 | H | D13 |
| 2317 | CN | D11 | A2 | H | D14 |
| 2318 | CN | D11 | A2 | H | D15 |
| 2319 | CN | D11 | A2 | H | D16 |
| 2320 | CN | D12 | A2 | H | D1 |
| 2321 | CN | D12 | A2 | H | D2 |
| 2322 | CN | D12 | A2 | H | D3 |
| 2323 | CN | D12 | A2 | H | D4 |
| 2324 | CN | D12 | A2 | H | D5 |
| 2325 | CN | D12 | A2 | H | D6 |
| 2326 | CN | D12 | A2 | H | D7 |
| 2327 | CN | D12 | A2 | H | D8 |
| 2328 | CN | D12 | A2 | H | D9 |

TABLE 1-16-continued

| No. | $R^1$ | $R^2$ | $R^3$ | $R^4$ | $R^5$ |
|---|---|---|---|---|---|
| 2329 | CN | D12 | A2 | H | D10 |
| 2330 | CN | D12 | A2 | H | D11 |
| 2331 | CN | D12 | A2 | H | D12 |
| 2332 | CN | D12 | A2 | H | D13 |
| 2333 | CN | D12 | A2 | H | D14 |
| 2334 | CN | D12 | A2 | H | D15 |
| 2335 | CN | D12 | A2 | H | D16 |
| 2336 | CN | D13 | A2 | H | D1 |
| 2337 | CN | D13 | A2 | H | D2 |
| 2338 | CN | D13 | A2 | H | D3 |
| 2339 | CN | D13 | A2 | H | D4 |
| 2340 | CN | D13 | A2 | H | D5 |
| 2341 | CN | D13 | A2 | H | D6 |
| 2342 | CN | D13 | A2 | H | D7 |
| 2343 | CN | D13 | A2 | H | D8 |
| 2344 | CN | D13 | A2 | H | D9 |
| 2345 | CN | D13 | A2 | H | D10 |
| 2346 | CN | D13 | A2 | H | D11 |
| 2347 | CN | D13 | A2 | H | D12 |
| 2348 | CN | D13 | A2 | H | D13 |
| 2349 | CN | D13 | A2 | H | D14 |
| 2350 | CN | D13 | A2 | H | D15 |
| 2351 | CN | D13 | A2 | H | D16 |
| 2352 | CN | D14 | A2 | H | D1 |
| 2353 | CN | D14 | A2 | H | D2 |
| 2354 | CN | D14 | A2 | H | D3 |
| 2355 | CN | D14 | A2 | H | D4 |
| 2356 | CN | D14 | A2 | H | D5 |
| 2357 | CN | D14 | A2 | H | D6 |
| 2358 | CN | D14 | A2 | H | D7 |
| 2359 | CN | D14 | A2 | H | D8 |
| 2360 | CN | D14 | A2 | H | D9 |
| 2361 | CN | D14 | A2 | H | D10 |
| 2362 | CN | D14 | A2 | H | D11 |
| 2363 | CN | D14 | A2 | H | D12 |
| 2364 | CN | D14 | A2 | H | D13 |
| 2365 | CN | D14 | A2 | H | D14 |
| 2366 | CN | D14 | A2 | H | D15 |
| 2367 | CN | D14 | A2 | H | D16 |
| 2368 | CN | D15 | A2 | H | D1 |
| 2369 | CN | D15 | A2 | H | D2 |
| 2370 | CN | D15 | A2 | H | D3 |
| 2371 | CN | D15 | A2 | H | D4 |
| 2372 | CN | D15 | A2 | H | D5 |
| 2373 | CN | D15 | A2 | H | D6 |
| 2374 | CN | D15 | A2 | H | D7 |
| 2375 | CN | D15 | A2 | H | D8 |
| 2376 | CN | D15 | A2 | H | D9 |
| 2377 | CN | D15 | A2 | H | D10 |
| 2378 | CN | D15 | A2 | H | D11 |
| 2379 | CN | D15 | A2 | H | D12 |
| 2380 | CN | D15 | A2 | H | D13 |
| 2381 | CN | D15 | A2 | H | D14 |
| 2382 | CN | D15 | A2 | H | D15 |
| 2383 | CN | D15 | A2 | H | D16 |
| 2384 | CN | D16 | A2 | H | D1 |
| 2385 | CN | D16 | A2 | H | D2 |
| 2386 | CN | D16 | A2 | H | D3 |
| 2387 | CN | D16 | A2 | H | D4 |
| 2388 | CN | D16 | A2 | H | D5 |
| 2389 | CN | D16 | A2 | H | D6 |
| 2390 | CN | D16 | A2 | H | D7 |
| 2391 | CN | D16 | A2 | H | D8 |
| 2392 | CN | D16 | A2 | H | D9 |
| 2393 | CN | D16 | A2 | H | D10 |
| 2394 | CN | D16 | A2 | H | D11 |
| 2395 | CN | D16 | A2 | H | D12 |
| 2396 | CN | D16 | A2 | H | D13 |
| 2397 | CN | D16 | A2 | H | D14 |
| 2398 | CN | D16 | A2 | H | D15 |
| 2399 | CN | D16 | A2 | H | D16 |
| 2400 | CN | A1 | D1 | D1 | D1 |

TABLE 1-17

| No. | $R^1$ | $R^2$ | $R^3$ | $R^4$ | $R^5$ |
|---|---|---|---|---|---|
| 2401 | CN | A1 | D1 | D1 | D2 |
| 2402 | CN | A1 | D1 | D1 | D3 |
| 2403 | CN | A1 | D1 | D1 | D4 |
| 2404 | CN | A1 | D1 | D1 | D5 |
| 2405 | CN | A1 | D1 | D1 | D6 |
| 2406 | CN | A1 | D1 | D2 | D1 |
| 2407 | CN | A1 | D1 | D2 | D2 |
| 2408 | CN | A1 | D1 | D2 | D3 |
| 2409 | CN | A1 | D1 | D2 | D4 |
| 2410 | CN | A1 | D1 | D2 | D5 |
| 2411 | CN | A1 | D1 | D2 | D6 |
| 2412 | CN | A1 | D1 | D3 | D1 |
| 2413 | CN | A1 | D1 | D3 | D2 |
| 2414 | CN | A1 | D1 | D3 | D3 |
| 2415 | CN | A1 | D1 | D3 | D4 |
| 2416 | CN | A1 | D1 | D3 | D5 |
| 2417 | CN | A1 | D1 | D3 | D6 |
| 2418 | CN | A1 | D1 | D4 | D1 |
| 2419 | CN | A1 | D1 | D4 | D2 |
| 2420 | CN | A1 | D1 | D4 | D3 |
| 2421 | CN | A1 | D1 | D4 | D4 |
| 2422 | CN | A1 | D1 | D4 | D5 |
| 2423 | CN | A1 | D1 | D4 | D6 |
| 2424 | CN | A1 | D1 | D5 | D1 |
| 2425 | CN | A1 | D1 | D5 | D2 |
| 2426 | CN | A1 | D1 | D5 | D3 |
| 2427 | CN | A1 | D1 | D5 | D4 |
| 2428 | CN | A1 | D1 | D5 | D5 |
| 2429 | CN | A1 | D1 | D5 | D6 |
| 2430 | CN | A1 | D1 | D6 | D1 |
| 2431 | CN | A1 | D1 | D6 | D2 |
| 2432 | CN | A1 | D1 | D6 | D3 |
| 2433 | CN | A1 | D1 | D6 | D4 |
| 2434 | CN | A1 | D1 | D6 | D5 |
| 2435 | CN | A1 | D1 | D6 | D6 |
| 2436 | CN | A1 | D2 | D1 | D1 |
| 2437 | CN | A1 | D2 | D1 | D2 |
| 2438 | CN | A1 | D2 | D1 | D3 |
| 2439 | CN | A1 | D2 | D1 | D4 |
| 2440 | CN | A1 | D2 | D1 | D5 |
| 2441 | CN | A1 | D2 | D1 | D6 |
| 2442 | CN | A1 | D2 | D2 | D1 |
| 2443 | CN | A1 | D2 | D2 | D2 |
| 2444 | CN | A1 | D2 | D2 | D3 |
| 2445 | CN | A1 | D2 | D2 | D4 |
| 2446 | CN | A1 | D2 | D2 | D5 |
| 2447 | CN | A1 | D2 | D2 | D6 |
| 2448 | CN | A1 | D2 | D3 | D1 |
| 2449 | CN | A1 | D2 | D3 | D2 |
| 2450 | CN | A1 | D2 | D3 | D3 |
| 2451 | CN | A1 | D2 | D3 | D4 |
| 2452 | CN | A1 | D2 | D3 | D5 |
| 2453 | CN | A1 | D2 | D3 | D6 |
| 2454 | CN | A1 | D2 | D4 | D1 |
| 2455 | CN | A1 | D2 | D4 | D2 |
| 2456 | CN | A1 | D2 | D4 | D3 |
| 2457 | CN | A1 | D2 | D4 | D4 |
| 2458 | CN | A1 | D2 | D4 | D5 |
| 2459 | CN | A1 | D2 | D4 | D6 |
| 2460 | CN | A1 | D2 | D5 | D1 |
| 2461 | CN | A1 | D2 | D5 | D2 |
| 2462 | CN | A1 | D2 | D5 | D3 |
| 2463 | CN | A1 | D2 | D5 | D4 |
| 2464 | CN | A1 | D2 | D5 | D5 |
| 2465 | CN | A1 | D2 | D5 | D6 |
| 2466 | CN | A1 | D2 | D6 | D1 |
| 2467 | CN | A1 | D2 | D6 | D2 |
| 2468 | CN | A1 | D2 | D6 | D3 |
| 2469 | CN | A1 | D2 | D6 | D4 |
| 2470 | CN | A1 | D2 | D6 | D5 |
| 2471 | CN | A1 | D2 | D6 | D6 |
| 2472 | CN | A1 | D3 | D1 | D1 |
| 2473 | CN | A1 | D3 | D1 | D2 |
| 2474 | CN | A1 | D3 | D1 | D3 |
| 2475 | CN | A1 | D3 | D1 | D4 |
| 2476 | CN | A1 | D3 | D1 | D5 |
| 2477 | CN | A1 | D3 | D1 | D6 |
| 2478 | CN | A1 | D3 | D2 | D1 |

TABLE 1-17-continued

| No. | $R^1$ | $R^2$ | $R^3$ | $R^4$ | $R^5$ |
|---|---|---|---|---|---|
| 2479 | CN | A1 | D3 | D2 | D2 |
| 2480 | CN | A1 | D3 | D2 | D3 |
| 2481 | CN | A1 | D3 | D2 | D4 |
| 2482 | CN | A1 | D3 | D2 | D5 |
| 2483 | CN | A1 | D3 | D2 | D6 |
| 2484 | CN | A1 | D3 | D3 | D1 |
| 2485 | CN | A1 | D3 | D3 | D2 |
| 2486 | CN | A1 | D3 | D3 | D3 |
| 2487 | CN | A1 | D3 | D3 | D4 |
| 2488 | CN | A1 | D3 | D3 | D5 |
| 2489 | CN | A1 | D3 | D3 | D6 |
| 2490 | CN | A1 | D3 | D4 | D1 |
| 2491 | CN | A1 | D3 | D4 | D2 |
| 2492 | CN | A1 | D3 | D4 | D3 |
| 2493 | CN | A1 | D3 | D4 | D4 |
| 2494 | CN | A1 | D3 | D4 | D5 |
| 2495 | CN | A1 | D3 | D4 | D6 |
| 2496 | CN | A1 | D3 | D5 | D1 |
| 2497 | CN | A1 | D3 | D5 | D2 |
| 2498 | CN | A1 | D3 | D5 | D3 |
| 2499 | CN | A1 | D3 | D5 | D4 |
| 2500 | CN | A1 | D3 | D5 | D5 |
| 2501 | CN | A1 | D3 | D5 | D6 |
| 2502 | CN | A1 | D3 | D6 | D1 |
| 2503 | CN | A1 | D3 | D6 | D2 |
| 2504 | CN | A1 | D3 | D6 | D3 |
| 2505 | CN | A1 | D3 | D6 | D4 |
| 2506 | CN | A1 | D3 | D6 | D5 |
| 2507 | CN | A1 | D3 | D6 | D6 |
| 2508 | CN | A1 | D4 | D1 | D1 |
| 2509 | CN | A1 | D4 | D1 | D2 |
| 2510 | CN | A1 | D4 | D1 | D3 |
| 2511 | CN | A1 | D4 | D1 | D4 |
| 2512 | CN | A1 | D4 | D1 | D5 |
| 2513 | CN | A1 | D4 | D1 | D6 |
| 2514 | CN | A1 | D4 | D2 | D1 |
| 2515 | CN | A1 | D4 | D2 | D2 |
| 2516 | CN | A1 | D4 | D2 | D3 |
| 2517 | CN | A1 | D4 | D2 | D4 |
| 2518 | CN | A1 | D4 | D2 | D5 |
| 2519 | CN | A1 | D4 | D2 | D6 |
| 2520 | CN | A1 | D4 | D3 | D1 |
| 2521 | CN | A1 | D4 | D3 | D2 |
| 2522 | CN | A1 | D4 | D3 | D3 |
| 2523 | CN | A1 | D4 | D3 | D4 |
| 2524 | CN | A1 | D4 | D3 | D5 |
| 2525 | CN | A1 | D4 | D3 | D6 |
| 2526 | CN | A1 | D4 | D4 | D1 |
| 2527 | CN | A1 | D4 | D4 | D2 |
| 2528 | CN | A1 | D4 | D4 | D3 |
| 2529 | CN | A1 | D4 | D4 | D4 |
| 2530 | CN | A1 | D4 | D4 | D5 |
| 2531 | CN | A1 | D4 | D4 | D6 |
| 2532 | CN | A1 | D4 | D5 | D1 |
| 2533 | CN | A1 | D4 | D5 | D2 |
| 2534 | CN | A1 | D4 | D5 | D3 |
| 2535 | CN | A1 | D4 | D5 | D4 |
| 2536 | CN | A1 | D4 | D5 | D5 |
| 2537 | CN | A1 | D4 | D5 | D6 |
| 2538 | CN | A1 | D4 | D6 | D1 |
| 2539 | CN | A1 | D4 | D6 | D2 |
| 2540 | CN | A1 | D4 | D6 | D3 |
| 2541 | CN | A1 | D4 | D6 | D4 |
| 2542 | CN | A1 | D4 | D6 | D5 |
| 2543 | CN | A1 | D4 | D6 | D6 |
| 2544 | CN | A1 | D5 | D1 | D1 |
| 2545 | CN | A1 | D5 | D1 | D2 |
| 2546 | CN | A1 | D5 | D1 | D3 |
| 2547 | CN | A1 | D5 | D1 | D4 |
| 2548 | CN | A1 | D5 | D1 | D5 |
| 2549 | CN | A1 | D5 | D1 | D6 |
| 2550 | CN | A1 | D5 | D2 | D1 |

TABLE 1-18

| No. | $R^1$ | $R^2$ | $R^3$ | $R^4$ | $R^5$ |
|---|---|---|---|---|---|
| 2551 | CN | A1 | D5 | D2 | D2 |
| 2552 | CN | A1 | D5 | D2 | D3 |
| 2553 | CN | A1 | D5 | D2 | D4 |
| 2554 | CN | A1 | D5 | D2 | D5 |
| 2555 | CN | A1 | D5 | D2 | D6 |
| 2556 | CN | A1 | D5 | D3 | D1 |
| 2557 | CN | A1 | D5 | D3 | D2 |
| 2558 | CN | A1 | D5 | D3 | D3 |
| 2559 | CN | A1 | D5 | D3 | D4 |
| 2560 | CN | A1 | D5 | D3 | D5 |
| 2561 | CN | A1 | D5 | D3 | D6 |
| 2562 | CN | A1 | D5 | D4 | D1 |
| 2563 | CN | A1 | D5 | D4 | D2 |
| 2564 | CN | A1 | D5 | D4 | D3 |
| 2565 | CN | A1 | D5 | D4 | D4 |
| 2566 | CN | A1 | D5 | D4 | D5 |
| 2567 | CN | A1 | D5 | D4 | D6 |
| 2568 | CN | A1 | D5 | D5 | D1 |
| 2569 | CN | A1 | D5 | D5 | D2 |
| 2570 | CN | A1 | D5 | D5 | D3 |
| 2571 | CN | A1 | D5 | D5 | D4 |
| 2572 | CN | A1 | D5 | D5 | D5 |
| 2573 | CN | A1 | D5 | D5 | D6 |
| 2574 | CN | A1 | D5 | D6 | D1 |
| 2575 | CN | A1 | D5 | D6 | D2 |
| 2576 | CN | A1 | D5 | D6 | D3 |
| 2577 | CN | A1 | D5 | D6 | D4 |
| 2578 | CN | A1 | D5 | D6 | D5 |
| 2579 | CN | A1 | D5 | D6 | D6 |
| 2580 | CN | A1 | D6 | D1 | D1 |
| 2581 | CN | A1 | D6 | D1 | D2 |
| 2582 | CN | A1 | D6 | D1 | D3 |
| 2583 | CN | A1 | D6 | D1 | D4 |
| 2584 | CN | A1 | D6 | D1 | D5 |
| 2585 | CN | A1 | D6 | D1 | D6 |
| 2586 | CN | A1 | D6 | D2 | D1 |
| 2587 | CN | A1 | D6 | D2 | D2 |
| 2588 | CN | A1 | D6 | D2 | D3 |
| 2589 | CN | A1 | D6 | D2 | D4 |
| 2590 | CN | A1 | D6 | D2 | D5 |
| 2591 | CN | A1 | D6 | D2 | D6 |
| 2592 | CN | A1 | D6 | D3 | D1 |
| 2593 | CN | A1 | D6 | D3 | D2 |
| 2594 | CN | A1 | D6 | D3 | D3 |
| 2595 | CN | A1 | D6 | D3 | D4 |
| 2596 | CN | A1 | D6 | D3 | D5 |
| 2597 | CN | A1 | D6 | D3 | D6 |
| 2598 | CN | A1 | D6 | D4 | D1 |
| 2599 | CN | A1 | D6 | D4 | D2 |
| 2600 | CN | A1 | D6 | D4 | D3 |
| 2601 | CN | A1 | D6 | D4 | D4 |
| 2602 | CN | A1 | D6 | D4 | D5 |
| 2603 | CN | A1 | D6 | D4 | D6 |
| 2604 | CN | A1 | D6 | D5 | D1 |
| 2605 | CN | A1 | D6 | D5 | D2 |
| 2606 | CN | A1 | D6 | D5 | D3 |
| 2607 | CN | A1 | D6 | D5 | D4 |
| 2608 | CN | A1 | D6 | D5 | D5 |
| 2609 | CN | A1 | D6 | D5 | D6 |
| 2610 | CN | A1 | D6 | D6 | D1 |
| 2611 | CN | A1 | D6 | D6 | D2 |
| 2612 | CN | A1 | D6 | D6 | D3 |
| 2613 | CN | A1 | D6 | D6 | D4 |
| 2614 | CN | A1 | D6 | D6 | D5 |
| 2615 | CN | A1 | D6 | D6 | D6 |
| 2616 | CN | A2 | D1 | D1 | D1 |
| 2617 | CN | A2 | D1 | D1 | D2 |
| 2618 | CN | A2 | D1 | D1 | D3 |
| 2619 | CN | A2 | D1 | D1 | D4 |
| 2620 | CN | A2 | D1 | D1 | D5 |
| 2621 | CN | A2 | D1 | D1 | D6 |
| 2622 | CN | A2 | D1 | D2 | D1 |
| 2623 | CN | A2 | D1 | D2 | D2 |
| 2624 | CN | A2 | D1 | D2 | D3 |
| 2625 | CN | A2 | D1 | D2 | D4 |
| 2626 | CN | A2 | D1 | D2 | D5 |
| 2627 | CN | A2 | D1 | D2 | D6 |
| 2628 | CN | A2 | D1 | D3 | D1 |

TABLE 1-18-continued

| No. | $R^1$ | $R^2$ | $R^3$ | $R^4$ | $R^5$ |
|---|---|---|---|---|---|
| 2629 | CN | A2 | D1 | D3 | D2 |
| 2630 | CN | A2 | D1 | D3 | D3 |
| 2631 | CN | A2 | D1 | D3 | D4 |
| 2632 | CN | A2 | D1 | D3 | D5 |
| 2633 | CN | A2 | D1 | D3 | D6 |
| 2634 | CN | A2 | D1 | D4 | D1 |
| 2635 | CN | A2 | D1 | D4 | D2 |
| 2636 | CN | A2 | D1 | D4 | D3 |
| 2637 | CN | A2 | D1 | D4 | D4 |
| 2638 | CN | A2 | D1 | D4 | D5 |
| 2639 | CN | A2 | D1 | D4 | D6 |
| 2640 | CN | A2 | D1 | D5 | D1 |
| 2641 | CN | A2 | D1 | D5 | D2 |
| 2642 | CN | A2 | D1 | D5 | D3 |
| 2643 | CN | A2 | D1 | D5 | D4 |
| 2644 | CN | A2 | D1 | D5 | D5 |
| 2645 | CN | A2 | D1 | D5 | D6 |
| 2646 | CN | A2 | D1 | D6 | D1 |
| 2647 | CN | A2 | D1 | D6 | D2 |
| 2648 | CN | A2 | D1 | D6 | D3 |
| 2649 | CN | A2 | D1 | D6 | D4 |
| 2650 | CN | A2 | D1 | D6 | D5 |
| 2651 | CN | A2 | D1 | D6 | D6 |
| 2652 | CN | A2 | D2 | D1 | D1 |
| 2653 | CN | A2 | D2 | D1 | D2 |
| 2654 | CN | A2 | D2 | D1 | D3 |
| 2655 | CN | A2 | D2 | D1 | D4 |
| 2656 | CN | A2 | D2 | D1 | D5 |
| 2657 | CN | A2 | D2 | D1 | D6 |
| 2658 | CN | A2 | D2 | D2 | D1 |
| 2659 | CN | A2 | D2 | D2 | D2 |
| 2660 | CN | A2 | D2 | D2 | D3 |
| 2661 | CN | A2 | D2 | D2 | D4 |
| 2662 | CN | A2 | D2 | D2 | D5 |
| 2663 | CN | A2 | D2 | D2 | D6 |
| 2664 | CN | A2 | D2 | D3 | D1 |
| 2665 | CN | A2 | D2 | D3 | D2 |
| 2666 | CN | A2 | D2 | D3 | D3 |
| 2667 | CN | A2 | D2 | D3 | D4 |
| 2668 | CN | A2 | D2 | D3 | D5 |
| 2669 | CN | A2 | D2 | D3 | D6 |
| 2670 | CN | A2 | D2 | D4 | D1 |
| 2671 | CN | A2 | D2 | D4 | D2 |
| 2672 | CN | A2 | D2 | D4 | D3 |
| 2673 | CN | A2 | D2 | D4 | D4 |
| 2674 | CN | A2 | D2 | D4 | D5 |
| 2675 | CN | A2 | D2 | D4 | D6 |
| 2676 | CN | A2 | D2 | D5 | D1 |
| 2677 | CN | A2 | D2 | D5 | D2 |
| 2678 | CN | A2 | D2 | D5 | D3 |
| 2679 | CN | A2 | D2 | D5 | D4 |
| 2680 | CN | A2 | D2 | D5 | D5 |
| 2681 | CN | A2 | D2 | D5 | D6 |
| 2682 | CN | A2 | D2 | D6 | D1 |
| 2683 | CN | A2 | D2 | D6 | D2 |
| 2684 | CN | A2 | D2 | D6 | D3 |
| 2685 | CN | A2 | D2 | D6 | D4 |
| 2686 | CN | A2 | D2 | D6 | D5 |
| 2687 | CN | A2 | D2 | D6 | D6 |
| 2688 | CN | A2 | D3 | D1 | D1 |
| 2689 | CN | A2 | D3 | D1 | D2 |
| 2690 | CN | A2 | D3 | D1 | D3 |
| 2691 | CN | A2 | D3 | D1 | D4 |
| 2692 | CN | A2 | D3 | D1 | D5 |
| 2693 | CN | A2 | D3 | D1 | D6 |
| 2694 | CN | A2 | D3 | D2 | D1 |
| 2695 | CN | A2 | D3 | D2 | D2 |
| 2696 | CN | A2 | D3 | D2 | D3 |
| 2697 | CN | A2 | D3 | D2 | D4 |
| 2698 | CN | A2 | D3 | D2 | D5 |
| 2699 | CN | A2 | D3 | D2 | D6 |
| 2700 | CN | A2 | D3 | D3 | D1 |

TABLE 1-19

| No. | $R^1$ | $R^2$ | $R^3$ | $R^4$ | $R^5$ |
|---|---|---|---|---|---|
| 2701 | CN | A2 | D3 | D3 | D2 |
| 2702 | CN | A2 | D3 | D3 | D3 |
| 2703 | CN | A2 | D3 | D3 | D4 |
| 2704 | CN | A2 | D3 | D3 | D5 |
| 2705 | CN | A2 | D3 | D3 | D6 |
| 2706 | CN | A2 | D3 | D4 | D1 |
| 2707 | CN | A2 | D3 | D4 | D2 |
| 2708 | CN | A2 | D3 | D4 | D3 |
| 2709 | CN | A2 | D3 | D4 | D4 |
| 2710 | CN | A2 | D3 | D4 | D5 |
| 2711 | CN | A2 | D3 | D4 | D6 |
| 2712 | CN | A2 | D3 | D5 | D1 |
| 2713 | CN | A2 | D3 | D5 | D2 |
| 2714 | CN | A2 | D3 | D5 | D3 |
| 2715 | CN | A2 | D3 | D5 | D4 |
| 2716 | CN | A2 | D3 | D5 | D5 |
| 2717 | CN | A2 | D3 | D5 | D6 |
| 2718 | CN | A2 | D3 | D6 | D1 |
| 2719 | CN | A2 | D3 | D6 | D2 |
| 2720 | CN | A2 | D3 | D6 | D3 |
| 2721 | CN | A2 | D3 | D6 | D4 |
| 2722 | CN | A2 | D3 | D6 | D5 |
| 2723 | CN | A2 | D3 | D6 | D6 |
| 2724 | CN | A2 | D4 | D1 | D1 |
| 2725 | CN | A2 | D4 | D1 | D2 |
| 2726 | CN | A2 | D4 | D1 | D3 |
| 2727 | CN | A2 | D4 | D1 | D4 |
| 2728 | CN | A2 | D4 | D1 | D5 |
| 2729 | CN | A2 | D4 | D1 | D6 |
| 2730 | CN | A2 | D4 | D2 | D1 |
| 2731 | CN | A2 | D4 | D2 | D2 |
| 2732 | CN | A2 | D4 | D2 | D3 |
| 2733 | CN | A2 | D4 | D2 | D4 |
| 2734 | CN | A2 | D4 | D2 | D5 |
| 2735 | CN | A2 | D4 | D2 | D6 |
| 2736 | CN | A2 | D4 | D3 | D1 |
| 2737 | CN | A2 | D4 | D3 | D2 |
| 2738 | CN | A2 | D4 | D3 | D3 |
| 2739 | CN | A2 | D4 | D3 | D4 |
| 2740 | CN | A2 | D4 | D3 | D5 |
| 2741 | CN | A2 | D4 | D3 | D6 |
| 2742 | CN | A2 | D4 | D4 | D1 |
| 2743 | CN | A2 | D4 | D4 | D2 |
| 2744 | CN | A2 | D4 | D4 | D3 |
| 2745 | CN | A2 | D4 | D4 | D4 |
| 2746 | CN | A2 | D4 | D4 | D5 |
| 2747 | CN | A2 | D4 | D4 | D6 |
| 2748 | CN | A2 | D4 | D5 | D1 |
| 2749 | CN | A2 | D4 | D5 | D2 |
| 2750 | CN | A2 | D4 | D5 | D3 |
| 2751 | CN | A2 | D4 | D5 | D4 |
| 2752 | CN | A2 | D4 | D5 | D5 |
| 2753 | CN | A2 | D4 | D5 | D6 |
| 2754 | CN | A2 | D4 | D6 | D1 |
| 2755 | CN | A2 | D4 | D6 | D2 |
| 2756 | CN | A2 | D4 | D6 | D3 |
| 2757 | CN | A2 | D4 | D6 | D4 |
| 2758 | CN | A2 | D4 | D6 | D5 |
| 2759 | CN | A2 | D4 | D6 | D6 |
| 2760 | CN | A2 | D5 | D1 | D1 |
| 2761 | CN | A2 | D5 | D1 | D2 |
| 2762 | CN | A2 | D5 | D1 | D3 |
| 2763 | CN | A2 | D5 | D1 | D4 |
| 2764 | CN | A2 | D5 | D1 | D5 |
| 2765 | CN | A2 | D5 | D1 | D6 |
| 2766 | CN | A2 | D5 | D2 | D1 |
| 2767 | CN | A2 | D5 | D2 | D2 |
| 2768 | CN | A2 | D5 | D2 | D3 |
| 2769 | CN | A2 | D5 | D2 | D4 |
| 2770 | CN | A2 | D5 | D2 | D5 |
| 2771 | CN | A2 | D5 | D2 | D6 |
| 2772 | CN | A2 | D5 | D3 | D1 |
| 2773 | CN | A2 | D5 | D3 | D2 |
| 2774 | CN | A2 | D5 | D3 | D3 |
| 2775 | CN | A2 | D5 | D3 | D4 |
| 2776 | CN | A2 | D5 | D3 | D5 |
| 2777 | CN | A2 | D5 | D3 | D6 |
| 2778 | CN | A2 | D5 | D4 | D1 |

TABLE 1-19-continued

| No. | $R^1$ | $R^2$ | $R^3$ | $R^4$ | $R^5$ |
|---|---|---|---|---|---|
| 2779 | CN | A2 | D5 | D4 | D2 |
| 2780 | CN | A2 | D5 | D4 | D3 |
| 2781 | CN | A2 | D5 | D4 | D4 |
| 2782 | CN | A2 | D5 | D4 | D5 |
| 2783 | CN | A2 | D5 | D4 | D6 |
| 2784 | CN | A2 | D5 | D5 | D1 |
| 2785 | CN | A2 | D5 | D5 | D2 |
| 2786 | CN | A2 | D5 | D5 | D3 |
| 2787 | CN | A2 | D5 | D5 | D4 |
| 2788 | CN | A2 | D5 | D5 | D5 |
| 2789 | CN | A2 | D5 | D5 | D6 |
| 2790 | CN | A2 | D5 | D6 | D1 |
| 2791 | CN | A2 | D5 | D6 | D2 |
| 2792 | CN | A2 | D5 | D6 | D3 |
| 2793 | CN | A2 | D5 | D6 | D4 |
| 2794 | CN | A2 | D5 | D6 | D5 |
| 2795 | CN | A2 | D5 | D6 | D6 |
| 2796 | CN | A2 | D6 | D1 | D1 |
| 2797 | CN | A2 | D6 | D1 | D2 |
| 2798 | CN | A2 | D6 | D1 | D3 |
| 2799 | CN | A2 | D6 | D1 | D4 |
| 2800 | CN | A2 | D6 | D1 | D5 |
| 2801 | CN | A2 | D6 | D1 | D6 |
| 2802 | CN | A2 | D6 | D2 | D1 |
| 2803 | CN | A2 | D6 | D2 | D2 |
| 2804 | CN | A2 | D6 | D2 | D3 |
| 2805 | CN | A2 | D6 | D2 | D4 |
| 2806 | CN | A2 | D6 | D2 | D5 |
| 2807 | CN | A2 | D6 | D2 | D6 |
| 2808 | CN | A2 | D6 | D3 | D1 |
| 2809 | CN | A2 | D6 | D3 | D2 |
| 2810 | CN | A2 | D6 | D3 | D3 |
| 2811 | CN | A2 | D6 | D3 | D4 |
| 2812 | CN | A2 | D6 | D3 | D5 |
| 2813 | CN | A2 | D6 | D3 | D6 |
| 2814 | CN | A2 | D6 | D4 | D1 |
| 2815 | CN | A2 | D6 | D4 | D2 |
| 2816 | CN | A2 | D6 | D4 | D3 |
| 2817 | CN | A2 | D6 | D4 | D4 |
| 2818 | CN | A2 | D6 | D4 | D5 |
| 2819 | CN | A2 | D6 | D4 | D6 |
| 2820 | CN | A2 | D6 | D5 | D1 |
| 2821 | CN | A2 | D6 | D5 | D2 |
| 2822 | CN | A2 | D6 | D5 | D3 |
| 2823 | CN | A2 | D6 | D5 | D4 |
| 2824 | CN | A2 | D6 | D5 | D5 |
| 2825 | CN | A2 | D6 | D5 | D6 |
| 2826 | CN | A2 | D6 | D6 | D1 |
| 2827 | CN | A2 | D6 | D6 | D2 |
| 2828 | CN | A2 | D6 | D6 | D3 |
| 2829 | CN | A2 | D6 | D6 | D4 |
| 2830 | CN | A2 | D6 | D6 | D5 |
| 2831 | CN | A2 | D6 | D6 | D6 |
| 2832 | CN | A1 | H | D1 | D1 |
| 2833 | CN | A1 | H | D1 | D2 |
| 2834 | CN | A1 | H | D1 | D3 |
| 2835 | CN | A1 | H | D1 | D4 |
| 2836 | CN | A1 | H | D1 | D5 |
| 2837 | CN | A1 | H | D1 | D6 |
| 2838 | CN | A1 | H | D1 | D7 |
| 2839 | CN | A1 | H | D1 | D8 |
| 2840 | CN | A1 | H | D1 | D9 |
| 2841 | CN | A1 | H | D1 | D10 |
| 2842 | CN | A1 | H | D1 | D11 |
| 2843 | CN | A1 | H | D1 | D12 |
| 2844 | CN | A1 | H | D1 | D13 |
| 2845 | CN | A1 | H | D1 | D14 |
| 2846 | CN | A1 | H | D1 | D15 |
| 2847 | CN | A1 | H | D1 | D16 |
| 2848 | CN | A1 | H | D2 | D1 |
| 2849 | CN | A1 | H | D2 | D2 |
| 2850 | CN | A1 | H | D2 | D3 |

TABLE 1-20

| No. | $R^1$ | $R^2$ | $R^3$ | $R^4$ | $R^5$ |
|---|---|---|---|---|---|
| 2851 | CN | A1 | H | D2 | D4 |
| 2852 | CN | A1 | H | D2 | D5 |
| 2853 | CN | A1 | H | D2 | D6 |
| 2854 | CN | A1 | H | D2 | D7 |
| 2855 | CN | A1 | H | D2 | D8 |
| 2856 | CN | A1 | H | D2 | D9 |
| 2857 | CN | A1 | H | D2 | D10 |
| 2858 | CN | A1 | H | D2 | D11 |
| 2859 | CN | A1 | H | D2 | D12 |
| 2860 | CN | A1 | H | D2 | D13 |
| 2861 | CN | A1 | H | D2 | D14 |
| 2862 | CN | A1 | H | D2 | D15 |
| 2863 | CN | A1 | H | D2 | D16 |
| 2864 | CN | A1 | H | D3 | D1 |
| 2865 | CN | A1 | H | D3 | D2 |
| 2866 | CN | A1 | H | D3 | D3 |
| 2867 | CN | A1 | H | D3 | D4 |
| 2868 | CN | A1 | H | D3 | D5 |
| 2869 | CN | A1 | H | D3 | D6 |
| 2870 | CN | A1 | H | D3 | D7 |
| 2871 | CN | A1 | H | D3 | D8 |
| 2872 | CN | A1 | H | D3 | D9 |
| 2873 | CN | A1 | H | D3 | D10 |
| 2874 | CN | A1 | H | D3 | D11 |
| 2875 | CN | A1 | H | D3 | D12 |
| 2876 | CN | A1 | H | D3 | D13 |
| 2877 | CN | A1 | H | D3 | D14 |
| 2878 | CN | A1 | H | D3 | D15 |
| 2879 | CN | A1 | H | D3 | D16 |
| 2880 | CN | A1 | H | D4 | D1 |
| 2881 | CN | A1 | H | D4 | D2 |
| 2882 | CN | A1 | H | D4 | D3 |
| 2883 | CN | A1 | H | D4 | D4 |
| 2884 | CN | A1 | H | D4 | D5 |
| 2885 | CN | A1 | H | D4 | D6 |
| 2886 | CN | A1 | H | D4 | D7 |
| 2887 | CN | A1 | H | D4 | D8 |
| 2888 | CN | A1 | H | D4 | D9 |
| 2889 | CN | A1 | H | D4 | D10 |
| 2890 | CN | A1 | H | D4 | D11 |
| 2891 | CN | A1 | H | D4 | D12 |
| 2892 | CN | A1 | H | D4 | D13 |
| 2893 | CN | A1 | H | D4 | D14 |
| 2894 | CN | A1 | H | D4 | D15 |
| 2895 | CN | A1 | H | D4 | D16 |
| 2896 | CN | A1 | H | D5 | D1 |
| 2897 | CN | A1 | H | D5 | D2 |
| 2898 | CN | A1 | H | D5 | D3 |
| 2899 | CN | A1 | H | D5 | D4 |
| 2900 | CN | A1 | H | D5 | D5 |
| 2901 | CN | A1 | H | D5 | D6 |
| 2902 | CN | A1 | H | D5 | D7 |
| 2903 | CN | A1 | H | D5 | D8 |
| 2904 | CN | A1 | H | D5 | D9 |
| 2905 | CN | A1 | H | D5 | D10 |
| 2906 | CN | A1 | H | D5 | D11 |
| 2907 | CN | A1 | H | D5 | D12 |
| 2908 | CN | A1 | H | D5 | D13 |
| 2909 | CN | A1 | H | D5 | D14 |
| 2910 | CN | A1 | H | D5 | D15 |
| 2911 | CN | A1 | H | D5 | D16 |
| 2912 | CN | A1 | H | D6 | D1 |
| 2913 | CN | A1 | H | D6 | D2 |
| 2914 | CN | A1 | H | D6 | D3 |
| 2915 | CN | A1 | H | D6 | D4 |
| 2916 | CN | A1 | H | D6 | D5 |
| 2917 | CN | A1 | H | D6 | D6 |
| 2918 | CN | A1 | H | D6 | D7 |
| 2919 | CN | A1 | H | D6 | D8 |
| 2920 | CN | A1 | H | D6 | D9 |
| 2921 | CN | A1 | H | D6 | D10 |
| 2922 | CN | A1 | H | D6 | D11 |
| 2923 | CN | A1 | H | D6 | D12 |
| 2924 | CN | A1 | H | D6 | D13 |
| 2925 | CN | A1 | H | D6 | D14 |
| 2926 | CN | A1 | H | D6 | D15 |
| 2927 | CN | A1 | H | D6 | D16 |
| 2928 | CN | A1 | H | D7 | D1 |

TABLE 1-20-continued

| No. | $R^1$ | $R^2$ | $R^3$ | $R^4$ | $R^5$ |
|---|---|---|---|---|---|
| 2929 | CN | A1 | H | D7 | D2 |
| 2930 | CN | A1 | H | D7 | D3 |
| 2931 | CN | A1 | H | D7 | D4 |
| 2932 | CN | A1 | H | D7 | D5 |
| 2933 | CN | A1 | H | D7 | D6 |
| 2934 | CN | A1 | H | D7 | D7 |
| 2935 | CN | A1 | H | D7 | D8 |
| 2936 | CN | A1 | H | D7 | D9 |
| 2937 | CN | A1 | H | D7 | D10 |
| 2938 | CN | A1 | H | D7 | D11 |
| 2939 | CN | A1 | H | D7 | D12 |
| 2940 | CN | A1 | H | D7 | D13 |
| 2941 | CN | A1 | H | D7 | D14 |
| 2942 | CN | A1 | H | D7 | D15 |
| 2943 | CN | A1 | H | D7 | D16 |
| 2944 | CN | A1 | H | D8 | D1 |
| 2945 | CN | A1 | H | D8 | D2 |
| 2946 | CN | A1 | H | D8 | D3 |
| 2947 | CN | A1 | H | D8 | D4 |
| 2948 | CN | A1 | H | D8 | D5 |
| 2949 | CN | A1 | H | D8 | D6 |
| 2950 | CN | A1 | H | D8 | D7 |
| 2951 | CN | A1 | H | D8 | D8 |
| 2952 | CN | A1 | H | D8 | D9 |
| 2953 | CN | A1 | H | D8 | D10 |
| 2954 | CN | A1 | H | D8 | D11 |
| 2955 | CN | A1 | H | D8 | D12 |
| 2956 | CN | A1 | H | D8 | D13 |
| 2957 | CN | A1 | H | D8 | D14 |
| 2958 | CN | A1 | H | D8 | D15 |
| 2959 | CN | A1 | H | D8 | D16 |
| 2960 | CN | A1 | H | D9 | D1 |
| 2961 | CN | A1 | H | D9 | D2 |
| 2962 | CN | A1 | H | D9 | D3 |
| 2963 | CN | A1 | H | D9 | D4 |
| 2964 | CN | A1 | H | D9 | D5 |
| 2965 | CN | A1 | H | D9 | D6 |
| 2966 | CN | A1 | H | D9 | D7 |
| 2967 | CN | A1 | H | D9 | D8 |
| 2968 | CN | A1 | H | D9 | D9 |
| 2969 | CN | A1 | H | D9 | D10 |
| 2970 | CN | A1 | H | D9 | D11 |
| 2971 | CN | A1 | H | D9 | D12 |
| 2972 | CN | A1 | H | D9 | D13 |
| 2973 | CN | A1 | H | D9 | D14 |
| 2974 | CN | A1 | H | D9 | D15 |
| 2975 | CN | A1 | H | D9 | D16 |
| 2976 | CN | A1 | H | D10 | D1 |
| 2977 | CN | A1 | H | D10 | D2 |
| 2978 | CN | A1 | H | D10 | D3 |
| 2979 | CN | A1 | H | D10 | D4 |
| 2980 | CN | A1 | H | D10 | D5 |
| 2981 | CN | A1 | H | D10 | D6 |
| 2982 | CN | A1 | H | D10 | D7 |
| 2983 | CN | A1 | H | D10 | D8 |
| 2984 | CN | A1 | H | D10 | D9 |
| 2985 | CN | A1 | H | D10 | D10 |
| 2986 | CN | A1 | H | D10 | D11 |
| 2987 | CN | A1 | H | D10 | D12 |
| 2988 | CN | A1 | H | D10 | D13 |
| 2989 | CN | A1 | H | D10 | D14 |
| 2990 | CN | A1 | H | D10 | D15 |
| 2991 | CN | A1 | H | D10 | D16 |
| 2992 | CN | A1 | H | D11 | D1 |
| 2993 | CN | A1 | H | D11 | D2 |
| 2994 | CN | A1 | H | D11 | D3 |
| 2995 | CN | A1 | H | D11 | D4 |
| 2996 | CN | A1 | H | D11 | D5 |
| 2997 | CN | A1 | H | D11 | D6 |
| 2998 | CN | A1 | H | D11 | D7 |
| 2999 | CN | A1 | H | D11 | D8 |
| 3000 | CN | A1 | H | D11 | D9 |

TABLE 1-21

| No. | $R^1$ | $R^2$ | $R^3$ | $R^4$ | $R^5$ |
|---|---|---|---|---|---|
| 3001 | CN | A1 | H | D11 | D10 |
| 3002 | CN | A1 | H | D11 | D11 |
| 3003 | CN | A1 | H | D11 | D12 |
| 3004 | CN | A1 | H | D11 | D13 |
| 3005 | CN | A1 | H | D11 | D14 |
| 3006 | CN | A1 | H | D11 | D15 |
| 3007 | CN | A1 | H | D11 | D16 |
| 3008 | CN | A1 | H | D12 | D1 |
| 3009 | CN | A1 | H | D12 | D2 |
| 3010 | CN | A1 | H | D12 | D3 |
| 3011 | CN | A1 | H | D12 | D4 |
| 3012 | CN | A1 | H | D12 | D5 |
| 3013 | CN | A1 | H | D12 | D6 |
| 3014 | CN | A1 | H | D12 | D7 |
| 3015 | CN | A1 | H | D12 | D8 |
| 3016 | CN | A1 | H | D12 | D9 |
| 3017 | CN | A1 | H | D12 | D10 |
| 3018 | CN | A1 | H | D12 | D11 |
| 3019 | CN | A1 | H | D12 | D12 |
| 3020 | CN | A1 | H | D12 | D13 |
| 3021 | CN | A1 | H | D12 | D14 |
| 3022 | CN | A1 | H | D12 | D15 |
| 3023 | CN | A1 | H | D12 | D16 |
| 3024 | CN | A1 | H | D13 | D1 |
| 3025 | CN | A1 | H | D13 | D2 |
| 3026 | CN | A1 | H | D13 | D3 |
| 3027 | CN | A1 | H | D13 | D4 |
| 3028 | CN | A1 | H | D13 | D5 |
| 3029 | CN | A1 | H | D13 | D6 |
| 3030 | CN | A1 | H | D13 | D7 |
| 3031 | CN | A1 | H | D13 | D8 |
| 3032 | CN | A1 | H | D13 | D9 |
| 3033 | CN | A1 | H | D13 | D10 |
| 3034 | CN | A1 | H | D13 | D11 |
| 3035 | CN | A1 | H | D13 | D12 |
| 3036 | CN | A1 | H | D13 | D13 |
| 3037 | CN | A1 | H | D13 | D14 |
| 3038 | CN | A1 | H | D13 | D15 |
| 3039 | CN | A1 | H | D13 | D16 |
| 3040 | CN | A1 | H | D14 | D1 |
| 3041 | CN | A1 | H | D14 | D2 |
| 3042 | CN | A1 | H | D14 | D3 |
| 3043 | CN | A1 | H | D14 | D4 |
| 3044 | CN | A1 | H | D14 | D5 |
| 3045 | CN | A1 | H | D14 | D6 |
| 3046 | CN | A1 | H | D14 | D7 |
| 3047 | CN | A1 | H | D14 | D8 |
| 3048 | CN | A1 | H | D14 | D9 |
| 3049 | CN | A1 | H | D14 | D10 |
| 3050 | CN | A1 | H | D14 | D11 |
| 3051 | CN | A1 | H | D14 | D12 |
| 3052 | CN | A1 | H | D14 | D13 |
| 3053 | CN | A1 | H | D14 | D14 |
| 3054 | CN | A1 | H | D14 | D15 |
| 3055 | CN | A1 | H | D14 | D16 |
| 3056 | CN | A1 | H | D15 | D1 |
| 3057 | CN | A1 | H | D15 | D2 |
| 3058 | CN | A1 | H | D15 | D3 |
| 3059 | CN | A1 | H | D15 | D4 |
| 3060 | CN | A1 | H | D15 | D5 |
| 3061 | CN | A1 | H | D15 | D6 |
| 3062 | CN | A1 | H | D15 | D7 |
| 3063 | CN | A1 | H | D15 | D8 |
| 3064 | CN | A1 | H | D15 | D9 |
| 3065 | CN | A1 | H | D15 | D10 |
| 3066 | CN | A1 | H | D15 | D11 |
| 3067 | CN | A1 | H | D15 | D12 |
| 3068 | CN | A1 | H | D15 | D13 |
| 3069 | CN | A1 | H | D15 | D14 |
| 3070 | CN | A1 | H | D15 | D15 |
| 3071 | CN | A1 | H | D15 | D16 |
| 3072 | CN | A1 | H | D16 | D1 |
| 3073 | CN | A1 | H | D16 | D2 |
| 3074 | CN | A1 | H | D16 | D3 |
| 3075 | CN | A1 | H | D16 | D4 |
| 3076 | CN | A1 | H | D16 | D5 |
| 3077 | CN | A1 | H | D16 | D6 |
| 3078 | CN | A1 | H | D16 | D7 |

TABLE 1-21-continued

| No. | $R^1$ | $R^2$ | $R^3$ | $R^4$ | $R^5$ |
|---|---|---|---|---|---|
| 3079 | CN | A1 | H | D16 | D8 |
| 3080 | CN | A1 | H | D16 | D9 |
| 3081 | CN | A1 | H | D16 | D10 |
| 3082 | CN | A1 | H | D16 | D11 |
| 3083 | CN | A1 | H | D16 | D12 |
| 3084 | CN | A1 | H | D16 | D13 |
| 3085 | CN | A1 | H | D16 | D14 |
| 3086 | CN | A1 | H | D16 | D15 |
| 3087 | CN | A1 | H | D16 | D16 |
| 3088 | CN | A2 | H | D1 | D1 |
| 3089 | CN | A2 | H | D1 | D2 |
| 3090 | CN | A2 | H | D1 | D3 |
| 3091 | CN | A2 | H | D1 | D4 |
| 3092 | CN | A2 | H | D1 | D5 |
| 3093 | CN | A2 | H | D1 | D6 |
| 3094 | CN | A2 | H | D1 | D7 |
| 3095 | CN | A2 | H | D1 | D8 |
| 3096 | CN | A2 | H | D1 | D9 |
| 3097 | CN | A2 | H | D1 | D10 |
| 3098 | CN | A2 | H | D1 | D11 |
| 3099 | CN | A2 | H | D1 | D12 |
| 3100 | CN | A2 | H | D1 | D13 |
| 3101 | CN | A2 | H | D1 | D14 |
| 3102 | CN | A2 | H | D1 | D15 |
| 3103 | CN | A2 | H | D1 | D16 |
| 3104 | CN | A2 | H | D2 | D1 |
| 3105 | CN | A2 | H | D2 | D2 |
| 3106 | CN | A2 | H | D2 | D3 |
| 3107 | CN | A2 | H | D2 | D4 |
| 3108 | CN | A2 | H | D2 | D5 |
| 3109 | CN | A2 | H | D2 | D6 |
| 3110 | CN | A2 | H | D2 | D7 |
| 3111 | CN | A2 | H | D2 | D8 |
| 3112 | CN | A2 | H | D2 | D9 |
| 3113 | CN | A2 | H | D2 | D10 |
| 3114 | CN | A2 | H | D2 | D11 |
| 3115 | CN | A2 | H | D2 | D12 |
| 3116 | CN | A2 | H | D2 | D13 |
| 3117 | CN | A2 | H | D2 | D14 |
| 3118 | CN | A2 | H | D2 | D15 |
| 3119 | CN | A2 | H | D2 | D16 |
| 3120 | CN | A2 | H | D3 | D1 |
| 3121 | CN | A2 | H | D3 | D2 |
| 3122 | CN | A2 | H | D3 | D3 |
| 3123 | CN | A2 | H | D3 | D4 |
| 3124 | CN | A2 | H | D3 | D5 |
| 3125 | CN | A2 | H | D3 | D6 |
| 3126 | CN | A2 | H | D3 | D7 |
| 3127 | CN | A2 | H | D3 | D8 |
| 3128 | CN | A2 | H | D3 | D9 |
| 3129 | CN | A2 | H | D3 | D10 |
| 3130 | CN | A2 | H | D3 | D11 |
| 3131 | CN | A2 | H | D3 | D12 |
| 3132 | CN | A2 | H | D3 | D13 |
| 3133 | CN | A2 | H | D3 | D14 |
| 3134 | CN | A2 | H | D3 | D15 |
| 3135 | CN | A2 | H | D3 | D16 |
| 3136 | CN | A2 | H | D4 | D1 |
| 3137 | CN | A2 | H | D4 | D2 |
| 3138 | CN | A2 | H | D4 | D3 |
| 3139 | CN | A2 | H | D4 | D4 |
| 3140 | CN | A2 | H | D4 | D5 |
| 3141 | CN | A2 | H | D4 | D6 |
| 3142 | CN | A2 | H | D4 | D7 |
| 3143 | CN | A2 | H | D4 | D8 |
| 3144 | CN | A2 | H | D4 | D9 |
| 3145 | CN | A2 | H | D4 | D10 |
| 3146 | CN | A2 | H | D4 | D11 |
| 3147 | CN | A2 | H | D4 | D12 |
| 3148 | CN | A2 | H | D4 | D13 |
| 3149 | CN | A2 | H | D4 | D14 |
| 3150 | CN | A2 | H | D4 | D15 |

TABLE 1-22

| No. | $R^1$ | $R^2$ | $R^3$ | $R^4$ | $R^5$ |
|---|---|---|---|---|---|
| 3151 | CN | A2 | H | D4 | D16 |
| 3152 | CN | A2 | H | D5 | D1 |
| 3153 | CN | A2 | H | D5 | D2 |
| 3154 | CN | A2 | H | D5 | D3 |
| 3155 | CN | A2 | H | D5 | D4 |
| 3156 | CN | A2 | H | D5 | D5 |
| 3157 | CN | A2 | H | D5 | D6 |
| 3158 | CN | A2 | H | D5 | D7 |
| 3159 | CN | A2 | H | D5 | D8 |
| 3160 | CN | A2 | H | D5 | D9 |
| 3161 | CN | A2 | H | D5 | D10 |
| 3162 | CN | A2 | H | D5 | D11 |
| 3163 | CN | A2 | H | D5 | D12 |
| 3164 | CN | A2 | H | D5 | D13 |
| 3165 | CN | A2 | H | D5 | D14 |
| 3166 | CN | A2 | H | D5 | D15 |
| 3167 | CN | A2 | H | D5 | D16 |
| 3168 | CN | A2 | H | D6 | D1 |
| 3169 | CN | A2 | H | D6 | D2 |
| 3170 | CN | A2 | H | D6 | D3 |
| 3171 | CN | A2 | H | D6 | D4 |
| 3172 | CN | A2 | H | D6 | D5 |
| 3173 | CN | A2 | H | D6 | D6 |
| 3174 | CN | A2 | H | D6 | D7 |
| 3175 | CN | A2 | H | D6 | D8 |
| 3176 | CN | A2 | H | D6 | D9 |
| 3177 | CN | A2 | H | D6 | D10 |
| 3178 | CN | A2 | H | D6 | D11 |
| 3179 | CN | A2 | H | D6 | D12 |
| 3180 | CN | A2 | H | D6 | D13 |
| 3181 | CN | A2 | H | D6 | D14 |
| 3182 | CN | A2 | H | D6 | D15 |
| 3183 | CN | A2 | H | D6 | D16 |
| 3184 | CN | A2 | H | D7 | D1 |
| 3185 | CN | A2 | H | D7 | D2 |
| 3186 | CN | A2 | H | D7 | D3 |
| 3187 | CN | A2 | H | D7 | D4 |
| 3188 | CN | A2 | H | D7 | D5 |
| 3189 | CN | A2 | H | D7 | D6 |
| 3190 | CN | A2 | H | D7 | D7 |
| 3191 | CN | A2 | H | D7 | D8 |
| 3192 | CN | A2 | H | D7 | D9 |
| 3193 | CN | A2 | H | D7 | D10 |
| 3194 | CN | A2 | H | D7 | D11 |
| 3195 | CN | A2 | H | D7 | D12 |
| 3196 | CN | A2 | H | D7 | D13 |
| 3197 | CN | A2 | H | D7 | D14 |
| 3198 | CN | A2 | H | D7 | D15 |
| 3199 | CN | A2 | H | D7 | D16 |
| 3200 | CN | A2 | H | D8 | D1 |
| 3201 | CN | A2 | H | D8 | D2 |
| 3202 | CN | A2 | H | D8 | D3 |
| 3203 | CN | A2 | H | D8 | D4 |
| 3204 | CN | A2 | H | D8 | D5 |
| 3205 | CN | A2 | H | D8 | D6 |
| 3206 | CN | A2 | H | D8 | D7 |
| 3207 | CN | A2 | H | D8 | D8 |
| 3208 | CN | A2 | H | D8 | D9 |
| 3209 | CN | A2 | H | D8 | D10 |
| 3210 | CN | A2 | H | D8 | D11 |
| 3211 | CN | A2 | H | D8 | D12 |
| 3212 | CN | A2 | H | D8 | D13 |
| 3213 | CN | A2 | H | D8 | D14 |
| 3214 | CN | A2 | H | D8 | D15 |
| 3215 | CN | A2 | H | D8 | D16 |
| 3216 | CN | A2 | H | D9 | D1 |
| 3217 | CN | A2 | H | D9 | D2 |
| 3218 | CN | A2 | H | D9 | D3 |
| 3219 | CN | A2 | H | D9 | D4 |
| 3220 | CN | A2 | H | D9 | D5 |
| 3221 | CN | A2 | H | D9 | D6 |
| 3222 | CN | A2 | H | D9 | D7 |
| 3223 | CN | A2 | H | D9 | D8 |
| 3224 | CN | A2 | H | D9 | D9 |
| 3225 | CN | A2 | H | D9 | D10 |
| 3226 | CN | A2 | H | D9 | D11 |
| 3227 | CN | A2 | H | D9 | D12 |
| 3228 | CN | A2 | H | D9 | D13 |

TABLE 1-22-continued

| No. | $R^1$ | $R^2$ | $R^3$ | $R^4$ | $R^5$ |
|---|---|---|---|---|---|
| 3229 | CN | A2 | H | D9 | D14 |
| 3230 | CN | A2 | H | D9 | D15 |
| 3231 | CN | A2 | H | D9 | D16 |
| 3232 | CN | A2 | H | D10 | D1 |
| 3233 | CN | A2 | H | D10 | D2 |
| 3234 | CN | A2 | H | D10 | D3 |
| 3235 | CN | A2 | H | D10 | D4 |
| 3236 | CN | A2 | H | D10 | D5 |
| 3237 | CN | A2 | H | D10 | D6 |
| 3238 | CN | A2 | H | D10 | D7 |
| 3239 | CN | A2 | H | D10 | D8 |
| 3240 | CN | A2 | H | D10 | D9 |
| 3241 | CN | A2 | H | D10 | D10 |
| 3242 | CN | A2 | H | D10 | D11 |
| 3243 | CN | A2 | H | D10 | D12 |
| 3244 | CN | A2 | H | D10 | D13 |
| 3245 | CN | A2 | H | D10 | D14 |
| 3246 | CN | A2 | H | D10 | D15 |
| 3247 | CN | A2 | H | D10 | D16 |
| 3248 | CN | A2 | H | D11 | D1 |
| 3249 | CN | A2 | H | D11 | D2 |
| 3250 | CN | A2 | H | D11 | D3 |
| 3251 | CN | A2 | H | D11 | D4 |
| 3252 | CN | A2 | H | D11 | D5 |
| 3253 | CN | A2 | H | D11 | D6 |
| 3254 | CN | A2 | H | D11 | D7 |
| 3255 | CN | A2 | H | D11 | D8 |
| 3256 | CN | A2 | H | D11 | D9 |
| 3257 | CN | A2 | H | D11 | D10 |
| 3258 | CN | A2 | H | D11 | D11 |
| 3259 | CN | A2 | H | D11 | D12 |
| 3260 | CN | A2 | H | D11 | D13 |
| 3261 | CN | A2 | H | D11 | D14 |
| 3262 | CN | A2 | H | D11 | D15 |
| 3263 | CN | A2 | H | D11 | D16 |
| 3264 | CN | A2 | H | D12 | D1 |
| 3265 | CN | A2 | H | D12 | D2 |
| 3266 | CN | A2 | H | D12 | D3 |
| 3267 | CN | A2 | H | D12 | D4 |
| 3268 | CN | A2 | H | D12 | D5 |
| 3269 | CN | A2 | H | D12 | D6 |
| 3270 | CN | A2 | H | D12 | D7 |
| 3271 | CN | A2 | H | D12 | D8 |
| 3272 | CN | A2 | H | D12 | D9 |
| 3273 | CN | A2 | H | D12 | D10 |
| 3274 | CN | A2 | H | D12 | D11 |
| 3275 | CN | A2 | H | D12 | D12 |
| 3276 | CN | A2 | H | D12 | D13 |
| 3277 | CN | A2 | H | D12 | D14 |
| 3278 | CN | A2 | H | D12 | D15 |
| 3279 | CN | A2 | H | D12 | D16 |
| 3280 | CN | A2 | H | D13 | D1 |
| 3281 | CN | A2 | H | D13 | D2 |
| 3282 | CN | A2 | H | D13 | D3 |
| 3283 | CN | A2 | H | D13 | D4 |
| 3284 | CN | A2 | H | D13 | D5 |
| 3285 | CN | A2 | H | D13 | D6 |
| 3286 | CN | A2 | H | D13 | D7 |
| 3287 | CN | A2 | H | D13 | D8 |
| 3288 | CN | A2 | H | D13 | D9 |
| 3289 | CN | A2 | H | D13 | D10 |
| 3290 | CN | A2 | H | D13 | D11 |
| 3291 | CN | A2 | H | D13 | D12 |
| 3292 | CN | A2 | H | D13 | D13 |
| 3293 | CN | A2 | H | D13 | D14 |
| 3294 | CN | A2 | H | D13 | D15 |
| 3295 | CN | A2 | H | D13 | D16 |
| 3296 | CN | A2 | H | D14 | D1 |
| 3297 | CN | A2 | H | D14 | D2 |
| 3298 | CN | A2 | H | D14 | D3 |
| 3299 | CN | A2 | H | D14 | D4 |
| 3300 | CN | A2 | H | D14 | D5 |

TABLE 1-23

| No. | $R^1$ | $R^2$ | $R^3$ | $R^4$ | $R^5$ |
|---|---|---|---|---|---|
| 3301 | CN | A2 | H | D14 | D6 |
| 3302 | CN | A2 | H | D14 | D7 |
| 3303 | CN | A2 | H | D14 | D8 |
| 3304 | CN | A2 | H | D14 | D9 |
| 3305 | CN | A2 | H | D14 | D10 |
| 3306 | CN | A2 | H | D14 | D11 |
| 3307 | CN | A2 | H | D14 | D12 |
| 3308 | CN | A2 | H | D14 | D13 |
| 3309 | CN | A2 | H | D14 | D14 |
| 3310 | CN | A2 | H | D14 | D15 |
| 3311 | CN | A2 | H | D14 | D16 |
| 3312 | CN | A2 | H | D15 | D1 |
| 3313 | CN | A2 | H | D15 | D2 |
| 3314 | CN | A2 | H | D15 | D3 |
| 3315 | CN | A2 | H | D15 | D4 |
| 3316 | CN | A2 | H | D15 | D5 |
| 3317 | CN | A2 | H | D15 | D6 |
| 3318 | CN | A2 | H | D15 | D7 |
| 3319 | CN | A2 | H | D15 | D8 |
| 3320 | CN | A2 | H | D15 | D9 |
| 3321 | CN | A2 | H | D15 | D10 |
| 3322 | CN | A2 | H | D15 | D11 |
| 3323 | CN | A2 | H | D15 | D12 |
| 3324 | CN | A2 | H | D15 | D13 |
| 3325 | CN | A2 | H | D15 | D14 |
| 3326 | CN | A2 | H | D15 | D15 |
| 3327 | CN | A2 | H | D15 | D16 |
| 3328 | CN | A2 | H | D16 | D1 |
| 3329 | CN | A2 | H | D16 | D2 |
| 3330 | CN | A2 | H | D16 | D3 |
| 3331 | CN | A2 | H | D16 | D4 |
| 3332 | CN | A2 | H | D16 | D5 |
| 3333 | CN | A2 | H | D16 | D6 |
| 3334 | CN | A2 | H | D16 | D7 |
| 3335 | CN | A2 | H | D16 | D8 |
| 3336 | CN | A2 | H | D16 | D9 |
| 3337 | CN | A2 | H | D16 | D10 |
| 3338 | CN | A2 | H | D16 | D11 |
| 3339 | CN | A2 | H | D16 | D12 |
| 3340 | CN | A2 | H | D16 | D13 |
| 3341 | CN | A2 | H | D16 | D14 |
| 3342 | CN | A2 | H | D16 | D15 |
| 3343 | CN | A2 | H | D16 | D16 |
| 3344 | A1 | CN | D1 | D1 | D1 |
| 3345 | A1 | CN | D1 | D1 | D2 |
| 3346 | A1 | CN | D1 | D1 | D3 |
| 3347 | A1 | CN | D1 | D1 | D4 |
| 3348 | A1 | CN | D1 | D1 | D5 |
| 3349 | A1 | CN | D1 | D1 | D6 |
| 3350 | A1 | CN | D1 | D2 | D1 |
| 3351 | A1 | CN | D1 | D2 | D2 |
| 3352 | A1 | CN | D1 | D2 | D3 |
| 3353 | A1 | CN | D1 | D2 | D4 |
| 3354 | A1 | CN | D1 | D2 | D5 |
| 3355 | A1 | CN | D1 | D2 | D6 |
| 3356 | A1 | CN | D1 | D3 | D1 |
| 3357 | A1 | CN | D1 | D3 | D2 |
| 3358 | A1 | CN | D1 | D3 | D3 |
| 3359 | A1 | CN | D1 | D3 | D4 |
| 3360 | A1 | CN | D1 | D3 | D5 |
| 3361 | A1 | CN | D1 | D3 | D6 |
| 3362 | A1 | CN | D1 | D4 | D1 |
| 3363 | A1 | CN | D1 | D4 | D2 |
| 3364 | A1 | CN | D1 | D4 | D3 |
| 3365 | A1 | CN | D1 | D4 | D4 |
| 3366 | A1 | CN | D1 | D4 | D5 |
| 3367 | A1 | CN | D1 | D4 | D6 |
| 3368 | A1 | CN | D1 | D5 | D1 |
| 3369 | A1 | CN | D1 | D5 | D2 |
| 3370 | A1 | CN | D1 | D5 | D3 |
| 3371 | A1 | CN | D1 | D5 | D4 |
| 3372 | A1 | CN | D1 | D5 | D5 |
| 3373 | A1 | CN | D1 | D5 | D6 |
| 3374 | A1 | CN | D1 | D6 | D1 |
| 3375 | A1 | CN | D1 | D6 | D2 |
| 3376 | A1 | CN | D1 | D6 | D3 |
| 3377 | A1 | CN | D1 | D6 | D4 |
| 3378 | A1 | CN | D1 | D6 | D5 |

TABLE 1-23-continued

| No. | $R^1$ | $R^2$ | $R^3$ | $R^4$ | $R^5$ |
|---|---|---|---|---|---|
| 3379 | A1 | CN | D1 | D6 | D6 |
| 3380 | A1 | CN | D2 | D1 | D1 |
| 3381 | A1 | CN | D2 | D1 | D2 |
| 3382 | A1 | CN | D2 | D1 | D3 |
| 3383 | A1 | CN | D2 | D1 | D4 |
| 3384 | A1 | CN | D2 | D1 | D5 |
| 3385 | A1 | CN | D2 | D1 | D6 |
| 3386 | A1 | CN | D2 | D2 | D1 |
| 3387 | A1 | CN | D2 | D2 | D2 |
| 3388 | A1 | CN | D2 | D2 | D3 |
| 3389 | A1 | CN | D2 | D2 | D4 |
| 3390 | A1 | CN | D2 | D2 | D5 |
| 3391 | A1 | CN | D2 | D2 | D6 |
| 3392 | A1 | CN | D2 | D3 | D1 |
| 3393 | A1 | CN | D2 | D3 | D2 |
| 3394 | A1 | CN | D2 | D3 | D3 |
| 3395 | A1 | CN | D2 | D3 | D4 |
| 3396 | A1 | CN | D2 | D3 | D5 |
| 3397 | A1 | CN | D2 | D3 | D6 |
| 3398 | A1 | CN | D2 | D4 | D1 |
| 3399 | A1 | CN | D2 | D4 | D2 |
| 3400 | A1 | CN | D2 | D4 | D3 |
| 3401 | A1 | CN | D2 | D4 | D4 |
| 3402 | A1 | CN | D2 | D4 | D5 |
| 3403 | A1 | CN | D2 | D4 | D6 |
| 3404 | A1 | CN | D2 | D5 | D1 |
| 3405 | A1 | CN | D2 | D5 | D2 |
| 3406 | A1 | CN | D2 | D5 | D3 |
| 3407 | A1 | CN | D2 | D5 | D4 |
| 3408 | A1 | CN | D2 | D5 | D5 |
| 3409 | A1 | CN | D2 | D5 | D6 |
| 3410 | A1 | CN | D2 | D6 | D1 |
| 3411 | A1 | CN | D2 | D6 | D2 |
| 3412 | A1 | CN | D2 | D6 | D3 |
| 3413 | A1 | CN | D2 | D6 | D4 |
| 3414 | A1 | CN | D2 | D6 | D5 |
| 3415 | A1 | CN | D2 | D6 | D6 |
| 3416 | A1 | CN | D3 | D1 | D1 |
| 3417 | A1 | CN | D3 | D1 | D2 |
| 3418 | A1 | CN | D3 | D1 | D3 |
| 3419 | A1 | CN | D3 | D1 | D4 |
| 3420 | A1 | CN | D3 | D1 | D5 |
| 3421 | A1 | CN | D3 | D1 | D6 |
| 3422 | A1 | CN | D3 | D2 | D1 |
| 3423 | A1 | CN | D3 | D2 | D2 |
| 3424 | A1 | CN | D3 | D2 | D3 |
| 3425 | A1 | CN | D3 | D2 | D4 |
| 3426 | A1 | CN | D3 | D2 | D5 |
| 3427 | A1 | CN | D3 | D2 | D6 |
| 3428 | A1 | CN | D3 | D3 | D1 |
| 3429 | A1 | CN | D3 | D3 | D2 |
| 3430 | A1 | CN | D3 | D3 | D3 |
| 3431 | A1 | CN | D3 | D3 | D4 |
| 3432 | A1 | CN | D3 | D3 | D5 |
| 3433 | A1 | CN | D3 | D3 | D6 |
| 3434 | A1 | CN | D3 | D4 | D1 |
| 3435 | A1 | CN | D3 | D4 | D2 |
| 3436 | A1 | CN | D3 | D4 | D3 |
| 3437 | A1 | CN | D3 | D4 | D4 |
| 3438 | A1 | CN | D3 | D4 | D5 |
| 3439 | A1 | CN | D3 | D4 | D6 |
| 3440 | A1 | CN | D3 | D5 | D1 |
| 3441 | A1 | CN | D3 | D5 | D2 |
| 3442 | A1 | CN | D3 | D5 | D3 |
| 3443 | A1 | CN | D3 | D5 | D4 |
| 3444 | A1 | CN | D3 | D5 | D5 |
| 3445 | A1 | CN | D3 | D5 | D6 |
| 3446 | A1 | CN | D3 | D6 | D1 |
| 3447 | A1 | CN | D3 | D6 | D2 |
| 3448 | A1 | CN | D3 | D6 | D3 |
| 3449 | A1 | CN | D3 | D6 | D4 |
| 3450 | A1 | CN | D3 | D6 | D5 |

TABLE 1-24

| No. | $R^1$ | $R^2$ | $R^3$ | $R^4$ | $R^5$ |
|---|---|---|---|---|---|
| 3451 | A1 | CN | D3 | D6 | D6 |
| 3452 | A1 | CN | D4 | D1 | D1 |
| 3453 | A1 | CN | D4 | D1 | D2 |
| 3454 | A1 | CN | D4 | D1 | D3 |
| 3455 | A1 | CN | D4 | D1 | D4 |
| 3456 | A1 | CN | D4 | D1 | D5 |
| 3457 | A1 | CN | D4 | D1 | D6 |
| 3458 | A1 | CN | D4 | D2 | D1 |
| 3459 | A1 | CN | D4 | D2 | D2 |
| 3460 | A1 | CN | D4 | D2 | D3 |
| 3461 | A1 | CN | D4 | D2 | D4 |
| 3462 | A1 | CN | D4 | D2 | D5 |
| 3463 | A1 | CN | D4 | D2 | D6 |
| 3464 | A1 | CN | D4 | D3 | D1 |
| 3465 | A1 | CN | D4 | D3 | D2 |
| 3466 | A1 | CN | D4 | D3 | D3 |
| 346? | A1 | CN | D4 | D3 | D4 |
| 3468 | A1 | CN | D4 | D3 | D5 |
| 3469 | A1 | CN | D4 | D3 | D6 |
| 3470 | A1 | CN | D4 | D4 | D1 |
| 3471 | A1 | CN | D4 | D4 | D2 |
| 3472 | A1 | CN | D4 | D4 | D3 |
| 3473 | A1 | CN | D4 | D4 | D4 |
| 3474 | A1 | CN | D4 | D4 | D5 |
| 3475 | A1 | CN | D4 | D4 | D6 |
| 3476 | A1 | CN | D4 | D5 | D1 |
| 3477 | A1 | CN | D4 | D5 | D2 |
| 3478 | A1 | CN | D4 | D5 | D3 |
| 3479 | A1 | CN | D4 | D5 | D4 |
| 3480 | A1 | CN | D4 | D5 | D5 |
| 3481 | A1 | CN | D4 | D5 | D6 |
| 3482 | A1 | CN | D4 | D6 | D1 |
| 3483 | A1 | CN | D4 | D6 | D2 |
| 3484 | A1 | CN | D4 | D6 | D3 |
| 3485 | A1 | CN | D4 | D6 | D4 |
| 3486 | A1 | CN | D4 | D6 | D5 |
| 3487 | A1 | CN | D4 | D5 | D6 |
| 3488 | A1 | CN | D5 | D1 | D1 |
| 3489 | A1 | CN | D5 | D1 | D2 |
| 3490 | A1 | CN | D5 | D1 | D3 |
| 3491 | A1 | CN | D5 | D1 | D4 |
| 3492 | A1 | CN | D5 | D1 | D5 |
| 3493 | A1 | CN | D5 | D1 | D6 |
| 3494 | A1 | CN | D5 | D2 | D1 |
| 3495 | A1 | CN | D5 | D2 | D2 |
| 3496 | A1 | CN | D5 | D2 | D3 |
| 3497 | A1 | CN | D5 | D1 | D4 |
| 3498 | A1 | CN | D5 | D2 | D5 |
| 3499 | A1 | CN | D5 | D2 | D6 |
| 3500 | A1 | CN | D5 | D3 | D1 |
| 3501 | A1 | CN | D5 | D3 | D2 |
| 35D2 | A1 | CN | D5 | D3 | D3 |
| 3503 | A1 | CN | D5 | D3 | D4 |
| 3504 | A1 | CN | D5 | D3 | D5 |
| 3505 | A1 | CN | D5 | D3 | D6 |
| 3506 | A1 | CN | D5 | D4 | D1 |
| 3507 | A1 | CN | D5 | D4 | D7 |
| 3508 | A1 | CN | D5 | D4 | D3 |
| 3509 | A1 | CN | D5 | D4 | D4 |
| 3510 | A1 | CN | D5 | D4 | D5 |
| 3511 | A1 | CN | D5 | D4 | D6 |
| 3512 | A1 | CN | D5 | D5 | D1 |
| 3513 | A1 | CN | D5 | D5 | D2 |
| 3514 | A1 | CN | D5 | D5 | D3 |
| 3515 | A1 | CN | D5 | D5 | D4 |
| 3516 | A1 | CN | D5 | D5 | D5 |
| 3517 | A1 | CN | D5 | D5 | D5 |
| 3518 | A1 | CN | D5 | D6 | D1 |
| 3519 | A1 | CN | D5 | D6 | D2 |
| 3520 | A1 | CN | D5 | D6 | D2 |
| 3521 | A1 | CN | D5 | D6 | D4 |
| 3522 | A1 | CN | D5 | D6 | D5 |
| 3523 | A1 | CN | D5 | D6 | D6 |
| 3524 | A1 | CN | D6 | D1 | D1 |
| 3525 | A1 | CN | D6 | D1 | D2 |
| 3526 | A1 | CN | D6 | D1 | D3 |
| 3527 | A1 | CN | D6 | D1 | D4 |
| 3528 | A1 | CN | D6 | D1 | D1 |

TABLE 1-24-continued

| No. | $R^1$ | $R^2$ | $R^3$ | $R^4$ | $R^5$ |
|---|---|---|---|---|---|
| 3529 | A1 | CN | D6 | D1 | D1 |
| 3530 | A1 | CN | D6 | D2 | D1 |
| 3531 | A1 | CN | D6 | D2 | D2 |
| 3532 | A1 | CN | D6 | D2 | D3 |
| 3533 | A1 | CN | D6 | D2 | D4 |
| 3534 | A1 | CN | D6 | D2 | D5 |
| 3535 | A1 | CN | D5 | D2 | D6 |
| 3536 | A1 | CN | D5 | D3 | D6 |
| 3537 | A1 | CN | D6 | D5 | D6 |
| 3538 | A1 | CN | D6 | D5 | D6 |
| 3539 | A1 | CN | D6 | D3 | D4 |
| 3540 | A1 | CN | D6 | D3 | 05 |
| 3541 | A1 | CN | D6 | D3 | D6 |
| 3542 | A1 | CN | D6 | D4 | D1 |
| 3543 | A1 | CN | D6 | D4 | D2 |
| 3544 | A1 | CN | D6 | D4 | D5 |
| 3545 | A1 | CN | D6 | D4 | D4 |
| 3546 | A1 | CN | D6 | D4 | D5 |
| 3547 | A1 | CN | D6 | D4 | D6 |
| 3548 | A1 | CN | D5 | D5 | D1 |
| 3549 | A1 | CN | D5 | D5 | D2 |
| 3550 | A1 | CN | D6 | D5 | D3 |
| 3551 | A1 | CN | D6 | D5 | D4 |
| 3552 | A1 | CN | D6 | D5 | D5 |
| 3553 | A1 | CN | D6 | D5 | D6 |
| 3554 | A1 | CN | D6 | D5 | D1 |
| 3555 | A1 | CN | D6 | D6 | D2 |
| 3556 | A1 | CN | D6 | D6 | D3 |
| 3557 | A1 | CN | D6 | D6 | D4 |
| 3558 | A1 | CN | D6 | D6 | D5 |
| 3559 | A1 | CN | D6 | D6 | D6 |
| 3560 | A2 | CN | D1 | D1 | D1 |
| 3561 | A2 | CN | D1 | D1 | D2 |
| 3562 | A2 | CN | D1 | D1 | D3 |
| 3563 | A2 | CN | D1 | D1 | D4 |
| 3564 | A2 | CN | D1 | D1 | D5 |
| 3565 | A2 | CN | D1 | D1 | D6 |
| 3565 | A2 | CN | D1 | D2 | D1 |
| 3567 | A2 | CN | D1 | D2 | D2 |
| 3568 | A2 | CN | D1 | D2 | D3 |
| 3569 | A2 | CN | D1 | D2 | D4 |
| 3570 | A2 | CN | D1 | D7 | D5 |
| 3571 | A2 | CN | D1 | D2 | D6 |
| 3572 | A2 | CN | D1 | D3 | D1 |
| 3573 | A2 | CN | D1 | D3 | D2 |
| 3574 | A2 | CN | D1 | D3 | D3 |
| 357b | A2 | CN | D1 | D3 | D4 |
| 3576 | A2 | CN | D1 | D3 | D5 |
| 3577 | A2 | CN | D1 | D3 | D6 |
| 3578 | A2 | CN | D1 | D4 | D1 |
| 3579 | A2 | CN | D1 | D4 | D2 |
| 3580 | A2 | CN | D1 | D4 | D3 |
| 3581 | A2 | CN | D1 | D4 | D4 |
| 3582 | A2 | CN | D1 | D4 | D5 |
| 3583 | A2 | CN | D1 | D4 | D6 |
| 3584 | A2 | CN | D1 | D5 | D1 |
| 3585 | A2 | CN | D1 | D5 | D2 |
| 3586 | A2 | CN | D1 | D5 | D3 |
| 3587 | A2 | CN | D1 | D5 | D4 |
| 3588 | A2 | CN | D1 | D5 | D5 |
| 3589 | A2 | CN | D1 | D5 | D6 |
| 3590 | A2 | CN | D1 | D6 | D1 |
| 3591 | A2 | CN | D1 | D6 | D2 |
| 3592 | A2 | CN | D1 | D6 | D3 |
| 3593 | A2 | CN | D1 | D6 | D4 |
| 3594 | A2 | CN | D1 | D5 | D5 |
| 3595 | A2 | CN | D1 | D6 | D6 |
| 3596 | A2 | CN | D2 | D1 | D1 |
| 3597 | A2 | CN | D2 | D1 | D2 |
| 3598 | A2 | CN | D2 | D1 | D3 |
| 3599 | A2 | CN | D2 | D1 | D4 |
| 3600 | A2 | CN | D2 | D1 | D5 |

TABLE 1-25

| No. | $R^1$ | $R^2$ | $R^3$ | $R^4$ | $R^5$ |
|---|---|---|---|---|---|
| 3601 | A2 | CN | D2 | D1 | D6 |
| 3602 | A2 | CN | D2 | D2 | D1 |
| 3603 | A2 | CN | D2 | D2 | D2 |
| 3604 | A2 | CN | D2 | D2 | D3 |
| 3605 | A2 | CN | D2 | D2 | D4 |
| 3606 | A2 | CN | D2 | D2 | D5 |
| 3607 | A2 | CN | D2 | D2 | D6 |
| 3608 | A2 | CN | D2 | D3 | D1 |
| 3609 | A2 | CN | D2 | D3 | D2 |
| 3610 | A2 | CN | D2 | D3 | D3 |
| 3611 | A2 | CN | D2 | D3 | D4 |
| 3612 | A2 | CN | D2 | D3 | D5 |
| 3613 | A2 | CN | D2 | D3 | D6 |
| 3614 | A2 | CN | D2 | D4 | D1 |
| 3615 | A2 | CN | D2 | D4 | D2 |
| 3616 | A2 | CN | D2 | D4 | D3 |
| 3617 | A2 | CN | D2 | D4 | D4 |
| 3618 | A2 | CN | D2 | D4 | D5 |
| 3619 | A2 | CN | D2 | D4 | D6 |
| 3620 | A2 | CN | D2 | D5 | D1 |
| 3621 | A2 | CN | D2 | D5 | D2 |
| 3622 | A2 | CN | D2 | D5 | D3 |
| 3623 | A2 | CN | D2 | D5 | D3 |
| 3624 | A2 | CN | D2 | D5 | D5 |
| 3625 | A2 | CN | D2 | D5 | D6 |
| 3626 | A2 | CN | D2 | D6 | D1 |
| 3627 | A2 | CN | D2 | D6 | D2 |
| 3628 | A2 | CN | D2 | D6 | D3 |
| 3629 | A2 | CN | D2 | D6 | D4 |
| 3630 | A2 | CN | D2 | D6 | D5 |
| 3631 | A2 | CN | D2 | D6 | D6 |
| 3632 | A2 | CN | D3 | D1 | D1 |
| 3633 | A2 | CN | D3 | D1 | D2 |
| 3634 | A2 | CN | D3 | D1 | D3 |
| 3635 | A2 | CN | D3 | D1 | D4 |
| 3636 | A2 | CN | D3 | D1 | D5 |
| 3637 | A2 | CN | D3 | D1 | D6 |
| 3638 | A2 | CN | D3 | D2 | D1 |
| 3639 | A2 | CN | D3 | D2 | D2 |
| 3640 | A2 | CN | D3 | D2 | D3 |
| 3641 | A2 | CN | D3 | D2 | D4 |
| 3642 | A2 | CN | D3 | D2 | D5 |
| 3643 | A2 | CN | D3 | D2 | D6 |
| 3644 | A2 | CN | D3 | D3 | D1 |
| 3645 | A2 | CN | D3 | D3 | D2 |
| 3646 | A2 | CN | D3 | D3 | D3 |
| 3647 | A2 | CN | D3 | D3 | D4 |
| 3648 | A2 | CN | D3 | D3 | D5 |
| 3649 | A2 | CN | D3 | D3 | D6 |
| 3650 | A2 | CN | D3 | D4 | D1 |
| 3651 | A2 | CN | D3 | D4 | D2 |
| 3652 | A2 | CN | D3 | D4 | D3 |
| 3653 | A2 | CN | D3 | D4 | D4 |
| 3654 | A2 | CN | D3 | D4 | D5 |
| 3655 | A2 | CN | D3 | D4 | D6 |
| 3656 | A2 | CN | D3 | D5 | D1 |
| 3657 | A2 | CN | D3 | D5 | D2 |
| 3658 | A2 | CN | D3 | D5 | D3 |
| 3659 | A2 | CN | D3 | D5 | D4 |
| 3660 | A2 | CN | D3 | D5 | D5 |
| 3661 | A2 | CN | D3 | D5 | D6 |
| 3662 | A2 | CN | D3 | D6 | D1 |
| 3663 | A2 | CN | D3 | D6 | D2 |
| 3664 | A2 | CN | D3 | D6 | D3 |
| 3665 | A2 | CN | D3 | D6 | D4 |
| 3666 | A2 | CN | D3 | D6 | D5 |
| 3667 | A2 | CN | D3 | D6 | D6 |
| 3668 | A2 | CN | D4 | D1 | D1 |
| 3669 | A2 | CN | D4 | D1 | D2 |
| 3670 | A2 | CN | D4 | D1 | D3 |
| 3671 | A2 | CN | D4 | D1 | D4 |
| 3672 | A2 | CN | D4 | D1 | D5 |
| 3673 | A2 | CN | D4 | D1 | D5 |
| 3674 | A2 | CN | D4 | D2 | D1 |
| 3675 | A2 | CN | D4 | D2 | D2 |
| 3676 | A2 | CN | D4 | D2 | D3 |
| 3677 | A2 | CN | D4 | D2 | D4 |
| 3678 | A2 | CN | D4 | D2 | D5 |

TABLE 1-25-continued

| No. | $R^1$ | $R^2$ | $R^3$ | $R^4$ | $R^5$ |
|---|---|---|---|---|---|
| 3679 | A2 | CN | D4 | D2 | D6 |
| 3680 | A2 | CN | D4 | D3 | D1 |
| 3631 | A2 | CN | D4 | D3 | D2 |
| 3632 | A2 | CN | D4 | D3 | D3 |
| 3633 | A2 | CN | D4 | D3 | D4 |
| 3684 | A2 | CN | D4 | D3 | D5 |
| 3685 | A2 | CN | D4 | D3 | D6 |
| 3686 | A2 | CN | D4 | D4 | D1 |
| 3687 | A2 | CN | D4 | D4 | D2 |
| 3688 | A2 | CN | D4 | D4 | D3 |
| 3689 | A2 | CN | D4 | D4 | D4 |
| 3690 | A2 | CN | D4 | D4 | D5 |
| 3691 | A2 | CN | D4 | D4 | D6 |
| 3692 | A2 | CN | D4 | D5 | D1 |
| 3693 | A2 | CN | D4 | D5 | D2 |
| 3694 | A2 | CN | D4 | D5 | D3 |
| 3695 | A2 | CN | D4 | D5 | D4 |
| 3696 | A2 | CN | D4 | D5 | D5 |
| 3697 | A2 | CN | D4 | D5 | D6 |
| 3698 | A2 | CN | D4 | D6 | D1 |
| 3699 | A2 | CN | D4 | D6 | D2 |
| 3700 | A2 | CN | D4 | D6 | D3 |
| 3701 | A2 | CN | D4 | D6 | D4 |
| 37D2 | A2 | CN | D4 | D6 | D5 |
| 3703 | A2 | CN | D4 | D6 | D6 |
| 3704 | A2 | CN | D5 | D1 | D1 |
| 3705 | A2 | CN | D5 | D1 | D2 |
| 3706 | A2 | CN | D5 | D1 | D3 |
| 3707 | A2 | CN | D5 | D1 | D4 |
| 3708 | A2 | CN | D5 | D1 | D5 |
| 3709 | A2 | CN | D5 | D1 | D6 |
| 3710 | A2 | CN | D5 | D2 | D1 |
| 3711 | A2 | CN | D5 | D2 | D2 |
| 3712 | A2 | CN | D5 | D2 | D3 |
| 3713 | A2 | CN | D5 | D2 | D4 |
| 3714 | A2 | CN | D5 | D2 | D5 |
| 3715 | A2 | CN | D5 | D2 | D6 |
| 3716 | A2 | CN | D5 | D3 | D1 |
| 3717 | A2 | CN | D5 | D3 | D2 |
| 3718 | A2 | CN | D5 | D3 | D3 |
| 3719 | A2 | CN | D5 | D3 | D4 |
| 3720 | A2 | CN | D5 | D3 | D5 |
| 3721 | A2 | CN | D5 | D3 | D6 |
| 3722 | A2 | CN | D5 | D4 | D1 |
| 3723 | A2 | CN | D5 | D4 | D2 |
| 3724 | A2 | CN | D5 | D4 | D3 |
| 3725 | A2 | CN | D5 | D4 | D4 |
| 3726 | A2 | CN | D5 | D4 | D5 |
| 3727 | A2 | CN | D5 | D4 | D6 |
| 3728 | A2 | CN | D5 | D5 | D1 |
| 3729 | A2 | CN | D5 | D5 | D2 |
| 3730 | A2 | CN | D5 | D5 | D3 |
| 3731 | A2 | CN | D5 | D5 | D4 |
| 3732 | A2 | CN | D5 | D5 | D5 |
| 3733 | A2 | CN | D5 | D5 | D6 |
| 3734 | A2 | CN | D5 | D6 | D1 |
| 3735 | A2 | CN | D5 | D6 | D2 |
| 3736 | A2 | CN | D5 | D6 | D3 |
| 3737 | A2 | CN | D5 | D6 | D4 |
| 3738 | A2 | CN | D5 | D6 | D5 |
| 3739 | A2 | CN | D5 | D6 | D6 |
| 3740 | A2 | CN | D6 | D1 | D1 |
| 3741 | A2 | CN | D6 | D1 | D2 |
| 3742 | A2 | CN | D6 | D1 | D3 |
| 3743 | A2 | CN | D6 | D1 | D4 |
| 3744 | A2 | CN | D6 | D1 | D5 |
| 3745 | A2 | CN | D6 | D1 | D6 |
| 3746 | A2 | CN | D6 | D2 | D1 |
| 3747 | A2 | CN | D6 | D2 | D2 |
| 3748 | A2 | CN | D6 | D2 | D3 |
| 3749 | A2 | CN | D6 | D2 | D4 |
| 3750 | A2 | CN | D6 | D2 | D5 |

TABLE 1-26

| No. | $R^1$ | $R^2$ | $R^3$ | $R^4$ | $R^5$ |
|---|---|---|---|---|---|
| 3751 | A2 | CN | D6 | D2 | D6 |
| 3752 | A2 | CN | D6 | D3 | D1 |
| 3753 | A2 | CN | D6 | D3 | D2 |
| 3754 | A2 | CN | D6 | D3 | D3 |
| 3755 | A2 | CN | D6 | D3 | D4 |
| 3756 | A2 | CN | D6 | D3 | D5 |
| 3757 | A2 | CN | D6 | D3 | D6 |
| 3758 | A2 | CN | D6 | D4 | D1 |
| 3759 | A2 | CN | D6 | D4 | D2 |
| 3760 | A2 | CN | D6 | D4 | D3 |
| 3761 | A2 | CN | D6 | D4 | D4 |
| 3762 | A2 | CN | D6 | D4 | D5 |
| 3763 | A2 | CN | D6 | D4 | D6 |
| 3764 | A2 | CN | D6 | D5 | D1 |
| 3765 | A2 | CN | D6 | D5 | D2 |
| 3766 | A2 | CN | D6 | D5 | D3 |
| 3767 | A2 | CN | D6 | D5 | D4 |
| 3768 | A2 | CN | D6 | D5 | D5 |
| 3769 | A2 | CN | D6 | D5 | D6 |
| 3770 | A2 | CN | D6 | D6 | D1 |
| 3771 | A2 | CN | D6 | D6 | D2 |
| 3772 | A2 | CN | D6 | D6 | D3 |
| 3773 | A2 | CN | D6 | D6 | D4 |
| 3774 | A2 | CN | D6 | D6 | D5 |
| 3775 | A2 | CN | D6 | D6 | D6 |
| 3776 | D1 | CN | A1 | D1 | D1 |
| 3777 | D1 | CN | A1 | D1 | D2 |
| 3778 | D1 | CN | A1 | D1 | D3 |
| 3779 | D1 | CN | A1 | D1 | D4 |
| 3780 | D1 | CN | A1 | D1 | D5 |
| 3781 | D1 | CN | A1 | D1 | D6 |
| 3782 | D1 | CN | A1 | D2 | D1 |
| 3783 | D1 | CN | A1 | D2 | D2 |
| 3784 | D1 | CN | A1 | D2 | D3 |
| 3735 | D1 | CN | A1 | D2 | D4 |
| 3736 | D1 | CN | A1 | D2 | D5 |
| 3737 | D1 | CN | A1 | D2 | D6 |
| 3738 | D1 | CN | A1 | D3 | D1 |
| 3789 | D1 | CN | A1 | D3 | D2 |
| 3790 | D1 | CN | A1 | D3 | D3 |
| 3791 | D1 | CN | A1 | D3 | D4 |
| 3792 | D1 | CN | A1 | D3 | D5 |
| 3793 | D1 | CN | A1 | D3 | D6 |
| 3794 | D1 | CN | A1 | D4 | D1 |
| 3795 | D1 | CN | A1 | D4 | D2 |
| 3796 | D1 | CN | A1 | D4 | D3 |
| 3797 | D1 | CN | A1 | D4 | D4 |
| 3798 | D1 | CN | A1 | D4 | D5 |
| 3799 | D1 | CN | A1 | D4 | D6 |
| 3800 | D1 | CN | A1 | D5 | D1 |
| 3801 | D1 | CN | A1 | D5 | D2 |
| 38D2 | D1 | CN | A1 | D5 | D3 |
| 3803 | D1 | CN | A1 | D5 | D4 |
| 3804 | D1 | CN | A1 | D5 | D5 |
| 3805 | D1 | CN | A1 | D5 | D6 |
| 3806 | D1 | CN | A1 | D6 | D1 |
| 3807 | D1 | CN | A1 | D6 | D2 |
| 3808 | D1 | CN | A1 | D6 | D3 |
| 3809 | D1 | CN | A1 | D6 | D4 |
| 3810 | D1 | CN | A1 | D6 | D5 |
| 3811 | D1 | CN | A1 | D6 | D6 |
| 3812 | D2 | CN | A1 | D1 | D1 |
| 3813 | D2 | CN | A1 | D1 | D2 |
| 3814 | D2 | CN | A1 | D1 | D3 |
| 3815 | D2 | CN | A1 | D1 | D4 |
| 3816 | D2 | CN | A1 | D1 | D5 |
| 3817 | D2 | CN | A1 | D1 | D6 |
| 3818 | D2 | CN | A1 | D2 | D1 |
| 3819 | D2 | CN | A1 | D2 | D2 |
| 3820 | D2 | CN | A1 | D2 | D3 |
| 3821 | D2 | CN | A1 | D2 | D4 |
| 3822 | D2 | CN | A1 | D2 | D5 |
| 3823 | D2 | CN | A1 | D2 | D6 |
| 3824 | D2 | CN | A1 | D3 | D1 |
| 3825 | D2 | CN | A1 | D3 | D2 |
| 3826 | D2 | CN | A1 | D3 | D3 |
| 3827 | D2 | CN | A1 | D3 | D4 |
| 3828 | D2 | CN | A1 | D3 | D5 |

TABLE 1-26-continued

| No. | $R^1$ | $R^2$ | $R^3$ | $R^4$ | $R^5$ |
|---|---|---|---|---|---|
| 3829 | D2 | CN | A1 | D3 | D6 |
| 3830 | D2 | CN | A1 | D4 | D1 |
| 3831 | D2 | CN | A1 | D4 | D2 |
| 3832 | D2 | CN | A1 | D4 | D3 |
| 3833 | D2 | CN | A1 | D4 | D4 |
| 3834 | D2 | CN | A1 | D4 | D5 |
| 3835 | D2 | CN | A1 | D4 | D6 |
| 3836 | D2 | CN | A1 | D5 | D1 |
| 3837 | D2 | CN | A1 | D5 | D2 |
| 3838 | D2 | CN | A1 | D5 | D3 |
| 3839 | D2 | CN | A1 | D5 | D4 |
| 3840 | D2 | CN | A1 | D5 | D5 |
| 3841 | D2 | CN | A1 | D5 | D6 |
| 3842 | D2 | CN | A1 | D6 | D1 |
| 3843 | D2 | CN | A1 | D6 | D2 |
| 3844 | D2 | CN | A1 | D6 | D3 |
| 3845 | D2 | CN | A1 | D6 | D4 |
| 3846 | D2 | CN | A1 | D6 | D5 |
| 3847 | D2 | CN | A1 | D6 | D6 |
| 3848 | D3 | CN | A1 | D1 | D1 |
| 3849 | D3 | CN | A1 | D1 | D2 |
| 3850 | D3 | CN | A1 | D1 | D3 |
| 3851 | D3 | CN | A1 | D1 | D4 |
| 3852 | D3 | CN | A1 | D1 | D5 |
| 3853 | D3 | CN | A1 | D1 | D6 |
| 3854 | D3 | CN | A1 | D2 | D1 |
| 3855 | D3 | CN | A1 | D2 | D2 |
| 3856 | D3 | CN | A1 | D2 | D3 |
| 3857 | D3 | CN | A1 | D2 | D4 |
| 3858 | D3 | CN | A1 | D2 | D5 |
| 3859 | D3 | CN | A1 | D2 | D6 |
| 3860 | D3 | CN | A1 | D3 | D1 |
| 3861 | D3 | CN | A1 | D3 | D2 |
| 3862 | D3 | CN | A1 | D3 | D3 |
| 3863 | D3 | CN | A1 | D3 | D4 |
| 3864 | D3 | CN | A1 | D3 | D5 |
| 3865 | D3 | CN | A1 | D3 | D6 |
| 3866 | D3 | CN | A1 | D4 | D1 |
| 3867 | D3 | CN | A1 | D4 | D2 |
| 3868 | D3 | CN | A1 | D4 | D3 |
| 3869 | D3 | CN | A1 | D4 | D4 |
| 3870 | D3 | CN | A1 | D4 | D5 |
| 3871 | D3 | CN | A1 | D4 | D6 |
| 3872 | D3 | CN | A1 | D5 | D1 |
| 3873 | D3 | CN | A1 | D5 | D2 |
| 3874 | D3 | CN | A1 | D5 | D3 |
| 3875 | D3 | CN | A1 | D5 | D4 |
| 3876 | D3 | CN | A1 | D5 | D5 |
| 3877 | D3 | CN | A1 | D5 | D6 |
| 3878 | D3 | CN | A1 | D6 | D1 |
| 3879 | D3 | CN | A1 | D6 | D2 |
| 3880 | D3 | CN | A1 | D6 | D3 |
| 3881 | D3 | CN | A1 | D6 | D4 |
| 3882 | D3 | CN | A1 | D6 | D5 |
| 3883 | D3 | CN | A1 | D6 | D6 |
| 3884 | D4 | CN | A1 | D1 | D1 |
| 3885 | D4 | CN | A1 | D1 | D2 |
| 3886 | D4 | CN | A1 | D1 | D3 |
| 3887 | D4 | CN | A1 | D1 | D4 |
| 3888 | D4 | CN | A1 | D1 | D5 |
| 3889 | D4 | CN | A1 | D1 | D6 |
| 3890 | D4 | CN | A1 | D2 | D1 |
| 3891 | D4 | CN | A1 | D2 | D2 |
| 3892 | D4 | CN | A1 | D2 | D3 |
| 3893 | D4 | CN | A1 | D2 | D4 |
| 3894 | D4 | CN | A1 | D2 | D5 |
| 3895 | D4 | CN | A1 | D2 | D6 |
| 3896 | D4 | CN | A1 | D3 | D1 |
| 3897 | D4 | CN | A1 | D3 | D2 |
| 3898 | D4 | CN | A1 | D3 | D3 |
| 3899 | D4 | CN | A1 | D3 | D4 |
| 3900 | D4 | CN | A1 | D3 | D5 |

TABLE 1-27

| No. | $R^1$ | R2 | $R^3$ | $R^4$ | $R^5$ |
|---|---|---|---|---|---|
| 3901 | D4 | CN | A1 | D3 | D6 |
| 3902 | D4 | CN | A1 | D4 | D1 |
| 3903 | D4 | CN | A1 | D4 | D2 |
| 3904 | D4 | CN | A1 | D4 | D3 |
| 3905 | D4 | CN | A1 | D4 | D4 |
| 3906 | D4 | CN | A1 | D4 | D5 |
| 3907 | D4 | CN | A1 | D4 | D6 |
| 3908 | D4 | CN | A1 | D5 | D1 |
| 3909 | D4 | CN | A1 | D5 | D2 |
| 3910 | D4 | CN | A1 | D5 | D3 |
| 3911 | D4 | CN | A1 | D5 | D4 |
| 3912 | D4 | CN | A1 | D5 | D5 |
| 3913 | D4 | CN | A1 | D5 | D6 |
| 3914 | D4 | CN | A1 | D6 | D1 |
| 3915 | D4 | CN | A1 | D6 | D2 |
| 3916 | D4 | CN | A1 | D6 | D3 |
| 3917 | D4 | CN | A1 | D6 | D4 |
| 3918 | D4 | CN | A1 | D6 | D5 |
| 3919 | D4 | CN | A1 | D6 | D6 |
| 3920 | D5 | CN | A1 | D1 | D1 |
| 3921 | D5 | CN | A1 | D1 | D2 |
| 3922 | D5 | CN | A1 | D1 | D3 |
| 3923 | D5 | CN | A1 | D1 | D4 |
| 3924 | D5 | CN | A1 | D1 | D5 |
| 3925 | D5 | CN | A1 | D1 | D6 |
| 3926 | D5 | CN | A1 | D2 | D1 |
| 3927 | D5 | CN | A1 | D2 | D2 |
| 3928 | D5 | CN | A1 | D2 | D3 |
| 3929 | D5 | CN | A1 | D2 | D4 |
| 3930 | D5 | CN | A1 | D2 | D5 |
| 3931 | D5 | CN | A1 | D2 | D6 |
| 3932 | D5 | CN | A1 | D3 | D1 |
| 3933 | D5 | CN | A1 | D3 | D2 |
| 3934 | D5 | CN | A1 | D3 | D3 |
| 3935 | D5 | CN | A1 | D3 | D4 |
| 3936 | D5 | CN | A1 | D3 | D5 |
| 3937 | D5 | CN | A1 | D3 | D6 |
| 3938 | D5 | CN | A1 | D4 | D1 |
| 3939 | D5 | CN | A1 | D4 | D2 |
| 3940 | D5 | CN | A1 | D4 | D3 |
| 3941 | D5 | CN | A1 | D4 | D4 |
| 3942 | D5 | CN | A1 | D4 | D5 |
| 3943 | D5 | CN | A1 | D4 | D6 |
| 3944 | D5 | CN | A1 | D5 | D1 |
| 3945 | D5 | CN | A1 | D5 | D2 |
| 3946 | D5 | CN | A1 | D5 | D3 |
| 3947 | D5 | CN | A1 | D5 | D4 |
| 3948 | D5 | CN | A1 | D5 | D5 |
| 3949 | D5 | CN | A1 | D5 | D6 |
| 3950 | D5 | CN | A1 | D6 | D1 |
| 3951 | D5 | CN | A1 | D6 | D2 |
| 3952 | D5 | CN | A1 | D6 | D3 |
| 3953 | D5 | CN | A1 | D6 | D4 |
| 3954 | D5 | CN | A1 | D6 | D5 |
| 3955 | D5 | CN | A1 | D6 | D6 |
| 3956 | D6 | CN | A1 | D1 | D1 |
| 3957 | D6 | CN | A1 | D1 | D2 |
| 3958 | D6 | CN | A1 | D1 | D3 |
| 3959 | D6 | CN | A1 | D1 | D4 |
| 3960 | D6 | CN | A1 | D1 | D5 |
| 3961 | D6 | CN | A1 | D1 | D6 |
| 3962 | D6 | CN | A1 | D2 | D1 |
| 3963 | D6 | CN | A1 | D2 | D2 |
| 3964 | D6 | CN | A1 | D2 | D3 |
| 3965 | D6 | CN | A1 | D2 | D4 |
| 3966 | D6 | CN | A1 | D2 | D5 |
| 3967 | D6 | CN | A1 | D2 | D6 |
| 3968 | D6 | CN | A1 | D3 | D1 |
| 3969 | D6 | CN | A1 | D3 | D2 |
| 3970 | D6 | CN | A1 | D3 | D3 |
| 3971 | D6 | CN | A1 | D3 | D4 |
| 3972 | D6 | CN | A1 | D3 | D5 |
| 3973 | D6 | CN | A1 | D3 | D6 |
| 3974 | D6 | CN | A1 | D4 | D1 |
| 3975 | D6 | CN | A1 | D4 | D2 |
| 3976 | D6 | CN | A1 | D4 | D3 |
| 3977 | D6 | CN | A1 | D4 | D4 |
| 3978 | D6 | CN | A1 | D4 | D5 |

TABLE 1-27-continued

| No. | $R^1$ | R2 | $R^3$ | $R^4$ | $R^5$ |
|---|---|---|---|---|---|
| 3979 | D6 | CN | A1 | D4 | D6 |
| 3980 | D6 | CN | A1 | D5 | D1 |
| 3981 | D6 | CN | A1 | D5 | D2 |
| 3982 | D6 | CN | A1 | D5 | D3 |
| 3983 | D6 | CN | A1 | D5 | D4 |
| 3984 | D6 | CN | A1 | D5 | D5 |
| 3985 | D6 | CN | A1 | D5 | D6 |
| 3986 | D6 | CN | A1 | D6 | D1 |
| 3987 | D6 | CN | A1 | D6 | D2 |
| 3988 | D6 | CN | A1 | D6 | D3 |
| 3989 | D6 | CN | A1 | D6 | D4 |
| 3990 | D6 | CN | A1 | D6 | D5 |
| 3991 | D6 | CN | A1 | D6 | D6 |
| 3992 | D1 | CN | A2 | D1 | D1 |
| 3993 | D1 | CN | A2 | D1 | D2 |
| 3994 | D1 | CN | A2 | D1 | D3 |
| 3995 | D1 | CN | A2 | D1 | D4 |
| 3996 | D1 | CN | A2 | D1 | D5 |
| 3997 | D1 | CN | A2 | D1 | D6 |
| 3998 | D1 | CN | A2 | D2 | D1 |
| 3999 | D1 | CN | A2 | D2 | D2 |
| 4000 | D1 | CN | A2 | D2 | D3 |
| 4001 | D1 | CN | A2 | D2 | D4 |
| 4002 | D1 | CN | A2 | D2 | D5 |
| 4003 | D1 | CN | A2 | D2 | D6 |
| 4004 | D1 | CN | A2 | D3 | D1 |
| 4005 | D1 | CN | A2 | D3 | D2 |
| 4006 | D1 | CN | A2 | D3 | D3 |
| 4007 | D1 | CN | A2 | D3 | D4 |
| 4008 | D1 | CN | A2 | D3 | D5 |
| 4009 | D1 | CN | A2 | D3 | D6 |
| 4010 | D1 | CN | A2 | D4 | D1 |
| 4011 | D1 | CN | A2 | D4 | D2 |
| 4012 | D1 | CN | A2 | D4 | D3 |
| 4013 | D1 | CN | A2 | D4 | D4 |
| 4014 | D1 | CN | A2 | D4 | D5 |
| 4015 | D1 | CN | A2 | D4 | D6 |
| 4016 | D1 | CN | A2 | D5 | D1 |
| 4017 | D1 | CN | A2 | D5 | D2 |
| 4018 | D1 | CN | A2 | D5 | D3 |
| 4019 | D1 | CN | A2 | D5 | D4 |
| 4020 | D1 | CN | A2 | D5 | D5 |
| 4021 | D1 | CN | A2 | D5 | D6 |
| 4022 | D1 | CN | A2 | D6 | D1 |
| 4023 | D1 | CN | A2 | D6 | D2 |
| 4024 | D1 | CN | A2 | D6 | D3 |
| 4025 | D1 | CN | A2 | D6 | D4 |
| 4026 | D1 | CN | A2 | D6 | D5 |
| 4027 | D1 | CN | A2 | D6 | D6 |
| 4028 | D2 | CN | A2 | D1 | D1 |
| 4029 | D2 | CN | A2 | D1 | D2 |
| 4030 | D2 | CN | A2 | D1 | D3 |
| 4031 | D2 | CN | A2 | D1 | D4 |
| 4032 | D2 | CN | A2 | D1 | D5 |
| 4033 | D2 | CN | A2 | D1 | D6 |
| 4034 | D2 | CN | A2 | D2 | D1 |
| 4035 | D2 | CN | A2 | D2 | D2 |
| 4036 | D2 | CN | A2 | D2 | D3 |
| 4037 | D2 | CN | A2 | D2 | D4 |
| 4038 | D2 | CN | A2 | D2 | D5 |
| 4039 | D2 | CN | A2 | D2 | D6 |
| 4040 | D2 | CN | A2 | D3 | D1 |
| 4041 | D2 | CN | A2 | D3 | D2 |
| 4042 | D2 | CN | A2 | D3 | D3 |
| 4043 | D2 | CN | A2 | D3 | D4 |
| 4044 | D2 | CN | A2 | D3 | D5 |
| 4045 | D2 | CN | A2 | D3 | D6 |
| 4046 | D2 | CN | A2 | D4 | D1 |
| 4047 | D2 | CN | A2 | D4 | D2 |
| 4048 | D2 | CN | A2 | D4 | D3 |
| 4049 | D2 | CN | A2 | D4 | D4 |
| 4050 | D2 | CN | A2 | D4 | D5 |

TABLE 1-28

| No. | $R^1$ | $R^2$ | $R^3$ | $R^4$ | $R^5$ |
|---|---|---|---|---|---|
| 4051 | D2 | CN | A2 | D4 | D6 |
| 4052 | D2 | CN | A2 | D5 | D1 |
| 4053 | D2 | CN | A2 | D5 | D2 |
| 4054 | D2 | CN | A2 | D5 | D3 |
| 4055 | D2 | CN | A2 | D5 | D4 |
| 4056 | D2 | CN | A2 | D5 | D5 |
| 4057 | D2 | CN | A2 | D5 | D6 |
| 4058 | D2 | CN | A2 | D6 | D1 |
| 4059 | D2 | CN | A2 | D6 | D2 |
| 4060 | D2 | CN | A2 | D6 | D3 |
| 4061 | D2 | CN | A2 | D6 | D4 |
| 4062 | D2 | CN | A2 | D6 | D5 |
| 4063 | D2 | CN | A2 | D6 | D6 |
| 4064 | D3 | CN | A2 | D3 | D1 |
| 4065 | D3 | CN | A2 | D3 | D2 |
| 4066 | D3 | CN | A2 | D3 | D3 |
| 4067 | D3 | CN | A2 | D1 | D4 |
| 4068 | D3 | CN | A2 | D1 | D5 |
| 4069 | D3 | CN | A2 | D1 | D6 |
| 4070 | D3 | CN | A2 | D2 | D1 |
| 4071 | D3 | CN | A2 | D2 | D2 |
| 4072 | D3 | CN | A2 | D2 | D3 |
| 4073 | D3 | CN | A2 | D2 | D3 |
| 4074 | D3 | CN | A2 | D2 | D5 |
| 4075 | D3 | CN | A2 | D2 | D6 |
| 4076 | D3 | CN | A2 | D3 | D1 |
| 4077 | D3 | CN | A2 | D3 | D2 |
| 4078 | D3 | CN | A2 | D3 | D3 |
| 4079 | D3 | CN | A2 | D3 | D4 |
| 4080 | D3 | CN | A2 | D3 | D5 |
| 4081 | D3 | CN | A2 | D3 | D6 |
| 4082 | D3 | CN | A2 | D4 | D1 |
| 4083 | D3 | CN | A2 | D4 | D2 |
| 4084 | D3 | CN | A2 | D4 | D3 |
| 4085 | D3 | CN | A2 | D4 | D4 |
| 4086 | D3 | CN | A2 | D4 | D5 |
| 4087 | D3 | CN | A2 | D4 | D6 |
| 4088 | D3 | CN | A2 | D5 | D1 |
| 4089 | D3 | CN | A2 | D5 | D2 |
| 4090 | D3 | CN | A2 | D5 | D3 |
| 4091 | D3 | CN | A2 | D5 | D4 |
| 4092 | D3 | CN | A2 | D5 | D5 |
| 4093 | D3 | CN | A2 | D5 | D6 |
| 4094 | D3 | CN | A2 | D6 | D1 |
| 4095 | D3 | CN | A2 | D6 | D2 |
| 4096 | D3 | CN | A2 | D6 | D3 |
| 4097 | D3 | CN | A2 | D6 | D4 |
| 4098 | D3 | CN | A2 | D6 | D5 |
| 4099 | D3 | CN | A2 | D6 | D6 |
| 4100 | D4 | CN | A2 | D1 | D1 |
| 4101 | D4 | CN | A2 | D1 | D2 |
| 4102 | D4 | CN | A2 | D1 | D3 |
| 4103 | D4 | CN | A2 | D1 | D4 |
| 4104 | D4 | CN | A2 | D1 | D5 |
| 4105 | D4 | CN | A2 | D1 | D6 |
| 4106 | D4 | CN | A2 | D2 | D1 |
| 4107 | D4 | CN | A2 | D2 | D2 |
| 4108 | D4 | CN | A2 | D2 | D3 |
| 4109 | D4 | CN | A2 | D2 | D4 |
| 4110 | D4 | CN | A2 | D2 | D5 |
| 4111 | D4 | CN | A2 | D2 | D6 |
| 4112 | D4 | CN | A2 | D3 | D3 |
| 4113 | D4 | CN | A2 | D3 | D2 |
| 4114 | D4 | CN | A2 | D3 | D3 |
| 4115 | D4 | CN | A2 | D3 | D4 |
| 4116 | D4 | CN | A2 | D3 | D5 |
| 4117 | D4 | CN | A2 | D3 | D6 |
| 4118 | D4 | CN | A2 | D4 | D1 |
| 4119 | D4 | CN | A2 | D4 | D2 |
| 4120 | D4 | CN | A2 | D4 | D3 |
| 4121 | D4 | CN | A2 | D4 | D4 |
| 4122 | D4 | CN | A2 | D4 | D5 |
| 4123 | Da | CN | A2 | D3 | D5 |
| 4124 | D4 | CN | A2 | D5 | D1 |
| 4125 | D4 | CN | A2 | D5 | D2 |
| 4126 | D4 | CN | A2 | D5 | D3 |
| 4127 | D4 | CN | A2 | D5 | D4 |
| 4128 | D4 | CN | A2 | D5 | D5 |

TABLE 1-28-continued

| No. | $R^1$ | $R^2$ | $R^3$ | $R^4$ | $R^5$ |
|---|---|---|---|---|---|
| 4129 | D4 | CN | A2 | D5 | D6 |
| 4130 | D4 | CN | A2 | D6 | D1 |
| 4131 | D4 | CN | A2 | D6 | D2 |
| 4132 | D4 | CN | A2 | D6 | D3 |
| 4133 | D4 | CN | A2 | D6 | D4 |
| 4134 | D4 | CN | A2 | D6 | D5 |
| 4135 | D4 | CN | A2 | D6 | D6 |
| 4136 | D5 | CN | A2 | D1 | D1 |
| 4137 | D5 | CN | A2 | D1 | D2 |
| 4138 | D5 | CN | A2 | D1 | D3 |
| 4139 | D5 | CN | A2 | D1 | D4 |
| 4140 | D5 | CN | A2 | D1 | D5 |
| 4141 | D5 | CN | A2 | D1 | D6 |
| 4142 | D5 | CN | A2 | D2 | D1 |
| 4143 | D5 | CN | A2 | D2 | D2 |
| 4144 | D5 | CN | A2 | D2 | D3 |
| 4145 | D5 | CN | A2 | D2 | D4 |
| 4146 | D5 | CN | A2 | D2 | D5 |
| 4147 | D5 | CN | A2 | D2 | D6 |
| 4148 | D5 | CN | A2 | D3 | D1 |
| 4149 | D5 | CN | A2 | D3 | D2 |
| 4150 | D5 | CN | A2 | D3 | D3 |
| 4151 | D5 | CN | A2 | D3 | D4 |
| 4152 | D5 | CN | A2 | D3 | D5 |
| 4153 | D5 | CN | A2 | D3 | D6 |
| 4154 | D5 | CN | A2 | D4 | D1 |
| 4155 | D5 | CN | A2 | D4 | D2 |
| 4156 | D5 | CN | A2 | D4 | D3 |
| 4157 | D5 | CN | A2 | D4 | D4 |
| 4158 | D5 | CN | A2 | D4 | D5 |
| 4159 | D5 | CN | A2 | D4 | D6 |
| 4160 | D5 | CN | A2 | D5 | D1 |
| 4161 | D5 | CN | A2 | D5 | D2 |
| 4162 | D5 | CN | A2 | D5 | D3 |
| 4163 | D5 | CN | A2 | D5 | D4 |
| 4164 | D5 | CN | A2 | D5 | D5 |
| 4165 | D5 | CN | A2 | D5 | D6 |
| 4166 | D5 | CN | A2 | D6 | D1 |
| 4167 | D5 | CN | A2 | D6 | D2 |
| 4168 | D5 | CN | A2 | D6 | D3 |
| 4169 | D5 | CN | A2 | D6 | D4 |
| 4170 | D5 | CN | A2 | D6 | D5 |
| 4171 | D5 | CN | A2 | D6 | D6 |
| 4172 | D6 | CN | A2 | D1 | D1 |
| 4173 | D6 | CN | A2 | D1 | D2 |
| 4174 | D6 | CN | A2 | D1 | D3 |
| 4175 | D6 | CN | A2 | D1 | D4 |
| 4176 | D6 | CN | A2 | D1 | D5 |
| 4177 | D6 | CN | A2 | D1 | D6 |
| 4178 | D6 | CN | A2 | D2 | D1 |
| 4179 | D6 | CN | A2 | D2 | D2 |
| 4180 | D6 | CN | A2 | D2 | D3 |
| 4181 | D6 | CN | A2 | D2 | D4 |
| 4182 | D6 | CN | A2 | D2 | D5 |
| 4183 | D6 | CN | A2 | D2 | D6 |
| 4184 | D6 | CN | A2 | D3 | D1 |
| 4185 | D6 | CN | A2 | D3 | D2 |
| 4186 | D6 | CN | A2 | D3 | D3 |
| 4187 | D6 | CN | A2 | D3 | D4 |
| 4188 | D6 | CN | A2 | D3 | D5 |
| 4189 | D6 | CN | A2 | D3 | D6 |
| 4190 | D6 | CN | A2 | D4 | D1 |
| 4191 | D6 | CN | A2 | D4 | D2 |
| 4192 | D6 | CN | A2 | D4 | D3 |
| 4193 | D6 | CN | A2 | D4 | D4 |
| 4194 | D6 | CN | A2 | D4 | D5 |
| 4195 | D6 | CN | A2 | D4 | D6 |
| 4196 | D6 | CN | A2 | D5 | D1 |
| 4197 | D6 | CN | A2 | D5 | D2 |
| 4198 | D6 | CN | A2 | D5 | D3 |
| 4199 | D6 | CN | A2 | D5 | D4 |
| 4200 | D6 | CN | A2 | D5 | D5 |

TABLE 1-29

| No. | $R^1$ | $R^2$ | $R^3$ | $R^4$ | $R^5$ |
|---|---|---|---|---|---|
| 4201 | D6 | CN | A2 | D5 | D6 |
| 4202 | D6 | CN | A2 | D6 | D1 |
| 4203 | D6 | CN | A2 | D6 | D2 |
| 4204 | D5 | CN | A2 | D6 | D3 |
| 4205 | D5 | CN | A2 | D6 | D4 |
| 4206 | D6 | CN | A2 | D6 | D5 |
| 4207 | D6 | CN | A2 | D6 | D6 |
| 4208 | D1 | CN | A1 | H | D1 |
| 4209 | D1 | CN | A1 | H | D2 |
| 4210 | D1 | CN | A1 | H | D3 |
| 4211 | D1 | CN | A1 | H | D4 |
| 4212 | D1 | CN | A1 | H | D5 |
| 4213 | D1 | CN | A1 | H | D6 |
| 4214 | D1 | CN | A1 | H | D7 |
| 4215 | D1 | CN | A1 | H | D8 |
| 4216 | D1 | CN | A1 | H | D9 |
| 421? | D1 | CN | A1 | H | D10 |
| 4218 | D1 | CN | A1 | H | D11 |
| 4219 | D1 | CN | A1 | H | D12 |
| 4220 | D1 | CN | A1 | H | D13 |
| 4221 | D3 | CN | A1 | H | D14 |
| 4222 | D1 | CN | A1 | H | D15 |
| 4223 | D1 | CN | A1 | H | D16 |
| 4224 | D2 | CN | A1 | H | D1 |
| 4225 | D2 | CN | A1 | H | D2 |
| 4226 | D2 | CN | A1 | H | D3 |
| 4227 | D2 | CN | A1 | H | D4 |
| 4228 | D2 | CN | A1 | H | D5 |
| 4229 | D2 | CN | A1 | H | D5 |
| 4230 | D2 | CN | A1 | H | D7 |
| 4231 | DZ | CN | A1 | H | D8 |
| 4232 | D2 | CN | A1 | H | D9 |
| 4233 | D2 | CN | A1 | H | D10 |
| 4234 | D2 | CN | A1 | H | D11 |
| 4235 | D2 | CN | A1 | H | D12 |
| 4236 | D2 | CN | A1 | H | D13 |
| 4237 | D2 | CN | A1 | H | D14 |
| 4238 | D2 | CN | A1 | H | D15 |
| 4239 | D2 | CN | A1 | H | D16 |
| 4240 | D3 | CN | A1 | H | D11 |
| 4241 | D3 | CN | A1 | H | D2 |
| 4242 | D3 | CN | A1 | H | D3 |
| 4243 | D3 | CN | A1 | H | D4 |
| 4244 | D3 | CN | A1 | H | D5 |
| 4245 | D3 | CN | A1 | H | D6 |
| 4246 | D3 | CN | A1 | H | D7 |
| 4247 | D3 | CN | A1 | H | D8 |
| 4248 | D3 | CN | A1 | H | D9 |
| 4249 | D3 | CN | A1 | H | D10 |
| 4250 | D3 | CN | A1 | H | D11 |
| 4251 | D3 | CN | A1 | H | D12 |
| 4252 | D3 | CN | A1 | H | D13 |
| 4253 | D3 | CN | A1 | H | D14 |
| 4254 | D3 | CN | A1 | H | D15 |
| 4255 | D3 | CN | A1 | H | D16 |
| 4256 | D4 | CN | A1 | H | D1 |
| 4257 | D4 | CN | A1 | H | D2 |
| 4258 | D4 | CN | A1 | H | D3 |
| 4259 | D4 | CN | A1 | H | D4 |
| 4260 | D4 | CN | A1 | H | D5 |
| 4261 | D4 | CN | A1 | H | D6 |
| 4262 | D4 | CN | A1 | H | D7 |
| 4263 | D4 | CN | A1 | H | D8 |
| 4264 | D4 | CN | A1 | H | D9 |
| 4265 | D4 | CN | A1 | H | D10 |
| 4266 | D4 | CN | A1 | H | D11 |
| 4267 | D4 | CN | A1 | H | D12 |
| 4268 | D4 | CN | A1 | H | D13 |
| 4269 | D4 | CN | A1 | H | D14 |
| 4270 | D4 | CN | A1 | H | D15 |
| 4271 | D4 | CN | A1 | H | D16 |
| 4272 | D5 | CN | A1 | H | D1 |
| 4273 | D5 | CN | A1 | H | D2 |
| 4274 | D5 | CN | A1 | H | D3 |
| 4275 | D5 | CN | A1 | H | D4 |
| 4276 | D5 | CN | A1 | H | D5 |
| 4277 | D5 | CN | A1 | H | D6 |
| 4278 | D5 | CN | A1 | H | D7 |

TABLE 1-29-continued

| No. | $R^1$ | $R^2$ | $R^3$ | $R^4$ | $R^5$ |
|---|---|---|---|---|---|
| 4279 | D5 | CN | A1 | H | D8 |
| 4280 | D5 | CN | A1 | H | D9 |
| 4281 | D5 | CN | A1 | H | D10 |
| 4282 | D5 | CN | A1 | H | D11 |
| 4283 | D5 | CN | A1 | H | D11 |
| 4284 | D5 | CN | A1 | H | D13 |
| 4285 | D5 | CN | A1 | H | D14 |
| 4286 | D5 | CN | A1 | H | D15 |
| 4287 | D5 | CN | A1 | H | D16 |
| 4288 | D6 | CN | A1 | H | D1 |
| 4289 | D6 | CN | A1 | H | D2 |
| 4290 | D6 | CN | A1 | H | D3 |
| 4291 | D6 | CN | A1 | H | D4 |
| 4292 | D6 | CN | A1 | H | D5 |
| 4293 | D6 | CN | A1 | H | D6 |
| 4294 | D6 | CN | A1 | H | D7 |
| 4295 | D6 | CN | A1 | H | D8 |
| 4296 | D6 | CN | A1 | H | D9 |
| 4297 | D6 | CN | A1 | H | D10 |
| 4298 | D6 | CN | A1 | H | D11 |
| 4299 | D6 | CN | A1 | H | D12 |
| 4300 | D6 | CN | A1 | H | D13 |
| 4301 | D6 | CN | A1 | H | D14 |
| 4302 | D6 | CN | A1 | H | D15 |
| 4303 | D6 | CN | A1 | H | D16 |
| 4304 | D7 | CN | A1 | H | D1 |
| 4305 | D7 | CN | A1 | H | D2 |
| 4306 | D7 | CN | A1 | H | D3 |
| 4307 | D7 | CN | A1 | H | D4 |
| 4308 | D7 | CN | A1 | H | D5 |
| 4309 | D7 | CN | A1 | H | D6 |
| 4310 | D7 | CN | A1 | H | D2 |
| 4311 | D7 | CN | A1 | H | D8 |
| 4312 | D7 | CN | A1 | H | D9 |
| 4313 | D7 | CN | A1 | H | D10 |
| 4314 | D7 | CN | A1 | H | D11 |
| 4315 | D7 | CN | A1 | H | D12 |
| 4316 | D7 | CN | A1 | H | D13 |
| 4317 | D7 | CN | A1 | H | D14 |
| 4318 | D7 | CN | A1 | H | D15 |
| 4319 | D7 | CN | A1 | H | D16 |
| 4320 | D8 | CN | A1 | H | D1 |
| 4321 | D8 | CN | A1 | H | D2 |
| 4322 | D8 | CN | A1 | H | D3 |
| 4323 | D8 | CN | A1 | H | D4 |
| 4324 | D8 | CN | A1 | H | D5 |
| 4325 | D8 | CN | A1 | H | D6 |
| 4326 | D8 | CN | A1 | H | D7 |
| 4327 | D8 | CN | A1 | H | D8 |
| 4328 | D8 | CN | A1 | H | D9 |
| 4329 | D8 | CN | A1 | H | D10 |
| 4330 | D8 | CN | A1 | H | D11 |
| 4331 | D6 | CN | A1 | H | D12 |
| 4332 | D8 | CN | A1 | H | D13 |
| 4333 | D8 | CN | A1 | H | D14 |
| 4334 | D8 | CN | A1 | H | D15 |
| 4335 | D8 | CN | A1 | H | D16 |
| 4336 | D9 | CN | A1 | H | D1 |
| 4337 | D9 | CN | A1 | H | D2 |
| 4338 | D9 | CN | A1 | H | D3 |
| 4339 | D9 | CN | A1 | H | D4 |
| 4340 | D9 | CN | A1 | H | D5 |
| 4341 | D9 | CN | A1 | H | D6 |
| 4342 | D9 | CN | A1 | H | D7 |
| 4343 | D9 | CN | A1 | H | D8 |
| 4344 | D9 | CN | A1 | H | D9 |
| 4345 | D9 | CN | A1 | H | D10 |
| 4346 | D9 | CN | A1 | H | D11 |
| 4347 | D9 | CN | A1 | H | D12 |
| 4348 | D9 | CN | A1 | H | D13 |
| 4349 | D9 | CN | A1 | H | D14 |
| 4350 | D9 | CN | A1 | H | D15 |

TABLE 1-30

| No. | $R^1$ | $R^2$ | $R^3$ | $R^4$ | $R^5$ |
|---|---|---|---|---|---|
| 4351 | D9 | CN | A1 | H | D16 |
| 4352 | D10 | CN | A1 | H | D1 |
| 4353 | D10 | CN | A1 | H | D2 |
| 4354 | D10 | CN | A1 | H | D3 |
| 4355 | D10 | CN | A1 | H | D4 |
| 4356 | D10 | CN | A1 | H | D5 |
| 4357 | D10 | CN | A1 | H | D6 |
| 4358 | D10 | CN | A1 | H | D7 |
| 4359 | D10 | CN | A1 | H | D8 |
| 4360 | D10 | CN | A1 | H | D9 |
| 4361 | D10 | CN | A1 | H | D10 |
| 4362 | D10 | CN | A1 | H | D11 |
| 4363 | D10 | CN | A1 | H | D12 |
| 4364 | D10 | CN | A1 | H | D13 |
| 4365 | D10 | CN | A1 | H | D14 |
| 4366 | D10 | CN | A1 | H | D16 |
| 4367 | D10 | CN | A1 | H | D16 |
| 4368 | D11 | CN | A1 | H | D1 |
| 4369 | D11 | CN | A1 | H | D2 |
| 4370 | D11 | CN | A1 | H | D3 |
| 4371 | D11 | CN | A1 | H | D4 |
| 4372 | D11 | CN | A1 | H | D5 |
| 4373 | D11 | CN | A1 | H | D6 |
| 4374 | D11 | CN | A1 | H | D7 |
| 4375 | D11 | CN | A1 | H | D8 |
| 4376 | D11 | CN | A1 | H | D9 |
| 4377 | D11 | CN | A1 | H | D10 |
| 4378 | D11 | CN | A1 | H | D11 |
| 4379 | D11 | CN | A1 | H | D12 |
| 4380 | D11 | CN | A1 | H | D13 |
| 4381 | D11 | CN | A1 | H | D14 |
| 4382 | D11 | CN | A1 | H | D15 |
| 4383 | D11 | CN | A1 | H | D16 |
| 4384 | D12 | CN | A1 | H | D1 |
| 4385 | D12 | CN | A1 | H | D2 |
| 4386 | D12 | CN | A1 | H | D3 |
| 4387 | D12 | CN | A1 | H | D4 |
| 4388 | D12 | CN | A1 | H | D5 |
| 4389 | D12 | CN | A1 | H | D6 |
| 4390 | D12 | CN | A1 | H | D7 |
| 4391 | D12 | CN | A1 | H | D8 |
| 4392 | D12 | CN | A1 | H | D9 |
| 4393 | D12 | CN | A1 | H | D10 |
| 4394 | D12 | CN | A1 | H | D11 |
| 4395 | D12 | CN | A1 | H | D12 |
| 4396 | D12 | CN | A1 | H | D13 |
| 4397 | D12 | CN | A1 | H | D14 |
| 4398 | D12 | CN | A1 | H | D15 |
| 4399 | D12 | CN | A1 | H | D16 |
| 4400 | D13 | CN | A1 | H | D1 |
| 4401 | D13 | CN | A1 | H | D2 |
| 4402 | D13 | CN | A1 | H | D3 |
| 4403 | D13 | CN | A1 | H | D4 |
| 4404 | D13 | CN | A1 | H | D5 |
| 4405 | D13 | CN | A1 | H | D6 |
| 4406 | D13 | CN | A1 | H | D7 |
| 4407 | D13 | CN | A1 | H | D6 |
| 4408 | D13 | CN | A1 | H | D9 |
| 4409 | D13 | CN | A1 | H | D10 |
| 4410 | D13 | CN | A1 | H | D11 |
| 4411 | D13 | CN | A1 | H | D12 |
| 4412 | D13 | CN | A1 | H | D13 |
| 4413 | D13 | CN | A1 | H | D14 |
| 4414 | D13 | CN | A1 | H | D15 |
| 4415 | D13 | CN | A1 | H | D16 |
| 4416 | D14 | CN | A1 | H | D1 |
| 4417 | D14 | CN | A1 | H | D2 |
| 4418 | D14 | CN | A1 | H | D3 |
| 4419 | D14 | CN | A1 | H | D4 |
| 4420 | D14 | CN | A1 | H | D5 |
| 4421 | D14 | CN | A1 | H | D6 |
| 4422 | D14 | CN | A1 | H | D7 |
| 4423 | D14 | CN | A1 | H | D8 |
| 4424 | D14 | CN | A1 | H | D9 |
| 4425 | D14 | CN | A1 | H | D10 |
| 4426 | D14 | CN | A1 | H | D11 |
| 4427 | D14 | CN | A1 | H | D12 |
| 4428 | D14 | CN | A1 | H | D13 |

TABLE 1-30-continued

| No. | $R^1$ | $R^2$ | $R^3$ | $R^4$ | $R^5$ |
|---|---|---|---|---|---|
| 4429 | D14 | CN | A1 | H | D14 |
| 4430 | D14 | CN | A1 | H | D15 |
| 4431 | D14 | CN | A1 | H | D16 |
| 4432 | D15 | CN | A1 | H | D1 |
| 4433 | D15 | CN | A1 | H | D2 |
| 4434 | D15 | CN | A1 | H | D3 |
| 4435 | D15 | CN | A1 | H | D4 |
| 4436 | D15 | CN | A1 | H | D5 |
| 4437 | D15 | CN | A1 | H | D6 |
| 4438 | D15 | CN | A1 | H | D7 |
| 4439 | D15 | CN | A1 | H | D8 |
| 4440 | D15 | CN | A1 | H | D9 |
| 4441 | D15 | CN | A1 | H | D10 |
| 4442 | D15 | CN | A1 | H | D11 |
| 4443 | D15 | CN | A1 | H | D12 |
| 4444 | D15 | CN | A1 | H | D13 |
| 4445 | D15 | CN | A1 | H | D14 |
| 4446 | D15 | CN | A1 | H | D15 |
| 4447 | D15 | CN | A1 | H | D16 |
| 4448 | D16 | CN | A1 | H | D1 |
| 4449 | D16 | CN | A1 | H | D2 |
| 4450 | D16 | CN | A1 | H | D3 |
| 4451 | D16 | CN | A1 | H | D4 |
| 4452 | D16 | CN | A1 | H | D5 |
| 4453 | D16 | CN | A1 | H | D6 |
| 4454 | D16 | CN | A1 | H | D7 |
| 4455 | D16 | CN | A1 | H | D8 |
| 4456 | D16 | CN | A1 | H | D9 |
| 4457 | D16 | CN | A1 | H | D10 |
| 4458 | D16 | CN | A1 | H | D11 |
| 4459 | D16 | CN | A1 | H | D12 |
| 4460 | D16 | CN | A1 | H | D13 |
| 4461 | D16 | CN | A1 | H | D14 |
| 4462 | D16 | CN | A1 | H | D15 |
| 4463 | D16 | CN | A1 | H | D16 |
| 4464 | D1 | CN | A2 | H | D1 |
| 4465 | D1 | CN | A2 | H | D2 |
| 4466 | D1 | CN | A2 | H | D3 |
| 4467 | D1 | CN | A2 | H | D4 |
| 4468 | D1 | CN | A2 | H | D5 |
| 4469 | D1 | CN | A2 | H | D6 |
| 4470 | D1 | CN | A2 | H | D7 |
| 4471 | D1 | CN | A2 | H | D8 |
| 4472 | D1 | CN | A2 | H | D9 |
| 4473 | D1 | CN | A2 | H | D10 |
| 4474 | D1 | CN | A2 | H | D11 |
| 4475 | D1 | CN | A2 | H | D12 |
| 4476 | D1 | CN | A2 | H | D13 |
| 4477 | D1 | CN | A2 | H | D14 |
| 4478 | D1 | CN | A2 | H | D15 |
| 4479 | D1 | CN | A2 | H | D16 |
| 4480 | D2 | CN | A2 | H | D1 |
| 4481 | D2 | CN | A2 | H | D2 |
| 4482 | D2 | CN | A2 | H | D3 |
| 4483 | D2 | CN | A2 | H | D4 |
| 4484 | D2 | CN | A2 | H | D5 |
| 4485 | D2 | CN | A2 | H | D6 |
| 4486 | D2 | CN | A2 | H | D7 |
| 4487 | D2 | CN | A2 | H | D8 |
| 4488 | D2 | CN | A2 | H | D9 |
| 4489 | D2 | CN | A2 | H | D10 |
| 4490 | D2 | CN | A2 | H | D11 |
| 4491 | D2 | CN | A2 | H | D12 |
| 4492 | D2 | CN | A2 | H | D13 |
| 4493 | D2 | CN | A2 | H | D14 |
| 4494 | D2 | CN | A2 | H | D15 |
| 4495 | D2 | CN | A2 | H | D16 |
| 4496 | D3 | CN | A2 | H | D1 |
| 4497 | D3 | CN | A2 | H | D2 |
| 4498 | D3 | CN | A2 | H | D3 |
| 4499 | D3 | CN | A2 | H | D4 |
| 4500 | D3 | CN | A2 | H | D5 |

TABLE 1-31

| No. | $R^1$ | $R^2$ | $R^3$ | $R^4$ | $R^5$ |
|---|---|---|---|---|---|
| 4501 | D3 | CN | A2 | H | D6 |
| 4502 | D3 | CN | A2 | H | D7 |
| 4503 | D3 | CN | A2 | H | D5 |
| 4504 | D3 | CN | A2 | H | D9 |
| 4505 | D3 | CN | A2 | H | D10 |
| 4506 | D3 | CN | A2 | H | D11 |
| 4507 | D3 | CN | A2 | H | D12 |
| 4508 | D3 | CN | A2 | H | D13 |
| 4509 | D3 | CN | A2 | H | D14 |
| 4510 | D3 | CN | A2 | H | D15 |
| 4511 | D3 | CN | A2 | H | D16 |
| 4512 | D4 | CN | A2 | H | D1 |
| 4513 | D4 | CN | A2 | H | D2 |
| 4514 | D4 | CN | A2 | H | D3 |
| 4515 | D4 | CN | A2 | H | D4 |
| 4516 | D4 | CN | A2 | H | D5 |
| 4517 | D4 | CN | A2 | H | D6 |
| 4518 | D4 | CN | A2 | H | D7 |
| 4519 | D4 | CN | A2 | H | D8 |
| 4520 | D4 | CN | A2 | H | D9 |
| 4521 | D4 | CN | A2 | H | D10 |
| 4522 | D4 | CN | A2 | H | D11 |
| 4523 | D4 | CN | A2 | H | D12 |
| 4524 | D4 | CN | A2 | H | D13 |
| 4525 | D4 | CN | A2 | H | D14 |
| 4526 | D4 | CN | A2 | H | D15 |
| 4527 | D4 | CN | A2 | H | D16 |
| 4528 | D5 | CN | A2 | H | D1 |
| 4529 | D5 | CN | A2 | H | D2 |
| 4530 | D5 | CN | A2 | H | D3 |
| 4531 | D5 | CN | A2 | H | D4 |
| 4532 | D5 | CN | A2 | H | D5 |
| 4533 | D5 | CN | A2 | H | D6 |
| 4534 | D5 | CN | A2 | H | D7 |
| 4535 | D5 | CN | A2 | H | D8 |
| 4536 | D5 | CN | A2 | H | D9 |
| 4537 | D5 | CN | A2 | H | D10 |
| 4538 | D5 | CN | A2 | H | D11 |
| 4539 | D5 | CN | A2 | H | D12 |
| 4540 | D5 | CN | A2 | H | D13 |
| 4541 | D5 | CN | A2 | H | D14 |
| 4542 | D5 | CN | A2 | H | D15 |
| 4543 | D5 | CN | A2 | H | D16 |
| 4544 | D6 | CN | A2 | H | D1 |
| 4545 | D6 | CN | A2 | H | D2 |
| 4546 | D6 | CN | A2 | H | D3 |
| 4547 | D6 | CN | A2 | H | D4 |
| 4548 | D6 | CN | A2 | H | D5 |
| 4549 | D6 | CN | A2 | H | D6 |
| 4550 | D6 | CN | A2 | H | D7 |
| 4551 | D6 | CN | A2 | H | D8 |
| 4552 | D6 | CN | A2 | H | D9 |
| 4553 | D6 | CN | A2 | H | D10 |
| 4554 | D6 | CN | A2 | H | D11 |
| 4555 | D6 | CN | A2 | H | D17 |
| 4556 | D6 | CN | A2 | H | D13 |
| 4557 | D6 | CN | A2 | H | D14 |
| 4558 | D6 | CN | A2 | H | D15 |
| 4559 | D6 | CN | A2 | H | D16 |
| 4560 | D7 | CN | A2 | H | D1 |
| 4561 | D7 | CN | A2 | H | D2 |
| 4562 | D7 | CN | A2 | H | D3 |
| 4563 | D7 | CN | A2 | H | D4 |
| 4564 | D7 | CN | A2 | H | D5 |
| 4565 | D7 | CN | A2 | H | D6 |
| 4566 | D7 | CN | A2 | H | D7 |
| 4567 | D7 | CN | A2 | H | D8 |
| 4568 | D7 | CN | A2 | H | D9 |
| 4569 | D7 | CN | A2 | H | D10 |
| 4570 | D7 | CN | A2 | H | D11 |
| 4571 | D7 | CN | A2 | H | D12 |
| 4572 | D7 | CN | A2 | H | D13 |
| 4573 | D7 | CN | A2 | H | D14 |
| 4574 | D7 | CN | A2 | H | D15 |
| 4575 | D7 | CN | A2 | H | D16 |
| 4576 | D8 | CN | A2 | H | D1 |
| 4577 | D8 | CN | A2 | H | D2 |
| 4578 | D8 | CN | A2 | H | D3 |

TABLE 1-31-continued

| No. | $R^1$ | $R^2$ | $R^3$ | $R^4$ | $R^5$ |
|---|---|---|---|---|---|
| 4579 | D8 | CN | A2 | H | D4 |
| 4580 | D8 | CN | A2 | H | D5 |
| 4581 | D8 | CN | A2 | H | D6 |
| 4582 | D8 | CN | A2 | H | D7 |
| 4583 | D8 | CN | A2 | H | D8 |
| 4584 | D8 | CN | A2 | H | D9 |
| 4585 | D8 | CN | A2 | H | D10 |
| 4586 | D8 | CN | A2 | H | D11 |
| 4587 | D8 | CN | A2 | H | D12 |
| 4588 | D8 | CN | A2 | H | D13 |
| 4589 | D8 | CN | A2 | H | D14 |
| 4590 | D8 | CN | A2 | H | D15 |
| 4591 | D8 | CN | A2 | H | D16 |
| 4592 | D9 | CN | A2 | H | D1 |
| 4593 | D9 | CN | A2 | H | D2 |
| 4594 | D9 | CN | A2 | H | D3 |
| 4595 | D9 | CN | A2 | H | D4 |
| 4596 | D9 | CN | A2 | H | D5 |
| 4597 | D9 | CN | A2 | H | D6 |
| 4598 | D9 | CN | A2 | H | D7 |
| 4599 | D9 | CN | A2 | H | D8 |
| 4600 | D9 | CN | A2 | H | D9 |
| 4601 | D9 | CN | A2 | H | D10 |
| 4602 | D9 | CN | A2 | H | D11 |
| 4603 | D9 | CN | A2 | H | D12 |
| 4604 | D9 | CN | A2 | H | D13 |
| 4605 | D9 | CN | A2 | H | D14 |
| 4606 | D9 | CN | A2 | H | D15 |
| 4607 | D9 | CN | A2 | H | D16 |
| 4608 | D10 | CN | A2 | H | D1 |
| 4609 | D10 | CN | A2 | H | D2 |
| 4610 | D10 | CN | A2 | H | D3 |
| 4611 | D10 | CN | A2 | H | D4 |
| 4612 | D10 | CN | A2 | H | D5 |
| 4613 | D10 | CN | A2 | H | D6 |
| 4614 | D10 | CN | A2 | H | D7 |
| 4615 | D10 | CN | A2 | H | D8 |
| 4616 | D10 | CN | A2 | H | D9 |
| 4617 | D10 | CN | A2 | H | D10 |
| 4618 | D10 | CN | A2 | H | D11 |
| 4619 | D10 | CN | A2 | H | D12 |
| 4620 | D10 | CN | A2 | H | D13 |
| 4621 | D10 | CN | A2 | H | D14 |
| 4622 | D10 | CN | A2 | H | D15 |
| 4623 | D10 | CN | A2 | H | D16 |
| 4624 | D11 | CN | A2 | H | D1 |
| 4625 | D11 | CN | A2 | H | D2 |
| 4626 | D11 | CN | A2 | H | D3 |
| 4627 | D11 | CN | A2 | H | D4 |
| 4628 | D11 | CN | A2 | H | D5 |
| 4629 | D11 | CN | A2 | H | D6 |
| 4630 | D11 | CN | A2 | H | D7 |
| 4631 | D11 | CN | A2 | H | D8 |
| 4632 | D11 | CN | A2 | H | D9 |
| 4633 | D11 | CN | A2 | H | D10 |
| 4634 | D11 | CN | A2 | H | D11 |
| 4635 | D11 | CN | A2 | H | D12 |
| 4636 | D11 | CN | A2 | H | D13 |
| 4637 | D11 | CN | A2 | H | D14 |
| 4638 | D11 | CN | A2 | H | D15 |
| 4639 | D11 | CN | A2 | H | D16 |
| 4640 | D12 | CN | A2 | H | D1 |
| 4641 | D12 | CN | A2 | H | D2 |
| 4642 | D12 | CN | A2 | H | D3 |
| 4643 | D12 | CN | A2 | H | D4 |
| 4644 | D12 | CN | A2 | H | D5 |
| 4645 | D12 | CN | A2 | H | D6 |
| 4646 | D12 | CN | A2 | H | D7 |
| 4647 | D12 | CN | A2 | H | D8 |
| 4648 | D12 | CN | A2 | H | D9 |
| 4649 | D12 | CN | A2 | H | D10 |
| 4650 | D12 | CN | A2 | H | D11 |

TABLE 1-32

| No. | $R^1$ | $R^2$ | $R^3$ | $R^4$ | $R^5$ |
|---|---|---|---|---|---|
| 4651 | D12 | CN | A2 | H | D12 |
| 4652 | D12 | CN | A2 | H | D13 |
| 4653 | D12 | CN | A2 | H | D14 |
| 4654 | D12 | CN | A2 | H | D15 |
| 4655 | D12 | CN | A2 | H | D16 |
| 4656 | D13 | CN | A2 | H | D1 |
| 4657 | D13 | CN | A2 | H | D2 |
| 4658 | D13 | CN | A2 | H | D3 |
| 4659 | D13 | CN | A2 | H | D4 |
| 4660 | D13 | CN | A2 | H | D5 |
| 4661 | D13 | CN | A2 | H | D6 |
| 4662 | D13 | CN | A2 | H | D7 |
| 4663 | D13 | CN | A2 | H | D8 |
| 4664 | D13 | CN | A2 | H | D9 |
| 4665 | D13 | CN | A2 | H | D10 |
| 4666 | D13 | CN | A2 | H | D11 |
| 4667 | D13 | CN | A2 | H | D12 |
| 4668 | D13 | CN | A2 | H | D13 |
| 4669 | D13 | CN | A2 | H | D14 |
| 4670 | D13 | CN | A2 | H | D15 |
| 4671 | D13 | CN | A2 | H | D16 |
| 4672 | D14 | CN | A2 | H | D1 |
| 4673 | D14 | CN | A2 | H | D2 |
| 4674 | D14 | CN | A2 | H | D3 |
| 4675 | D14 | CN | A2 | H | D4 |
| 4676 | D14 | CN | A2 | H | D5 |
| 4677 | D14 | CN | A2 | H | D6 |
| 4678 | D14 | CN | A2 | H | D7 |
| 4679 | D14 | CN | A2 | H | D8 |
| 4680 | D14 | CN | A2 | H | D9 |
| 4681 | D14 | CN | A2 | H | D10 |
| 4682 | D14 | CN | A2 | H | D11 |
| 4683 | D14 | CN | A2 | H | D12 |
| 4684 | D14 | CN | A2 | H | D13 |
| 4685 | D14 | CN | A2 | H | D14 |
| 4686 | D14 | CN | A2 | H | D15 |
| 4687 | D14 | CN | A2 | H | D16 |
| 4688 | D15 | CN | A2 | H | D1 |
| 4689 | D15 | CN | A2 | H | D2 |
| 4690 | D15 | CN | A2 | H | D3 |
| 4691 | D15 | CN | A2 | H | D4 |
| 4692 | D15 | CN | A2 | H | D5 |
| 4693 | D15 | CN | A2 | H | D6 |
| 4694 | D15 | CN | A2 | H | D7 |
| 4695 | D15 | CN | A2 | H | D8 |
| 4696 | D15 | CN | A2 | H | D9 |
| 4697 | D15 | CN | A2 | H | D10 |
| 4698 | D15 | CN | A2 | H | D11 |
| 4699 | D15 | CN | A2 | H | D12 |
| 4700 | D15 | CN | A2 | H | D13 |
| 4701 | D15 | CN | A2 | H | D14 |
| 4702 | D15 | CN | A2 | H | D15 |
| 4703 | D15 | CN | A2 | H | D16 |
| 4704 | D16 | CN | A2 | H | D1 |
| 4705 | D16 | CN | A2 | H | D2 |
| 4706 | D16 | CN | A2 | H | D3 |
| 4707 | D16 | CN | A2 | H | D4 |
| 4708 | D16 | CN | A2 | H | D5 |
| 4709 | D16 | CN | A2 | H | D6 |
| 4710 | D16 | CN | A2 | H | D7 |
| 4711 | D16 | CN | A2 | H | D8 |
| 4712 | D16 | CN | A2 | H | D9 |
| 4713 | D16 | CN | A2 | H | D10 |
| 4714 | D16 | CN | A2 | H | D11 |
| 4715 | D16 | CN | A2 | H | D12 |
| 4716 | D16 | CN | A2 | H | D13 |
| 4717 | D16 | CN | A2 | H | D14 |
| 4718 | D16 | CN | A2 | H | D15 |
| 4719 | D16 | CN | A2 | H | D16 |
| 4720 | D1 | CN | D1 | A1 | D1 |
| 4721 | D1 | CN | D1 | A1 | D2 |
| 4722 | D1 | CN | D1 | A1 | D3 |
| 4723 | D1 | CN | D1 | A1 | D4 |
| 4724 | D1 | CN | D1 | A1 | D5 |
| 4725 | D1 | CN | D1 | A1 | D6 |
| 4726 | D1 | CN | D2 | A1 | D1 |
| 4727 | D1 | CN | D2 | A1 | D2 |
| 4728 | D1 | CN | D2 | A1 | D3 |

TABLE 1-32-continued

| No. | $R^1$ | $R^2$ | $R^3$ | $R^4$ | $R^5$ |
|---|---|---|---|---|---|
| 4729 | D1 | CN | D2 | A1 | D4 |
| 4730 | D1 | CN | D2 | A1 | D5 |
| 4731 | D1 | CN | D2 | A1 | D6 |
| 4732 | D1 | CN | D3 | A1 | D1 |
| 4733 | D1 | CN | D3 | A1 | D2 |
| 4734 | D1 | CN | D3 | A1 | D3 |
| 4735 | D1 | CN | D3 | A1 | D4 |
| 4736 | D1 | CN | D3 | A1 | D5 |
| 4737 | D1 | CN | D3 | A1 | D6 |
| 4738 | D1 | CN | D4 | A1 | D1 |
| 4739 | D1 | CN | D4 | A1 | D2 |
| 4740 | D1 | CN | D4 | A1 | D3 |
| 4741 | D1 | CN | D4 | A1 | D4 |
| 4742 | D1 | CN | D4 | A1 | D5 |
| 4743 | D1 | CN | D4 | A1 | D6 |
| 4744 | D1 | CN | D5 | A1 | D1 |
| 4745 | D1 | CN | D5 | A1 | D2 |
| 4746 | D1 | CN | D5 | A1 | D3 |
| 4747 | D1 | CN | D5 | A1 | D4 |
| 4748 | D1 | CN | D5 | A1 | D5 |
| 4749 | D1 | CN | D5 | A1 | D6 |
| 4750 | D1 | CN | D6 | A1 | D1 |
| 4751 | D1 | CN | D6 | A1 | D2 |
| 4752 | D1 | CN | D6 | A1 | D3 |
| 4753 | D1 | CN | D6 | A1 | D4 |
| 4754 | D1 | CN | D6 | A1 | D5 |
| 4755 | D1 | CN | D6 | A1 | D6 |
| 4756 | D2 | CN | D1 | A1 | D1 |
| 4757 | D2 | CN | D1 | A1 | D2 |
| 4758 | D2 | CN | D1 | A1 | D3 |
| 4759 | D2 | CN | D1 | A1 | D4 |
| 4760 | D2 | CN | D1 | A1 | D5 |
| 4761 | D2 | CN | D1 | A1 | D6 |
| 4762 | D2 | CN | D2 | A1 | D1 |
| 4763 | D2 | CN | D2 | A1 | D2 |
| 4764 | D2 | CN | D2 | A1 | D3 |
| 4765 | D2 | CN | D2 | A1 | D4 |
| 4766 | D2 | CN | D2 | A1 | D5 |
| 4767 | D2 | CN | D2 | A1 | D6 |
| 4768 | D2 | CN | D3 | A1 | D1 |
| 4769 | D2 | CN | D3 | A1 | D2 |
| 4770 | D2 | CN | D3 | A1 | D3 |
| 4771 | D2 | CN | D3 | A1 | D4 |
| 4772 | D2 | CN | D3 | A1 | D5 |
| 4773 | D2 | CN | D3 | A1 | D6 |
| 4774 | D2 | CN | D4 | A1 | D1 |
| 4775 | D2 | CN | D4 | A1 | D2 |
| 4776 | D2 | CN | D4 | A1 | D3 |
| 4777 | D2 | CN | D4 | A1 | D4 |
| 4778 | D2 | CN | D4 | A1 | D5 |
| 4779 | D2 | CN | D4 | A1 | D6 |
| 4780 | D2 | CN | D5 | A1 | D1 |
| 4781 | D2 | CN | D5 | A1 | D2 |
| 4782 | D2 | CN | D5 | A1 | D3 |
| 4783 | D2 | CN | D5 | A1 | D4 |
| 4784 | D2 | CN | D5 | A1 | D5 |
| 4785 | D2 | CN | D5 | A1 | D6 |
| 4786 | D2 | CN | D6 | A1 | D1 |
| 4787 | D2 | CN | D6 | A1 | D2 |
| 4788 | D2 | CN | D6 | A1 | D3 |
| 4789 | D2 | CN | D6 | A1 | D4 |
| 4790 | D2 | CN | D6 | A1 | D5 |
| 4791 | D2 | CN | D6 | A1 | D6 |
| 4792 | D3 | CN | D1 | A1 | D1 |
| 4793 | D3 | CN | D1 | A1 | D2 |
| 4794 | D3 | CN | D1 | A1 | D3 |
| 4795 | D3 | CN | D1 | A1 | D4 |
| 4796 | D3 | CN | D1 | A1 | D5 |
| 4797 | D3 | CN | D1 | A1 | D6 |
| 4798 | D3 | CN | D2 | A1 | D1 |
| 4799 | D3 | CN | D2 | A1 | D2 |
| 4800 | D3 | CN | D2 | A1 | D3 |

TABLE 1-33

| No.4 | $R^1$ | $R^2$ | $R^3$ | $R^4$ | $R^5$ |
|---|---|---|---|---|---|
| 4801 | D3 | CN | D2 | A1 | D4 |
| 4802 | D3 | CN | D2 | A1 | D5 |
| 4803 | D3 | CN | D2 | A1 | D6 |
| 4804 | D3 | CN | D3 | A1 | D1 |
| 4805 | D3 | CN | D5 | A1 | D2 |
| 4806 | D3 | CN | D5 | A1 | D3 |
| 4807 | D3 | CN | D3 | A1 | D4 |
| 4808 | D3 | CN | D3 | A1 | D5 |
| 4809 | D3 | CN | D3 | A1 | D6 |
| 4810 | D3 | CN | D4 | A1 | D1 |
| 4811 | D3 | CN | D4 | A1 | D2 |
| 4812 | D3 | CN | D4 | A1 | D3 |
| 4813 | D3 | CN | D4 | A1 | D4 |
| 4814 | D3 | CN | D4 | A1 | D5 |
| 4815 | D3 | CN | D4 | A1 | D6 |
| 4816 | D3 | CN | D5 | A1 | D1 |
| 4817 | D3 | CN | D5 | A1 | D2 |
| 4818 | D3 | CN | D5 | A1 | D3 |
| 4819 | D3 | CN | D5 | A1 | D4 |
| 4820 | D3 | CN | D5 | A1 | D5 |
| 4821 | D3 | CN | D5 | A1 | D6 |
| 4822 | D3 | CN | D6 | A1 | D1 |
| 4823 | D3 | CN | D6 | A1 | D2 |
| 4824 | D3 | CN | D6 | A1 | D3 |
| 4825 | D3 | CN | D6 | A1 | D4 |
| 4826 | D3 | CN | D6 | A1 | D5 |
| 4827 | D3 | CN | D6 | A1 | D6 |
| 4828 | D4 | CN | D1 | A1 | D1 |
| 4829 | D4 | CN | D1 | A1 | D2 |
| 4830 | D4 | CN | D1 | A1 | D3 |
| 4831 | D4 | CN | D1 | A1 | D4 |
| 4832 | D4 | CN | D1 | A1 | D5 |
| 4833 | D4 | CN | D1 | A1 | D6 |
| 4834 | D4 | CN | D2 | A1 | D1 |
| 4835 | D4 | CN | D2 | A1 | D2 |
| 4836 | D4 | CN | D2 | A1 | D3 |
| 4837 | D4 | CN | D2 | A1 | D4 |
| 4838 | D4 | CN | D2 | A1 | D5 |
| 4839 | D4 | CN | D2 | A1 | D6 |
| 4840 | D4 | CN | D3 | A1 | D1 |
| 4841 | D4 | CN | D3 | A1 | D2 |
| 4842 | D4 | CN | D3 | A1 | D3 |
| 4843 | D4 | CN | D3 | A1 | D4 |
| 4844 | D4 | CN | D3 | A1 | D5 |
| 4845 | D4 | CN | D3 | A1 | D6 |
| 4846 | D4 | CN | D4 | A1 | D1 |
| 4847 | D4 | CN | D4 | A1 | D2 |
| 4848 | D4 | CN | D4 | A1 | D3 |
| 4849 | D4 | CN | D4 | A1 | D4 |
| 4850 | D4 | CN | D4 | A1 | D5 |
| 4851 | D4 | CN | D4 | A1 | D6 |
| 4852 | D4 | CN | D5 | A1 | D1 |
| 4853 | D4 | CN | D5 | A1 | D2 |
| 4854 | D4 | CN | D5 | A1 | D3 |
| 4855 | D4 | CN | D5 | A1 | D4 |
| 4856 | D4 | CN | D5 | A1 | D5 |
| 4857 | D4 | CN | D5 | A1 | D6 |
| 4858 | D4 | CN | D6 | A1 | D1 |
| 4859 | D4 | CN | D6 | A1 | D2 |
| 4860 | D4 | CN | D6 | A1 | D3 |
| 4861 | D4 | CN | D6 | A1 | D4 |
| 4862 | D4 | CN | D6 | A1 | D5 |
| 4863 | D4 | CN | D6 | A1 | D6 |
| 4864 | D5 | CN | D1 | A1 | D1 |
| 4865 | D5 | CN | D1 | A1 | D2 |
| 4866 | D5 | CN | D1 | A1 | D3 |
| 4867 | D5 | CN | D1 | A1 | D4 |
| 4868 | D5 | CN | D1 | A1 | D5 |
| 4869 | D5 | CN | D1 | A1 | D6 |
| 4870 | D5 | CN | D2 | A1 | D1 |
| 4871 | D5 | CN | D2 | A1 | D2 |
| 4872 | D5 | CN | D2 | A1 | D3 |
| 4873 | D5 | CN | D2 | A1 | D4 |
| 4874 | D5 | CN | D2 | A1 | D5 |
| 4875 | D5 | CN | D2 | A1 | D6 |
| 4876 | D5 | CN | D3 | A1 | D1 |
| 4877 | D5 | CN | D3 | A1 | D2 |
| 4878 | D5 | CN | D3 | A1 | D3 |

TABLE 1-33-continued

| No.4 | $R^1$ | $R^2$ | $R^3$ | $R^4$ | $R^5$ |
|---|---|---|---|---|---|
| 4879 | D5 | CN | D3 | A1 | D4 |
| 4880 | D5 | CN | D3 | A1 | D5 |
| 4881 | D5 | CN | D3 | A1 | D6 |
| 4882 | D5 | CN | D4 | A1 | D1 |
| 4883 | D5 | CN | D4 | A1 | D2 |
| 4884 | D5 | CN | D4 | A1 | D3 |
| 4885 | D5 | CN | D4 | A1 | D4 |
| 4886 | D5 | CN | D4 | A1 | D5 |
| 4887 | D5 | CN | D4 | A1 | D6 |
| 4888 | D5 | CN | D5 | A1 | D1 |
| 4889 | D5 | CN | D5 | A1 | D2 |
| 4890 | D5 | CN | D5 | A1 | D3 |
| 4891 | D5 | CN | D5 | A1 | D4 |
| 4892 | D5 | CN | D5 | A1 | D5 |
| 4893 | D5 | CN | D5 | A1 | D6 |
| 4894 | D5 | CN | D6 | A1 | D1 |
| 4895 | D5 | CN | D6 | A1 | D2 |
| 4896 | D5 | CN | D6 | A1 | D3 |
| 4897 | D5 | CN | D6 | A1 | D4 |
| 4898 | D5 | CN | D6 | A1 | D5 |
| 4899 | D5 | CN | D6 | A1 | D6 |
| 4900 | D6 | CN | D1 | A1 | D1 |
| 4901 | D6 | CN | D1 | A1 | D2 |
| 49D2 | D6 | CN | D1 | A1 | D3 |
| 4903 | D6 | CN | D1 | A1 | D4 |
| 4904 | D6 | CN | D1 | A1 | D5 |
| 4905 | D6 | CN | D1 | A1 | D6 |
| 4906 | D6 | CN | D2 | A1 | D1 |
| 4907 | D6 | CN | D2 | A1 | D2 |
| 4908 | D6 | CN | D2 | A1 | D3 |
| 4909 | D6 | CN | D2 | A1 | D4 |
| 4910 | D6 | CN | D2 | A1 | D5 |
| 4911 | D6 | CN | D2 | A1 | D6 |
| 4912 | D6 | CN | D3 | A1 | D1 |
| 4913 | D6 | CN | D3 | A1 | D2 |
| 4914 | D6 | CN | D3 | A1 | D3 |
| 4915 | D6 | CN | D3 | A1 | D4 |
| 4916 | D6 | CN | D3 | A1 | D5 |
| 4917 | D6 | CN | D3 | A1 | D6 |
| 4918 | D6 | CN | D4 | A1 | D1 |
| 4919 | D6 | CN | D4 | A1 | D2 |
| 4920 | D6 | CN | D4 | A1 | D3 |
| 4921 | D6 | CN | D4 | A1 | D4 |
| 4922 | D6 | CN | D4 | A1 | D5 |
| 4923 | D6 | CN | D4 | A1 | D6 |
| 4924 | D6 | CN | D5 | A1 | D1 |
| 4925 | D6 | CN | D5 | A1 | D2 |
| 4926 | D6 | CN | D5 | A1 | D3 |
| 4927 | D6 | CN | D5 | A1 | D4 |
| 4928 | D6 | CN | D5 | A1 | D5 |
| 4929 | D6 | CN | D5 | A1 | D6 |
| 4930 | D6 | CN | D6 | A1 | D1 |
| 4931 | D6 | CN | D6 | A1 | D2 |
| 4932 | D6 | CN | D6 | A1 | D3 |
| 4933 | D6 | CN | D6 | A1 | D4 |
| 4934 | D6 | CN | D6 | A1 | D5 |
| 4935 | D6 | CN | D6 | A1 | D6 |
| 4936 | D1 | CN | D1 | A2 | D1 |
| 4937 | D1 | CN | D1 | A2 | D2 |
| 4938 | D1 | CN | D1 | A2 | D3 |
| 4939 | D1 | CN | D1 | A2 | D4 |
| 4940 | D1 | CN | D1 | A2 | D5 |
| 4941 | D1 | CN | D1 | A2 | D6 |
| 4942 | D1 | CN | D2 | A2 | D1 |
| 4943 | D1 | CN | D2 | A2 | D2 |
| 4944 | D1 | CN | D2 | A2 | D3 |
| 4945 | D1 | CN | D2 | A2 | D4 |
| 4946 | D1 | CN | D2 | A2 | D5 |
| 4947 | D1 | CN | D2 | A2 | D6 |
| 4948 | D1 | CN | D3 | A2 | D1 |
| 4949 | D1 | CN | D3 | A2 | D2 |
| 4950 | D1 | CN | D3 | A2 | D3 |

TABLE 1-34

| No. | $R^1$ | $R^2$ | $R^3$ | $R^4$ | $R^5$ |
|---|---|---|---|---|---|
| 4951 | D1 | CN | D3 | A2 | D4 |
| 4952 | D1 | CN | D3 | A2 | D5 |
| 4953 | D1 | CN | D3 | A2 | D6 |
| 4954 | D1 | CN | D4 | A2 | D1 |
| 4955 | D1 | CN | D4 | A2 | D2 |
| 4956 | D1 | CN | D4 | A2 | D3 |
| 4957 | D1 | CN | D4 | A2 | D4 |
| 4958 | D1 | CN | D4 | A2 | D5 |
| 4959 | D1 | CN | D4 | A2 | D6 |
| 4960 | D1 | CN | D5 | A2 | D1 |
| 4961 | D1 | CN | D5 | A2 | D2 |
| 4962 | D1 | CN | D5 | A2 | D3 |
| 4963 | D1 | CN | D5 | A2 | D4 |
| 4964 | D1 | CN | D5 | A2 | D5 |
| 4965 | D1 | CN | D5 | A2 | D6 |
| 4966 | D1 | CN | D6 | A2 | D1 |
| 4967 | D1 | CN | D6 | A2 | D2 |
| 4968 | D1 | CN | D5 | A2 | D3 |
| 4969 | D1 | CN | D6 | A2 | D4 |
| 4970 | D1 | CN | D6 | A2 | D5 |
| 4971 | D1 | CN | D6 | A2 | D6 |
| 4972 | D2 | CN | D1 | A2 | D1 |
| 4973 | D2 | CN | D1 | A2 | D2 |
| 4974 | D2 | CN | D1 | A2 | D3 |
| 4975 | D2 | CN | D1 | A2 | D4 |
| 4976 | D2 | CN | D1 | A2 | D5 |
| 4977 | D2 | CN | D1 | A2 | D6 |
| 4978 | D2 | CN | D2 | A2 | D1 |
| 4979 | D2 | CN | D2 | A2 | D2 |
| 4980 | D2 | CN | D2 | A2 | D3 |
| 4981 | D2 | CN | D2 | A2 | D4 |
| 4982 | D2 | CN | D2 | A2 | D5 |
| 4983 | D2 | CN | D2 | A2 | D6 |
| 4984 | D2 | CN | D3 | A2 | D1 |
| 4985 | D2 | CN | D3 | A2 | D2 |
| 4986 | D2 | CN | D3 | A2 | D3 |
| 4987 | D2 | CN | D3 | A2 | D4 |
| 4988 | D2 | CN | D3 | A2 | D5 |
| 4989 | D2 | CN | D3 | A2 | D6 |
| 4990 | D2 | CN | D4 | A2 | D1 |
| 4991 | D2 | CN | D4 | A2 | D2 |
| 4992 | D2 | CN | D4 | A2 | D3 |
| 4993 | D2 | CN | D4 | A2 | D4 |
| 4994 | D2 | CN | D4 | A2 | D5 |
| 4995 | D2 | CN | D4 | A2 | D6 |
| 4996 | D2 | CN | D5 | A2 | D1 |
| 4997 | D2 | CN | D5 | A2 | D2 |
| 4998 | D2 | CN | D5 | A2 | D3 |
| 4999 | D2 | CN | D5 | A2 | D4 |
| 5000 | D2 | CN | D5 | A2 | D5 |
| 5001 | D2 | CN | D5 | A2 | D6 |
| 5002 | D2 | CN | D6 | A2 | D1 |
| 5003 | D2 | CN | D6 | A2 | D2 |
| 5004 | D2 | CN | D6 | A2 | D3 |
| 5005 | D2 | CN | D6 | A2 | D4 |
| 5006 | D2 | CN | D6 | A2 | D5 |
| 5007 | D2 | CN | D6 | A2 | D6 |
| 5008 | D3 | CN | D1 | A2 | D1 |
| 5009 | D3 | CN | D1 | A2 | D2 |
| 5010 | D3 | CN | D1 | A2 | D3 |
| 5011 | D3 | CN | D1 | A2 | D4 |
| 5012 | D3 | CN | D1 | A2 | D5 |
| 5013 | D3 | CN | D1 | A2 | D6 |
| 5014 | D3 | CN | D2 | A2 | D1 |
| 5015 | D3 | CN | D2 | A2 | D2 |
| 5016 | D3 | CN | D2 | A2 | D3 |
| 5017 | D3 | CN | D2 | A2 | D4 |
| 5018 | D3 | CN | D2 | A2 | D5 |
| 5019 | D3 | CN | D2 | A2 | D6 |
| 5020 | D3 | CN | D3 | A2 | D1 |
| 5021 | D3 | CN | D3 | A2 | D2 |
| 5022 | D3 | CN | D3 | A2 | D3 |
| 5023 | D3 | CN | D3 | A2 | D4 |
| 5024 | D3 | CN | D3 | A2 | D5 |
| 5025 | D3 | CN | D3 | A2 | D6 |
| 5026 | D3 | CN | D4 | A2 | D1 |
| 5027 | D3 | CN | D4 | A2 | D2 |
| 5028 | D3 | CN | D4 | A2 | D3 |

TABLE 1-34-continued

| No. | $R^1$ | $R^2$ | $R^3$ | $R^4$ | $R^5$ |
|---|---|---|---|---|---|
| 5029 | D3 | CN | D4 | A2 | D4 |
| 5030 | D3 | CN | D4 | A2 | D5 |
| 5031 | D3 | CN | D4 | A2 | D6 |
| 5032 | D3 | CN | D5 | A2 | D1 |
| 5033 | D3 | CN | D5 | A2 | D2 |
| 5034 | D3 | CN | D5 | A2 | D3 |
| 5035 | D3 | CN | D5 | A2 | D4 |
| 5036 | D3 | CN | D5 | A2 | D5 |
| 5037 | D3 | CN | D5 | A2 | D6 |
| 5038 | D3 | CN | D6 | A2 | D1 |
| 5039 | D3 | CN | D6 | A2 | D2 |
| 5040 | D3 | CN | D6 | A2 | D3 |
| 5041 | D3 | CN | D6 | A2 | D4 |
| 5042 | D3 | CN | D6 | A2 | D5 |
| 5043 | D3 | CN | D6 | A2 | D6 |
| 5044 | D4 | CN | D1 | A2 | D1 |
| 5045 | D4 | CN | D1 | A2 | D2 |
| 5046 | D4 | CN | D1 | A2 | D3 |
| 5047 | D4 | CN | D1 | A2 | D4 |
| 5048 | D4 | CN | D1 | A2 | D5 |
| 5049 | D4 | CN | D1 | A2 | D6 |
| 5050 | D4 | CN | D2 | A2 | D1 |
| 5051 | D4 | CN | D2 | A2 | D2 |
| 5052 | D4 | CN | D2 | A2 | D3 |
| 5053 | D4 | CN | D2 | A2 | D4 |
| 5054 | D4 | CN | D2 | A2 | D5 |
| 5055 | D4 | CN | D2 | A2 | D6 |
| 5056 | D4 | CN | D3 | A2 | D1 |
| 5057 | D4 | CN | D3 | A2 | D2 |
| 5058 | D4 | CN | D3 | A2 | D3 |
| 5059 | D4 | CN | D3 | A2 | D4 |
| 5060 | D4 | CN | D3 | A2 | D5 |
| 5061 | D4 | CN | D3 | A2 | D6 |
| 5062 | D4 | CN | D4 | A2 | D1 |
| 5063 | D4 | CN | D4 | A2 | D2 |
| 5064 | D4 | CN | D4 | A2 | D3 |
| 5065 | D4 | CN | D4 | A2 | D4 |
| 5066 | D4 | CN | D4 | A2 | D5 |
| 5067 | D4 | CN | D4 | A2 | D6 |
| 5068 | D4 | CN | D5 | A2 | D1 |
| 5069 | D4 | CN | D5 | A2 | D2 |
| 5070 | D4 | CN | D5 | A2 | D3 |
| 5071 | D4 | CN | D5 | A2 | D4 |
| 5072 | D4 | CN | D5 | A2 | D5 |
| 5073 | D4 | CN | D5 | A2 | D6 |
| 5074 | D4 | CN | D6 | A2 | D1 |
| 5075 | D4 | CN | D6 | A2 | D2 |
| 5076 | D4 | CN | D6 | A2 | D3 |
| 5077 | D4 | CN | D6 | A2 | D4 |
| 5078 | D4 | CN | D6 | A2 | D5 |
| 5079 | D4 | CN | D6 | A2 | D6 |
| 5080 | D5 | CN | D1 | A2 | D1 |
| 5081 | D5 | CN | D1 | A2 | D2 |
| 5082 | D5 | CN | D1 | A2 | D3 |
| 5083 | D5 | CN | D1 | A2 | D4 |
| 5084 | D5 | CN | D1 | A2 | D5 |
| 5085 | D5 | CN | D1 | A2 | D6 |
| 5086 | D5 | CN | D2 | A2 | D1 |
| 5087 | D5 | CN | D2 | A2 | D2 |
| 5088 | D5 | CN | D2 | A2 | D3 |
| 5089 | D5 | CN | D2 | A2 | D4 |
| 5090 | D5 | CN | D2 | A2 | D5 |
| 5091 | D5 | CN | D2 | A2 | D6 |
| 5092 | D5 | CN | D5 | A2 | D1 |
| 5093 | D5 | CN | D3 | A2 | D2 |
| 5094 | D5 | CN | D3 | A2 | D3 |
| 5095 | D5 | CN | D3 | A2 | D4 |
| 5096 | D5 | CN | D3 | A2 | D5 |
| 5097 | D5 | CN | D3 | A2 | D6 |
| 5098 | D5 | CN | D4 | A2 | D1 |
| 5099 | D5 | CN | D4 | A2 | D2 |
| 5100 | D5 | CN | D4 | A2 | D3 |

TABLE 1-35

| No. | $R^1$ | $R^2$ | $R^3$ | $R^4$ | $R^5$ |
|---|---|---|---|---|---|
| 5101 | D5 | CN | D4 | A2 | D4 |
| 5102 | D5 | CN | D4 | A2 | D5 |
| 5103 | D5 | CN | D4 | A2 | D6 |
| 5104 | D5 | CN | D5 | A2 | D1 |
| 5105 | D5 | CN | D5 | A2 | D2 |
| 5106 | D5 | CN | D5 | A2 | D3 |
| 5107 | D5 | CN | D5 | A2 | D4 |
| 5108 | D5 | CN | D5 | A2 | D5 |
| 5109 | D5 | CN | D5 | A2 | D6 |
| 5110 | D5 | CN | D6 | A2 | D1 |
| 5111 | D5 | CN | D6 | A2 | D2 |
| 5112 | D5 | CN | D6 | A2 | D3 |
| 5113 | D5 | CN | D6 | A2 | D3 |
| 5114 | D5 | CN | D6 | A2 | D5 |
| 5115 | D5 | CN | D6 | A2 | D6 |
| 5116 | D6 | CN | D1 | A2 | D1 |
| 5117 | D6 | CN | D1 | A2 | D2 |
| 5118 | D6 | CN | D1 | A2 | D3 |
| 5119 | D6 | CN | D1 | A2 | D4 |
| 5120 | D6 | CN | D1 | A2 | D5 |
| 5121 | D6 | CN | D1 | A2 | D5 |
| 5122 | D6 | CN | D2 | A2 | D1 |
| 5123 | D6 | CN | D2 | A2 | D2 |
| 5124 | D6 | CN | D2 | A2 | D3 |
| 5125 | D6 | CN | D2 | A2 | D4 |
| 5126 | D6 | CN | D2 | A2 | D5 |
| 5127 | D6 | CN | D2 | A2 | D6 |
| 5128 | D6 | CN | D3 | A2 | D1 |
| 5129 | D6 | CN | D3 | A2 | D2 |
| 5130 | D6 | CN | D3 | A2 | D3 |
| 5131 | D6 | CN | D3 | A2 | D4 |
| 5132 | D6 | CN | D3 | A2 | D5 |
| 5133 | D6 | CN | D3 | A2 | D6 |
| 5134 | D6 | CN | D4 | A2 | D1 |
| 5135 | D6 | CN | D4 | A2 | D2 |
| 5136 | D5 | CN | D4 | A2 | D3 |
| 5137 | D5 | CN | D4 | A2 | D4 |
| 5138 | D5 | CN | D4 | A2 | D5 |
| 5139 | D5 | CN | D4 | A2 | D6 |
| 5140 | D6 | CN | D5 | A2 | D1 |
| 5141 | D6 | CN | D5 | A2 | D2 |
| 5142 | D6 | CN | D5 | A2 | D3 |
| 5143 | D6 | CN | D5 | A2 | D4 |
| 5144 | D6 | CN | D5 | A2 | D5 |
| 5145 | D6 | CN | D5 | A2 | D6 |
| 5146 | D6 | CN | D6 | A2 | D1 |
| 5147 | D6 | CN | D6 | A2 | D2 |
| 5148 | D6 | CN | D6 | A2 | D3 |
| 5149 | D6 | CN | D6 | A2 | D4 |
| 5150 | D6 | CN | D6 | A2 | D5 |
| 5151 | D6 | CN | D6 | A2 | D6 |
| 5152 | D1 | CN | H | A1 | D1 |
| 5153 | D1 | CN | H | A1 | D2 |
| 5154 | D1 | CN | H | A1 | D3 |
| 5155 | D1 | CN | H | A1 | D4 |
| 5156 | D1 | CN | H | A1 | D5 |
| 5157 | D1 | CN | H | A1 | D6 |
| 5158 | D1 | CN | H | A1 | D7 |
| 5159 | D1 | CN | H | A1 | D8 |
| 5160 | D1 | CN | H | A1 | D9 |
| 5161 | D1 | CN | H | A1 | D10 |
| 5162 | D1 | CN | H | A1 | D11 |
| 5163 | D1 | CN | H | A1 | D12 |
| 5164 | D1 | CN | H | A1 | D13 |
| 5165 | D1 | CN | H | A1 | D14 |
| 5166 | D1 | CN | H | A1 | D15 |
| 5167 | D1 | CN | H | A1 | D16 |
| 5168 | D2 | CN | H | A1 | D1 |
| 5169 | D2 | CN | H | A1 | D2 |
| 5170 | D2 | CN | H | A1 | D3 |
| 5171 | D2 | CN | H | A1 | D4 |
| 5172 | D2 | CN | H | A1 | D5 |
| 5173 | D2 | CN | H | A1 | D6 |
| 5174 | D2 | CN | H | A1 | D7 |
| 5175 | D2 | CN | H | A1 | D5 |
| 5176 | D2 | CN | H | A1 | D9 |
| 5177 | D2 | CN | H | A1 | D10 |
| 5178 | D2 | CN | H | A1 | D11 |

TABLE 1-35-continued

| No. | $R^1$ | $R^2$ | $R^3$ | $R^4$ | $R^5$ |
|---|---|---|---|---|---|
| 5179 | D2 | CN | H | A1 | D12 |
| 5180 | D2 | CN | H | A1 | D13 |
| 5181 | D2 | CN | H | A1 | D14 |
| 5182 | D2 | CN | H | A1 | D15 |
| 5183 | D2 | CN | H | A1 | D16 |
| 5184 | D3 | CN | H | A1 | D1 |
| 5185 | D3 | CN | H | A1 | D2 |
| 5186 | D3 | CN | H | A1 | D3 |
| 5187 | D3 | CN | H | A1 | D4 |
| 5188 | D3 | CN | H | A1 | D5 |
| 5189 | D3 | CN | H | A1 | D6 |
| 5190 | D3 | CN | H | A1 | D7 |
| 5191 | D3 | CN | H | A1 | D8 |
| 5192 | D3 | CN | H | A1 | D9 |
| 5193 | D3 | CN | H | A1 | D10 |
| 5194 | D3 | CN | H | A1 | D11 |
| 5195 | D3 | CN | H | A1 | D12 |
| 5196 | D3 | CN | H | A1 | D13 |
| 5197 | D3 | CN | H | A1 | D14 |
| 5198 | D3 | CN | H | A1 | D15 |
| 5199 | D3 | CN | H | A1 | D16 |
| 5200 | D4 | CN | H | A1 | D1 |
| 5201 | D4 | CN | H | A1 | D2 |
| 5202 | D4 | CN | H | A1 | D3 |
| 5203 | D4 | CN | H | A1 | D4 |
| 5204 | D4 | CN | H | A1 | D5 |
| 5205 | D4 | CN | H | A1 | D6 |
| 5206 | D4 | CN | H | A1 | D7 |
| 5207 | D4 | CN | H | A1 | D8 |
| 5208 | D4 | CN | H | A1 | D9 |
| 5209 | D4 | CN | H | A1 | D10 |
| 5210 | D4 | CN | H | A1 | D11 |
| 5211 | D4 | CN | H | A1 | D12 |
| 5212 | D4 | CN | H | A1 | D13 |
| 5213 | D4 | CN | H | A1 | D14 |
| 5214 | D4 | CN | H | A1 | D15 |
| 5215 | D4 | CN | H | A1 | D16 |
| 5216 | D5 | CN | H | A1 | D1 |
| 5217 | D5 | CN | H | A1 | D2 |
| 5218 | D5 | CN | H | A1 | D3 |
| 5219 | D5 | CN | H | A1 | D4 |
| 5220 | D5 | CN | H | A1 | D5 |
| 5221 | D5 | CN | H | A1 | D6 |
| 5222 | D5 | CN | H | A1 | D7 |
| 5223 | D5 | CN | H | A1 | D8 |
| 5224 | D5 | CN | H | A1 | D9 |
| 5225 | D5 | CN | H | A1 | D10 |
| 5226 | D5 | CN | H | A1 | D11 |
| 5227 | D5 | CN | H | A1 | D12 |
| 5228 | D5 | CN | H | A1 | D13 |
| 5229 | D5 | CN | H | A1 | D14 |
| 5230 | D5 | CN | H | A1 | D15 |
| 5231 | D5 | CN | H | A1 | D16 |
| 5232 | D6 | CN | H | A1 | D1 |
| 5233 | D6 | CN | H | A1 | D2 |
| 5234 | D6 | CN | H | A1 | D3 |
| 5235 | D6 | CN | H | A1 | D4 |
| 5236 | D5 | CN | H | A1 | D5 |
| 5237 | D5 | CN | H | A1 | D6 |
| 5238 | D5 | CN | H | A1 | D7 |
| 5239 | D5 | CN | H | A1 | D8 |
| 5240 | D6 | CN | H | A1 | D9 |
| 5241 | D6 | CN | H | A1 | D10 |
| 5242 | D6 | CN | H | A1 | D11 |
| 5243 | D6 | CN | H | A1 | D12 |
| 5244 | D6 | CN | H | A1 | D13 |
| 5245 | D6 | CN | H | A1 | D14 |
| 5246 | D6 | CN | H | A1 | D15 |
| 5247 | D6 | CN | H | A1 | D16 |
| 5248 | D7 | CN | H | A1 | D1 |
| 5249 | D7 | CN | H | A1 | D2 |
| 5250 | D7 | CN | H | A1 | D3 |

TABLE 1-36

| No. | $R^1$ | $R^2$ | $R^3$ | $R^4$ | $R^5$ |
|---|---|---|---|---|---|
| 5251 | D7 | CN | H | A1 | D4 |
| 5252 | D7 | CN | H | A1 | D5 |
| 5253 | D7 | CN | H | A1 | D6 |
| 5254 | D7 | CN | H | A1 | D7 |
| 5255 | D7 | CN | H | A1 | D8 |
| 5256 | D7 | CN | H | A1 | D9 |
| 5257 | D7 | CN | H | A1 | D10 |
| 5258 | D7 | CN | H | A1 | D11 |
| 5259 | D7 | CN | H | A1 | D12 |
| 5260 | D7 | CN | H | A1 | D13 |
| 5261 | D7 | CN | H | A1 | D14 |
| 5262 | D7 | CN | H | A1 | D15 |
| 5263 | D7 | CN | H | A1 | D16 |
| 5264 | D8 | CN | H | A1 | D1 |
| 5265 | D8 | CN | H | A1 | D2 |
| 5266 | D8 | ON | H | A1 | D3 |
| 5267 | D8 | CN | H | A1 | D4 |
| 5268 | D8 | CN | H | A1 | D5 |
| 5269 | D8 | CN | H | A1 | D6 |
| 5270 | D8 | CN | H | A1 | D7 |
| 5271 | D8 | CN | H | A1 | D8 |
| 5272 | D8 | CN | H | A1 | D9 |
| 5273 | D8 | CN | H | A1 | D10 |
| 5274 | D8 | CN | H | A1 | D11 |
| 5275 | D5 | CN | H | A1 | D12 |
| 5276 | D8 | CN | H | A1 | D13 |
| 5277 | D8 | CN | H | A1 | D14 |
| 5278 | D8 | CN | H | A1 | D15 |
| 5279 | D8 | CN | H | A1 | D16 |
| 5280 | D9 | CN | H | A1 | D1 |
| 5281 | D9 | CN | H | A1 | D2 |
| 5282 | D9 | CN | H | A1 | D3 |
| 5283 | D9 | CN | H | A1 | D4 |
| 5284 | D9 | CN | H | A1 | D5 |
| 5285 | D9 | CN | H | A1 | D6 |
| 5286 | D9 | CN | H | A1 | D7 |
| 5287 | D9 | CN | H | A1 | D8 |
| 5288 | D9 | CN | H | A1 | D9 |
| 5289 | D9 | CN | H | A1 | D10 |
| 5290 | D9 | CN | H | A1 | D11 |
| 5291 | D9 | CN | H | A1 | D12 |
| 5292 | D9 | CN | H | A1 | D13 |
| 5293 | D9 | CN | H | A1 | D14 |
| 5294 | D9 | CN | H | A1 | D15 |
| 5295 | D9 | CN | H | A1 | D16 |
| 5296 | D10 | CN | H | A1 | D1 |
| 5297 | D10 | CN | H | A1 | D2 |
| 5298 | D10 | CN | H | A1 | D3 |
| 5299 | D10 | CN | H | A1 | D4 |
| 5300 | D10 | CN | H | A1 | D5 |
| 5301 | D10 | CN | H | A1 | D6 |
| 5302 | D10 | CN | H | A1 | D7 |
| 5303 | D10 | CN | H | A1 | D8 |
| 5304 | D10 | CN | H | A1 | D9 |
| 5305 | D10 | CN | H | A1 | D10 |
| 5306 | D10 | CN | H | A1 | D11 |
| 5307 | D10 | CN | H | A1 | D12 |
| 5308 | D10 | CN | H | A1 | D13 |
| 5309 | D10 | CN | H | A1 | D14 |
| 5310 | D10 | CN | H | A1 | D15 |
| 5311 | D10 | CN | H | A1 | D16 |
| 5312 | D11 | CN | H | A1 | D1 |
| 5313 | D11 | CN | H | A1 | D2 |
| 5314 | D11 | CN | H | A1 | D3 |
| 5315 | D11 | CN | H | A1 | D4 |
| 5316 | D11 | CN | H | A1 | D5 |
| 5317 | D11 | CN | H | A1 | D6 |
| 5318 | D11 | CN | H | A1 | D7 |
| 5319 | D11 | CN | H | A1 | D8 |
| 5320 | D11 | CN | H | A1 | D9 |
| 5321 | D11 | CN | H | A1 | D10 |
| 5322 | D11 | CN | H | A1 | D11 |
| 5323 | D11 | CN | H | A1 | D12 |
| 5324 | D11 | CN | H | A1 | D13 |
| 5325 | D11 | CN | H | A1 | D14 |
| 5326 | D11 | CN | H | A1 | D15 |
| 5327 | D11 | CN | H | A1 | D16 |
| 5328 | D12 | CN | H | A1 | D1 |

TABLE 1-36-continued

| No. | $R^1$ | $R^2$ | $R^3$ | $R^4$ | $R^5$ |
|---|---|---|---|---|---|
| 5329 | D12 | CN | H | A1 | D2 |
| 5330 | D12 | CN | H | A1 | D3 |
| 5331 | D12 | CN | H | A1 | D4 |
| 5332 | D12 | CN | H | A1 | D5 |
| 5333 | D12 | CN | H | A1 | D6 |
| 5334 | D12 | CN | H | A1 | D7 |
| 5335 | D12 | CN | H | A1 | D5 |
| 5336 | D12 | CN | H | A1 | D9 |
| 5337 | D12 | CN | H | A1 | D10 |
| 5338 | D12 | CN | H | A1 | D11 |
| 5339 | D12 | CN | H | A1 | D12 |
| 5340 | D12 | CN | H | A1 | D13 |
| 5341 | D12 | CN | H | A1 | D14 |
| 5342 | D12 | CN | H | A1 | D15 |
| 5343 | D12 | CN | H | A1 | D16 |
| 5344 | D13 | CN | H | A1 | D1 |
| 5345 | D13 | CN | H | A1 | D2 |
| 5346 | D13 | CN | H | A1 | D3 |
| 5347 | D13 | CN | H | A1 | D4 |
| 5348 | D13 | CN | H | A1 | D5 |
| 5349 | D13 | CN | H | A1 | D6 |
| 5350 | D13 | CN | H | A1 | D7 |
| 5351 | D13 | CN | H | A1 | D8 |
| 5352 | D13 | CN | H | A1 | D9 |
| 5353 | D13 | CN | H | A1 | D10 |
| 5354 | D13 | CN | H | A1 | D11 |
| 5355 | D13 | CN | H | A1 | D12 |
| 5356 | D13 | CN | H | A1 | D13 |
| 5357 | D13 | CN | H | A1 | D14 |
| 5358 | D13 | CN | H | A1 | D15 |
| 5359 | D13 | CN | H | A1 | D16 |
| 5360 | D14 | CN | H | A1 | D1 |
| 5361 | D14 | CN | H | A1 | D2 |
| 5362 | D14 | CN | H | A1 | D3 |
| 5363 | D14 | CN | H | A1 | D4 |
| 5364 | D14 | CN | H | A1 | D5 |
| 5365 | D14 | CN | H | A1 | D6 |
| 5366 | D14 | CN | H | A1 | D7 |
| 5367 | D14 | CN | H | A1 | D8 |
| 5368 | D14 | CN | H | A1 | D9 |
| 5369 | D14 | CN | H | A1 | D10 |
| 5370 | D14 | CN | H | A1 | D11 |
| 5371 | D14 | CN | H | A1 | D12 |
| 5372 | D14 | CN | H | A1 | D13 |
| 5373 | D14 | CN | H | A1 | D14 |
| 5374 | D14 | CN | H | A1 | D15 |
| 5375 | D14 | CN | H | A1 | D16 |
| 5376 | D15 | CN | H | A1 | D1 |
| 5377 | D15 | CN | H | A1 | D2 |
| 5378 | D15 | CN | H | A1 | D3 |
| 5379 | D15 | CN | H | A1 | D4 |
| 5380 | D15 | CN | H | A1 | D5 |
| 5381 | D15 | CN | H | A1 | D6 |
| 5382 | D15 | CN | H | A1 | D7 |
| 5383 | D15 | CN | H | A1 | D5 |
| 5384 | D15 | CN | H | A1 | D9 |
| 5385 | D15 | CN | H | A1 | D10 |
| 5386 | D15 | CN | H | A1 | D11 |
| 5387 | D15 | CN | H | A1 | D12 |
| 5388 | D15 | CN | H | A1 | D13 |
| 5389 | D15 | CN | H | A1 | D14 |
| 5390 | D15 | CN | H | A1 | D15 |
| 5391 | D1b | CN | H | A1 | D16 |
| 5392 | D16 | CN | H | A1 | D1 |
| 5393 | D16 | CN | H | A1 | D2 |
| 5394 | D16 | CN | H | A1 | D3 |
| 5395 | D16 | CN | H | A1 | D4 |
| 5396 | D16 | CN | H | A1 | D5 |
| 5397 | D16 | CN | H | A1 | D6 |
| 5398 | D16 | CN | H | A1 | D7 |
| 5399 | D16 | CN | H | A1 | D8 |
| 5400 | D16 | CN | H | A1 | D9 |

TABLE 1-37

| No. | $R^1$ | $R^2$ | $R^3$ | $R^4$ | $R^5$ |
|---|---|---|---|---|---|
| 5401 | D16 | CN | H | A1 | D10 |
| 5402 | D16 | CN | H | A1 | D11 |
| 5403 | D16 | CN | H | A1 | D12 |
| 5404 | D16 | CN | H | A1 | D13 |
| 5405 | D16 | CN | H | A1 | D14 |
| 5406 | D16 | CN | H | A1 | D15 |
| 5407 | D16 | CN | H | A1 | D16 |
| 5408 | D1 | CN | H | A2 | D1 |
| 5409 | D1 | CN | H | A2 | D2 |
| 5410 | D1 | CN | H | A2 | D3 |
| 5411 | D1 | CN | H | A2 | D4 |
| 5412 | D1 | CN | H | A2 | D5 |
| 5413 | D1 | CN | H | A2 | D6 |
| 5414 | D1 | CN | H | A2 | D7 |
| 5415 | D1 | CN | H | A2 | D8 |
| 5416 | D1 | CN | H | A2 | D9 |
| 5417 | D1 | CN | H | A2 | D10 |
| 5418 | D1 | CN | H | A2 | D11 |
| 5419 | D1 | CN | H | A2 | D12 |
| 5420 | D1 | CN | H | A2 | D13 |
| 5421 | D1 | CN | H | A2 | D14 |
| 5422 | D1 | CN | H | A2 | D15 |
| 5423 | D1 | CN | H | A2 | D16 |
| 5424 | D2 | CN | H | A2 | D1 |
| 5425 | D2 | CN | H | A2 | D2 |
| 5426 | D2 | CN | H | A2 | D3 |
| 5427 | D2 | CN | H | A2 | D4 |
| 5428 | D2 | CN | H | A2 | D5 |
| 5429 | D2 | CN | H | A2 | D6 |
| 5430 | D2 | CN | H | A2 | D7 |
| 5431 | D2 | CN | H | A2 | D8 |
| 5432 | D2 | CN | H | A2 | D9 |
| 5433 | D2 | CN | H | A2 | D10 |
| 5434 | D2 | CN | H | A2 | D11 |
| 5435 | D2 | CN | H | A2 | D12 |
| 5436 | D2 | CN | H | A2 | D13 |
| 5437 | D2 | CN | H | A2 | D14 |
| 5438 | D2 | CN | H | A2 | D15 |
| 5439 | D2 | CN | H | A2 | D16 |
| 5440 | D3 | CN | H | A2 | D1 |
| 5441 | D3 | CN | H | A2 | D2 |
| 5442 | D3 | CN | H | A2 | D3 |
| 5443 | D3 | CN | H | A2 | D4 |
| 5444 | D3 | CN | H | A2 | D5 |
| 5445 | D3 | CN | H | A2 | D6 |
| 5446 | D3 | CN | H | A2 | D7 |
| 5447 | D3 | CN | H | A2 | D5 |
| 5448 | D3 | CN | H | A2 | D9 |
| 5449 | D3 | CN | H | A2 | D10 |
| 5450 | D3 | CN | H | A2 | D11 |
| 5451 | D3 | CN | H | A2 | D12 |
| 5452 | D3 | CN | H | A2 | D13 |
| 5453 | D3 | CN | H | A2 | D14 |
| 5454 | D3 | CN | H | A2 | D15 |
| 5455 | D3 | CN | H | A2 | D16 |
| 5456 | D4 | CN | H | A2 | D1 |
| 5457 | D4 | CN | H | A2 | D2 |
| 5458 | D4 | CN | H | A2 | D3 |
| 5459 | D4 | CN | H | A2 | D4 |
| 5460 | D4 | CN | H | A2 | D5 |
| 5461 | D4 | CN | H | A2 | D6 |
| 5462 | D4 | CN | H | A2 | D7 |
| 5463 | D4 | CN | H | A2 | D8 |
| 5464 | D4 | CN | H | A2 | D9 |
| 5465 | D4 | CN | H | A2 | D10 |
| 5466 | D4 | CN | H | A2 | D11 |
| 5467 | D4 | CN | H | A2 | D12 |
| 5468 | D4 | CN | H | A2 | D13 |
| 5469 | D4 | CN | H | A2 | D14 |
| 5470 | D4 | CN | H | A2 | D15 |
| 5471 | D4 | CN | H | A2 | D16 |
| 5472 | D5 | CN | H | A2 | D1 |
| 5473 | D5 | CN | H | A2 | D2 |
| 5474 | D5 | CN | H | A2 | D3 |
| 5475 | D5 | CN | H | A2 | D4 |
| 5476 | D5 | CN | H | A2 | D5 |
| 5477 | D5 | CN | H | A2 | D6 |
| 5478 | D5 | CN | H | A2 | D7 |

TABLE 1-37-continued

| No. | $R^1$ | $R^2$ | $R^3$ | $R^4$ | $R^5$ |
|---|---|---|---|---|---|
| 5479 | D5 | CN | H | A2 | D8 |
| 5480 | D5 | CN | H | A2 | D9 |
| 5481 | D5 | CN | H | A2 | D10 |
| 5482 | D5 | CN | H | A2 | D11 |
| 5483 | D5 | CN | H | A2 | D12 |
| 5484 | D5 | CN | H | A2 | D13 |
| 5485 | D5 | CN | H | A2 | D14 |
| 5486 | D5 | CN | H | A2 | D15 |
| 5487 | D5 | CN | H | A2 | D16 |
| 5488 | D6 | CN | H | A2 | D1 |
| 5489 | D6 | CN | H | A2 | D2 |
| 5490 | D6 | CN | H | A2 | D3 |
| 5491 | D6 | CN | H | A2 | D4 |
| 5492 | D6 | CN | H | A2 | D5 |
| 5493 | D6 | CN | H | A2 | D5 |
| 5494 | D6 | CN | H | A2 | D7 |
| 5495 | D6 | CN | H | A2 | D5 |
| 5496 | D6 | CN | H | A2 | D9 |
| 5497 | D6 | CN | H | A2 | D10 |
| 5498 | D6 | CN | H | A2 | D11 |
| 5499 | D6 | CN | H | A2 | D12 |
| 5500 | D6 | CN | H | A2 | D13 |
| 5501 | D6 | CN | H | A2 | D14 |
| 5502 | D6 | CN | H | A2 | D15 |
| 5503 | D6 | CN | H | A2 | D16 |
| 5504 | D7 | CN | H | A2 | D1 |
| 5505 | D7 | CN | H | A2 | D2 |
| 5506 | D7 | CN | H | A2 | D3 |
| 5507 | D7 | CN | H | A2 | D4 |
| 5508 | D7 | CN | H | A2 | D5 |
| 5509 | D7 | CN | H | A2 | D6 |
| 5510 | D7 | CN | H | A2 | D7 |
| 5511 | D7 | CN | H | A2 | D8 |
| 5512 | D7 | CN | H | A2 | D9 |
| 5513 | D7 | CN | H | A2 | D10 |
| 5514 | D7 | CN | H | A2 | D11 |
| 5515 | D7 | CN | H | A2 | D12 |
| 5516 | D7 | CN | H | A2 | D13 |
| 5517 | D7 | CN | H | A2 | D14 |
| 5518 | D7 | CN | H | A2 | D15 |
| 5519 | D7 | CN | H | A2 | D16 |
| 5520 | D8 | CN | H | A2 | D1 |
| 5521 | D8 | CN | H | A2 | D2 |
| 5522 | D8 | CN | H | A2 | D3 |
| 5523 | D8 | CN | H | A2 | D4 |
| 5524 | D8 | CN | H | A2 | D5 |
| 5525 | D8 | CN | H | A2 | D6 |
| 5526 | D8 | CN | H | A2 | D7 |
| 5527 | D8 | CN | H | A2 | D8 |
| 5528 | D8 | CN | H | A2 | D9 |
| 5529 | D8 | CN | H | A2 | D10 |
| 5530 | D8 | CN | H | A2 | D11 |
| 5531 | D8 | CN | H | A2 | D12 |
| 5532 | D8 | CN | H | A2 | D13 |
| 5533 | D8 | CN | H | A2 | D14 |
| 5534 | D8 | CN | H | A2 | D15 |
| 5535 | D8 | CN | H | A2 | D16 |
| 5536 | D9 | CN | H | A2 | D1 |
| 5537 | D9 | CN | H | A2 | D2 |
| 5538 | D9 | CN | H | A2 | D3 |
| 5539 | D9 | CN | H | A2 | D4 |
| 5540 | D9 | CN | H | A2 | D5 |
| 5541 | D9 | CN | H | A2 | D6 |
| 5542 | D9 | CN | H | A2 | D7 |
| 5543 | D9 | CN | H | A2 | D8 |
| 5544 | D9 | CN | H | A2 | D9 |
| 5545 | D9 | CN | H | A2 | D10 |
| 5546 | D9 | CN | H | A2 | D11 |
| 5547 | D9 | CN | H | A2 | D12 |
| 5548 | D9 | CN | H | A2 | D13 |
| 5549 | D9 | CN | H | A2 | D14 |
| 5550 | D9 | CN | H | A2 | D15 |

TABLE 1-38

| No. | $R^1$ | $R^2$ | $R^3$ | $R^4$ | $R^5$ |
|---|---|---|---|---|---|
| 5551 | D9 | CN | H | A2 | D16 |
| 5552 | D10 | CN | H | A2 | D1 |
| 5553 | D10 | CN | H | A2 | D2 |
| 5554 | D10 | CN | H | A2 | D3 |
| 5555 | D10 | CN | H | A2 | D4 |
| 5556 | D10 | CN | H | A2 | D5 |
| 5557 | D10 | CN | H | A2 | D6 |
| 5558 | D10 | CN | H | A2 | D7 |
| 5559 | D10 | CN | H | A2 | D8 |
| 5560 | D10 | CN | H | A2 | D9 |
| 5561 | D10 | CN | H | A2 | D10 |
| 5562 | D10 | CN | H | A2 | D11 |
| 5563 | D10 | CN | H | A2 | D12 |
| 5564 | D10 | CN | H | A2 | D13 |
| 5565 | D10 | CN | H | A2 | D14 |
| 5566 | D10 | CN | H | A2 | D15 |
| 5567 | D10 | CN | H | A2 | D16 |
| 5568 | D11 | CN | H | A2 | D1 |
| 5569 | D11 | CN | H | A2 | D2 |
| 5570 | D11 | CN | H | A2 | D3 |
| 5571 | D11 | CN | H | A2 | D4 |
| 5572 | D11 | CN | H | A2 | D5 |
| 5573 | D11 | CN | H | A2 | D6 |
| 5574 | D11 | CN | H | A2 | D7 |
| 5575 | D11 | CN | H | A2 | D8 |
| 5576 | D11 | CN | H | A2 | D9 |
| 5577 | D11 | CN | H | A2 | D10 |
| 5578 | D11 | CN | H | A2 | D11 |
| 5579 | D11 | CN | H | A2 | D12 |
| 5580 | D11 | CN | H | A2 | D13 |
| 5581 | D11 | CN | H | A2 | D14 |
| 5582 | D11 | CN | H | A2 | D15 |
| 5583 | D11 | CN | H | A2 | D16 |
| 5584 | D12 | CN | H | A2 | D1 |
| 5585 | D12 | CN | H | A2 | D2 |
| 5586 | D12 | CN | H | A2 | D3 |
| 5587 | D12 | CN | H | A2 | D4 |
| 5588 | D12 | CN | H | A2 | D5 |
| 5589 | D12 | CN | H | A2 | D6 |
| 5590 | D12 | CN | H | A2 | D7 |
| 5591 | D12 | CN | H | A2 | D8 |
| 5592 | D12 | CN | H | A2 | D9 |
| 5593 | D12 | CN | H | A2 | D10 |
| 5594 | D12 | CN | H | A2 | D11 |
| 5595 | D12 | CN | H | A2 | D12 |
| 5596 | D12 | CN | H | A2 | D13 |
| 5597 | D12 | CN | H | A2 | D14 |
| 5598 | D12 | CN | H | A2 | D15 |
| 5599 | D12 | CN | H | A2 | D16 |
| 5600 | D13 | CN | H | A2 | D1 |
| 5601 | D13 | CN | H | A2 | D2 |
| 5602 | D13 | CN | H | A2 | D3 |
| 5603 | D13 | CN | H | A2 | D4 |
| 5604 | D13 | CN | H | A2 | D5 |
| 5605 | D13 | CN | H | A2 | D6 |
| 5606 | D13 | CN | H | A2 | D7 |
| 5607 | D13 | CN | H | A2 | D8 |
| 5608 | D13 | CN | H | A2 | D9 |
| 5609 | D13 | CN | H | A2 | D10 |
| 5610 | D13 | CN | H | A2 | D11 |
| 5611 | D13 | CN | H | A2 | D12 |
| 5612 | D13 | CN | H | A2 | D13 |
| 5613 | D13 | CN | H | A2 | D14 |
| 5614 | D13 | CN | H | A2 | D15 |
| 5615 | D13 | CN | H | A2 | D16 |
| 5616 | D14 | CN | H | A2 | D1 |
| 5617 | D14 | CN | H | A2 | D2 |
| 5618 | D14 | CN | H | A2 | D3 |
| 5619 | D14 | CN | H | A2 | D4 |
| 5620 | D14 | CN | H | A2 | D5 |
| 5621 | D14 | CN | H | A2 | D6 |
| 5622 | D14 | CN | H | A2 | D7 |
| 5623 | D14 | CN | H | A2 | D8 |
| 5624 | D14 | CN | H | A2 | D9 |
| 5625 | D14 | CN | H | A2 | D10 |
| 5626 | D14 | CN | H | A2 | D11 |
| 5627 | D14 | CN | H | A2 | D12 |
| 5628 | D14 | CN | H | A2 | D13 |

TABLE 1-38-continued

| No. | $R^1$ | $R^2$ | $R^3$ | $R^4$ | $R^5$ |
|---|---|---|---|---|---|
| 5629 | D14 | CN | H | A2 | D14 |
| 5630 | D14 | CN | H | A2 | D15 |
| 5631 | D14 | CN | H | A2 | D16 |
| 5632 | D15 | CN | H | A2 | D1 |
| 5633 | D15 | CN | H | A2 | D2 |
| 5634 | D15 | CN | H | A2 | D3 |
| 5635 | D15 | CN | H | A2 | D4 |
| 5636 | D15 | CN | H | A2 | D5 |
| 5637 | D15 | CN | H | A2 | D6 |
| 5638 | D15 | CN | H | A2 | D7 |
| 5639 | D15 | CN | H | A2 | D8 |
| 5640 | D15 | CN | H | A2 | D9 |
| 5641 | D15 | CN | H | A2 | D10 |
| 5642 | D15 | CN | H | A2 | D11 |
| 5643 | D15 | CN | H | A2 | D12 |
| 5644 | D15 | CN | H | A2 | D13 |
| 5645 | D15 | CN | H | A2 | D14 |
| 5646 | D15 | CN | H | A2 | D15 |
| 5647 | D15 | CN | H | A2 | D16 |
| 5648 | D15 | CN | H | A2 | D1 |
| 5649 | D16 | CN | H | A2 | D2 |
| 5650 | D16 | CN | H | A2 | D3 |
| 5651 | D16 | CN | H | A2 | D4 |
| 5652 | D16 | CN | H | A2 | D5 |
| 5653 | D16 | CN | H | A2 | D6 |
| 5654 | D16 | CN | H | A2 | D7 |
| 5655 | D16 | CN | H | A2 | D8 |
| 5656 | D16 | CN | H | A2 | D9 |
| 5657 | D16 | CN | H | A2 | D10 |
| 5658 | D16 | CN | H | A2 | D11 |
| 5659 | D16 | CN | H | A2 | D12 |
| 5660 | D16 | CN | H | A2 | D13 |
| 5661 | D16 | CN | H | A2 | D14 |
| 5662 | D16 | CN | H | A2 | D15 |
| 5663 | D16 | CN | H | A2 | D16 |

[Synthesis Method of Compound Represented by Formula (I)]

The compound represented by the formula (I) can be synthesized by combining existing reactions. For example, a compound of the formula (I), in which $R^1$ is A, $R^2$ is H, $R^3$ is CN, and $R^4$ and $R^5$ are D, can be synthesized via an intermediate through the following reaction scheme.

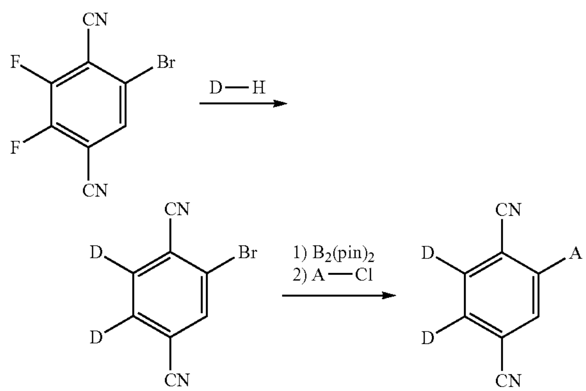

In this reaction scheme, halogenated terephthalonitrile is used as a starting material. Here, halogenated terephthalonitrile having a fluorine atom at a position where D is to be introduced and having a bromine atom at a position where A is to be introduced is prepared. For the halogenated terephthalonitrile, a reaction of D-H is caused in the presence of a catalyst so as to obtain an intermediate in which the fluorine atom is substituted with D. The intermediate is further reacted with bis(pinacolato)diboron in the presence of a catalyst, and further a reaction of A-Cl is caused so as to obtain a target compound in which the bromine atom is substituted with A.

The above reaction is an application of a conventionally known reaction, and conventionally known reaction conditions can be appropriately selected and used. For the details of the above reaction, synthesis examples to be described below can be referred to. Further, the compound represented by the formula (I) can also be synthesized by combining conventionally known other synthesis reactions.

A compound represented by the following formula (I'), which is a synthetic intermediate of the compound represented by the formula (I), includes a novel compound.

Formula (I')

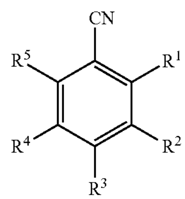

[$R^1$ to $R^5$ in the formula (I') satisfy the following condition 1 or condition 2, (condition 1) among $R^1$ to $R^5$, one is CN, another is a halogen atom, other p are each independently D, and the remaining 3-p is a hydrogen atom or a substituent (but, other than CN, A, and D).

(condition 2) among $R^1$ to $R^5$, one is CN, another is a first halogen atom, another is a second halogen atom, other p-1 are each independently D, and the remaining 3-p is a hydrogen atom or a substituent (but, other than CN, A, and D).

Here,

A is a group represented by Het-$L^A$-*, in which Het represents a substituted or unsubstituted heteroaryl group bonded via a carbon atom (meanwhile, at least two nitrogen atoms are included as ring skeleton-forming atoms of the heteroaryl group), $L^A$ represents a single bond or a substituted or unsubstituted arylene group, and * represents a bond position.

D is a group represented by the following formula (IIa), (IIb), (IIc) or (IId).

Formula (IIa)

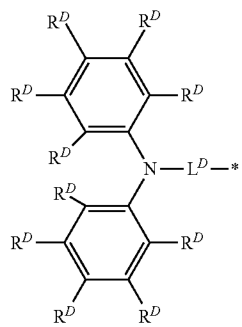

-continued

Formula (IIb)

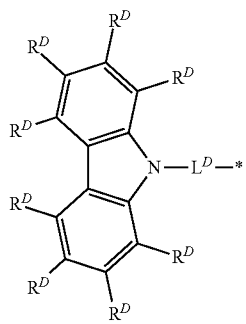

Formula (IIc)

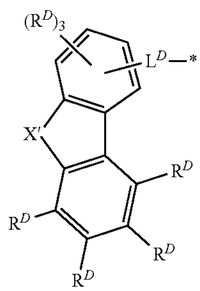

Formula (IId)

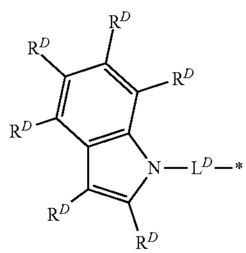

Here, X' represents N—$R^{D'}$, an oxygen atom or a sulfur atom, each $R^D$ independently represents a hydrogen atom, a deuterium atom, a substituted or unsubstituted alkyl group, a substituted or unsubstituted alkoxy group, a substituted or unsubstituted amino group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s may be bonded to each other to form a cyclic structure, $R^{D'}$ represents a hydrogen atom, a deuterium atom, a substituted or unsubstituted alkyl group, a substituted or unsubstituted aryl group, or a substituted or unsubstituted heteroaryl group, and $R^{D'}$ may be bonded to one or more other $R^D$'s to form a cyclic structure, each $L^D$ independently represents a single bond, a substituted or unsubstituted arylene group, or a substituted or unsubstituted heteroarylene group, and

* represents a bond position.

p is 2 or 3. The plurality of D's present in the molecule may be the same or different.]

The descriptions and preferable ranges of A, D, p, and 3-p substituents of the formula (I') can be made with reference to the corresponding descriptions of the formula (I).

In some embodiments, the condition 1 is satisfied. In some embodiments, p is 2. In some embodiments, p is 3. In some embodiments, the halogen atom is a bromine atom.

In some embodiments, the condition 2 is satisfied. In some embodiments, p is 2. In some embodiments, one of $R^1$ to $R^5$ is a hydrogen atom. In some embodiments, the halogen atom is a fluorine atom. In some embodiments, the halogen atom is a bromine atom.

Synthetic intermediates of Synthesis Examples 1 to 5 to be described below can be mentioned as a preferable example.

All the definitions of terms described in [0039] to [0101] of US2020/0168814A1 are incorporated herein, as a part of the present specification, and are used as definitions of terms of the present invention.

In some embodiments, the compound represented by the formula (I) is a light-emitting material.

In some embodiments, the compound represented by the formula (I) is a compound capable of emitting delayed fluorescence.

In some embodiments, the compound represented by the formula (I) exhibits excellent red emission.

In some embodiments, the compound represented by the formula (I) exhibits excellent durability.

In some embodiments of the present disclosure, the compound represented by the formula (1) is, when excited thermally or by an electronic means, able to emit light in a UV region, light of blue, green, yellow or orange in a visible region, in a red region (e.g., about 420 nm to about 500 nm, about 500 nm to about 600 nm, or about 600 nm to about 700 nm) or in a near IR region.

In some embodiments of the present disclosure, the compound represented by the formula (1) is, when excited thermally or by an electronic means, able to emit light of red or orange in a visible region (e.g., about 620 nm to about 780 nm, about 650 nm).

In some embodiments of the present disclosure, the compound represented by the formula (1) is, when excited thermally or by an electronic means, able to emit light of orange or yellow in a visible region (e.g., about 570 nm to about 620 nm, about 590 nm, about 570 nm).

In some embodiments of the present disclosure, the compound represented by the formula (1) is, when excited thermally or by an electronic means, able to emit light of green in a visible region (e.g., about 490 nm to about 575 nm, about 510 nm).

In some embodiments of the present disclosure, the compound represented by the formula (1) is, when excited thermally or by an electronic means, able to emit light of blue in a visible region (e.g., about 400 nm to about 490 nm, about 475 nm).

In some embodiments of the present disclosure, the compound represented by the formula (1) is, when excited thermally or by an electronic means, able to emit light in a UV region (e.g., about 280 to 400 nm).

In some embodiments of the present disclosure, the compound represented by the formula (1) is, when excited thermally or by an electronic means, able to emit light in an IR region (e.g., about 780 nm to 2 μm). In some embodiments of the present disclosure, the compound represented by the formula (I) is a charge transport material. In some embodiments of the present disclosure, the compound represented by the formula (I) is used for a charge transport layer. In some embodiments of the present disclosure, the compound represented by the formula (I), as a charge transport material, has high mobility, and is excellent in durability.

In some embodiments of the present disclosure, an organic semiconductor device using the compound represented by the formula (I), such as CMOS (complementary metal oxide semiconductor), can be manufactured. In some embodiments of the present disclosure, it is possible to manufacture an organic optical device such as an organic electroluminescence device or a solid-state image sensing device (for example, a CMOS image sensor) by using the compound represented by the formula (I).

Electronic characteristics of small-molecule chemical substance libraries can be calculated by known ab initio quantum chemistry calculation. For example, according to time-dependent density functional theory calculation using 6-31G* as a basis, and a functional group known as Becke's three parameters, Lee-Yang-Parr hybrid functionals, the Hartree-Fock equation (TD-DFT/B3LYP/6-31G*) is analyzed and molecular fractions (parts) having HOMO not lower than a specific threshold value and LUMO not higher than a specific threshold value can be screened, and the calculated triplet state of the parts is more than 2.75 eV.

With that, for example, in the presence of a HOMO energy (for example, ionizing potential) of −6.5 eV or more, a donor part ("D") can be selected. On the other hand, for example, in the presence of a LUMO energy (for example, electron affinity) of −0.5 eV or less, an acceptor part ("A") can be selected. A bridge part ("B") is a strong conjugated system, for example, capable of strictly limiting the acceptor part and the donor part in a specific three-dimensional configuration, and therefore prevents the donor part and the acceptor part from overlapping in the pai-conjugated system.

In some embodiments, a compound library is screened using at least one of the following characteristics.

1. Light emission around a specific wavelength.
2. A triplet state over a calculated specific energy level.
3. $\Delta E_{ST}$ value lower than a specific value.
4. Quantum yield more than a specific value.
5. HOMO level.
6. LUMO level.

In some embodiments, the difference ($\Delta E_{ST}$) between the lowest singlet excited state and the lowest triplet excited state at 77 K is less than about 0.5 eV, less than about 0.4 eV, less than about 0.3 eV, less than about 0.2 eV, or less than about 0.1 eV. In some embodiments, $\Delta E_{ST}$ value is less than about 0.09 eV, less than about 0.08 eV, less than about 0.07 eV, less than about 0.06 eV, less than about 0.05 eV, less than about 0.04 eV, less than about 0.03 eV, less than about 0.02 eV, or less than about 0.01 eV.

In some embodiments, the compound represented by the formula (1) shows a quantum yield of more than 25%, for example, about 30%, about 35%, about 40%, about 45%, about 50%, about 55%, about 60%, about 65%, about 70%, about 75%, about 80%, about 85%, about 90%, about 95% or more.

[Components Using Compound of the Present Disclosure]

In some embodiments, a solid-state film or layer is formed through combining with the compound represented by the formula (I), dispersing of the compound, covalent bonding with the compound, coating of the compound, carrying of the compound, or the co-use of one or more materials that associate with the compound (for example, small molecules, polymers, metals, metal complexes, etc.). For example, the compound represented by the formula (I) can be combined with an electrically active material to form a film. In some cases, the compound represented by the formula (I) may be combined with a hole transport polymer. In some cases, the compound represented by the formula (I) may be combined with an electron transport polymer. In some cases, the compound represented by the formula (I) may be combined with a hole transport polymer and an electron transport polymer. In some cases, the compound represented by the formula (I) may be combined with a copolymer having both a hole transport part and an electron transport part. According to the above embodiments, electrons and/or holes formed within the solid-state film or layer can interact with the compound represented by the formula (I).

[Film Formation]

In some embodiments, a film containing the compound represented by the formula (1) can be formed in a wet process. In a wet process, a solution prepared by dissolving a composition containing the compound of the present invention is applied onto a surface, and then the solvent is removed to form a film. The wet process includes a spin coating method, a slit coating method, an ink jet method (a spraying method), a gravure printing method, an offset printing method and flexographic printing method, which, however, are not limitative. In the wet process, an appropriate organic solvent capable of dissolving a composition containing the compound of the present invention is selected and used. In some embodiments, a substituent (for example, an alkyl group) capable of increasing the solubility in an organic solvent can be introduced into the compound to be contained in the composition.

In some embodiments, a film containing the compound of the present invention can be formed in a dry process. In some embodiments, a vacuum evaporation method is employable as a dry process, which, however, is not limitative. In the case where a vacuum evaporation method is employed, compounds to constitute a film can be co-evaporated from individual evaporation sources, or can be co-evaporated from a single evaporation source formed by mixing the compounds. In the case where a single evaporation source is used, a mixed powder prepared by mixing compound powders can be used, or a compression molded body prepared by compression-molding the mixed powder can be used, or a mixture prepared by heating and melting the constituent compounds and cooling the resulting melt can be used. In some embodiments, by co-evaporation under the condition where the evaporation rate (weight reduction rate) of the plural compounds contained in a single evaporation source is the same or is nearly the same, a film having a compositional ratio corresponding to the compositional ratio of the plural compounds contained in the evaporation source can be formed. When plural compounds are mixed in the same compositional ratio as the compositional ratio of the film to be formed to prepare an evaporation source, a film having a desired compositional ratio can be formed in a simplified manner. In some embodiments, the temperature at which the compounds to be co-evaporated has the same weight reduction ratio is specifically defined, and the temperature can be employed as the temperature of co-evaporation.

All the descriptions on use examples, a device, a display, a screen, etc., which are described in [0141] to [0169] and [0192] to [0242] of US2020/0168814A1, are incorporated herein as a part of the present specification, and are used as descriptions of the present invention.

In some embodiments of the present invention, the following compounds can be preferably used as host materials.

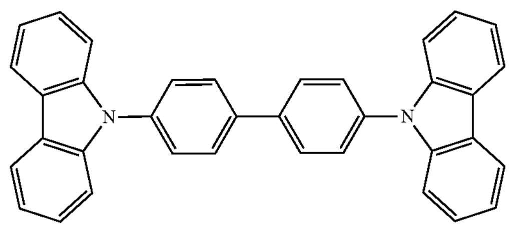

-continued
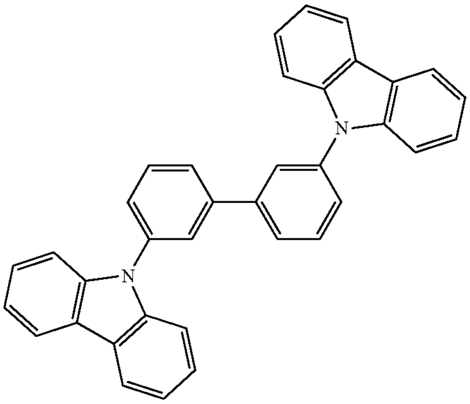
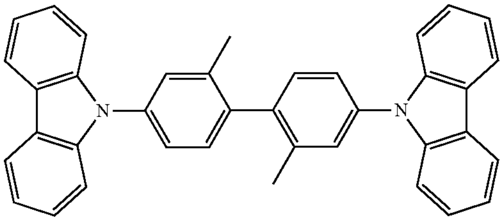
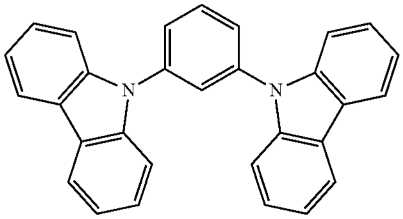
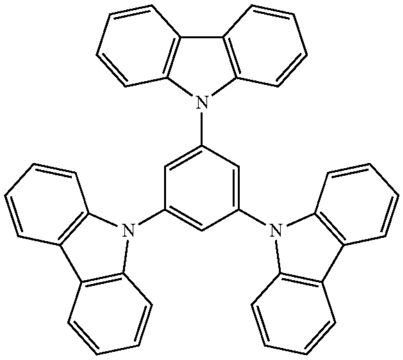
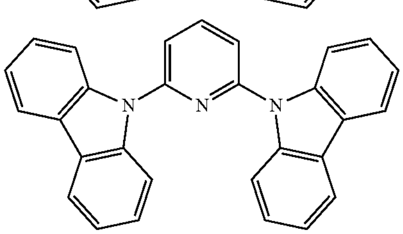
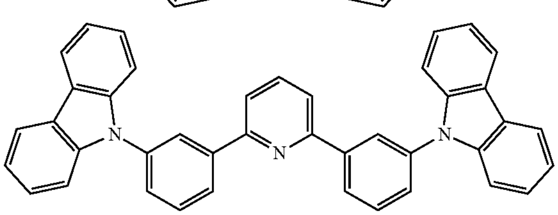
-continued
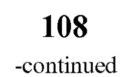
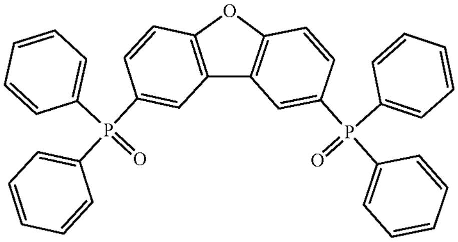
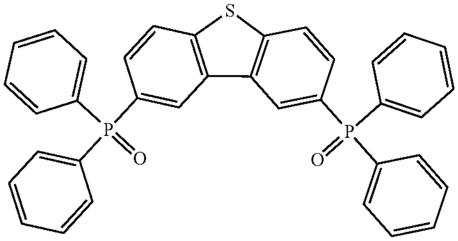
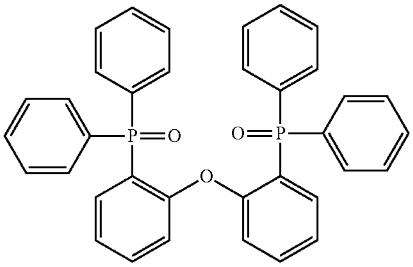
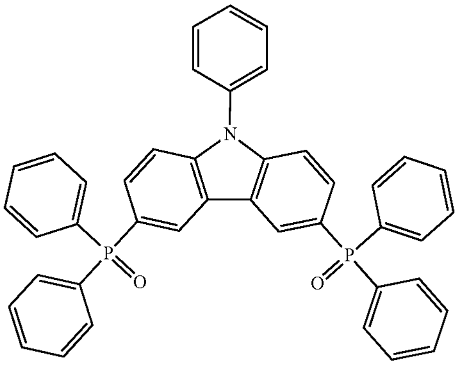
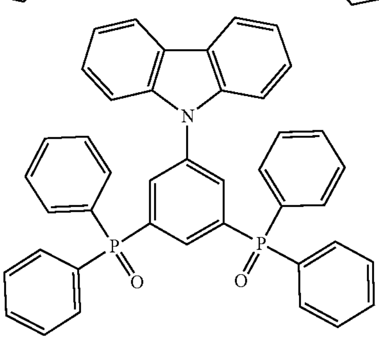
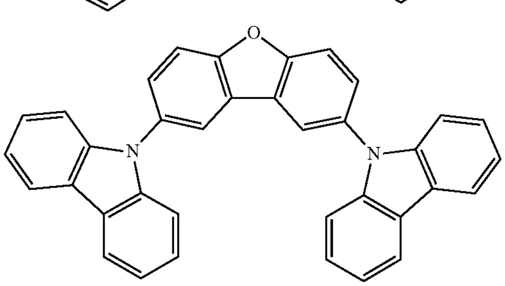

-continued
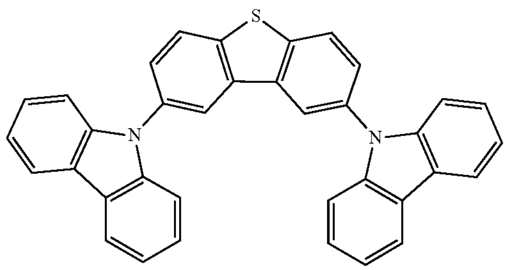
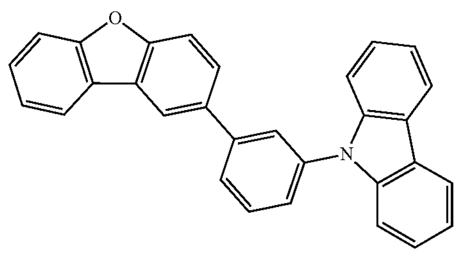
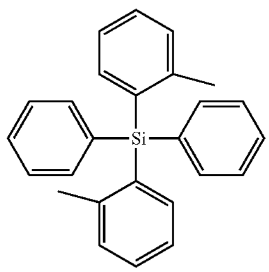
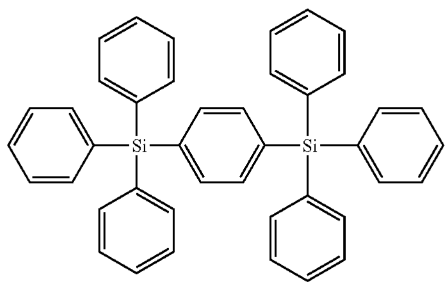
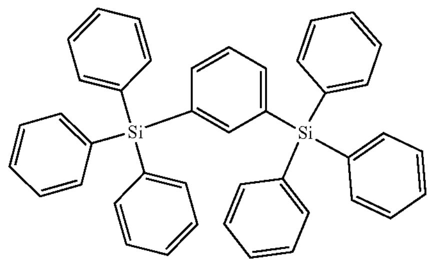
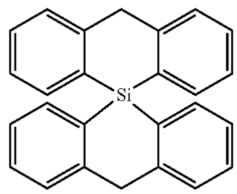
-continued
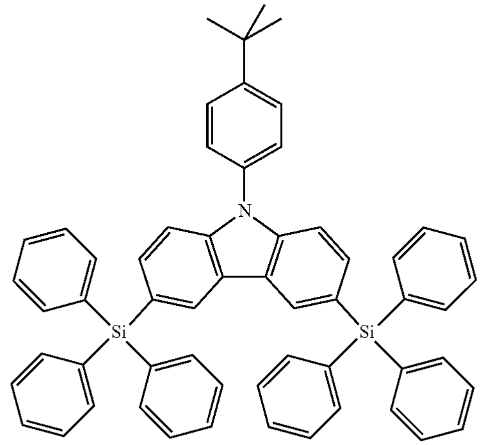
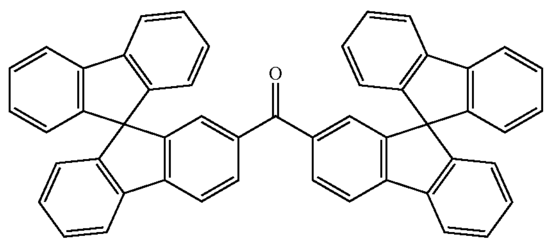
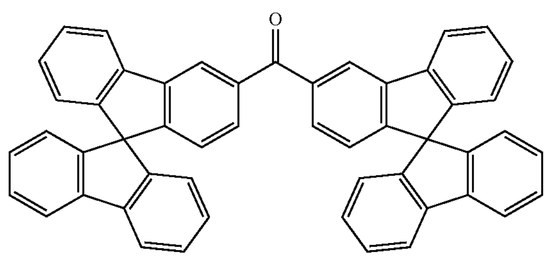
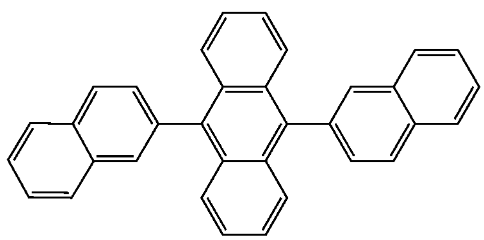
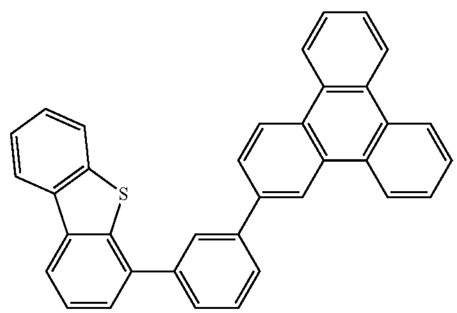

-continued
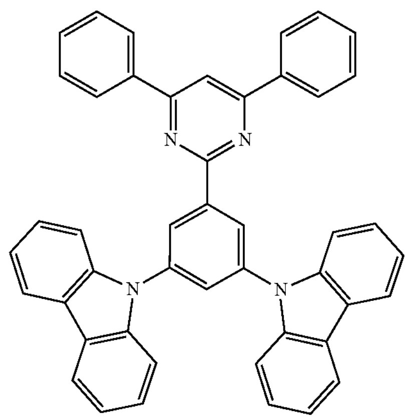
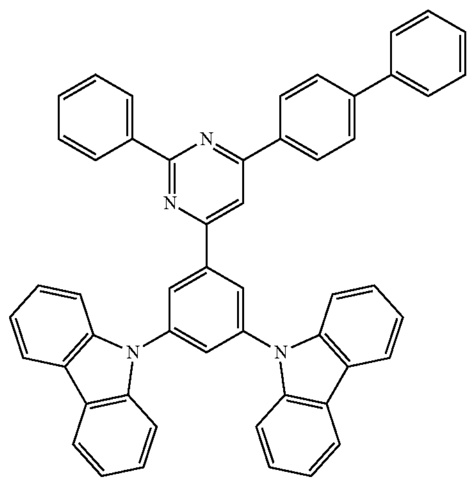
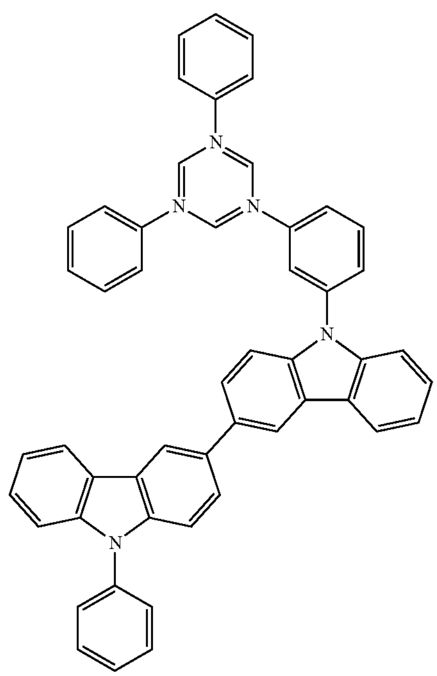
-continued
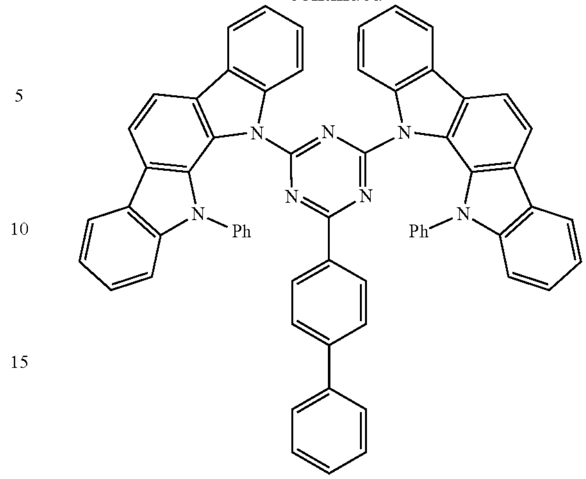
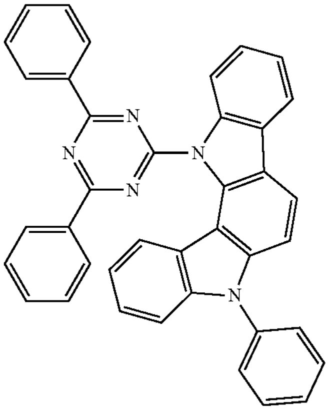
In some embodiments of the present invention, the following compounds can be preferably used as electron blocking materials.
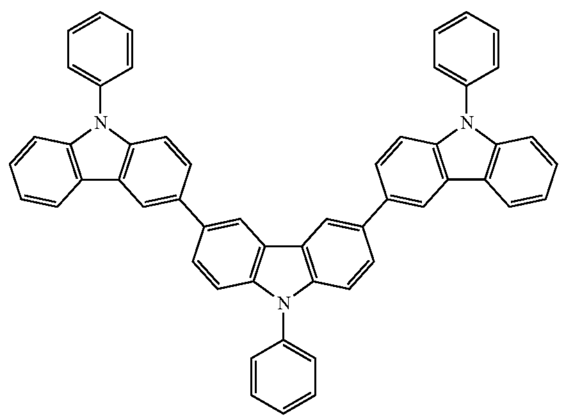

-continued
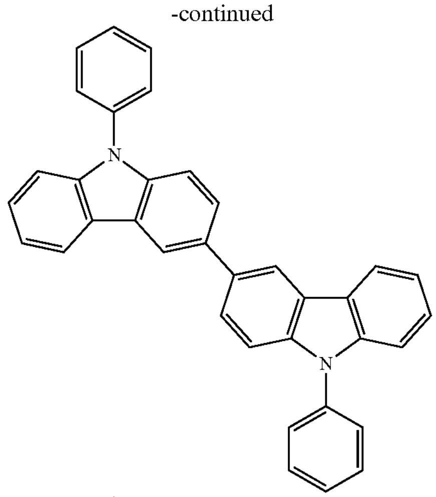
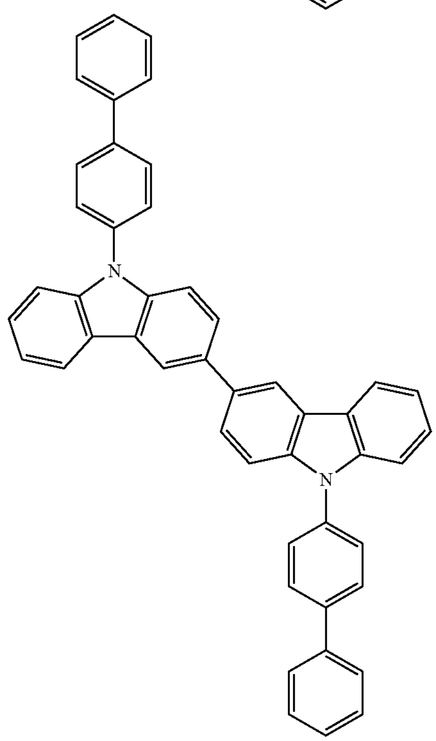
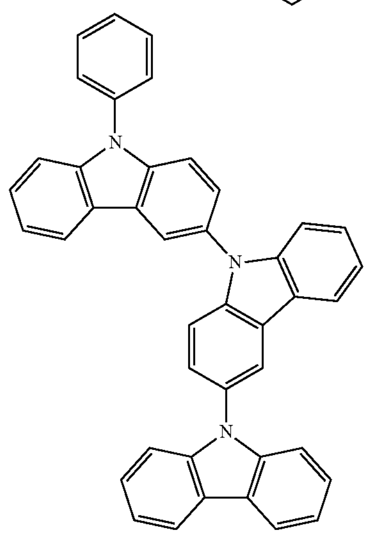
-continued
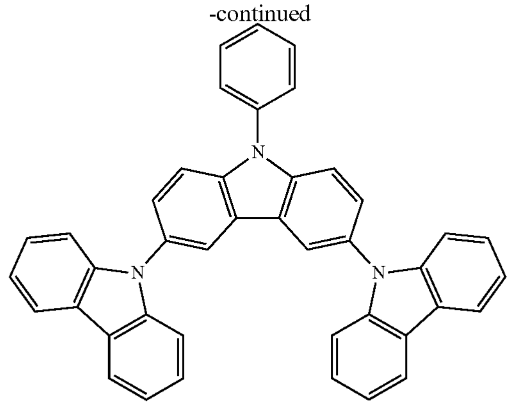
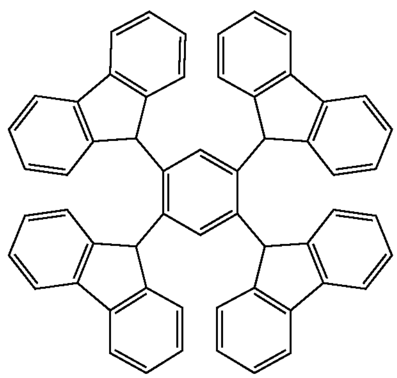
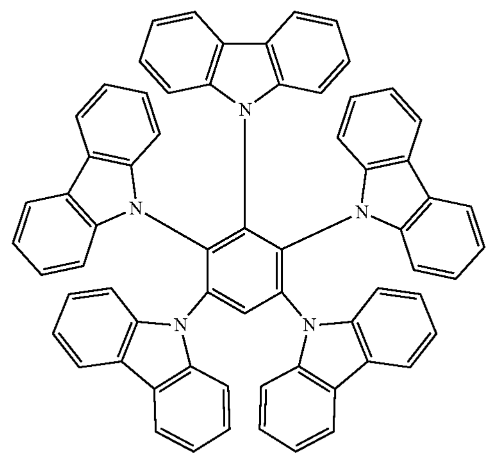
In some embodiments of the present invention, the following compounds can be preferably used as hole blocking materials.

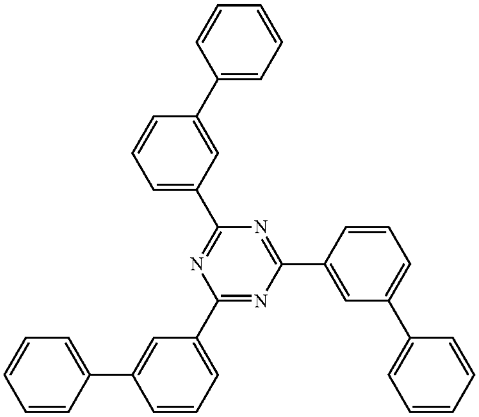
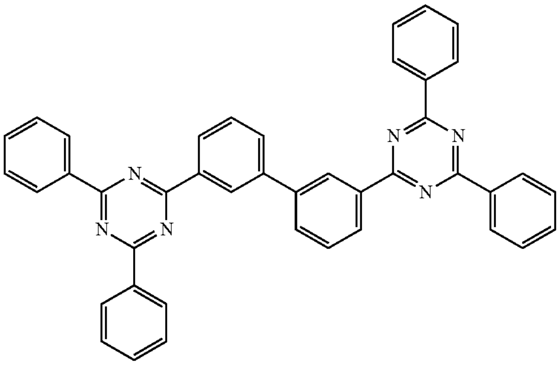
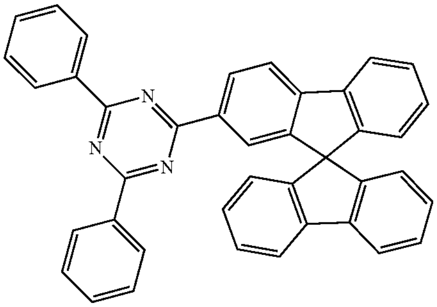
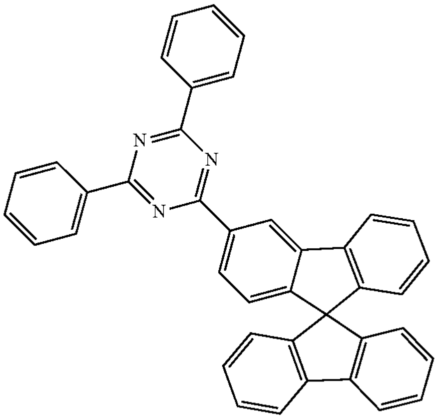
-continued
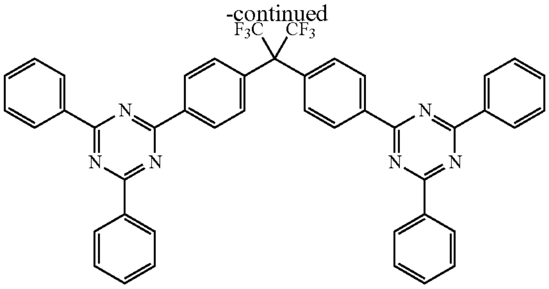
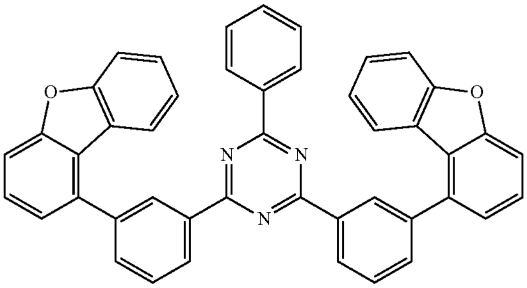
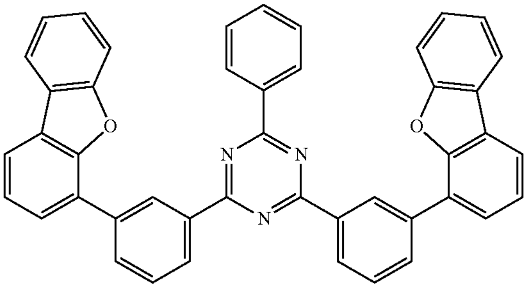
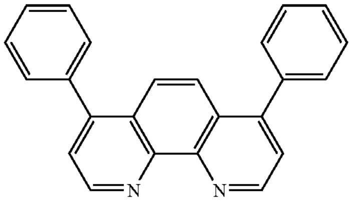
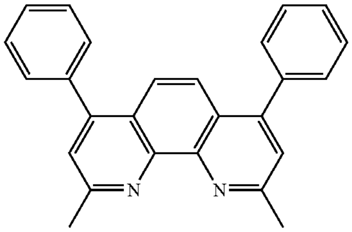
Hereinafter, preferable compounds that can be used as a hole injection material of an organic electroluminescence device will be exemplified.

$MoO_3$,

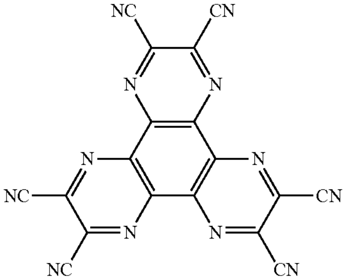

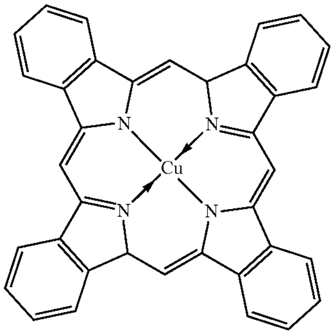

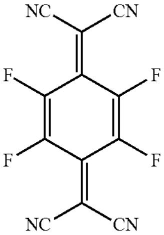

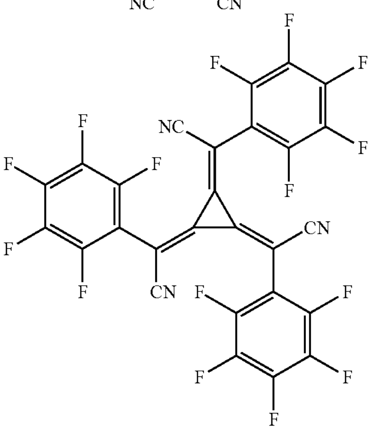

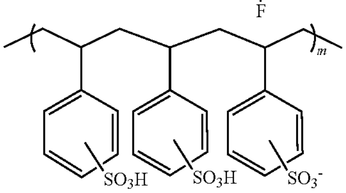

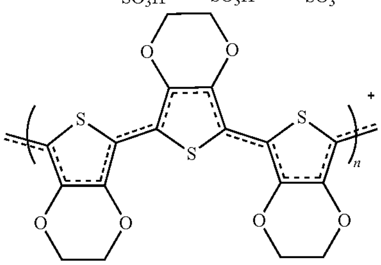

Next, preferable compounds that can be used as an electron injection material of an organic electroluminescence device will be exemplified.

LiF, CsF,

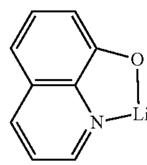

Further, preferable compounds as materials that can be added to each organic layer of an organic electroluminescence device will be exemplified. For example, addition as a stabilizing material, or the like may be taken into consideration.

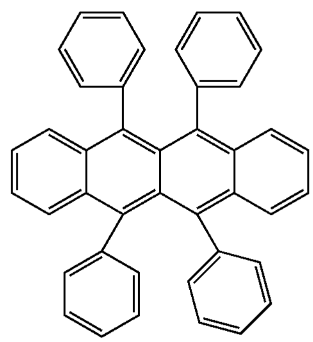

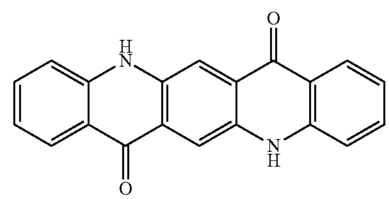

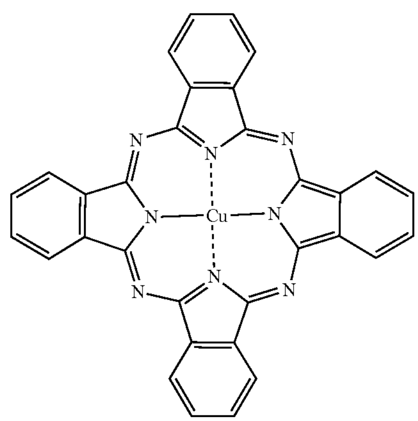

-continued

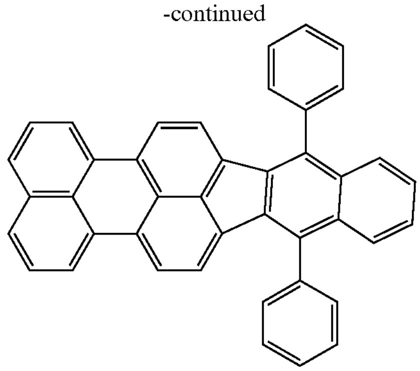

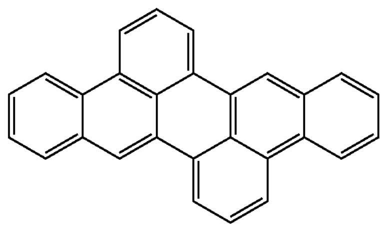

EXAMPLES

Hereinafter, the features of the present invention will be described in more detail with reference to Synthesis examples and Examples. The materials, the processing contents, the processing procedures, etc. illustrated below can be appropriately changed as long as they do not deviate from the gist of the present invention. Therefore, the scope of the present invention should not be construed as limiting to specific examples illustrated below. Further, the features of the following samples were evaluated by using NMR (manufactured by Bruker, nuclear magnetic resonance 500 MHz), LC/MS (manufactured by Waters, liquid chromatography mass spectrometer), AC3 (manufactured by RIKEN KEIKI), a high-performance UV/Vis/NIR spectrophotometer (manufactured by PerkinElmer, Lambda950), a fluorescence spectrophotometer (manufactured by Horiba, FluoroMax-4), a photonic multi-channel analyzer (manufactured by Hamamatsu Photonics, PMA-12 C10027-01), an absolute PL quantum yield measuring system (manufactured by Hamamatsu Photonics, C11347), an automatic current voltage luminance measuring system (manufactured by System GIKEN, ETS-170), a lifetime measuring system (manufactured by System GIKEN, EAS-26C) and a streak camera (manufactured by Hamamatsu Photonics, model C4334). Further, the compounds of Examples of the present application were used for manufacturing a device and the like after sublimation purification.

(Example 1) Synthesis of Compound 432

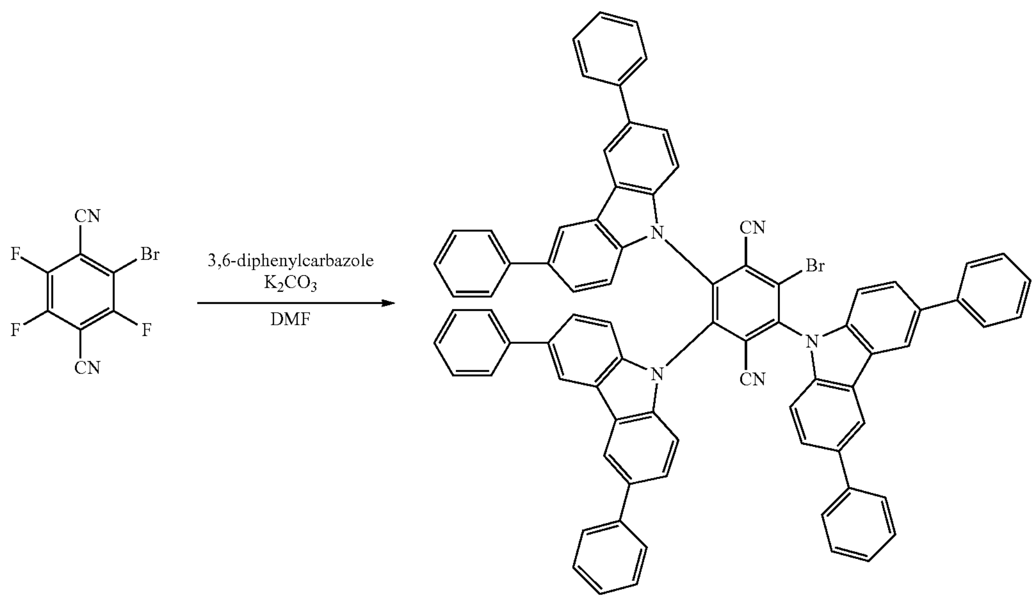

1

-continued

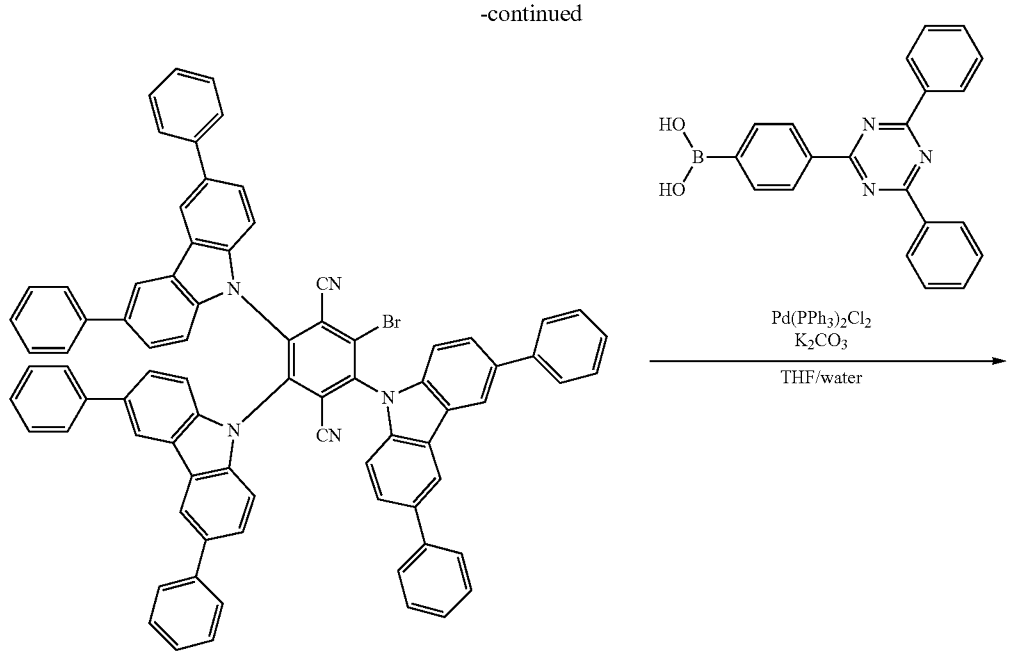

1

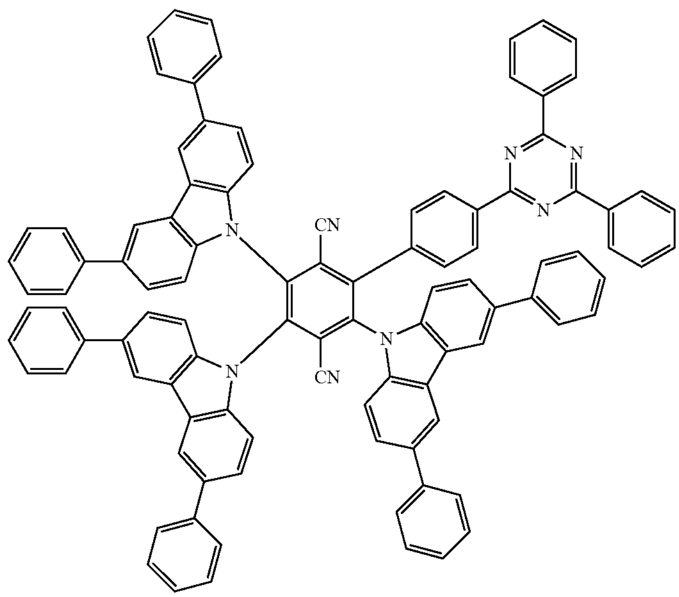

432

Synthesis of 2-bromo-3,5,6-tri(3,6-diphenylcarbazole-9-yl)-terephthalonitrile 1

A mixture of $K_2CO_3$ (829 mg, 6 mmol), carbazole (958 mg, 3 mmol) and 2,3,5,6-tetrafluoroterephthalonitrile (261 mg, 1 mmol) was stirred at 30° C. for 4 h in 5 mL of DMF (dimethylformamide). Water was added to the reaction solution, and, the precipitate was filtered and then washed with water and methanol. The crude product was purified with silica gel column chromatography (eluent: toluene) to obtain 1 as red powder (yield 676 mg, yield 58%).

$^1$H NMR (500 MHz, $CDCl_3$, δ): 8.50 (s, 2H), 7.89 (d, J=7 Hz, 2H), 7.86 (s, 2H), 7.71 (s, 2H), 7.79 (d, J=7 Hz, 4H), 7.57-7.28 (m, 32H), 7.14 (d, J=8 Hz, 2H), 7.04 (d, J=8 Hz, 2H).

MS (MALDI-TOF): 1158.91 $(M+H)^+$. Calcd for $C_{80}H_{48}BrN_5$: 1157.31.

Synthesis of 2-(4,6-diphenyl-1,3,5-triazine-2-yl) phenyl-3,5,6-tri(3,6-diphenylcarbazole-9yl)-terephthalonitrile (Compound 432)

A mixture of 2-bromo-3,5,6-tri(3,6-diphenylcarbazole-9-yl)-terephthalonitrile 1 (1.16 g, 1 mmol), (4-(4,6-diphenyl-1,3,5-triazine-2-yl)phenyl)boronic acid (0.522 g, 1.2 mmol), and $K_2CO_3$ (0.33 g, 2.5 mmol), in a mixture of THF and water (50 ml/25 mL), was degassed, and was filled with nitrogen. $Pd(PPh_3)_2Cl_2$ (70 mg, 0.1 μmol) was added to the solution, followed by stirring at 70° C. overnight. After the reaction solution was cooled, water was added thereto, and THF was removed in a vacuum. The obtained solid was washed with water. The crude product was purified with silica gel column chromatography (eluent: toluene), to obtain a red-orange solid compound 432 (yield 361 mg, yield 26%).

MS (MALDI-TOF): 1387.28 ($M+H^+$). Calcd for $C_{101}H_{62}N_8$: 1386.51.

(Example 2) Synthesis of Compound 433

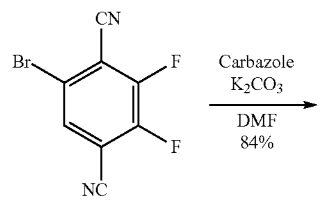

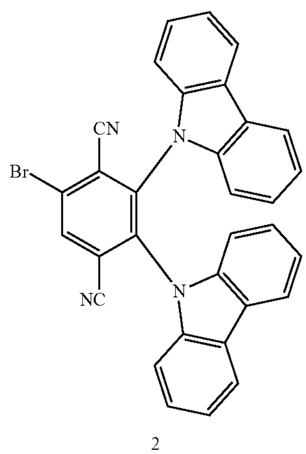

2

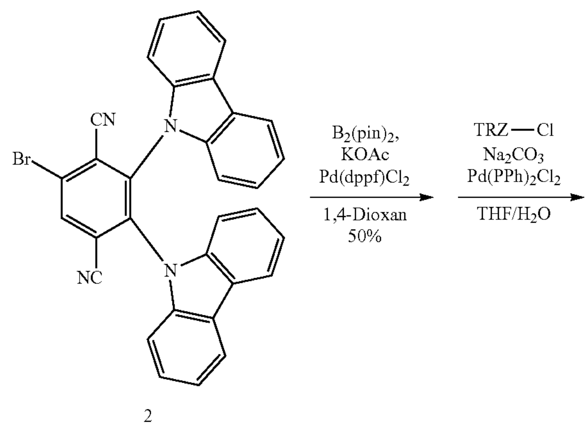

2

-continued

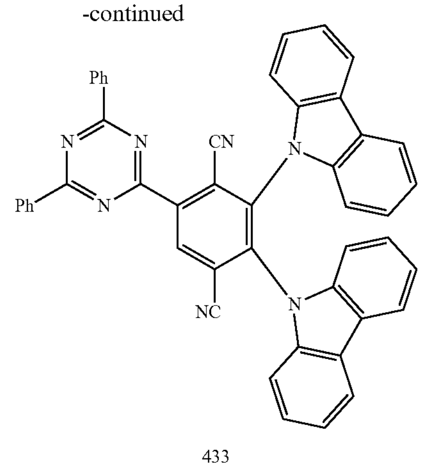

433

Synthesis of 5-bromo-2,3-bis(9H-carbazole-9-yl)-terephthalonitrile 2

A solution of $K_2CO_3$ (1.7 g, 12.35 mmol), carbazole (1.7 g, 9.88 mmol) and 5-bromo-2,3-difluoroterephthalonitrile (1.2 g, 4.94 mmol) in DMF (24 ml) was stirred at 50° C. for 4 h. The reaction of the reaction mixture was stopped with methanol and water. The precipitated powder was filtered, and washed with methanol, and then was purified with column chromatography (toluene only), and reprecipitated (toluene and hexane) so as to obtain 5-bromo-2,3-bis(9H-carbazole-9-yl)-terephthalonitrile 2 as orange powder with a yield of 84% (yield 2.22 g, 4.14 mmol).

$^1H$ NMR (500 MHz, $CDCl_3$, δ): 8.35 (s, 1H), 7.67 (m, 4H), 7.07 (m, 4H), 7.00 (m, 4H), 6.87 (m, 4H).

MS (ASAP): 537.1 ($M+H^+$). Calcd for $C_{32}H_{17}BrN_4$: 536.06.

Synthesis of 2,3-bis(9H-carbazole-9-yl)-5-(4,6-diphenyl-1,3,5-triazine-2-yl)-terephthalonitrile (Compound 433)

A mixture of 5-bromo-2,3-bis(9H-carbazole-9-yl)-terephthalonitrile 2 (1.80 g, 3.35 mmol), bis(pinacolato)diboron (1.28 g, 5.02 mmol), and potassium acetate (0.49 g, 5.02 mmol), in 1,4-dioxane (30 mL), was degassed, and was filled with nitrogen. $Pd(dppf)Cl_2$ (0.12 g, 0.17 mmol) was added to the solution, followed by stirring at 100° C. overnight. The reaction mixture was cooled to room temperature, and then water (15 mL), 2-chloro-4,6-diphenyl-1,3,5-triazine (1.34 g, 5.02 mmol), and sodium carbonate (1.06 g, 10.05 mmol) were added to the mixture. The mixture was degassed, and was filled with nitrogen again. $PdCl_2(PPh_3)$ (0.24 g, 0.33 mmol) and toluene (30 ml) were added to the mixture, followed by stirring at 100° C. for 7 h. The reaction mixture was concentrated under reduced pressure. Then, the precipitated powder was filtered and washed with methanol, and then was purified by filtration using washing of a short silica pad with dichlorobenzene. The resultant product was reprecipitated from dichlorobenzene and acetonitrile to obtain a compound 433 (yield 1.15 g, 1.67 mmol, yield 50%) as an orange solid.

$^1H$ NMR (500 MHz, $CDCl_3$, δ): 9.49 (s, 1H), 8.87 (d, J=8.0 Hz, 4H), 7.72-7.67 (m, 6H), 7.62 (t, J=7.0 Hz, 4H), 7.11-7.07 (m, 4H), 7.03 (t, J=7.5 Hz, 4H), 6.99-6.97 (m, 4H).

MS (ASAP): 690.4 ($M+H^+$). Calcd for $C_{47}H_{27}N_7$: 689.23.

(Example 3) Synthesis of Compound 450

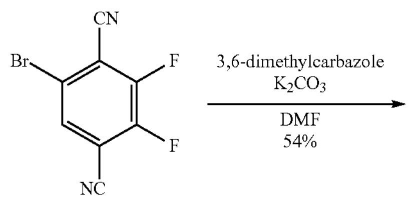

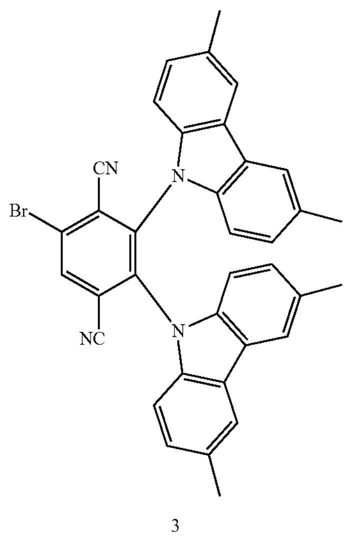

3

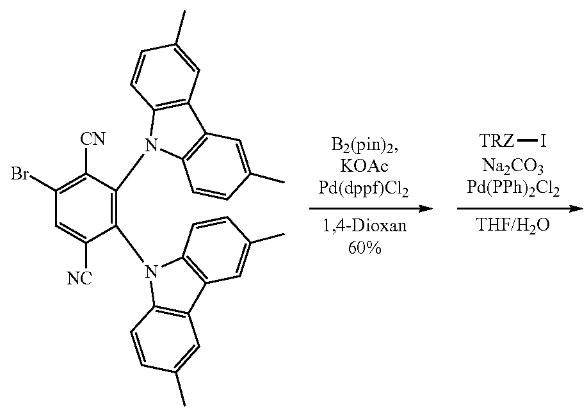

3

-continued

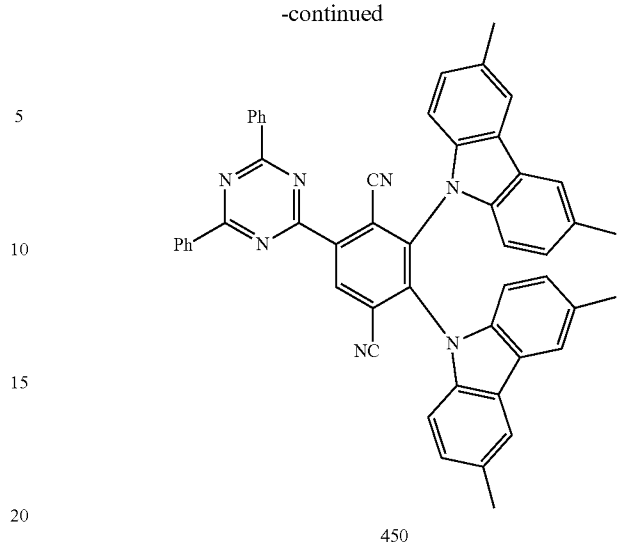

450

Synthesis of 5-bromo-2,3-bis(3,6-dimethyl-9H-carbazole-9-yl)-terephthalonitrile 3

A solution of $K_2CO_3$ (0.86 g, 6.22 mmol), 3,6-dimethyl-9H-carbazole (0.95 g, 4.94 mmol) and 5-bromo-2,3-difluoroterephthalonitrile (0.6 g, 2.47 mmol) in 15 mL of DMF was stirred at 50° C. for 4 h. The reaction of the reaction mixture was stopped with methanol and water. The precipitate was filtered and was washed with methanol, and then was purified through column chromatography using toluene as an eluent to obtain 5-bromo-2,3-bis (3,6-dimethyl-9H-carbazole-9-yl)-terephthalonitrile 3 (yield 0.81 g, 1.36 mmol) as orange powder with a yield of 54%.

$^1H$ NMR (500 MHz, $CDCl_3$, δ): 8.28 (s, 1H), 7.48 (s, 4H), 6.85 (d, J=8.0 Hz, 4H), 6.79 (t, J=9.0 Hz, 4H), 2.36 (s, 12H).

MS (ASAP): 593.2 (M+H$^+$). Calcd for $C_{36}H_{25}BrN_4$: 592.13.

Synthesis of 2,3-bis(3,6-dimethyl-9H-carbazole-9-yl)-5-(4,6-diphenyl-1,3,5-triazine-2-yl)-terephthalonitrile (Compound 450)

A mixture of 5-bromo-2,3-bis (3,6-dimethyl-9H-carbazole-9-yl)-terephthalonitrile 3 (0.80 g, 1.35 mmol), bis(pinacolato)diboron (0.52 g, 2.03 mmol), and potassium acetate (0.20 g, 2.03 mmol), in 1,4-dioxane (12 mL), was degassed, and was filled with nitrogen. $Pd(dppf)Cl_2$ (0.05 g, 0.07 mmol) was added to the solution, followed by stirring at 100° C. overnight. The reaction mixture was cooled to room temperature, and then water (6 mL), 2-chloro-4,6-diphenyl-1,3,5-triazine (0.73 g, 2.83 mmol), and sodium carbonate (0.43 g, 4.06 mmol) were added to the solution. The mixture was degassed, and was filled with nitrogen again. $PdCl_2(PPh_3)$ (0.10 g, 0.14 mmol) and toluene (12 ml) were added to the mixture, followed by stirring at 50° C. for 6 h. The reaction mixture was extracted with dichloromethane, and the resultant crude product was purified through column chromatography using toluene/hexane=5/1 as an eluent. The resultant product was reprecipitated from toluene and methanol to obtain a compound 450 (yield 0.60 g, 0.81 mmol, yield 60%) as an orange solid.

$^1H$ NMR (500 MHz, $CDCl_3$, δ): 9.39 (s, 1H), 8.84 (d, J=8.0 Hz, 4H), 7.66 (t, J=7.0 Hz, 2H), 7.60 (t, J=7.5 Hz, 4H), 7.52 (d, J=5.0 Hz, 4H), 6.91-6.87 (m, 8H), 2.38 (s, 12H).

MS (ASAP): 746.4 (M+H$^+$). Calcd for $C_{51}H_{35}N_7$: 745.30.

(Example 4) Synthesis of Compound 497

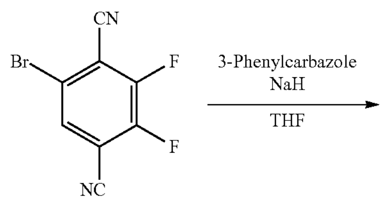

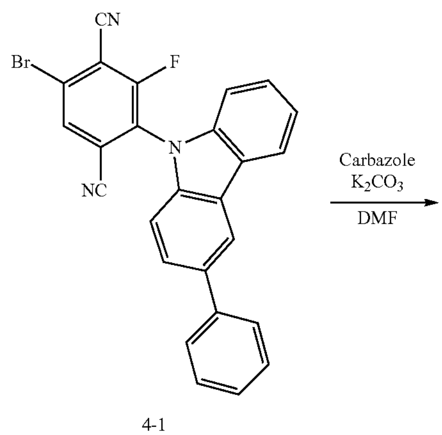

4-1

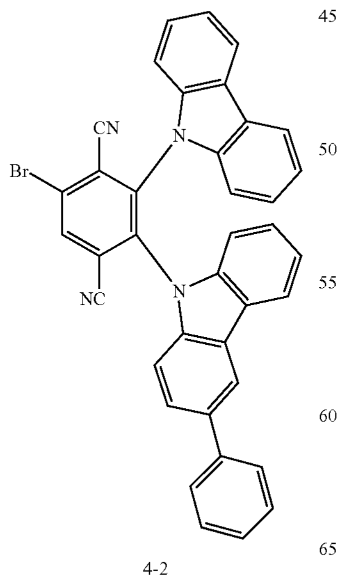

4-2

-continued

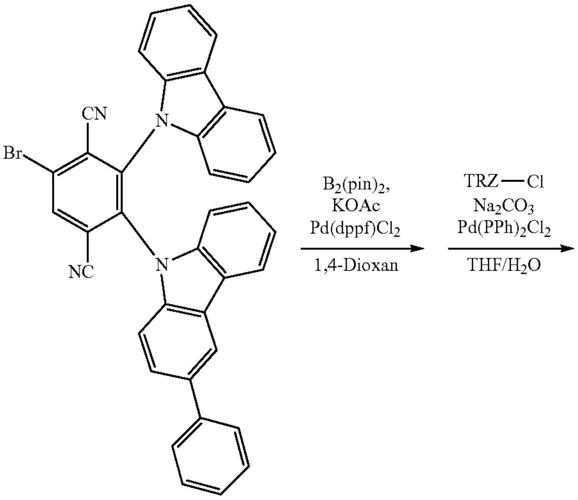

4-2

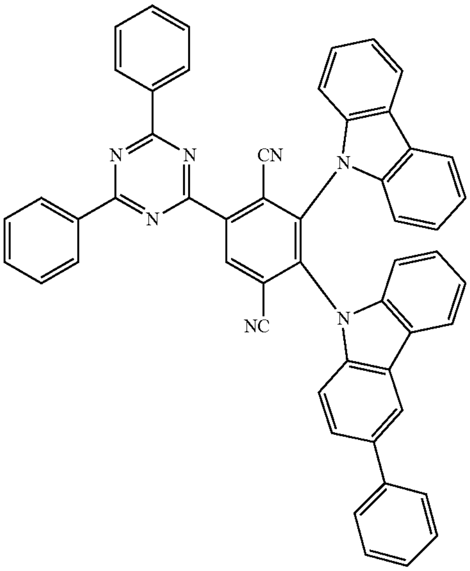

497

Synthesis of 5-bromo-2-fluoro-3-(3-phenylcarbazole-9-yl)-terephthalonitrile 4-1

3-phenylcarbazole (0.5 g, 2.06 mmol) was dissolved in 10 ml of THF, and 60% NaH (90 mg, 2.26 mmol) was slowly added thereto. The solution was stirred for 30 min. The reaction solution was added to 3-bromo-2,3-difluoroterephthalonitrile (0.5 g, 2.06 mmol) in THF (20 ml), and the mixed solution was stirred for 3 h. A saturated $NH_4Cl$ aqueous solution was carefully added to the reaction solution. After THF was evaporated, the resultant solid was washed with water. The obtained crude product was purified with silica gel column chromatography (eluent: toluene/hexane=7/3), to obtain 4-1 as yellow powder (yield 0.94 g, yield 98%).

MS (ASAP): 466.13 ($M+H^+$). Calcd for $C_{26}H_{13}BrFN_3$: 465.03.

Synthesis of 5-bromo-2-(9H-carbazole-9yl)-3-(3-phenylcarbazole-9-yl)-terephthalonitrile 4-2

A mixture of $K_2CO_3$ (0.556 g, 4.03 mmol), carbazole (0.505 g, 3.02 mmol) and 5-bromo-2-fluoro-3-(3-phenylcarbazole-9-yl)-terephthalonitrile 4-1 (0.94 g, 2.02 mmol) in 10 ml of DMF was stirred at 50° C. for 12 h. After the reaction solution was cooled, water was added thereto. The precipitate was filtered, washed with water, and dried. The crude product was purified through column chromatography (eluent: toluene/hexane=7/3) to obtain 4-2 as orange powder (yield 0.74 g, yield 60%).

MS (ASAP): 612.26 (M+H$^+$). Calcd for $C_{38}H_{21}BrN_4$: 612.09.

Synthesis of 2-(9H-carbazole-9yl)-3-(3-phenylcarbazole-9-yl)-5-(4,6-diphenyl-1,3,5-triazine-2-yl)-terephthalonitrile (Compound 497)

A mixture of 5-bromo-2-(9H-carbazole-9yl)-3-(3-phenylcarbazole-9-yl)-terephthalonitrile 4-2 (0.72 g, 1.17 mmol), bis(pinacolato)diboron (0.447 g, 1.76 mmol), and potassium acetate (0.173 g, 1.76 mmol), in 1,4-dioxane (10 mL), was degassed, and was filled with nitrogen. Pd(dppf)$Cl_2$ (43 g, 58.6 μmol) was added to the solution, followed by stirring at 100° C. overnight. After the reaction mixture was cooled to room temperature, 2-chloro-4,6-diphenyl-1,3,5-triazine (0.632 g, 1.76 mmol), and sodium carbonate (0.375 g, 3.52 mmol) and $PdCl_2(PPh_3)$ (0.24 g, 0.33 mmol), toluene (10 ml), and water (5 ml) were added to the solution, followed by stirring at 100° C. for 7 h. The reaction mixture was concentrated under reduced pressure, and the resultant crude product was filtered, washed with water, and purified through column chromatography (eluent: toluene/hexane=1:1 to 7:3) to obtain a compound 497 as an orange solid (yield 0.631 g, yield 70%).

$^1$H NMR (500 MHz, $CDCl_3$, δ): 9.5 (s, 1H), 8.87 (d, J=8 Hz, 4H), 7.89 (s, 1H), 7.75-7.61 (m, 9H), 7.55 (d, J=8 Hz, 2H), 7.44 (t, J=8 Hz, 2H), 7.33 (t, J=7 Hz, 1H), 7.25 (d, J=9 Hz, 1H), 7.11-6.71 (m, 10H).

MS (ASAP): 766.52 (M+H$^+$). Calcd for $C_{53}H_{31}N_7$: 765.26.

(Example 5) Synthesis of Compound 501

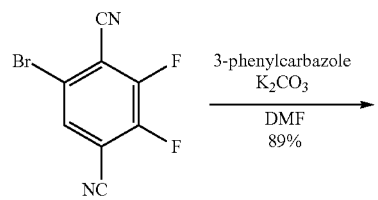

-continued

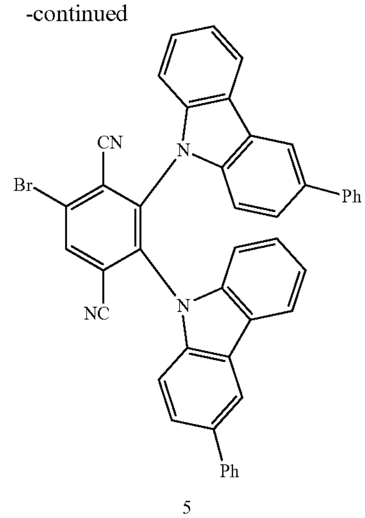

5

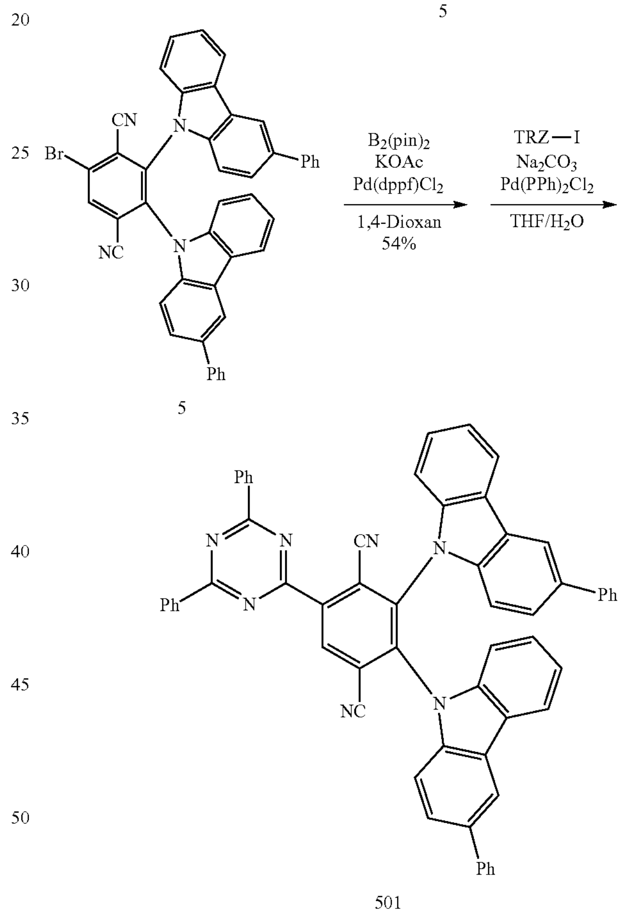

5

501

Synthesis of 5-bromo-2,3-bis(3-phenyl-9H-carbazole-9-yl)-terephthalonitrile 5

A solution of $K_2CO_3$ (0.71 g, 5.15 mmol), 3-phenyl-9H-carbazole (1.0 g, 4.12 mmol) and 5-bromo-2,3-difluoroterephthalonitrile (0.5 g, 2.06 mmol) in 10 mL of DMF was stirred at 50° C. for 4 h. The reaction of the reaction mixture was stopped with methanol and water. The precipitated powder was filtered, washed with methanol and purified through column chromatography using toluene as an eluent to obtain 5-bromo-2,3-bis(3-phenyl-9H-carbazole-9-yl)-terephthalonitrile 5 (yield 1.26 g, 1.83 mmol) as orange powder with a yield of 89%.

$^1$H NMR (500 MHz, $CDCl_3$, δ): 8.37 (s, 1H), 7.83 (s, 2H), 7.71 (d, J=7.5 Hz, 1H), 7.66 (d, J=7.5 Hz, 1H), 7.66 (t, J=8.0 Hz, 4H), 7.44-7.38 (m, 4H), 7.32 (t, J=7.5 Hz, 2H), 7.22 (d, J=8.5 Hz, 1H), 7.16-7.06 (m, 4H), 7.00-6.93 (m, 3H), 6.88-6.87 (m, 2H).

MS (ASAP): 689.3 ($M+H^+$). Calcd for $C_{44}H_{25}BrN_4$: 688.13.

Synthesis of 2,3-bis(3-phenyl-9H-carbazole-9-yl)-5-(4,6-diphenyl-1,3,5-triazine-2-yl)-terephthalonitrile (Compound 501)

A mixture of 5-bromo-2,3-bis(3-phenyl-9H-carbazole-9-yl)-terephthalonitrile 5 (1.25 g, 1.89 mmol), bis(pinacolato) diboron (0.72 g, 2.83 mmol), and potassium acetate (0.28 g, 2.83 mmol), in 1,4-dioxane (16 mL), was degassed, and was filled with nitrogen. $Pd(dppf)Cl_2$ (0.07 g, 0.10 mmol) was added to the solution, followed by stirring at 100° C. overnight. The reaction mixture was cooled to room temperature, and then water (8 mL), 2-iodide-4,6-diphenyl-1,3,5-triazine (1.02 g, 2.83 mmol), and sodium carbonate (0.60 g, 5.66 mmol) were added to the resultant product. The mixture was degassed, and was filled with nitrogen again. $PdCl_2(PPh_3)$ (0.13 g, 0.19 mmol) and toluene (16 ml) were added to the mixture, followed by stirring at 50° C. for 6 h. The reaction mixture was concentrated under reduced pressure, and the resultant crude product was filtered, washed with methanol, and purified through column chromatography using toluene as an eluent. The resultant product was reprecipitated from toluene and hexane to obtain a compound 501 (yield 0.86 g, 1.02 mmol, yield 54%) as an orange solid.

$^1$H NMR (500 MHz, $CDCl_3$, δ): 9.51 (s, 1H), 8.88 (d, J=7.5 Hz, 4H), 7.86 (s, 2H), 7.74 (d, J=7.5 Hz, 1H), 7.69 (t, J=7.5 Hz, 3H), 7.63 (t, J=7.5 Hz, 4H), 7.54 (t, J=8.5 Hz, 4H), 7.45-7.39 (m, 4H), 7.34-7.31 (m, 2H), 7.20-7.08 (m, 10H).

MS (ASAP): 842.6 ($M+H^+$). Calcd for $C_{59}H_{35}N_7$: 841.30.

(Example 6) Synthesis of Compound 3344

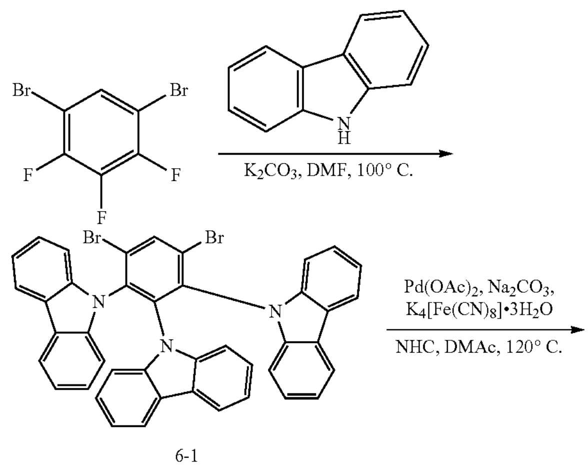

6-1

-continued

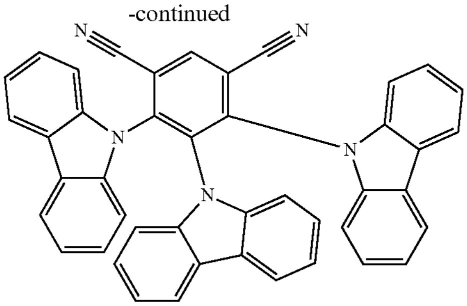

6-2

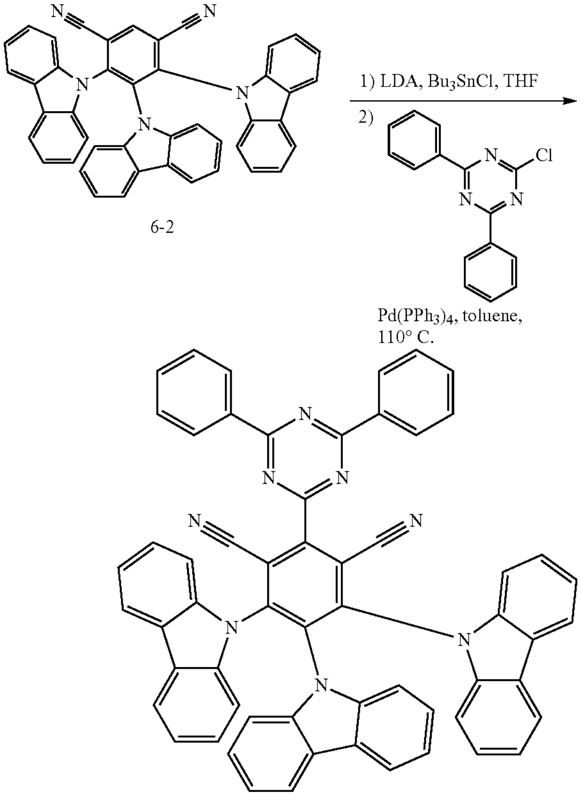

6-2

3344

Synthesis of 9,9',9"-(4,6-dibromobenzene-1,2,3-triyl)tris(9H-carbazole) 6-1

A mixture of 9H-carbazole (14.41 g, 86.25 mmol), 1,5-dibromo-2,3,4-trifluorobenzene (5.04 g, 17.25 mmol), and potassium carbonate (17.91 g, 129.4 mmol), in 60 ml of N-methyl-2-pyrollidone (NMP), was stirred under nitrogen atmosphere, at 140° C. for 17 h. The reaction mixture was poured on methanol to obtain a precipitate. After filtration, the resultant solid was washed with methanol to obtain an off-white cake. The mixture was purified through silica gel column chromatography using 1:1 (v/v) $CH_2Cl_2$/hexane as an eluent to obtain a white solid 6-1 (yield 10.04 g) with a yield of 79.6%.

$^1$H NMR (500 MHz, $CDC_3$, δ): 8.57 (s, 1H), 7.70 (d, J=7.5 Hz, 4H), 7.24 (d, J=7.5 Hz, 2H), 7.12 (d, J=8.0 Hz, 4H), 7.08-7.00 (m, 8H), 6.93 (d, J=8.0 Hz, 2H), 6.70 (t, J=7.5 Hz, 2H), 6.61 (t, J=7.5 Hz, 2H)

ASAP-MS (m/z): $[M+H]^+$ calcd. for $C_{42}H_{25}Br_2N_3$, 731.49; found 730.17.

Synthesis of 4,5,6-tri(9H-carbazole-9-yl)isophthalonitrile 6-2

To a flask, under an aerobic condition, 6-1 (0.14 g, 0.19 mmol), $Pd(OAc)_2$ (2.0 mg, 0.0038 mmol), $Na_2CO_3$ (0.048 g, 0.38 mmol), $K_4[Fe(CN)_6]\cdot 3H_2O$ (0.041 g, 0.096 mmol), 1,3-bis(2,6-diisopropylphenyl)-4,5-dihydro-1H-imidazole-3-imidiumchloride (NHC, 3.1 mg, 0.0038 mmol) and dimethylacetamide (3 mL) were added. The mixture was stirred at 120° C. for 22 h. After cooling to room temperature, the reaction of the mixture was stopped with water (20 ml), and an extraction with ethyl acetate (20 ml) was performed. The combined extracts were dried with $MgSO_4$, and evaporated in a vacuum. The crude residue was purified through silica gel column chromatography using 1:2 (v/v) hexane/$CHCl_3$ as an eluent to obtain a yellow solid 6-2 (yield 53.6 mg) with a yield of 44.9%.

$^1H$ NMR (500 MHz, $CDCl_3$, δ): 8.54 (s, 1H), 7.71 (d, J=8.0 Hz, 4H), 7.28 (d, J=8.0 Hz, 2H), 7.16-7.05 (m, 8H), 7.02-6.99 (m, 4H), 6.76 (t, J=7.5 Hz, 2H), 6.68 (d, J=8.0 Hz, 2H), 6.55 (t, J=7.5 Hz, 2H)

ASAP-MS (m/z): $[M+H]^+$ calcd. for $C_{44}H_{25}N_5$, 623.72; found 624.54.

Synthesis of 4,5,6-tri(9H-carbazole-9-yl)-2-(4,6-diphenyl-1,3,5-triazine-2-yl)isophthalonitrile (Compound 3344)

Under nitrogen, at −78° C., a lithium diisopropylamide solution (1.0 M in THF/hexane, 5.66 mL, 5.66 mmol) was added dropwise to a stirred solution of 6-2 (1.0 g, 1.6 mmol) and tributyn chloride (1.01 mL, 3.52 mmol) in anhydrous THF (350 ml). The reaction product was allowed to stand at room temperature, and was stirred overnight, and then was filtered through 5% by weight of $K_2CO_3$ on a silica gel plug by using $CH_2Cl_2$ as an eluent. The filtrate was concentrated in a vacuum. The resultant product was purified through silica gel column chromatography using 1:3 (v/v) hexane/$CH_2Cl_2$ as an eluent to obtain a yellow solid (1.38 g, 95.9%). A mixture of stannylated solid (1.38 g, 1.53 mmol), 2-chloro-4,6-diphenyl-1,3,5-triazine (449 mg, 1.68 mmol), and $Pd(PPh_3)_4$ (420 mg, 0.36 mmol) was placed in a double-necked round flask. After three cycles of exhaust and nitrogen re-filling were performed, 60 mL of toluene was added to the mixture, and the solution was stirred under reflux for 24 h. The solution was cooled to room temperature, filtered with a celite pad, and washed with toluene. The filtrate was concentrated in a vacuum. The resultant product was purified through silica gel column chromatography using 2:3 (v/v) hexane/$CHCl_3$ as an eluent to obtain a yellow solid compound 3344 (yield 186 mg, yield 32.0%).

$^1H$ NMR (500 MHz, $CDCl_3$, δ): 8.85 (d, J=7.5 Hz, 4H), 7.73 (d, J=7.5 Hz, 4H), 7.68-7.66 (m, 2H), 7.63-7.60 (m, 4H), 7.30 (d, J=7.5 Hz, 2H), 7.24 (d, J=7.5 Hz, 4H), 7.11-7.05 (m, 8H), 6.81-6.78 (m, 4H), 6.58 (t, J=7.5 Hz, 2H)

ASAP-MS (m/z): $[M+H]^+$ calcd. for $C_{59}H_{34}N_8$, 854.98; found 855.53.

Compounds 1 to 431, 434 to 449, 451 to 496, 498 to 500, 502 to 3343, and 3345 to 5663 can also be synthesized in the same manner as in the above synthesis examples.

(Example 1) Neat Film

Each of compounds synthesized in synthesis examples 1 to 6 was vapor-deposited on a quartz substrate by a vacuum deposition method under a condition of a vacuum degree of $10^{-3}$ Pa or less to form a thin film having a thickness of 70 nm.

(Example 2) Dope Film

Each of compounds synthesized in Synthesis Examples 1 to 6 and a host material were vapor-deposited on a quartz substrate by a vacuum deposition method under a condition of a vacuum degree of $10^{-3}$ Pa or less, from another vapor deposition source. Then, a thin film having a thickness of 100 nm was formed in which the concentration of each compound was 20% by weight.

(Example 3) Organic Electroluminescence Device

The principle on the features of the exemplified organic electroluminescence device will be described below.

In an organic electroluminescence device, carriers are injected into a light-emitting material from the anode and the cathode and then an excited state is formed in the light-emitting material, thereby emitting light. In the case of a carrier injection-type organic electroluminescence device, in general, 25% of all the generated excitons cause an excited singlet state, and the remaining excitons of 75% cause an excited triplet state. Therefore, the use of phosphorescence is light radiation from the excited triplet state, which enables high energy utilization. However, the excited triplet state has a long lifetime, thereby causing energy inactivation through the saturation of the excited state, and the interaction of excitons in the excited triplet state. As a result, in some cases, the quantum yield of the phosphorescence is usually not high. The delayed fluorescence material emits fluorescence through a mechanism in which the energy of excitons is shifted to the excited triplet state through intersystem crossing or the like, and then is shifted to the excited singlet state through inverse intersystem crossing or heat energy absorption due to triplet-triplet annihilation. It is thought that among the materials, a thermal activation-type delayed fluorescence material, which emits light through absorption of heat energy, is particularly useful for the organic electroluminescence device. When the delayed fluorescence material is used for the organic electroluminescence device, excitons in the excited singlet state usually emit fluorescence. Meanwhile, excitons in the excited triplet state emit fluorescence through intersystem crossing to the excited singlet state by absorbing the heat generated in the device. Here, the light emitted through inverse intersystem crossing from the excited triplet state to the excited singlet state is light emission from the excited singlet state, and thus has the same wavelength as fluorescence, but has a longer lifetime than normal fluorescence and phosphorescence (light radiation lifetime). Therefore, the light is observed as fluorescence delayed from normal fluorescence and phosphorescence. The above light may be defined as delayed fluorescence. By using the transition mechanism of thermal activation-type excitons, it is possible to raise the ratio in the excited singlet state of the compound, from the normally formed ratio of 25%, up to 25% or more through heat energy absorption after carrier injection. In the compound that emits strong fluorescence and delayed fluorescence at a low temperature below 100° C. intersystem crossing sufficiently occurs from the excited triplet state to the excited singlet state due to the heat of the device, thereby emitting delayed fluorescence. Thus, the use of the above compound can largely enhance the light radiation efficiency.

(Evaluation) Evaluation of Optical Characteristics

A sample was irradiated with light having a wavelength of 300 nm at 300K, whereby the emission spectrum was measured and assigned as fluorescence. A 77K spectrum was also measured, and was assigned as phosphorescence. The lowest singlet energy (S1) and the lowest triplet energy (T1) were estimated from emission of fluorescence and phosphorescence spectra, respectively. $\Delta E_{ST}$ was calculated from an energy gap between S1 and T1. PLQY was also measured from excitation light of 300 nm. The time-resolved spectrum was obtained by excitation light of 337 nm by using a streak camera. Then, a component having a short emission lifetime was assigned as fluorescence whereas a component having a long emission lifetime was assigned as delayed fluorescence. The lifetimes of the fluorescent component ($\tau_{prompt}$) and the delayed fluorescent component ($\tau_{delay}$) were calculated from decay curves.

The luminescence characteristics of compounds synthesized in Synthesis Examples 1 to 6 are superior to the luminescence characteristics of comparative compounds A and B. The luminescence characteristic mentioned herein means at least one characteristic of a physical property value and a device characteristic.

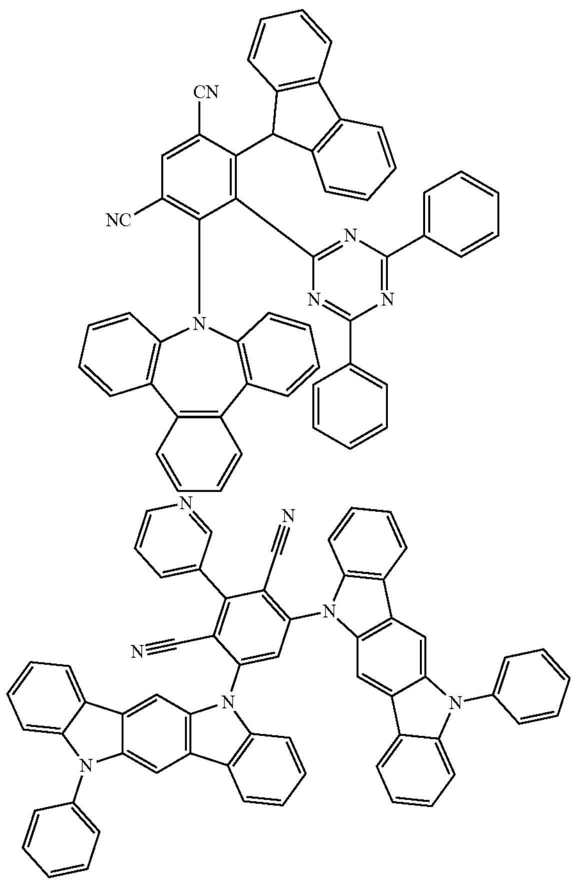

INDUSTRIAL APPLICABILITY

The compound of the present invention has excellent luminescence characteristics, and is also useful as a delayed fluorescence material. Thus, the light-emitting material of the present invention is effectively used for an organic optical device such as an organic electroluminescence device. Therefore, the present invention has high industrial applicability.

The invention claimed is:

1. A compound represented by the following formula (I):

Formula (I)

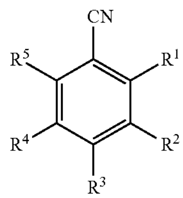

wherein, among $R^1$ to $R^5$, one is CN, another is A, other two or three groups are each independently D, and the remaining group is a hydrogen atom or a substituent other than CN, A, and D, wherein, A is a group represented by any of the following formulas (IIIa), (IIIb) and (IIIc):

Formula (IIIa)

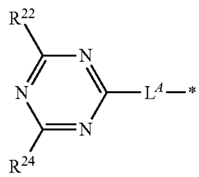

Formula (IIIb)

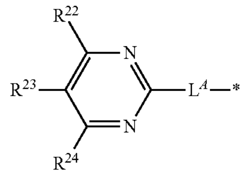

Formula (IIIc)

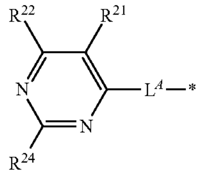

wherein each of $R^{21}$ to $R^{24}$ independently represents a hydrogen atom or a substituent, $L^A$ represents a single bond or a substituted or unsubstituted arylene group, and * represents a bond position, D is a group represented by the following formula (IIa), (IIb), (IIc) or (IId), Formula (IIa)

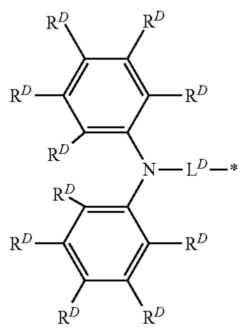

Formula (IIb)

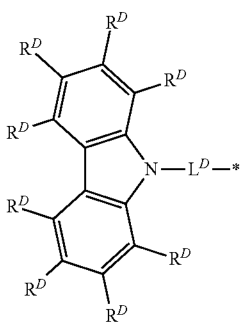

Formula (IIc)

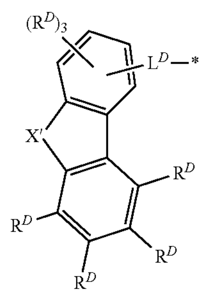

Formula (IId)

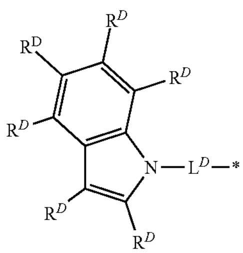

wherein X' represents N—$R^{D\prime}$, an oxygen atom or a sulfur atom, each $R^D$ independently represents a hydrogen atom, a deuterium atom, a substituted or unsubstituted alkyl group, a substituted or unsubstituted alkoxy group, a substituted or unsubstituted amino group, a substituted or unsubstituted aryl group, a substituted or unsubstituted aryloxy group, a substituted or unsubstituted heteroaryl group, a substituted or unsubstituted heteroaryloxy group or a silyl group, and two or more $R^D$'s in the formulae (IIb), (IIc) and (IId) may be bonded to each other to form a cyclic structure, $R^{D\prime}$ represents a hydrogen atom, a deuterium atom, a substituted or unsubstituted alkyl group, a substituted or unsubstituted aryl group, or a substituted or unsubstituted heteroaryl group, and $R^{D\prime}$ may be bonded to one or more other $R^D$'s to form a cyclic structure, each $L^D$ independently represents a single bond, a substituted or unsubstituted arylene group, or a substituted or unsubstituted heteroarylene group,

* represents a bond position, and a plurality of D's present in the molecule may be the same or different.

2. The compound according to claim 1, wherein $R^1$ is A.

3. The compound according to claim 1, wherein $R^3$ is CN.

4. The compound according to claim 3, wherein $R^2$ is H.

5. The compound according to claim 1, wherein $R^2$ is CN.

6. The compound according to claim 1, wherein D is a group represented by the formula (IIb).

7. The compound according to claim 1, wherein any one of $R^1$ to $R^5$ is a hydrogen atom.

8. The compound according to claim 1, wherein $L^D$ is a single bond.

9. The compound according to claim 1, wherein $L^D$ is a substituted or unsubstituted arylene group.

10. An organic optical device containing the compound according to claim 1.

11. The organic optical device according to claim 10, which is an organic light emitting diode (OLED).

* * * * *